United States Patent
Skulason et al.

(10) Patent No.: US 11,239,426 B2
(45) Date of Patent: Feb. 1, 2022

(54) ELECTROACTIVE COMPOUNDS

(71) Applicant: LG Chem, Ltd., Seoul (KR)

(72) Inventors: Hjalti Skulason, Buellton, CA (US); Viacheslav V. Diev, Wilmington, DE (US); Giang Dong Vo, Wilmington, DE (US); Weiying Gao, Landenberg, PA (US); Weishi Wu, Landenberg, PA (US); Norman Herron, Newark, DE (US); Michael Henry Howard, Jr., Montchanin, DE (US); Kalindi Dogra, Wilmington, DE (US); Yunlong Zou, Wilmington, DE (US)

(73) Assignee: LG Chem, Ltd.

( * ) Notice: Subject to any disclaimer, the term of this patent is extended or adjusted under 35 U.S.C. 154(b) by 244 days.

(21) Appl. No.: 16/463,184

(22) PCT Filed: Nov. 1, 2017

(86) PCT No.: PCT/US2017/059448
§ 371 (c)(1),
(2) Date: May 22, 2019

(87) PCT Pub. No.: WO2018/097937
PCT Pub. Date: May 31, 2018

(65) Prior Publication Data
US 2019/0378992 A1    Dec. 12, 2019

Related U.S. Application Data

(60) Provisional application No. 62/425,937, filed on Nov. 23, 2016.

(51) Int. Cl.
*H01L 51/00* (2006.01)
*C07D 493/04* (2006.01)
(Continued)

(52) U.S. Cl.
CPC ........ *H01L 51/0061* (2013.01); *C07C 211/61* (2013.01); *C07D 487/04* (2013.01);
(Continued)

(58) Field of Classification Search
None
See application file for complete search history.

(56) References Cited

U.S. PATENT DOCUMENTS

| 8,946,688 B2 | 2/2015 | Sunagawa et al. |
| 2004/0102577 A1 | 5/2004 | Hsu et al. |

(Continued)

FOREIGN PATENT DOCUMENTS

| CN | 104513662 A | 4/2015 |
| JP | 2002088062 A | 3/2002 |

(Continued)

OTHER PUBLICATIONS

Machine English translation of Jung et al. (KR-10-2014-0009838). Apr. 6, 2021.*

(Continued)

*Primary Examiner* — Jay Yang
(74) *Attorney, Agent, or Firm* — Lerner, David, Littenberg, Krumholz & Mentlik, LLP

(57) ABSTRACT

There is provided a compound having Formula (I), Formula (II), or Formula (III). The variables are described in detail herein.

(I)

(Continued)

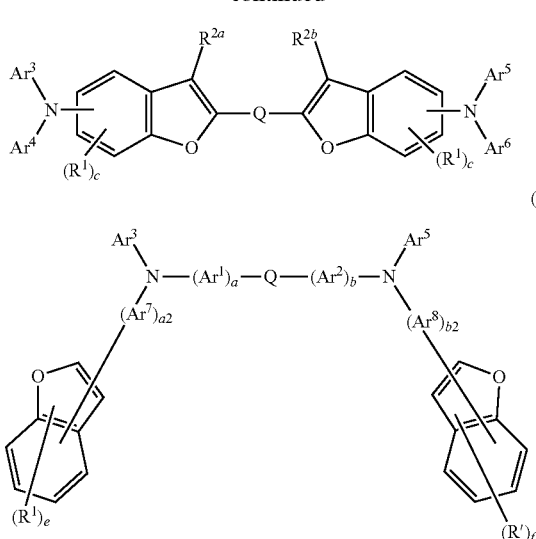

9 Claims, 2 Drawing Sheets

(51) Int. Cl.
| | |
|---|---|
| C09K 11/06 | (2006.01) |
| C07D 493/14 | (2006.01) |
| C07D 487/04 | (2006.01) |
| C07C 211/61 | (2006.01) |
| H01L 51/50 | (2006.01) |

(52) U.S. Cl.
CPC ......... *C07D 493/04* (2013.01); *C07D 493/14* (2013.01); *C09K 11/06* (2013.01); *H01L 51/006* (2013.01); *C07C 2603/54* (2017.05); *C09K 2211/1007* (2013.01); *C09K 2211/1014* (2013.01); *C09K 2211/1018* (2013.01); *H01L 51/0054* (2013.01); *H01L 51/0056* (2013.01); *H01L 51/0058* (2013.01); *H01L 51/0072* (2013.01); *H01L 51/0073* (2013.01); *H01L 51/5012* (2013.01)

(56) References Cited

U.S. PATENT DOCUMENTS

| | | |
|---|---|---|
| 2004/0127637 A1 | 7/2004 | Hsu et al. |
| 2005/0205860 A1 | 9/2005 | Hsu et al. |
| 2010/0032658 A1 | 2/2010 | Lee et al. |
| 2014/0239283 A1 | 8/2014 | Kimura et al. |
| 2014/0312340 A1 | 10/2014 | Funahashi et al. |
| 2015/0001494 A1 | 1/2015 | Kim et al. |
| 2016/0351817 A1 | 12/2016 | Kim et al. |
| 2016/0372664 A1 | 12/2016 | Ito et al. |
| 2017/0222155 A1 | 8/2017 | Cha et al. |
| 2017/0342318 A1 | 11/2017 | Kim et al. |
| 2019/0393420 A1 | 12/2019 | Takeda et al. |

FOREIGN PATENT DOCUMENTS

| | | | |
|---|---|---|---|
| JP | 2005075944 | A | 3/2005 |
| JP | 2010059147 | A | 3/2010 |
| JP | 2011153201 | A | 8/2011 |
| JP | 2012028711 | A | 2/2012 |
| JP | 2012059971 | A | 3/2012 |
| JP | 2012119592 | A | 6/2012 |
| JP | 2012521414 | A | 9/2012 |
| JP | 2012190863 | A | 10/2012 |
| JP | 2013530513 | A | 7/2013 |
| JP | 2013232521 | A | 11/2013 |
| JP | 2015007042 | A | 1/2015 |
| JP | 2017503773 | A | 2/2017 |
| JP | 2018157209 | A | 10/2018 |
| JP | 2019085387 | A | 6/2019 |
| KR | 20120065214 | A | 6/2012 |
| KR | 20130073700 | A | 7/2013 |
| KR | 10-2014-0009838 | * | 1/2014 |
| KR | 10-2015-0077513 | * | 7/2015 |
| KR | 20150077513 | A | 7/2015 |
| KR | 20160041391 | A | 4/2016 |
| KR | 20160084918 | A | 7/2016 |
| KR | 20160091196 | A | 8/2016 |
| KR | 20170082459 | A | 7/2017 |
| WO | 2006100896 | A1 | 9/2006 |
| WO | 2009018009 | A1 | 2/2009 |
| WO | 2010110553 | A2 | 9/2010 |
| WO | 201105334 | A1 | 1/2011 |
| WO | 2011074231 | A1 | 6/2011 |
| WO | 2011136484 | A1 | 11/2011 |
| WO | 2014010910 | A1 | 1/2014 |
| WO | 2015099486 | A1 | 7/2015 |
| WO | 2016108419 | A1 | 7/2016 |

OTHER PUBLICATIONS

Machine English translation of Kang et al. (KR-10-2015-0077513). Apr. 6, 2021.*
Search report from International Application No. PCT/US2017/059448, dated Jan. 30, 2018.
Frischeisen, Jörg, et al., "Determination of molecular dipole orientation in doped fluorescent organic thin films by photoluminescence measurements." Applied Physics Letters, vol. 96, 073302, published online Feb. 17, 2010.
Aniansson, E. A. G., et al., "Theory of the Kinetics of Micellar Equilibria and Quantitative Interpretation of Chemical Relaxation Studies of Micellar Solutoins of Ionic Surfactants." The Journal of Physical Chemistry, vol. 80, No. 9, Apr. 22, 1976, pp. 905-922.
Yempala, Thirumal, et al., "Simple and efficient synthesis of various dibenzofuran carbaldehydes." Synthetic Communications, published online Sep. 16, 2016, pp. 1905-1915.
Ji, Yong, et al., "Trace amount of Cu (ppm)-catalyzed intramolecular cyclization of 2-(gem-dibromovinyl)phenols(thiophenols) to 2-bromobenzofurans(thiophenes)." The Royal Society of Chemistry, published on Apr. 16, 2013.
Wang, Ying, "Photoconductive Polymers." Kirk-Othmer Encyclopedia of Chemical Technology, Fourth Edition, vol. 18, 1996, pp. 837-860.
CRC 5 Handbook of Chemistry and Physics, 81st Edition (2000-2001) (Book Not Included).

* cited by examiner

ELECTROACTIVE COMPOUNDS

CROSS-REFERENCE TO RELATED APPLICATIONS

The present application is a national phase entry under 35 U.S.C. § 371 of International Application No. PCT/KR2017/059448, filed Nov. 1, 2017, which claims priority from U.S. Provisional Application No. 62/425,937, filed Nov. 23, 2016, all of which are incorporated herein by reference.

BACKGROUND INFORMATION

Field of the Disclosure

This disclosure relates in general to electroactive compounds and their use in electronic devices.

Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules, such as anthracene, thiadiazole derivatives, and coumarin derivatives are known to show electroluminescence. Metal complexes, particularly iridium and platinum complexes are also known to show electroluminescence. In some cases these small molecule compounds are present as a dopant in a host material to improve processing and/or electronic properties.

There is a continuing need for new electroactive compounds that can be used as hosts or electroluminescent materials.

SUMMARY

There is provided a compound having Formula I

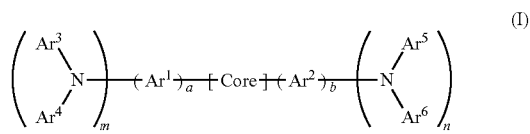

wherein:
Ar$^1$-Ar$^6$ are the same or different and are selected from the group consisting of hydrocarbon aryl groups, heteroaryl groups, and substituted derivatives thereof;
a and b are the same or different and are 0 or 1;
m and n are the same or different and are 0 or 1, with the proviso that a+b+m+n≥1; and
Core is selected from the group consisting of Formula IA, Formula IB, and Formula IC

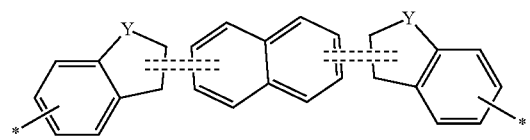

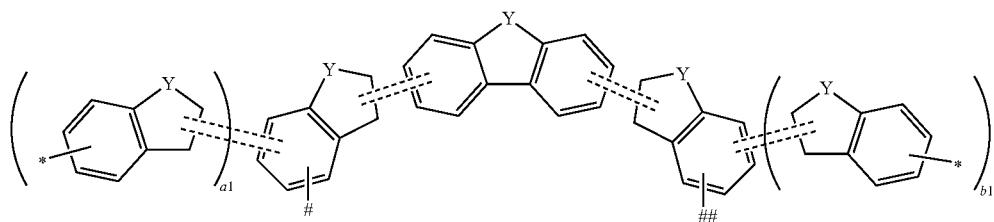

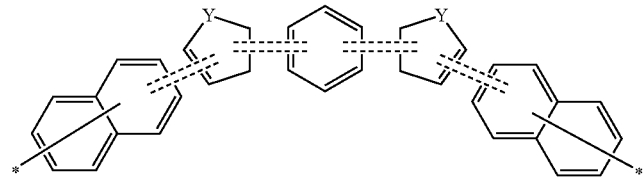

where:
Y is the same or different at each occurrence and is selected from the group consisting of O, S, Se, Te, NR$^2$, CR$^3$R$^4$, and SiR$^5$R$^6$;
R$^2$ is the same or different at each occurrence and is selected from the group consisting of alkyl, hydrocarbon aryl, heteroaryl, and substituted derivatives thereof;
R$^3$-R$^6$ are the same or different at each occurrence and are selected from the group consisting of alkyl, silyl, germyl, hydrocarbon aryl, heteroaryl, and substituted derivatives thereof, where R$^3$ and R$^4$ and/or R$^5$ and R$^6$ can be joined to form a cyclic group selected from the group consisting of cycloalkyl, silacycloalkyl, spirofluorenyl, silaspirofluorenyl, or a substituted derivative thereof;

a1 and b1 are the same or different and are 0 or 1;
a double dashed line between two rings indicates that the rings are fused together in any orientation;
* indicates a point of attachment in the identified formula; and
# and ## represent no bond or a point of attachment in the identified formula, such that when a1=0 then # is a point of attachment, when a1=1 then # is no bond, when b1=0 then ## is a point of attachment, and when b1=1 then ## is no bond;
and further wherein the Core may have one or more substituents selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

There is also provided a compound having Formula II or Formula III

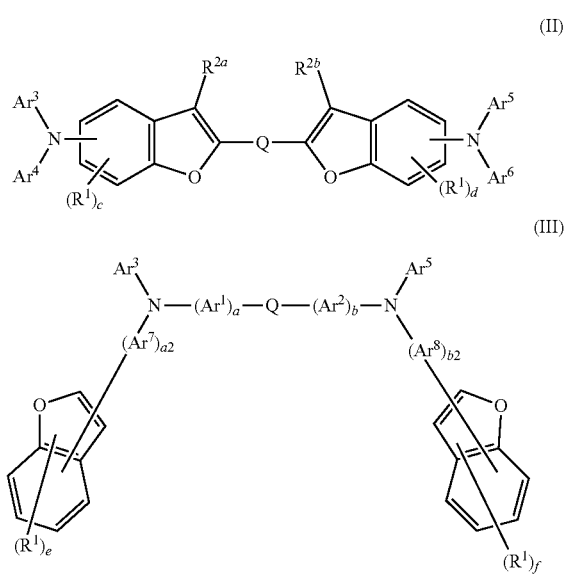

wherein:
Ar$^1$-Ar$^8$ are the same or different and are selected from hydrocarbon aryl groups, heteroaryl groups, and substituted derivatives thereof;
R$^1$ is the same or different at each occurrence and is selected from the group consisting of D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl, deuterated silyl, deuterated siloxane, deuterated siloxy, and deuterated germyl;
R$^{2a}$ and R$^{2b}$ are the same or different and are selected from the group consisting of H, D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl, deuterated silyl, deuterated siloxane, deuterated siloxy, and deuterated germyl;
Q is selected from the group consisting of a hydrocarbon aryl having 2 or more fused rings, a heteroaryl having 2 or more fused rings, and a substituted derivative thereof;

a, a2, b, and b2 are the same or different and are 0 or 1;
c and d are the same or different and are an integer of 0-3; and
e and f are the same or different and are an integer of 0-5.

There is also provided an organic electronic device comprising a first electrical contact, a second electrical contact and a photoactive layer therebetween, the photoactive layer comprising a compound having Formula I, Formula II, or Formula III.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
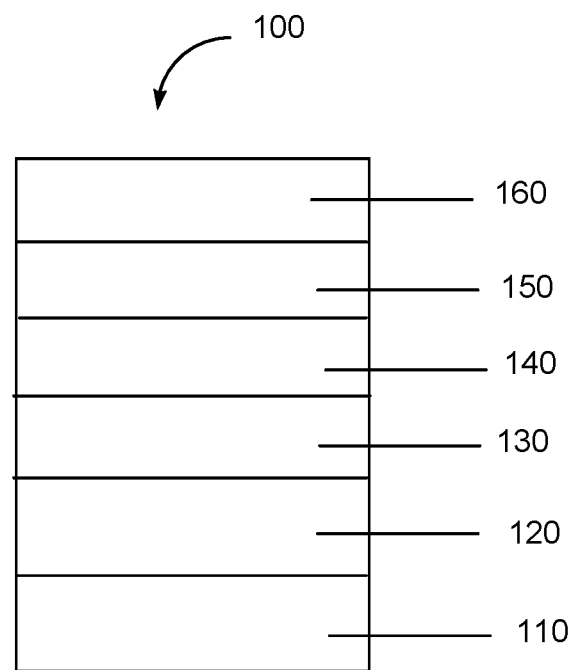
FIG. 1 includes an illustration of one example of an organic electronic device including a new compound described herein.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Compound Having Formula I, Compounds Having Formula II or Formula III, Devices, and finally Examples.

1. Definitions and Clarification of Terms

Before addressing details of embodiments described below, some terms are defined or clarified.

Unless otherwise specifically defined, R, R', R" and any other variables are generic designations. The specific definitions for a given formula herein are controlling for that formula.

The term "adjacent" as it refers to substituent groups refers to groups that are bonded to carbons that are joined together with a single or multiple bond. Exemplary adjacent R groups are shown below:

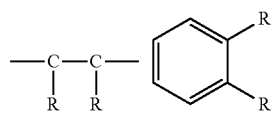

The term "alkoxy" is intended to mean the group RO—, where R is an alkyl group.

The term "alkyl" is intended to mean a group derived from an aliphatic hydrocarbon and includes a linear, a branched, or a cyclic group. A group "derived from" a compound, indicates the radical formed by removal of one or more H or D.

In some embodiments, an alkyl has from 1-20 carbon atoms.

The term "aromatic compound" is intended to mean an organic compound comprising at least one unsaturated cyclic group having 4n+2 delocalized pi electrons.

The term "aryl" is intended to mean a group derived from an aromatic hydrocarbon having one or more points of attachment. The term includes groups which have a single ring and those which have multiple rings which can be joined by a single bond or fused together. Hydrocarbon aryl groups have only carbon in the ring structures. Heteroaryl groups have at least one heteroatom in a ring structure.

The term "alkylaryl" is intended to mean an aryl group having one or more alkyl substituents.

The term "aryloxy" is intended to mean the group RO—, where R is an aryl group.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "deuterated" is intended to mean that at least one hydrogen ("H") has been replaced by deuterium ("D"). The term "deuterated analog" refers to a structural analog of a compound or group in which one or more available hydrogens have been replaced with deuterium. In a deuterated compound or deuterated analog, the deuterium is present in at least 100 times the natural abundance level. The term "% deuterated" or "% deuteration" is intended to mean the ratio of deuterons to the sum of protons plus deuterons, expressed as a percentage.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "germyl" refers to the group $R_3Ge$—, where R is the same or different at each occurrence and is H, D, C1-20 alkyl, deuterated alkyl, fluoroalkyl, aryl, or deuterated aryl.

The prefix "hetero" indicates that one or more carbon atoms have been replaced with a different atom. In some embodiments, the different atom is N, O, or S.

The term "host material" is intended to mean a material, usually in the form of a layer, to which a dopant may be added. The host material may or may not have electronic characteristic(s) or the ability to emit, receive, or filter radiation.

The terms "luminescent material", "emissive material" and "emitter" are intended to mean a material that emits light when activated by an applied voltage (such as in a light-emitting diode or light-emitting electrochemical cell). The term "blue luminescent material" is intended to mean a material capable of emitting radiation that has an emission maximum at a wavelength in a range of approximately 445-490 nm.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "N-heterocycle" or "N-heteroaryl" refers to a heteroaromatic compound or group having at least one nitrogen in an aromatic ring.

The term "N,O,S-heterocycle" or "N,O,S-heteroaryl" refers to a heteroaromatic compound or group having at least one heteroatom in an aromatic ring, where the heteroatom is N, O, or S. The N,O,S-heterocycle may have more than one type of heteroatom.

The term "organic electronic device" or sometimes just "electronic device" is intended to mean a device including one or more organic semiconductor layers or materials.

The term "photoactive" refers to a material or layer that emits light when activated by an applied voltage (such as in a light emitting diode or chemical cell) or responds to radiant energy and generates a signal with or without an applied bias voltage (such as in a photodetector or a photovoltaic cell). The photoactive material or layer is sometimes referred to as the emissive layer. The photoactive layer is abbreviated herein as "EML".

The term "silacycloalkyl" refers to a cyclic alkyl group where one or more carbons have been replaced with silicons.

The term "silaspirofluorenyl" refers to a spirofluorenyl group where the spiro carbon has been replaced with silicon.

The term "siloxane" refers to the group $R_3SiO(R_2Si)$—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

The term "siloxy" refers to the group $R_3SiO$—, where R is the same or different at each occurrence and is H, D, C1-20 alkyl, deuterated alkyl, fluoroalkyl, aryl, or deuterated aryl.

The term "silyl" refers to the group $R_3Si$—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

The term "spirofluorenyl" refers to a group derived from the compound below, where the central carbon is referred to as the spiro carbon.

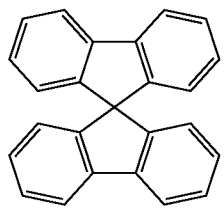 [SMILES: c1ccc2c(c1)-c1ccccc1C21c2ccccc2-c2ccccc21]

All groups may be unsubstituted or substituted. The substituent groups are discussed below. In a structure where a substituent bond passes through one or more rings as shown below,

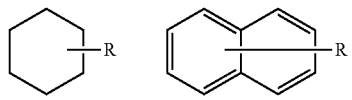

it is meant that the substituent R may be bonded at any available position on the one or more rings.

In any of the formulas or combination of formulas below, any subscript, such as a-h, k, p, q, r, s, a1, b1, and k1, that is present more than one time, may be the same or different at each occurrence.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic cell, and semiconductive member arts.

2. Compounds Having Formula I

In some embodiments, the compounds described herein have Formula I

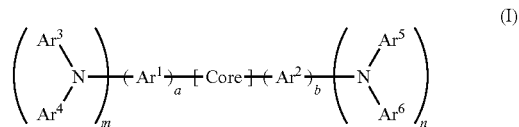

wherein:
$Ar^1$-$Ar^6$ are the same or different and are selected from the group consisting of hydrocarbon aryl groups, heteroaryl groups, and substituted derivatives thereof;
a and b are the same or different and are 0 or 1;
m and n are the same or different and are 0 or 1, with the proviso that a+b+m+n≥1; and
Core is selected from the group consisting of Formula IA, Formula IB, and Formula IC

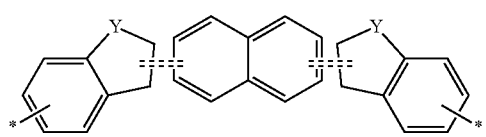

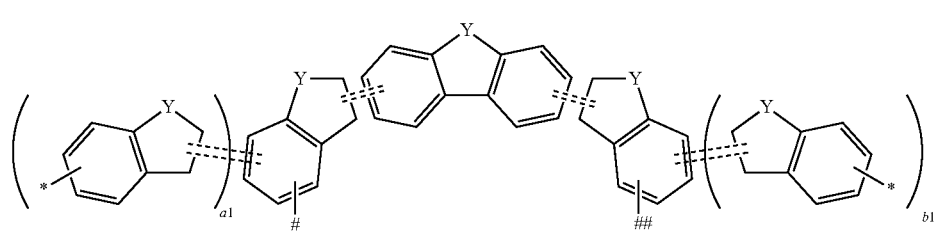

(IC)

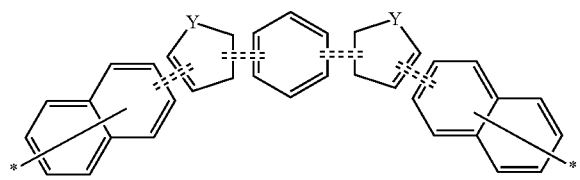

where:
Y is the same or different at each occurrence and is selected from the group consisting of O, S, Se, Te, $NR^2$, $CR^3R^4$, and $SiR^5R^6$;
$R^2$ is the same or different at each occurrence and is selected from the group consisting of alkyl, hydrocarbon aryl, heteroaryl, and substituted derivatives thereof;
$R^3$-$R^6$ are the same or different at each occurrence and are selected from the group consisting of alkyl, silyl, germyl, hydrocarbon aryl, heteroaryl, and substituted derivatives thereof, where $R^3$ and $R^4$ and/or $R^5$ and $R^6$ can be joined to form a cyclic group selected from the group consisting of cycloalkyl, silacycloalkyl, spirofluorenyl, silaspirofluorenyl, or a substituted derivative thereof;
a1 and b1 are the same or different and are 0 or 1;
a double dashed line between two rings indicates that the rings are fused together in any orientation;
* indicates a point of attachment in the identified formula; and
# and ## represent no bond or a point of attachment in the identified formula, such that when a1=0 then # is a point of attachment, when a1=1 then # is no bond, when b1=0 then ## is a point of attachment, and when b1=1 then ## is no bond;
and further wherein the Core may have one or more substituents selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

In Formula I, the Core group has one or two optional diarylamino substituents and one or two optional aryl spacer groups ($Ar^1$ and $Ar^2$).

In some embodiments of Formula I, there are no amino groups other that those explicitly shown in Formula I.

In some embodiments of Formula I, there are no more than 2 amino groups present.

In some embodiments of Formula I, m=n=0 and the compounds are useful as host materials.

In some embodiments of Formula I, m+n=1.

In some embodiments of Formula I, m=n=1.

In some embodiments, the compounds having Formula I where at least one of m and n is 1 are useful as emissive materials. In some embodiments, the compounds are blue emissive materials. They can be used alone or as a dopant in a host material.

In some embodiments, the compounds having Formula I where at m=n=1 are useful as emissive materials. In some embodiments, the compounds are blue emissive materials. They can be used alone or as a dopant in a host material.

In some embodiments, the compounds having Formula I where one or both of m and n is 1 have deep blue color. As used herein, the term "deep blue color" refers to a C.I.E. y-coordinate of less than 0.10, according to the C.I.E. chromaticity scale (Commission Internationale de L'Eclairage, 1931). In some embodiments, the compounds having Formula I have a photoluminescence y-coordinate of less than 0.10; in some embodiments, less than 0.090.

In some embodiments, the compounds having Formula I where one or both of m and n is 1 have a very narrow emission profile. In some embodiments, the emission profile has a width at half the maximum intensity (Full Width at Half Maximum, "FWHM") that is less than 75 nm; in some embodiments, less than 60 nm; in some embodiments, less than 50 nm; in some embodiments, less than 40 nm; in some embodiments, less than 30 nm. This is advantageous for display devices for producing more saturated color.

In some embodiments, the compounds having Formula I have a solubility in toluene of at least 10 mg/mL; in some embodiments, at least 15 mg/mL; in some embodiments, at least 20 mg/mL. This is advantageous for purification and for solution processing for optimal device performance.

In some embodiments, the compounds having Formula I have sublimation temperatures less than 750° C. at 10 torr; in some embodiments, less than 600° C. at 10 torr; in some embodiments, less than 500° C. at 10 torr. This is advantageous for purification.

In some embodiments, the compounds having Formula I where one or both of m and n is 1, have a high photoluminescence quantum yield ("PLQY"). The photoluminescence quantum yield is the ratio of photons emitted through photoluminescence to photons absorbed, and is expressed as a percentage of a standard compound. Increased PLQY can contribute to increased efficiency in devices. In some embodiments, the compounds of Formula I have a solution PLQY which is at least 90% of a standard of quinine bisulfate in 1 N sulfuric acid.

In some embodiments, devices including the compounds of Formula I have improved efficiencies. In some embodiments, the current efficiency of a device including Formula I is greater than 4.5 cd/A at 1000 nits; in some embodiments, greater than 5.0 cd/A at 1000 nits.

In some embodiments, devices including the compounds of Formula I have increased lifetime at an initial luminance of 1000 nits. In some embodiments, devices including the compounds of Formula I have a T70 greater than 1000 hours at 50° C. at a current density >15 mA/cm². As used herein, T70 refers to the time to reach 70% of initial luminance. In some embodiments, devices including the compounds of Formula I have a T70 greater than 1500 hours at 50° C.

In some embodiments, electroluminescent devices including the compounds of Formula I where one or both of m and n is 1 as emissive materials have deep blue color. In some embodiments, the C.I.E. x-coordinate is less than 0.15 and the C.I.E. y-coordinate is less than 0.10; in some embodiments, the y-coordinate is less than 0.090; in some embodiments, the y-coordinate is less than 0.080; in some embodiments, the y-coordinate is less than 0.070; in some embodiments, the y-coordinate is less than 0.060.

In some embodiments, the compounds of Formula I have a high degree of horizontal alignment in when doped in films. "Horizontal alignment" and "horizontal orientation" are intended to mean that the emissive dipoles lie parallel to the substrate. Increased horizontal alignment can contribute to higher efficiency in devices. In some embodiments, the compounds of Formula I have a horizontal orientation greater than 90%.

In some embodiments of Formula I, the compound is deuterated.

In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula I, deuteration is present on the Core group.

In some embodiments of Formula I, deuteration is present on one or both diarylamino groups.

In some embodiments of Formula I, deuteration is present on one or both of the aryl spacer groups.

In some embodiments of Formula I, deuteration is present on two or more of the Core group, a diarylamino group, and a spacer group.

In some embodiments of Formula I, a=0.
In some embodiments of Formula I, a=1.
In some embodiments of Formula I, a=1 and $Ar^1$ is selected from the group consisting of hydrocarbon aryl groups, heteroaryl groups, and substituted derivatives thereof, wherein substituted derivatives have only substituents selected from the group consisting of D, alkyl, silyl, germyl, deuterated alkyl, deuterated silyl, and deuterated germyl, and no other substituents.

In some embodiments of Formula I, a=1 and $Ar^1$ is an unsubstituted hydrocarbon aryl.

In some embodiments of Formula I, a=1 and $Ar^1$ is a hydrocarbon aryl or deuterated analog thereof having 6-30 ring carbons; in some embodiments 6-18 ring carbons.

In some embodiments of Formula I, a=1 and $Ar^1$ is a substituted hydrocarbon aryl, where the substituent is selected from the group consisting of D, alkyl, silyl, germyl, deuterated alkyl, deuterated silyl, and deuterated germyl.

In some embodiments of Formula I, a=1 and $Ar^1$ is selected from the group consisting of phenyl, biphenyl, terphenyl, 1-naphthyl, 2-naphthyl, anthracenyl, fluorenyl, phenanthryl, deuterated analogs thereof, and derivatives thereof having one or more substituents selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

In some embodiments of Formula I, a=1 and $Ar^1$ is selected from the group consisting of phenyl, biphenyl, terphenyl, 1-naphthyl, 2-naphthyl, anthracenyl, fluorenyl, phenanthryl, deuterated analogs thereof, and derivatives thereof having one or more substituents selected from the group consisting of D, alkyl, silyl, germyl, deuterated alkyl, deuterated silyl, and deuterated germyl.

In some embodiments of Formula I, a=1 and $Ar^1$ is selected from the group consisting of phenyl, biphenyl, naphthyl and substituted derivatives thereof.

In some embodiments of Formula I, a=1 and $Ar^1$ is selected from the group consisting of phenyl, biphenyl, naphthyl and deuterated analogs thereof.

In some embodiments of Formula I, a=1 and $Ar^1$ has Formula c

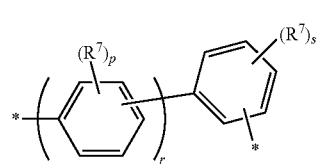

Formula c where:
$R^7$ is the same or different at each occurrence and is selected from the group consisting of D, alkyl, silyl, germyl, deuterated alkyl, deuterated silyl, deuterated germyl;
p is the same or different at each occurrence and is an integer from 0-4;
s is an integer from 0-4;
r is an integer from 0 to 5; and
* indicates a point of attachment in the identified formula.

In some embodiments of Formula c, p=s=0.
In some embodiments of Formula c, p>0.
In some embodiments of Formula c, s>0.
In some embodiments of Formula c, p>0 and $R^7$=D.
In some embodiments of Formula c, s>0 and $R^7$=D.
In some embodiments of Formula c, p>0 and $R^7$=alkyl or deuterated alkyl.
In some embodiments of Formula c, s>0 and $R^7$=alkyl or deuterated alkyl.
In some embodiments of Formula c, r=1-3.
In some embodiments of Formula I, a=1 and $Ar^1$ has Formula d

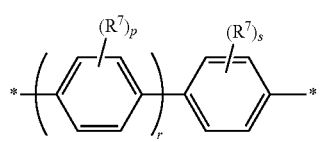

Formula d where $R^7$, p, r, s, and * are as in Formula c. All of the above-described embodiments for $R^7$, p, r, and s in Formula c, apply equally to $R^7$, p, r, and s in Formula d.

In some embodiments of Formula I, a=1 and $Ar^1$ is an unsubstituted heteroaryl.

In some embodiments of Formula I, a=1 and $Ar^1$ is a heteroaryl or deuterated analog thereof having 3-30 ring carbons; in some embodiments 3-18 ring carbons.

In some embodiments of Formula I, a=1 and $Ar^1$ is a substituted heteroaryl, where the substituent is selected from the group consisting of D, alkyl, silyl, germyl, deuterated alkyl, deuterated silyl, and deuterated germyl.

In some embodiments of Formula I, a=1 and $Ar^1$ is selected from the group consisting of heteroaryl and deuterated heteroaryl, where the heteroaryl has at least one ring atom which is selected from the group consisting of N, O, and S.

In some embodiments of Formula I, a=1 and $Ar^1$ is an N-heteroaryl or deuterated N-heteroaryl having at least one ring atom which is N.

In some embodiments, the N-heteroaryl is derived from a compound selected from the group consisting of pyrrole, pyridine, pyrimidine, carbazole, imidazole, benzimidazole, imidazolobenzimidazole, triazole, benzotriazole, triazolopyridine, indolocarbazole, phenanthroline, quinoline, isoquinoline, quinoxaline, indole, indoloindole, and substituted derivatives thereof.

In some embodiments of Formula I, a=1 and Ar¹ is an O-heteroaryl having at least one ring atom that is O.

In some embodiments, the O-heteroaryl is derived from a compound selected from the group consisting of furan, benzofuran, isobenzofuran, dibenzofuran, and substituted derivatives thereof.

In some embodiments of Formula I, a=1 and Ar¹ is present and is an S-heteroaryl having at least one ring atom which is S.

In some embodiments, the S-heteroaryl is derived from a compound selected form the group consisting of thiophene, benzothiophene, isobenzothiophene, dibenzothiophene, and substituted derivatives thereof.

In some embodiments of Formula I, a=1 and Ar¹ is an N,O-heteroaryl having at least one ring atom that is N and at least one ring atom that is O.

In some embodiments, the N,O-heteroaryl is derived from a compound selected from the group consisting of oxazole, benzoxazole, oxazine, phenoxazine, and substituted derivatives thereof.

In some embodiments of Formula I, b=0.
In some embodiments of Formula I, b=1.
All of the above-described embodiments for Ar¹ in Formula I apply equally to Ar² in Formula I.
In some embodiments of Formula I, Ar¹=Ar².
In some embodiments of Formula I, Ar¹≠Ar².
In some embodiments of Formula I, m=0.
In some embodiments of Formula I, m=1.
In some embodiments of Formula I, n=0.
In some embodiments of Formula I, n=1.
In some embodiments of Formula I, m=1 and Ar³ is selected from the group consisting of hydrocarbon aryl groups, heteroaryl groups, and substituted derivatives thereof, wherein substituted derivatives have only substituents selected from the group consisting of D, alkyl, silyl, germyl, deuterated alkyl, deuterated silyl, and deuterated germyl, and no other substituents.

In some embodiments of Formula I, m=1 and Ar³ has no more than two fused rings.

In some embodiments of Formula I, m=1 and Ar³ is not fluorene or substituted fluorene.

In some embodiments of Formula I, m=1 and Ar³ is not carbazole or substituted carbazole.

In some embodiments of Formula I, m=1 and Ar³ is a hydrocarbon aryl or deuterated analog thereof having 6-30 ring carbons; in some embodiments 6-18 ring carbons.

In some embodiments of Formula I, m=1 and Ar³ has Formula a

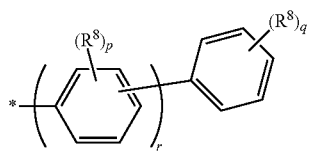

Formula a where:
R⁸ is the same or different at each occurrence and is selected from the group consisting of D, F, CN, alkyl, aryloxy, heteroaryl, alkoxy, siloxy, silyl, germyl, deuterated alkyl, deuterated aryloxy, deuterated heteroaryl, deuterated alkoxy, deuterated siloxane, deuterated silyl, deuterated germyl, where adjacent R⁸ groups can be joined together to form a fused ring;
p is the same or different at each occurrence and is an integer from 0-4;
q is an integer from 0-5;
r is an integer from 0 to 5; and
* indicates a point of attachment in the identified formula.
In some embodiments of Formula a, p=qs=0.
In some embodiments of Formula a, p>0.
In some embodiments of Formula a, q>0.
In some embodiments of Formula a, p>0 and R⁷=D.
In some embodiments of Formula a, q>0 and R⁷=D.
In some embodiments of Formula a, p>0 and R⁷=alkyl or deuterated alkyl.
In some embodiments of Formula a, q>0 and R⁷=alkyl or deuterated alkyl.
In some embodiments of Formula a, r=1-3.
In some embodiments of Formula I, m=1 and Ar³ has Formula b

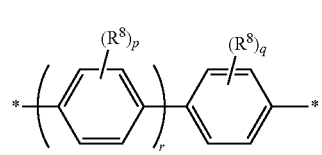

Formula b where R⁸, p, q, r and * are as in Formula a. All of the above-described embodiments for R⁷, p, q, and r in Formula a, apply equally to R⁷, p, q, and r in Formula b.

In some embodiments of Formula I, m=1 and Ar³ has Formula c

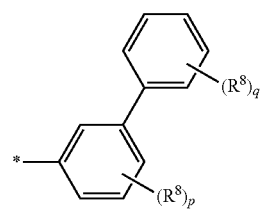

Formula c where R⁸, p, q, and * are as in Formula a.
In some embodiments of Formula a, p=0.
In some embodiments of Formula a, p=1.
In some embodiments of Formula a, p=2.
In some embodiments of Formula a, p=3.
In some embodiments of Formula a, p=4.
In some embodiments of Formula a, p>0.
In some embodiments of Formula a, q=0.
In some embodiments of Formula a, q=1.
In some embodiments of Formula a, q=2.
In some embodiments of Formula a, q=3.
In some embodiments of Formula a, q=4.
In some embodiments of Formula a, q=5.
In some embodiments of Formula a, q>0.
In some embodiments of Formula a, at least one of p and q is greater than 0 and at least one R⁸=D.
In some embodiments of Formula a, at least one of p and q is greater than 0 and at least one R⁸ is an alkyl or deuterated alkyl having 1-12 carbons; in some embodiments 1-8 carbons.

In some embodiments of Formula a, at least one of p and q is greater than 0 and at least one $R^8$ is a trialkylsilyl or deuterated trialkylsilyl.

In some embodiments, the alkyl moiety in the trialkyl silyl group has 1-8 carbons; in some embodiments, 1-3 carbons.

In some embodiments of Formula a, at least one of p and q is greater than 0 and at least one $R^8$ is an unsubstituted hydrocarbon aryl having 6-24 ring carbons.

In some embodiments of Formula a, at least one of p and q is greater than 0 and at least one $R^8$ is a hydrocarbon aryl having 6-24 ring carbons and having at least one substituent selected from the group consisting of D, alkyl, silyl, deuterated alkyl, deuterated silyl, and combinations thereof.

In some embodiments of Formula a, at least one of p and q is greater than 0 and at least one $R^8$ is selected from the group consisting of D, alkyl having 1-8 carbons, trialkylsilyl, phenyl, substituted phenyl, naphthyl, substituted naphthyl, biphenyl, substituted biphenyl, terphenyl, and substituted terphenyl, wherein the substituted groups have at least one substituent selected from the group consisting of D, alkyl, silyl, deuterated alkyl, deuterated silyl, and combinations thereof.

In some embodiments of Formula I, m=1 and $Ar^3$ is selected from the group consisting of phenyl, biphenyl, terphenyl, 1-naphthyl, 2-naphthyl, anthracenyl, fluorenyl, phenanthryl, and derivatives thereof having one or more substituents selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

In some embodiments of Formula I, m=1 and $Ar^3$ is selected from the group consisting of phenyl, biphenyl, terphenyl, 1-naphthyl, 2-naphthyl, anthracenyl, fluorenyl, phenanthryl, and derivatives thereof having one or more substituents selected from the group consisting of D, alkyl, silyl, germyl, deuterated alkyl, deuterated silyl, and deuterated germyl.

In some embodiments of Formula I, m=1 and $Ar^3$ has at least one substituent selected from the group consisting of D, F, CN, alkyl, alkoxy, silyl, siloxy, siloxane, germyl, hydrocarbon aryl, heteroaryl, diarylamino, carbazolyl, deuterated alkyl, deuterated alkoxy, deuterated silyl, deuterated siloxy, deuterated siloxane, deuterated germyl, deuterated hydrocarbon aryl, deuterated heteroaryl, deuterated diarylamino, and deuterated carbazolyl.

In some embodiments of Formula I, m=1 and $Ar^3$ has at least one substituent selected from the group consisting of D, F, CN, alkyl, alkoxy, silyl, siloxy, siloxane, germyl, hydrocarbon aryl, heteroaryl, deuterated alkyl, deuterated alkoxy, deuterated silyl, deuterated siloxy, deuterated siloxane, deuterated germyl, deuterated hydrocarbon aryl, and deuterated heteroaryl.

In some embodiments of Formula I, m=1 and $Ar^3$ has at least one substituent selected from the group consisting of D, alkyl, hydrocarbon aryl, heteroaryl, deuterated alkyl, deuterated hydrocarbon aryl, and deuterated heteroaryl.

All of the above-described embodiments for $Ar^3$ in Formula I apply equally to $Ar^4$, $Ar^5$, and $Ar^6$ in Formula I.

In some embodiments of Formula I, $Ar^3=Ar^4$.
In some embodiments of Formula I, $Ar^3\text{-}Ar^4$.
In some embodiments of Formula I, $Ar^5=Ar^6$.
In some embodiments of Formula I, $Ar^5 \neq Ar^6$.
In some embodiments of Formula I, $Ar^3=Ar^6$.
In some embodiments of Formula I, $Ar^4=Ar^5$.
In some embodiments of Formula I, $Ar^3=Ar^6$ and $Ar^4=Ar^5$.

In some embodiments of Formula I, $Ar^3$, $Ar^4$, $Ar^5$, and $Ar^6$ are all different.

In some embodiments of Formula I, m=1 and $Ar^3$ and $Ar^4$ are joined together to form a carbazolyl group. In some embodiments the carbazolyl group is unsubstituted. In some embodiments, the carbazolyl group has at least one substituent selected from the group consisting of D, alkyl, silyl, germyl, hydrocarbon aryl, deuterated alkyl, deuterated silyl, deuterated germyl, and deuterated hydrocarbon aryl.

In some embodiments of Formula I, n=1 and $Ar^5$ and $Ar^6$ are joined together to form a carbazolyl group. In some embodiments the carbazolyl group is unsubstituted. In some embodiments, the carbazolyl group has at least one substituent selected from the group consisting of D, alkyl, silyl, germyl, hydrocarbon aryl, deuterated alkyl, deuterated silyl, deuterated germyl, and deuterated hydrocarbon aryl.

In some embodiments of Formula I, the Core group has Formula IA

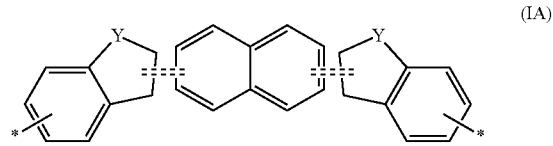

(IA)

where:
Y is the same or different at each occurrence and is selected from the group consisting of O, S, Se, Te, $NR^2$, $CR^3R^4$, and $SiR^5R^6$;
$R^2$ is the same or different at each occurrence and is selected from the group consisting of alkyl, hydrocarbon aryl, heteroaryl, and substituted derivatives thereof;
$R^3$-$R^6$ are the same or different at each occurrence and are selected from the group consisting of alkyl, silyl, germyl, hydrocarbon aryl, heteroaryl, and substituted derivatives thereof, where $R^3$ and $R^4$ and/or $R^5$ and $R^6$ can be joined to form a cyclic group selected from the group consisting of cycloalkyl, silacycloalkyl, spirofluorenyl, silaspirofluorenyl, or a substituted derivative thereof;
a double dashed line between two rings indicates that the rings are fused together in any orientation; and
* indicates a point of attachment in the identified formula;
and further wherein there may be one or more substituents selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

In some embodiments of Formula IA, Y=O.
In some embodiments of Formula IA, Y=S.
In some embodiments of Formula IA, Y=Se.
In some embodiments of Formula IA, Y=Te.
In some embodiments of Formula IA, Y=$NR^2$.
In some embodiments of Formula IA, Y=$CR^3R^4$.
In some embodiments of Formula IA, Y=$SiR^5R^6$.
In some embodiments of Formula IA, Y is selected from the group consisting of O, S, and Se.
In some embodiments of Formula IA, Y is selected from the group consisting of $CR^3R^4$ and $SiR^5R^6$.
In some embodiments of Formula IA, Y is selected from the group consisting of O, $NR^2$, and $CR^3R^4$.
In some embodiments of Formula IA, both Y are the same.

In some embodiments of Formula IA, $R^2$ is selected from the group consisting of alkyl, hydrocarbon aryl, heteroaryl, and substituted derivatives thereof, wherein the substituted derivatives have only substituents selected from the group consisting of D, alkyl, silyl, germyl, deuterated alkyl, deuterated silyl, and deuterated germyl, and no other substituents.

In some embodiments of Formula IA, $R^2$ is an unsubstituted hydrocarbon aryl having 6-30 ring carbons.

In some embodiments of Formula IA, $R^2$ is a hydrocarbon aryl having one or more substituents selected from the group consisting of D, alkyl, silyl, germyl, deuterated alkyl, deuterated silyl, and deuterated germyl.

In some embodiments of Formula IA, $R^2$ is selected from the group consisting of phenyl, biphenyl, terphenyl, 1-naphthyl, 2-naphthyl, anthracenyl, fluorenyl, phenanthryl, and derivatives thereof having one or more substituents selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

In some embodiments of Formula IA, $R^2$ is an unsubstituted heteroaryl.

In some embodiments of Formula IA, $R^2$ is an unsubstituted alkyl.

In some embodiments of Formula IA, $R^2$ is a heteroaryl having one or more substituents selected from the group consisting of D, alkyl, silyl, germyl, deuterated alkyl, deuterated silyl, and deuterated germyl.

In some embodiments of Formula IA, $R^2$ is an N-heteroaryl or substituted derivative thereof.

In some embodiments of Formula IA, $R^3$ is selected from the group consisting of substituted alkyl, substituted silyl, substituted germyl, substituted hydrocarbon aryl, and substituted heteroaryl, wherein the substitutent is selected from the group consisting of D, alkyl, silyl, germyl, deuterated alkyl, deuterated silyl, and deuterated germyl.

In some embodiments of Formula IA, $R^3$ is selected from the group consisting of substituted alkyl, substituted silyl, substituted germyl, substituted hydrocarbon aryl, and substituted heteroaryl, wherein the substitutent is only selected from the group consisting of D, alkyl, silyl, germyl, deuterated alkyl, deuterated silyl, and deuterated germyl, and no other substituents are present.

In some embodiments of Formula IA, $R^3$ is an alkyl having 1-20 carbon atoms or deuterated analog thereof; in some embodiments, 1-12 carbons.

In some embodiments of Formula IA, $R^3$ is an unsubstituted hydrocarbon aryl having 6-30 ring carbons.

In some embodiments of Formula IA, $R^3$ is a hydrocarbon aryl having one or more substituents selected from the group consisting of D, alkyl, silyl, germyl, deuterated alkyl, deuterated silyl, and deuterated germyl.

In some embodiments of Formula IA, $R^3$ is selected from the group consisting of phenyl, biphenyl, terphenyl, 1-naphthyl, 2-naphthyl, anthracenyl, fluorenyl, and derivatives thereof having one or more substituents selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

In some embodiments of Formula IA, $R^3$ is an unsubstituted heteroaryl.

In some embodiments of Formula IA, $R^3$ is a heteroaryl having one or more substituents selected from the group consisting of D, alkyl, silyl, germyl, deuterated alkyl, deuterated silyl, and deuterated germyl.

All of the above-described embodiments for $R^3$ in Formula IA, apply equally to $R^4$, $R^5$, and $R^6$ in Formula IA.

In some embodiments of Formula IA, $R^3$ and $R^4$ are joined to form a cyclic group selected from the group consisting of cycloalkyl, silacycloalkyl, spirofluorenyl, silaspirofluorenyl, or a substituted derivative thereof, wherein the substituents are selected from the group consisting of D, alkyl, silyl, germyl, deuterated alkyl, deuterated silyl, and deuterated germyl.

In some embodiments of Formula IA, $R^5$ and $R^6$ are joined to form a cyclic group selected from the group consisting of cycloalkyl, silacycloalkyl, spirofluorenyl, silaspirofluorenyl, or a substituted derivative thereof, wherein the substituents are selected from the group consisting of D, alkyl, silyl, germyl, deuterated alkyl, deuterated silyl, and deuterated germyl.

In some embodiments of Formula I, the Core group has a formula selected from the group consisting of Formula IA-a through Formula IA-t

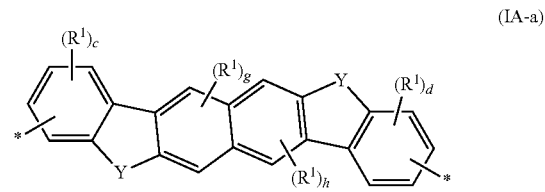

(IA-a)

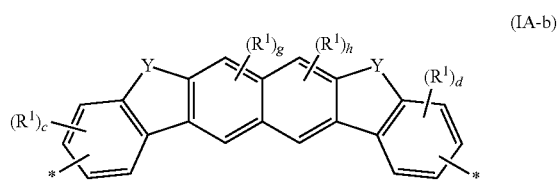

(IA-b)

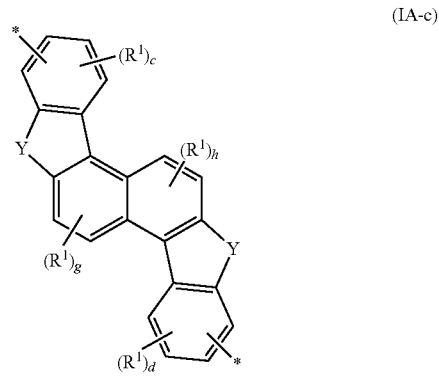

(IA-c)

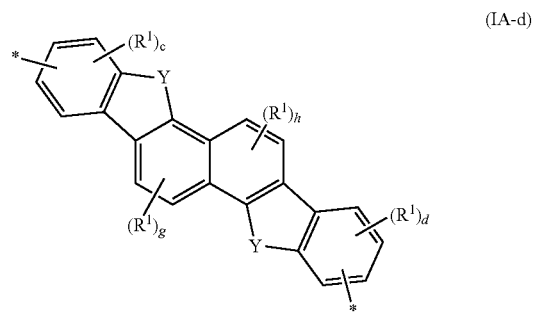

(IA-d)

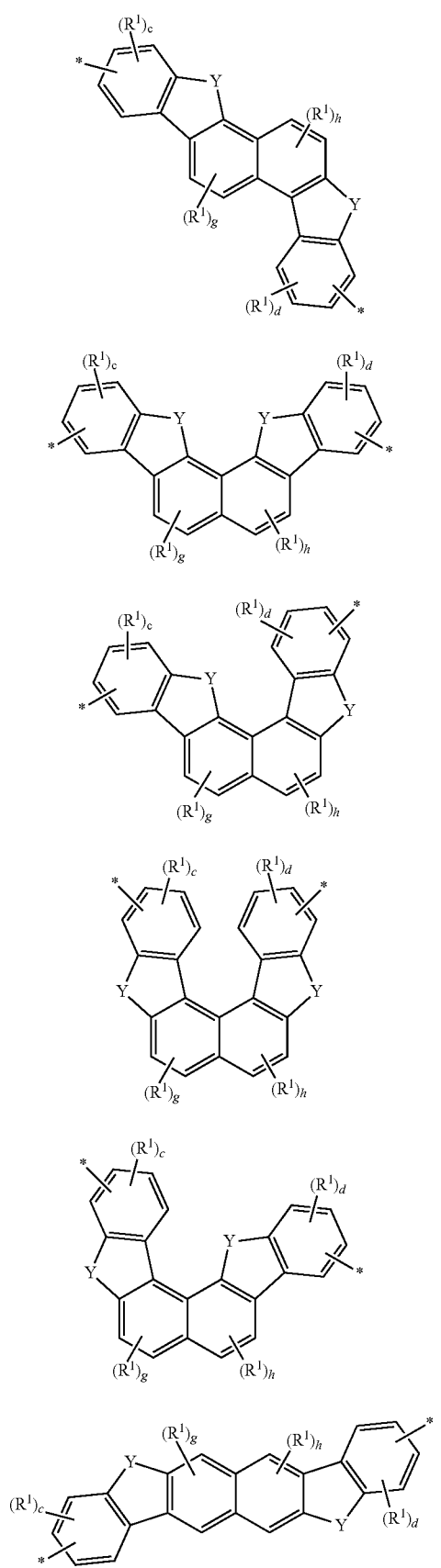
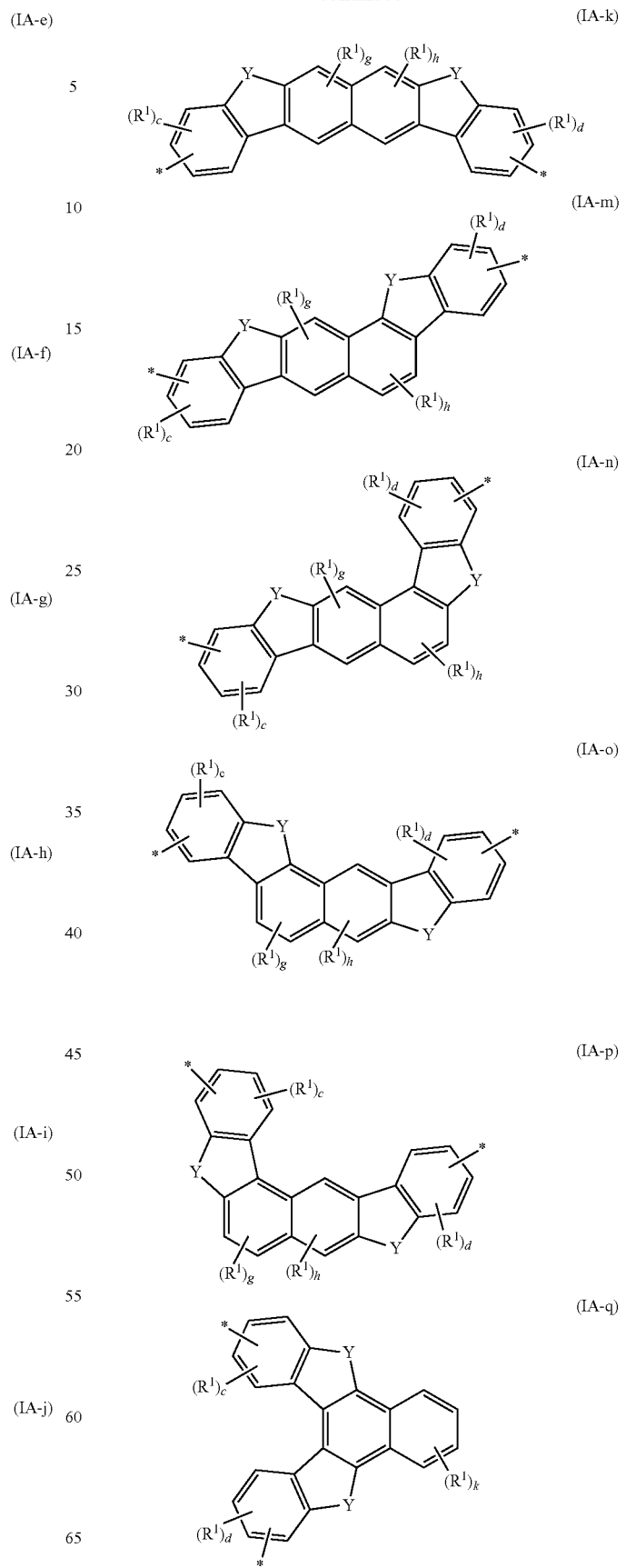

-continued

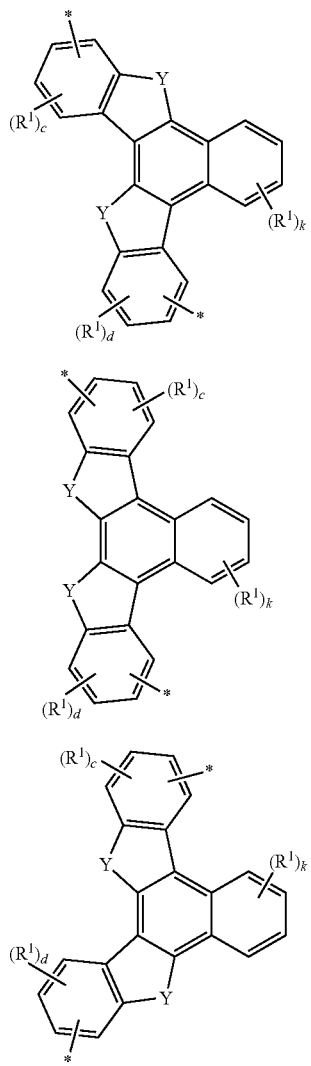

(IA-r)

(IA-s)

(IA-t)

where:
Y is the same or different at each occurrence and is selected from the group consisting of O, S, Se, Te, $NR^2$, $CR^3R^4$, and $SiR^5R^6$;
$R^1$ is the same or different at each occurrence and is selected from the group consisting of D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl deuterated silyl, deuterated siloxane, deuterated siloxy, and deuterated germyl;
$R^2$ is the same or different at each occurrence and is selected from the group consisting of alkyl, hydrocarbon aryl, heteroaryl, and substituted derivatives thereof;
$R^3$-$R^6$ are the same or different at each occurrence and are selected from the group consisting of alkyl, silyl, germyl, hydrocarbon aryl, heteroaryl, and substituted derivatives thereof, where $R^3$ and $R^4$ and/or $R^5$ and $R^6$ can be joined to form a cyclic group selected from the group consisting of cycloalkyl, silacycloalkyl, spirofluorenyl, silaspirofluorenyl, or a substituted derivative thereof;

c and d are the same or different and are an integer of 0-3;
g and h are the same or different and are an integer of 0-2;
k is an integer of 0-4; and
* indicates a point of attachment in the identified formula.
In some embodiments of Formula IA-a, c=0.
In some embodiments of Formula IA-a, c=1.
In some embodiments of Formula IA-a, c=2.
In some embodiments of Formula IA-a, c=3.
In some embodiments of Formula IA-a, c>0.
In some embodiments of Formula IA-a, d=0.
In some embodiments of Formula IA-a, d=1.
In some embodiments of Formula IA-a, d=2.
In some embodiments of Formula IA-a, d=3.
In some embodiments of Formula IA-a, d>0.
In some embodiments of Formula IA-a, g=0.
In some embodiments of Formula IA-a, g=1.
In some embodiments of Formula IA-a, g=2.
In some embodiments of Formula IA-a, g>0.
In some embodiments of Formula IA-a, h=0.
In some embodiments of Formula IA-a, h=1.
In some embodiments of Formula IA-a, h=2.
In some embodiments of Formula IA-a, h>0.
In some embodiments of Formula IA-a, at least one of c, d, g, and h is greater than 0 and at least one $R^1$ is D.
In some embodiments of Formula IA-a, at least one of c, d, g, and h is greater than 0 and at least one $R^1$ is a hydrocarbon aryl or substituted derivative having 6-18 ring carbons.
In some embodiments of Formula IA-a, at least one of c, d, g, and h is greater than 0 and at least one $R^1$ has Formula a, as defined above.
In some embodiments of Formula IA-a, at least one of c, d, g, and h is greater than 0 and at least one $R^1$ has Formula b, as defined above.
In some embodiments of Formula IA-a, at least one of c, d, g, and h is greater than 0 and at least one $R^1$ is selected from the group consisting of phenyl, biphenyl, terphenyl, alkyl-substituted derivatives thereof, silyl-substituted derivatives thereof, diarylamino-substituted derivatives thereof, and deuterated analogs thereof.
In some embodiments of Formula IA-a, at least one of c, d, g, and h is greater than 0 and at least one $R^1$ is selected from the group consisting of phenyl, biphenyl, terphenyl, alkyl-substituted derivatives thereof, silyl-substituted derivatives thereof, and deuterated analogs thereof.
In some embodiments of Formula IA-a, c=d=g=h=0.
All of the above-described embodiments for c, d, g, h, and $R^1$ in Formula IA-a, apply equally to c, d, g, h, and $R^1$ in Formulas IA-b through IA-p.
All of the above-described embodiments for Y in Formula IA, apply equally to Y in Formula IA-a through Formula IA-t.
All of the above described embodiments for $R^2$ in Formula IA, apply equally to $R^2$ in Formula IA-a through Formula IA-t.
All of the above-described embodiments for $R^3$, $R^4$, $R^5$, and $R^6$ in Formula IA, apply equally to $R^3$, $R^4$, $R^5$, and $R^6$ in Formula IA-a through Formula IA-t.
In some embodiments of Formula IA-q, k=0.
In some embodiments of Formula IA-q, k=1.
In some embodiments of Formula IA-q, k=2.
In some embodiments of Formula IA-q, k=3.
In some embodiments of Formula IA-q, k=4.
In some embodiments of Formula IA-q, k>0.
In some embodiments of Formula IA-q, at least one of c, d, and k is greater than 0 and at least one $R^1$ is D.

In some embodiments of Formula IA-q, at least one of c, d, and k is greater than 0 and at least one $R^1$ is a hydrocarbon aryl or substituted derivative having 6-18 ring carbons.

In some embodiments of Formula IA-q, at least one of c, d, and k is greater than 0 and at least one $R^1$ has Formula a, as defined above.

In some embodiments of Formula IA-q, at least one of c, d, and k is greater than 0 and at least one $R^1$ has Formula b, as defined above.

In some embodiments of Formula IA-q, at least one of c, d, and k is greater than 0 and at least one $R^1$ is selected from the group consisting of phenyl, biphenyl, terphenyl, alkyl-substituted derivatives thereof, silyl-substituted derivatives thereof, diarylamino-substituted derivatives thereof, and deuterated analogs thereof.

In some embodiments of Formula IA-q, at least one of c, d, and k is greater than 0 and at least one $R^1$ is selected from the group consisting of phenyl, biphenyl, terphenyl, alkyl-substituted derivatives thereof, silyl-substituted derivatives thereof, and deuterated analogs thereof.

In some embodiments of Formula IA-q, c=d=k=0.

All of the above-described embodiments for c, d, k, and $R^1$ in Formula IA-q, apply equally to c, d, k, and $R^1$ in Formulas IA-r through IA-t.

In some embodiments of Formula I, the Core group has Formula IA-a1, Formula IA-a2, Formula IA-b1, Formula IA-b2, Formula IA-c1, or Formula IA-c2.

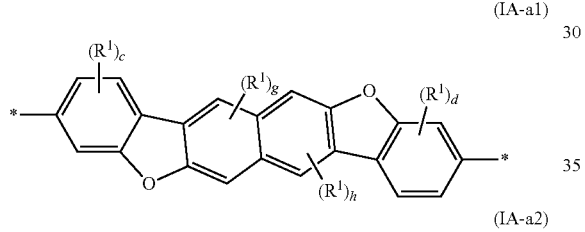
(IA-a1)

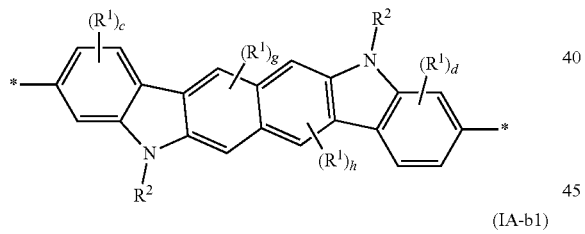
(IA-a2)

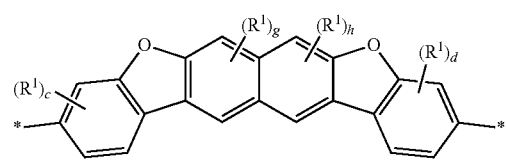
(IA-b1)

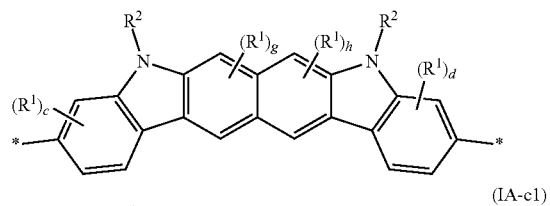
(IA-b2)

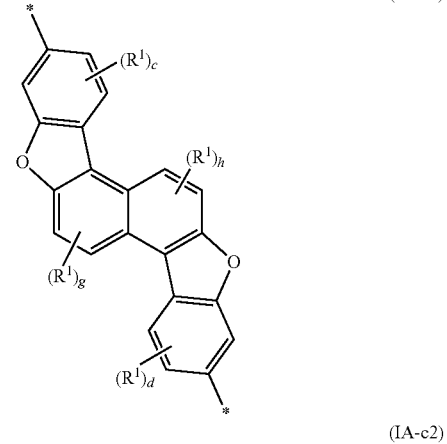
(IA-c1)

(IA-c2)

where c, d, g, h, $R^1$, and * are as defined above. All of the above-described embodiments for c, d, g, h, and $R^1$ in Formula IA-a, apply equally to c, d, g, h, and $R^1$ in Formula IA-a1, Formula IA-a2, Formula IA-b1, Formula IA-b2, Formula IA-c1, and Formula IA-c2.

In some embodiments of Formula I, the Core group has Formula IB

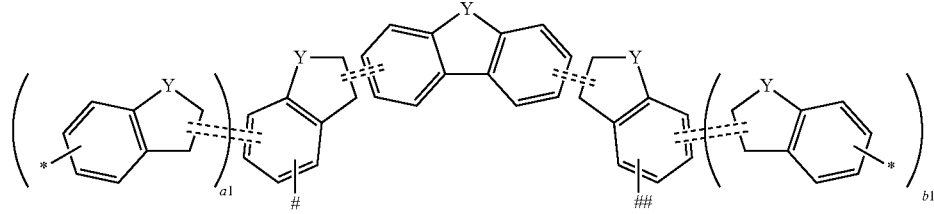
(IB)

where:
Y is the same or different at each occurrence and is selected from the group consisting of O, S, Se, Te, $NR^2$, $CR^3R^4$, and $SiR^5R^6$;
$R^2$ is the same or different at each occurrence and is selected from the group consisting of alkyl, hydrocarbon aryl, heteroaryl, and substituted derivatives thereof;
$R^3$-$R^6$ are the same or different at each occurrence and are selected from the group consisting of alkyl, silyl, germyl, hydrocarbon aryl, heteroaryl, and substituted derivatives thereof, where $R^3$ and $R^4$ and/or $R^5$ and $R^6$ can be joined to form a cyclic group selected from the group consisting of cycloalkyl, silacycloalkyl, spirofluorenyl, silaspirofluorenyl, or a substituted derivative thereof;
a1 and b1 are the same or different and are 0 or 1;
a double dashed line between two rings indicates that the rings are fused together in any orientation;
* indicates a point of attachment in the identified formula; and
# and ## represent no bond or a point of attachment in the identified formula, such that when a1=0 then # is a point of attachment, when a1=1 then # is no bond, when b1=0 then ## is a point of attachment, and when b1=1 then ## is no bond;
and further wherein there may be one or more substituents selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

In Formula IB, there are two terminal benzo groups. The Core group having Formula IB is attached to Formula I from the terminal benzo groups.

In some embodiments of Formula IB, a1=b1=0, and the Core group has the structure

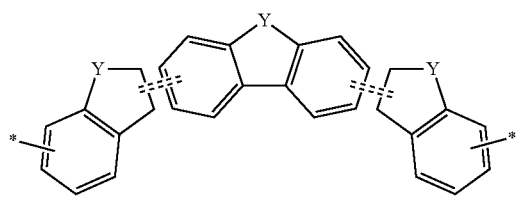

In some embodiments of Formula IB, a1=b1=1, and the Core group has the structure In some embodiments of Formula IB, a1=1 and b1=0, and the Core group has the structure

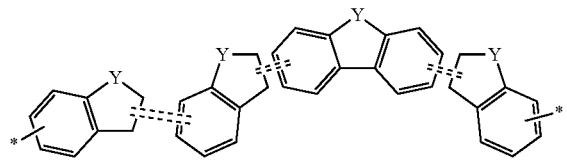

In some embodiments of Formula IB, a1=0 and b1=1, and the Core group has the structure

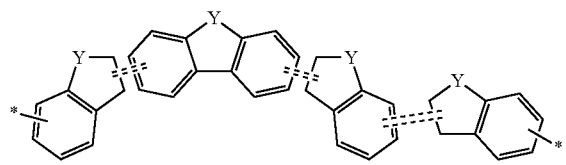

In the above four structures, * indicates a point of attachment in the identified formula.

In some embodiments of Formula IB, all Y groups are the same.

In some embodiments of Formula IB, at least one Y group is different from the other $Y^1$ through $Y^5$ groups.

All of the above-described embodiments for Y, $R^2$, $R^3$, $R^4$, $R^5$, and $R^6$ in Formula IA, apply equally to Y, $R^2$, $R^3$, $R^4$, $R^5$, and $R^6$ in Formula IB.

In some embodiments of Formula I, the Core group has one of Formula IB-a through IB-m below, although it is not limited to these isomers.

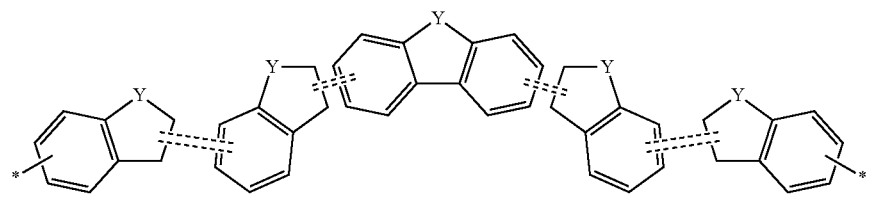

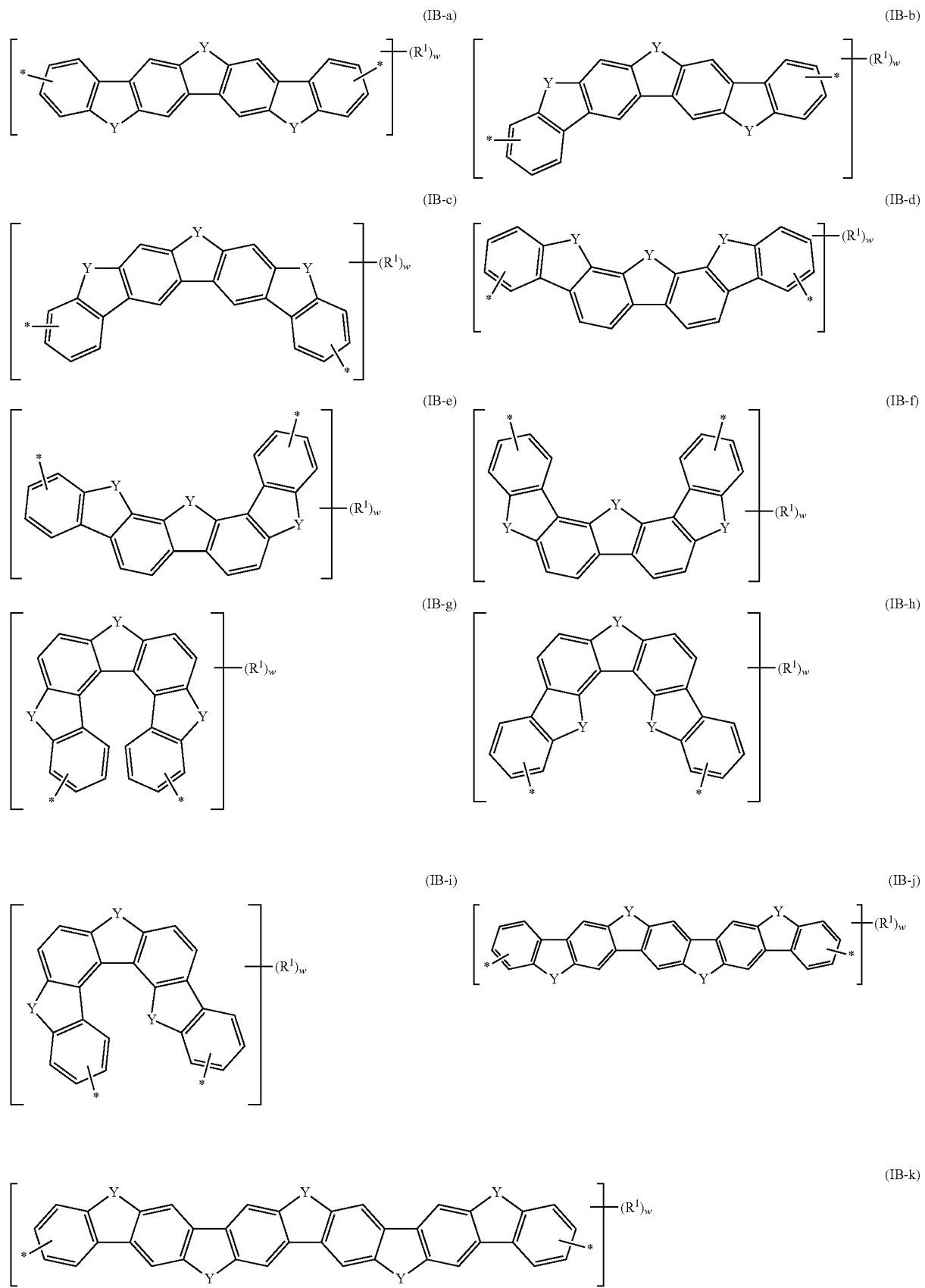

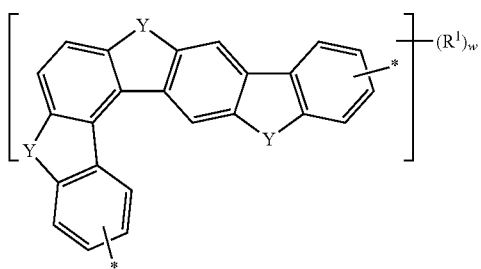
(IB-m)

where w is an integer from 0 to the maximum number of bonding positions available, and Y, $R^1$, and * are as defined above.

In some embodiments of Formula IB-a through Formula IB-m, w=0.
In some embodiments of Formula IB-a through Formula IB-m, w=1.
In some embodiments of Formula IB-a through Formula IB-m, w=2.
In some embodiments of Formula IB-a through Formula IB-m, w=3.
In some embodiments of Formula IB-a through Formula IB-m, w=4.
In some embodiments of Formula IB-a through Formula IB-m, w=5.
In some embodiments of Formula IB-a through Formula IB-m, w=6.
In some embodiments of Formula IB-a through Formula IB-m, w=7.
In some embodiments of Formula IB-a through Formula IB-m, w=8.
In some embodiments of Formula IB-a through Formula IB-m, w=9.
In some embodiments of Formula IB-a through Formula IB-m, w=10.
In some embodiments of Formula IB-a through Formula IB-m, w=11.
In some embodiments of Formula IB-a through Formula IB-m, w=12.
In some embodiments of Formula IB-a through Formula IB-m, w=the maximum number of bonding positions available.
In some embodiments of Formula IB-a through Formula IB-m, w>0.

All of the above-described embodiments for Y and $R^1$ in Formula IA-a, apply equally to Y and $R^1$ in Formula IB-a through Formula IB-m.

In some embodiments of Formula I, the Core group has one of Formula IB-aa through IB-mm below, although it is not limited to these isomers.

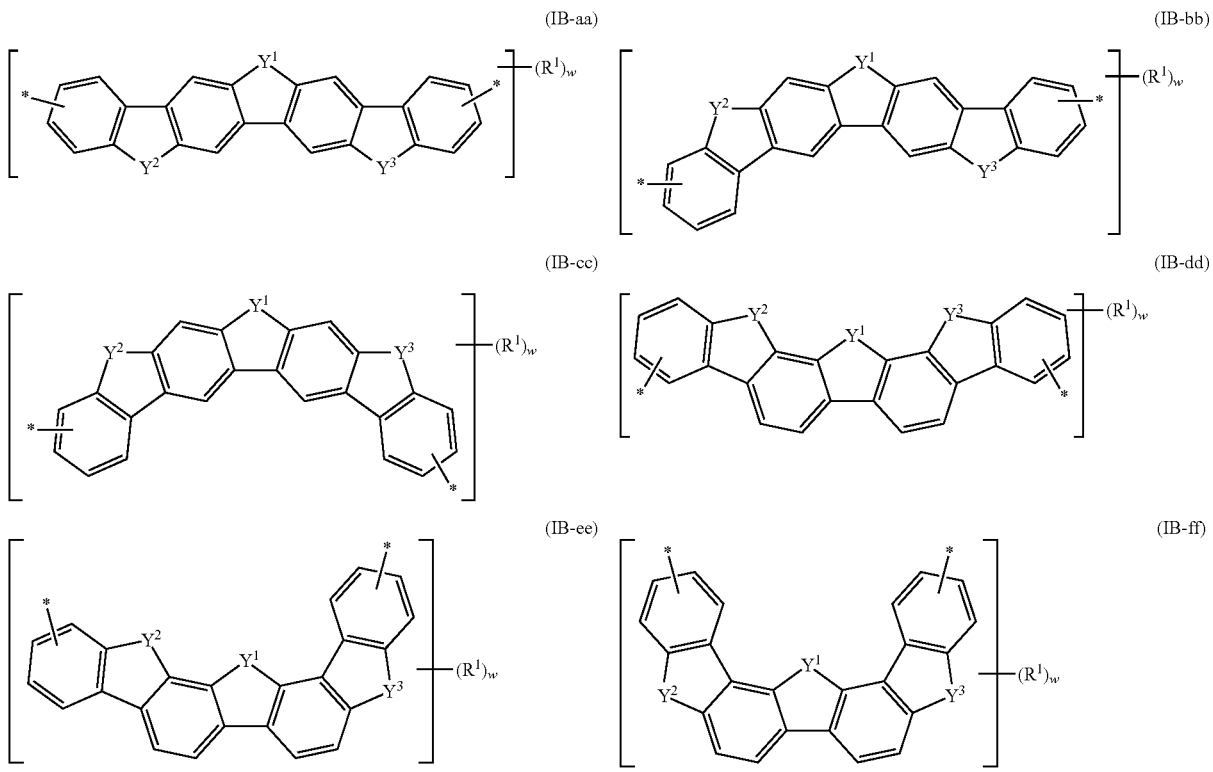

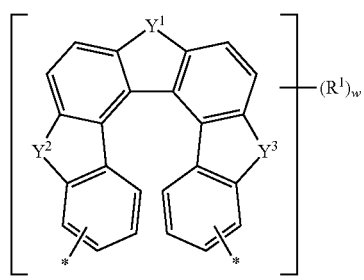
(IB-gg)

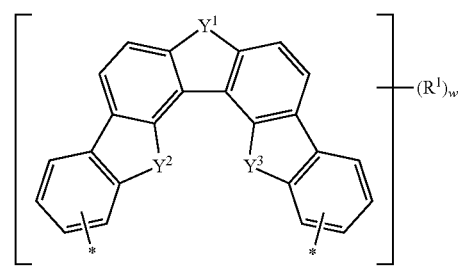
(IB-hh)

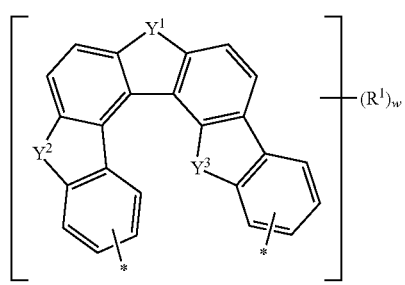
(IB-ii)

(IB-jj)

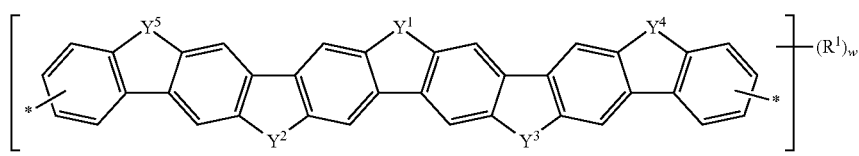
(IB-kk)

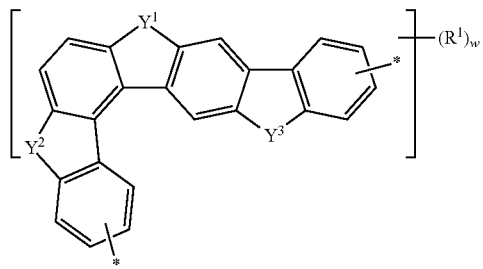
(IB-mm)

where w is an integer from 0 to the maximum number of bonding positions available, $Y^1$ through $Y^5$ are the same or different and are selected from the group consisting of O, S, Se, Te, $NR^2$, $CR^3R^4$, and $SiR^5R^6$, and $R^1$, and * are as defined above. At least one of $Y^1$ through $Y^5$ is different from the other $Y^1$ through $Y^5$ groups.

In some embodiments of Formulas IB-aa through IB-ii and IB-mm, $Y^1 \neq Y^2 = Y^3$.

In some embodiments of Formulas IB-aa through IB-ii and IB-mm, $Y^1 \neq Y^2 \neq Y^3$.

In some embodiments of Formulas IB-aa through IB-ii and IB-mm, $Y^1$ is selected from $CR^3R^4$ and $SiR^5R^6$, and $Y^2$ and $Y^3$ are selected from O, S, Se, and $NR^2$.

In some embodiments of Formulas IB-aa through IB-ii and IB-mm, $Y^1$ is $CR^3R^4$ and $Y^2$ and $Y^3$ are O.

In some embodiments of Formulas IB-aa through IB-ii and IB-mm, $Y^1$ is $CR^3R^4$ and $Y^2$ and $Y^3$ are $NR^2$.

In some embodiments of Formulas IB-jj and IB-kk, $Y^1$ is selected from $CR^3R^4$ and $SiR^5R^6$, and $Y^2$ through $Y^5$ are selected from O, S, Se, and $NR^2$.

In some embodiments of Formulas IB-jj and IB-kk, $Y^1$ is $CR^3R^4$, and $Y^2$ through $Y^5$ are O.

In some embodiments of Formulas IB-jj and IB-kk, $Y^1$ is $CR^3R^4{}^6$, and $Y^2$ through $Y^5$ are $NR^2$.

All of the above-described embodiments for $R^1$ and w in Formula IA-a, apply equally to $R^1$ and w in Formula IB-aa through Formula IB-mm.

In some embodiments of Formula I, the Core group has Formula IB-a1, IB-b1, IB-c1, IB-aa1, IB-bb1, or IB-cc1.

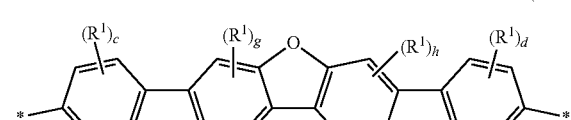
(IB-a1)

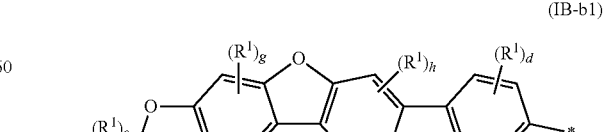
(IB-b1)

-continued

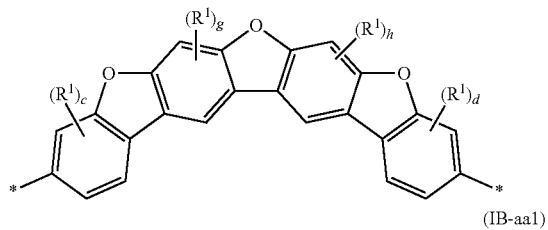
(IB-c1)

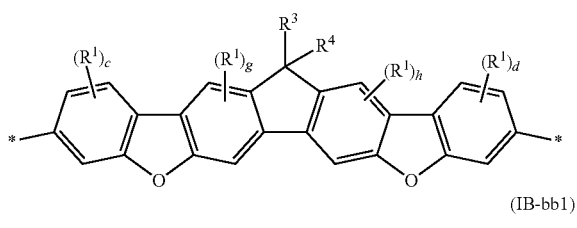
(IB-aa1)

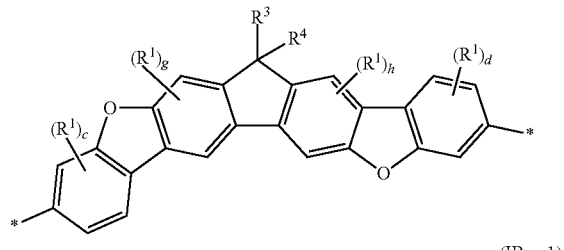
(IB-bb1)

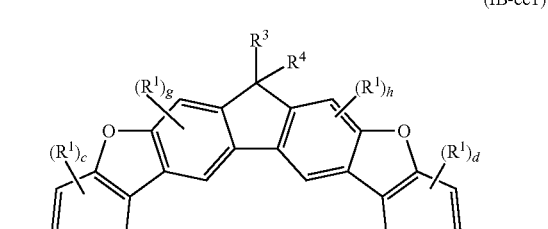
(IB-cc1)

where c, d, g, h, $R^1$, $R^3$, $R^4$ and * are as defined above. All of the above-described embodiments for c, d, g, h, $R^1$, $R^3$, and $R^4$ in Formula IA-a, apply equally to c, d, g, h, $R^1$, $R^3$, and $R^4$ in Formula IB-a1, IB-b1, IB-c1, IB-aa1, IB-bb1, and IB-cc1.

In some embodiments of Formula I, the Core group has Formula IC

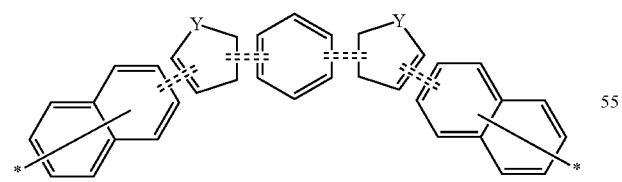
(IC)

where:
Y is the same or different at each occurrence and is selected from the group consisting of O, S, Se, Te, $NR^2$, $CR^3R^4$, and $SiR^5R^6$;
$R^2$ is the same or different at each occurrence and is selected from the group consisting of alkyl, hydrocarbon aryl, heteroaryl, and substituted derivatives thereof;

$R^3$-$R^6$ are the same or different at each occurrence and are selected from the group consisting of alkyl, silyl, germyl, hydrocarbon aryl, heteroaryl, and substituted derivatives thereof, where $R^3$ and $R^4$ and/or $R^5$ and $R^6$ can be joined to form a cyclic group selected from the group consisting of cycloalkyl, silacycloalkyl, spirofluorenyl, silaspirofluorenyl, or a substituted derivative thereof;

a double dashed line between two rings indicates that the rings are fused together in any orientation; and

* indicates a point of attachment in the identified formula;

and further wherein there may be one or more substituents selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

In some embodiments of Formula IC, both Y groups are the same.

All of the above-described embodiments for Y, $R^2$, $R^3$, $R^4$, $R^5$, and $R^6$ in Formula IA, apply equally to Y, $R^2$, $R^3$, $R^4$, $R^5$, and $R^6$ in Formula IC.

In some embodiments of Formula I, the Core group has one of Formula IC-a through IC-p below

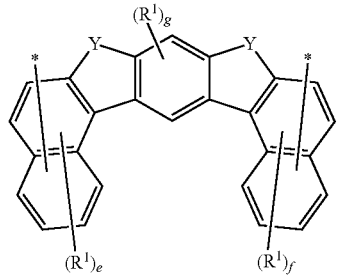
(IC-a)

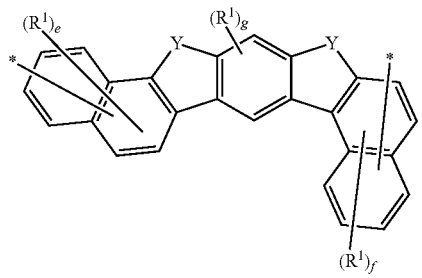
(IC-b)

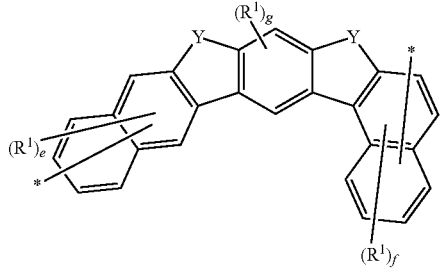
(IC-c)

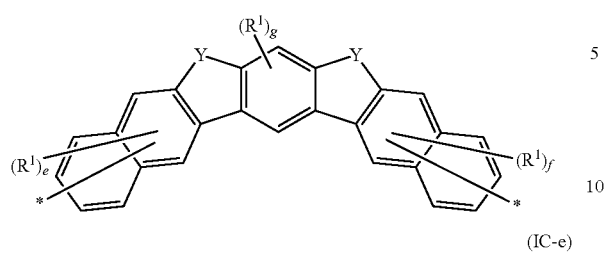
(IC-d)
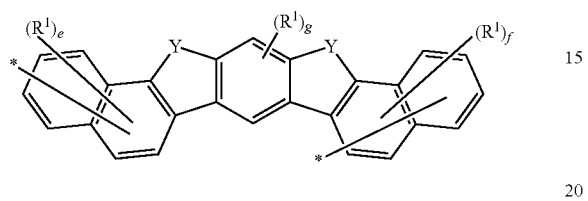
(IC-e)
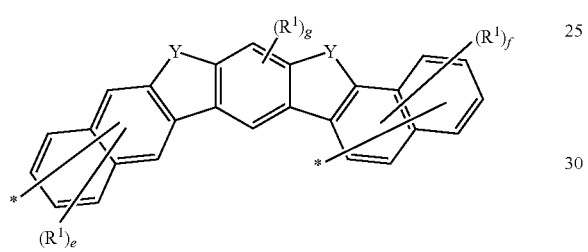
(IC-f)
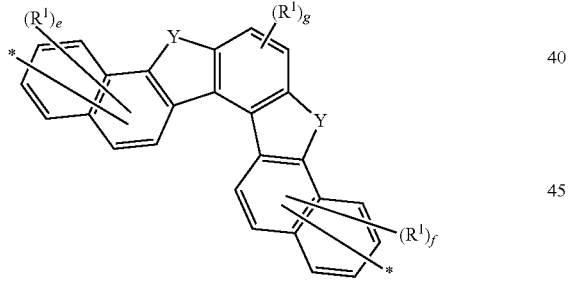
(IC-g)
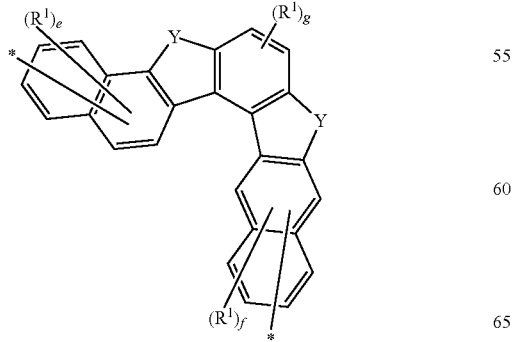
(IC-h)
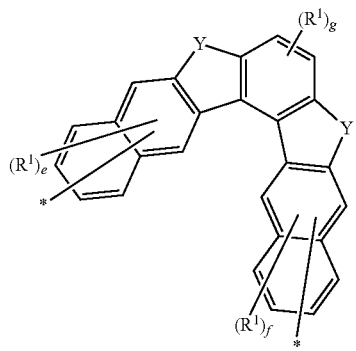
(IC-i)
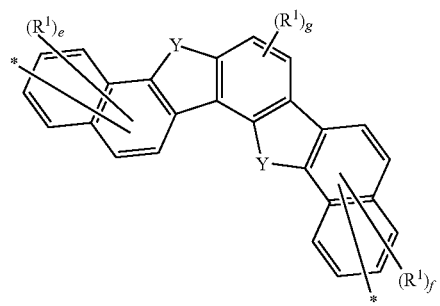
(IC-j)
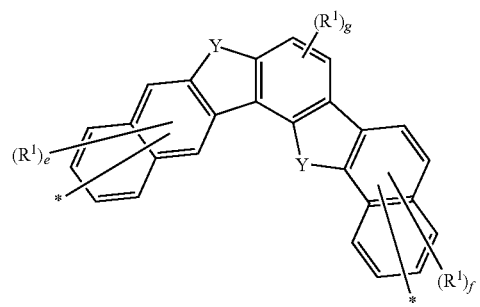
(IC-k)
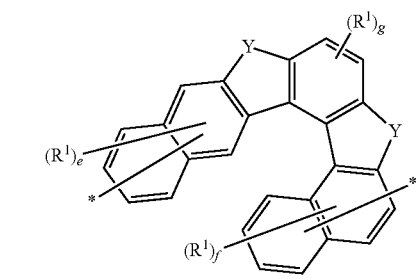
(IC-m)
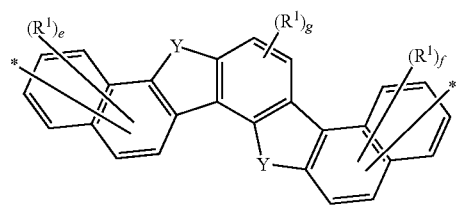
(IC-n)

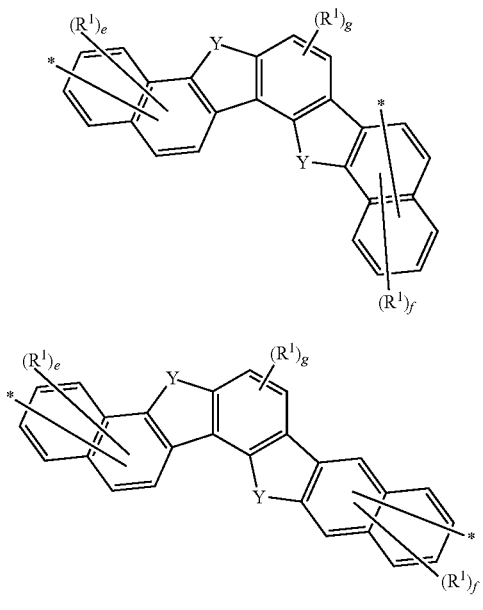

(IC-o)

(IC-p)

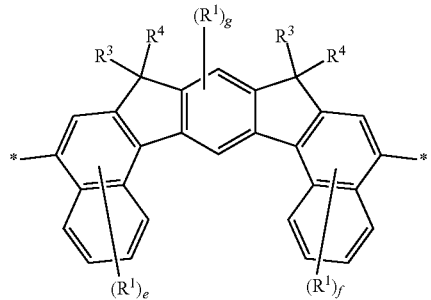

(IC-a1)

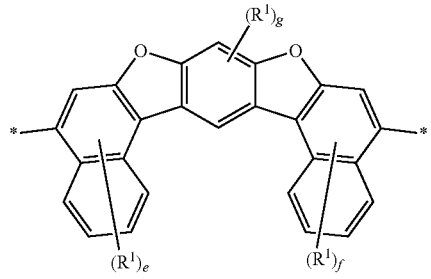

(IC-a2)

where e and f are the same or different and are an integer from 0-5, and Y, $R^1$, g, h, and * are as defined above.

In some embodiments of Formula IC-a through Formula IC-p, e=0.

In some embodiments of Formula IC-a through Formula IC-p, e=1.

In some embodiments of Formula IC-a through Formula IC-p, e=2.

In some embodiments of Formula IC-a through Formula IC-p, e=3.

In some embodiments of Formula IC-a through Formula IC-p, e=4.

In some embodiments of Formula IC-a through Formula IC-p, e=5.

In some embodiments of Formula IC-a through Formula IC-p, e>0.

In some embodiments of Formula IC-a through Formula IC-p, f=0.

In some embodiments of Formula IC-a through Formula IC-p, f=1.

In some embodiments of Formula IC-a through Formula IC-p, f=2.

In some embodiments of Formula IC-a through Formula IC-p, f=3.

In some embodiments of Formula IC-a through Formula IC-p, f=4.

In some embodiments of Formula IC-a through Formula IC-p, f=5.

In some embodiments of Formula IC-a through Formula IC-p, f>0.

In some embodiments of Formula IC-a through Formula IC-p, e=f.

In some embodiments of Formula IC-a through Formula IC-p, e≠f.

All of the above-described embodiments for Y, $R^1$, g, and h in Formula IA-a, apply equally to Y, $R^1$, g, and h in Formula IC-a through Formula IC-p.

In some embodiments of Formula I, the Core group has Formula IC-a1 or IC-a2 where $R^1$, $R^3$, $R^4$, e, f, g, and * are as defined above. All of the above-described embodiments for $R^1$, $R^3$, $R^4$, and g in Formula IA, Formula IA-a, and Formulas IC-a through IC-p, apply equally to $R^1$, $R^3$, $R^4$, e, f, and g in Formula IC-a1 and IC-a2.

In some embodiments of Formula I, exclusive of the core, there are no groups having more than 2 fused rings. In some embodiments, there are also no substituents on the core having more than 2 fused rings.

In some embodiments of Formula I, there are no pyrene groups.

In some embodiments of Formula I, exclusive of the core, there are no fluorene groups. In some embodiments, there are also no fluorene substituents on the core.

In some embodiments of Formula I, exclusive of the core, there are no carbazole groups. In some embodiments, there are no carbazole substituents on the core.

In some embodiments of Formula I, there are no spiro groups. In some embodiments, there are also no spiro substituents on the core.

In some embodiments of Formula I, at least one Y includes a heteroatom.

Any of the above embodiments of the above formulas can be combined with one or more of the other embodiments, so long as they are not mutually exclusive. For example, in Formula I, the embodiment in which a=1 and $Ar^1$ is selected from the group consisting of phenyl, biphenyl, terphenyl, 1-naphthyl, 2-naphthyl, anthracenyl, fluorenyl, phenanthryl, and derivatives thereof having one or more substituents selected from the group consisting of D, alkyl, silyl, germyl, deuterated alkyl, deuterated silyl, and deuterated germyl can be combined with the embodiment where $Ar^3$ has Formula b and with the embodiments where $Ar^3=Ar^6$. The same is true for the other non-mutually-exclusive embodiments discussed above. The skilled person would understand which embodiments were mutually exclusive and would thus readily be able to determine the combinations of embodiments that are contemplated by the present application.

The compounds of Formula I can be made using any technique that will yield a C—C, C—N, C—O, C—S, or C—Si bond. A variety of such techniques are known, such as Suzuki, Yamamoto, Stille, Negishi, and metal-catalyzed C—N couplings as well as metal catalyzed and oxidative direct arylation.

Deuterated compounds can be prepared in a similar manner using deuterated precursor materials or, more generally, by treating the non-deuterated compound with deuterated solvent, such as benzene-d6, in the presence of a Bronsted or Lewis acid H/D exchange catalyst, such as trifluoromethanesulfonic acid, aluminum trichloride or ethyl aluminum dichloride. Deuteration reactions have also been described in published PCT application WO2011/053334.

Exemplary preparations are given in the Examples.

Examples of compounds having Formula I include, but are not limited to, the compounds shown below.

Compound IA-1

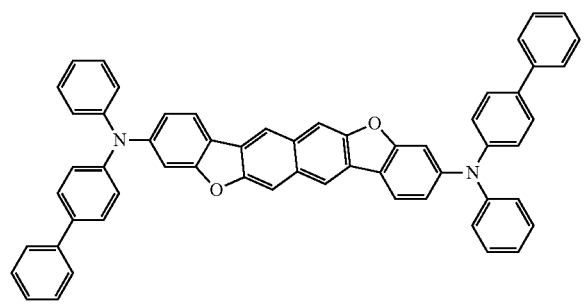

Compound IA-2

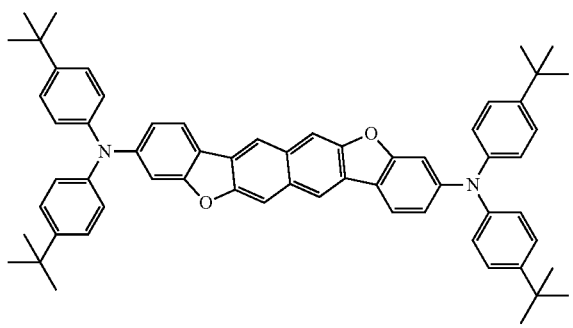

Compound IA-3

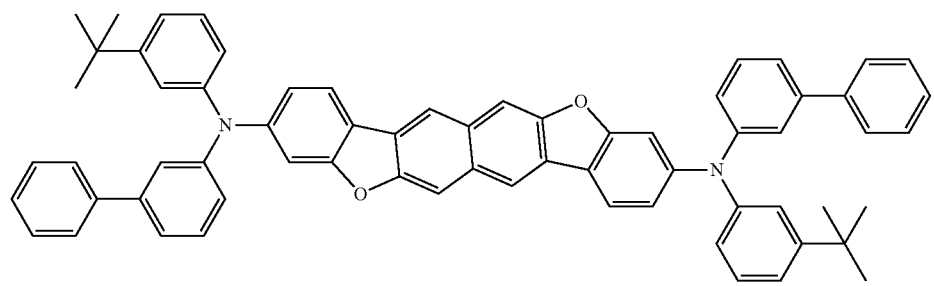

Compound IA-4

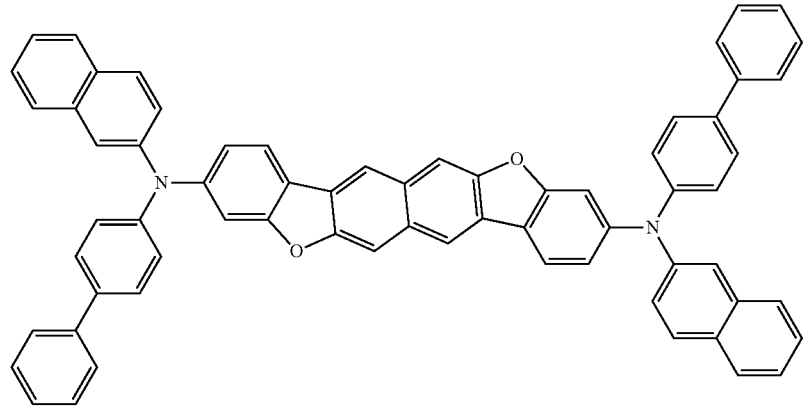

Compound IA-5

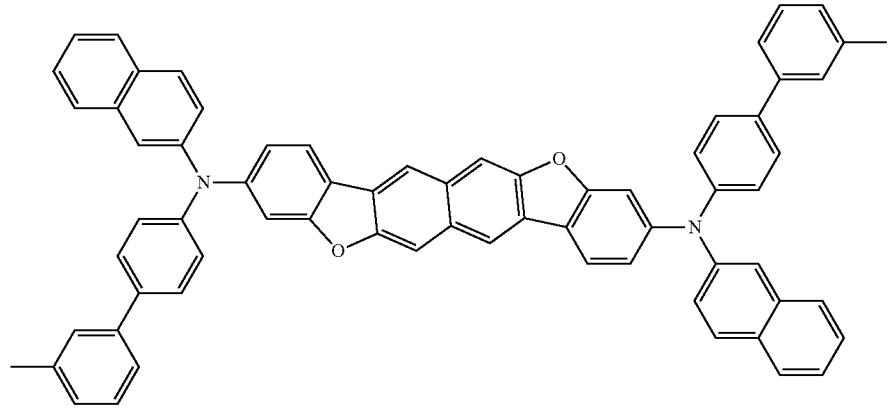

-continued
Compound IA-6
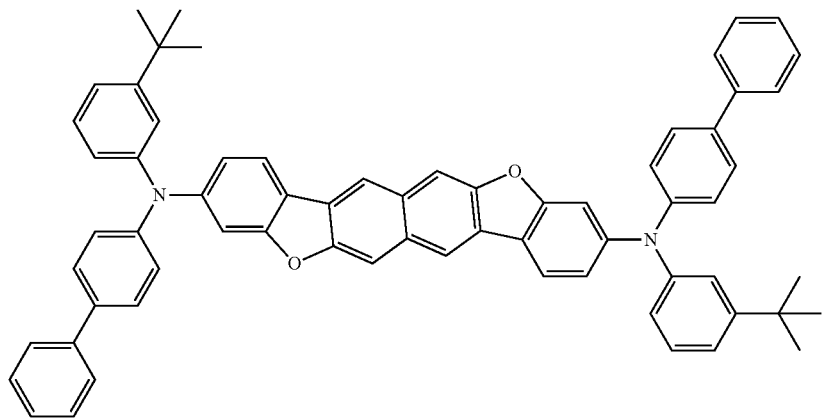
Compound IA-7
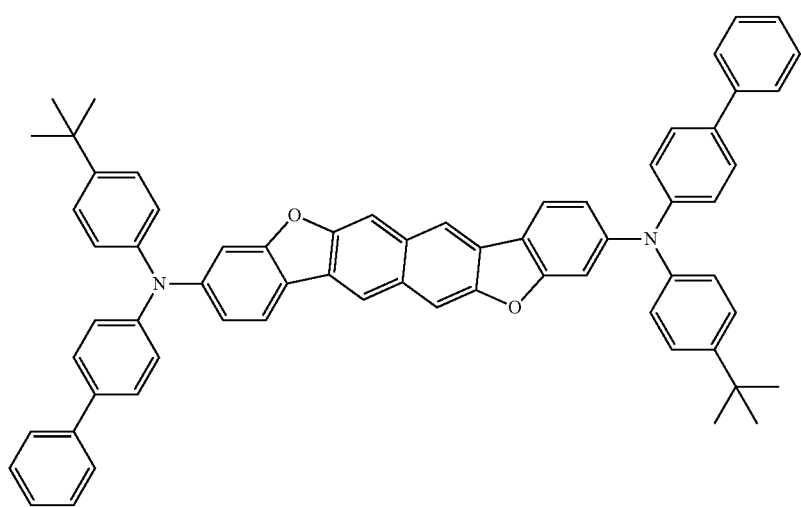
Compound IA-8
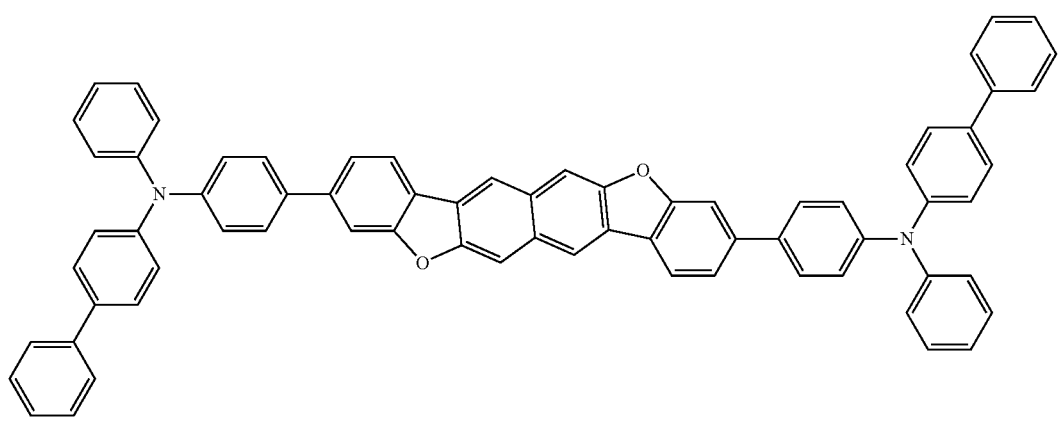

Compound IA-9
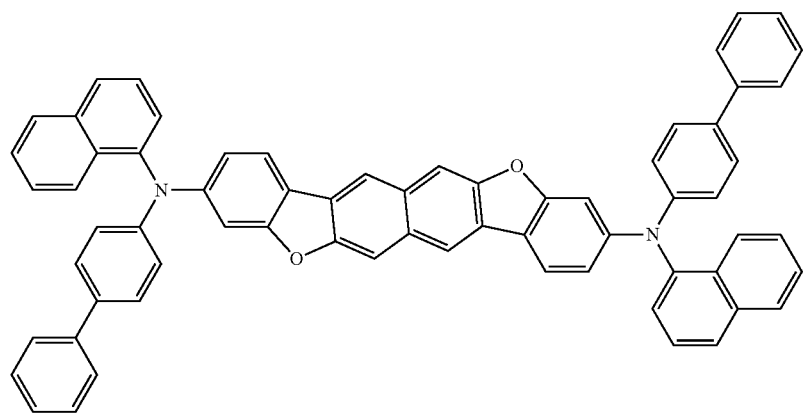
Compound IA-10
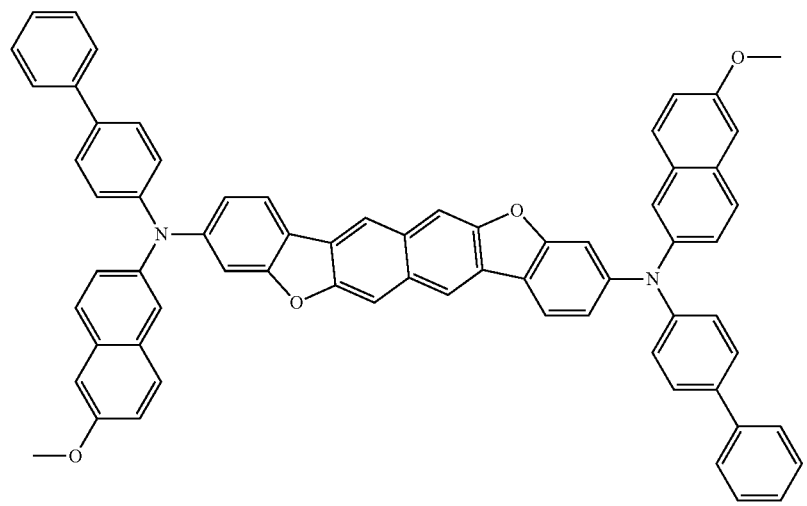
Compound IA-11
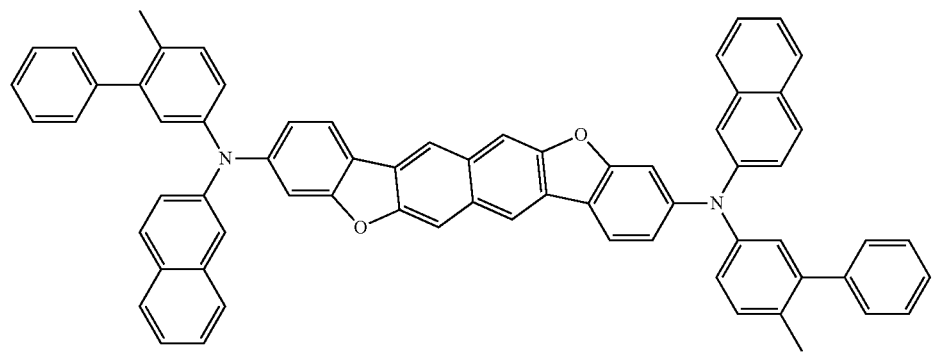

-continued
Compound IA-12
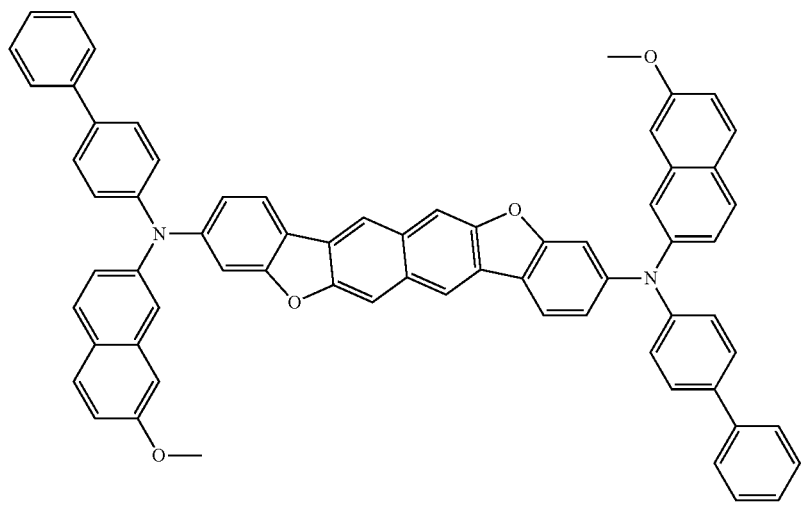
Compound IA-13
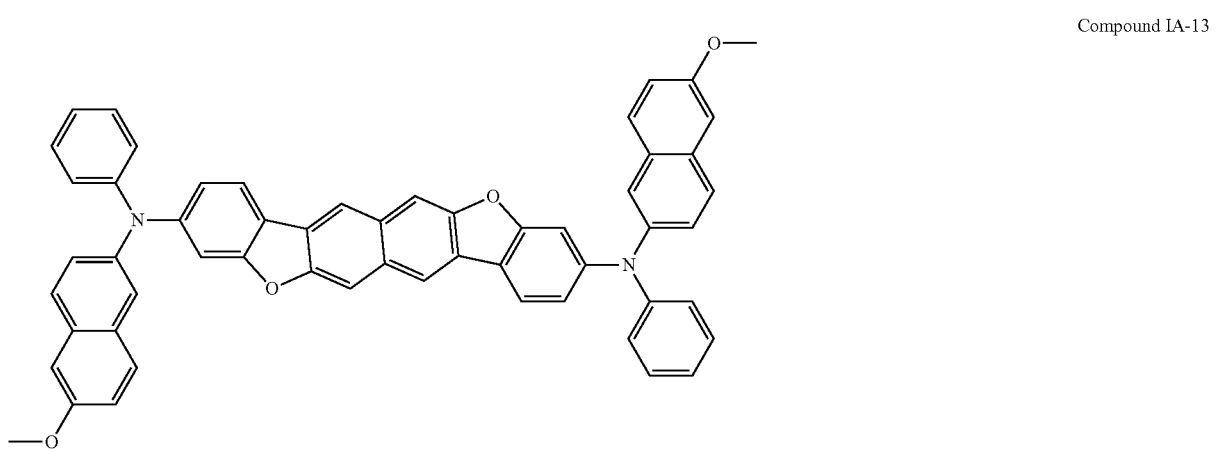
Compound IA-14
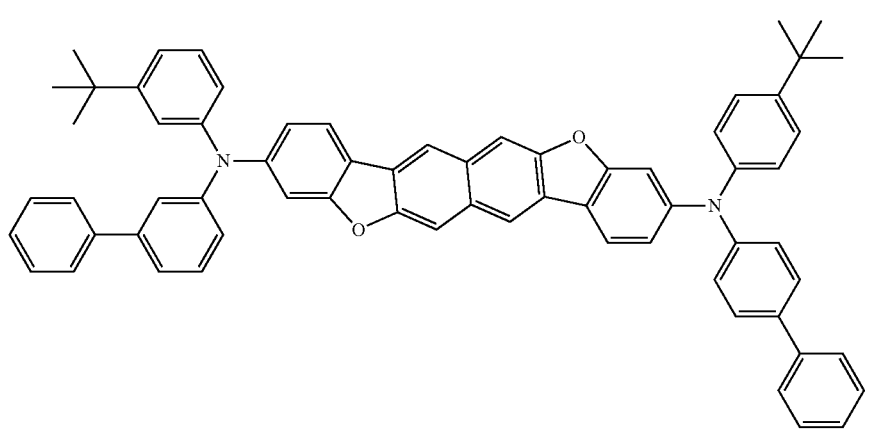

-continued
Compound IA-15
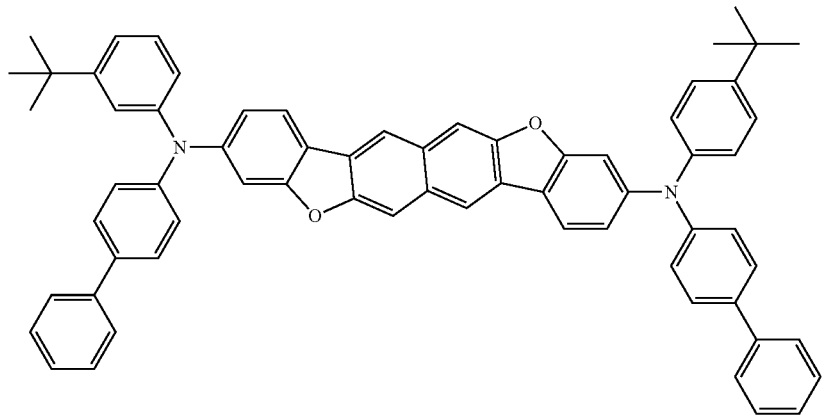
Compound IA-16
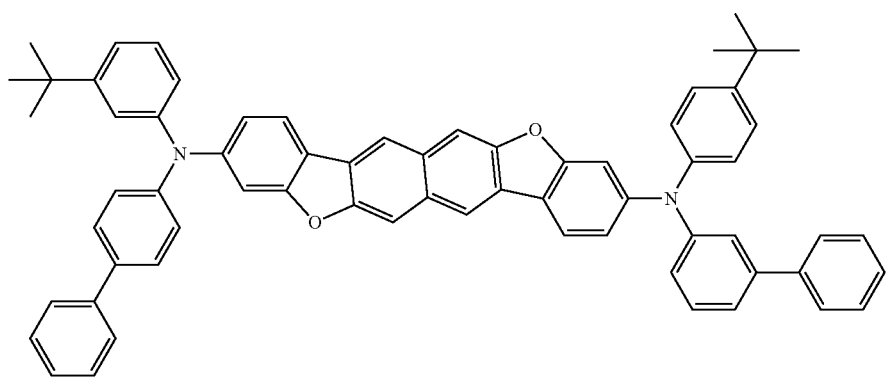
Compound IA-17
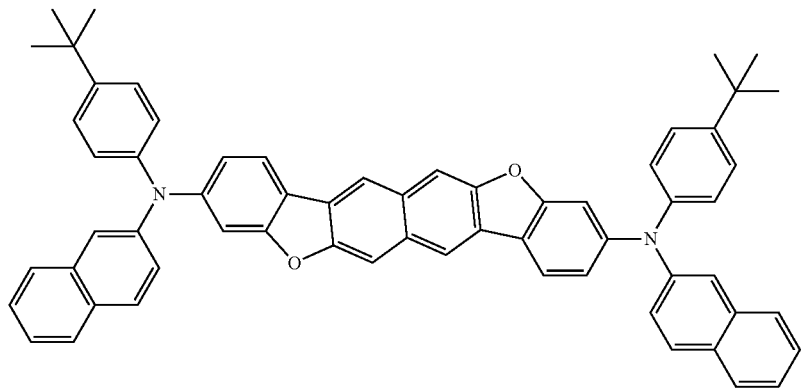
Compound IA-18
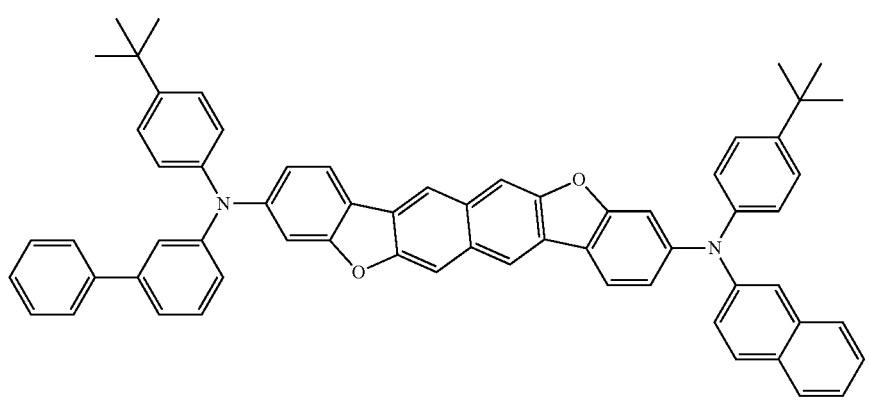

-continued
Compound IA-19
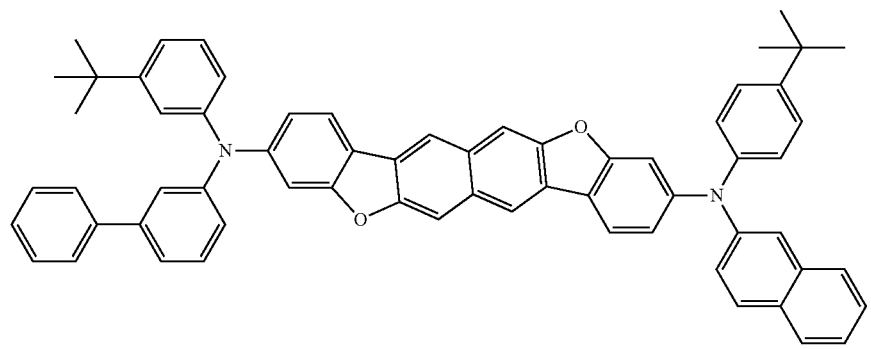
Compound IA-20
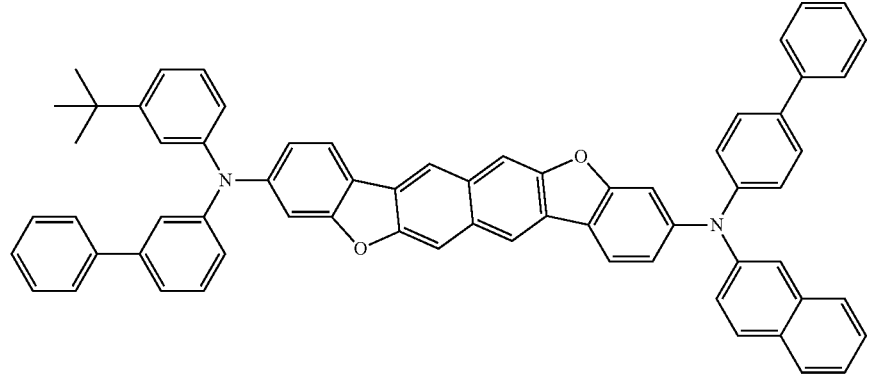
Compound IA-21
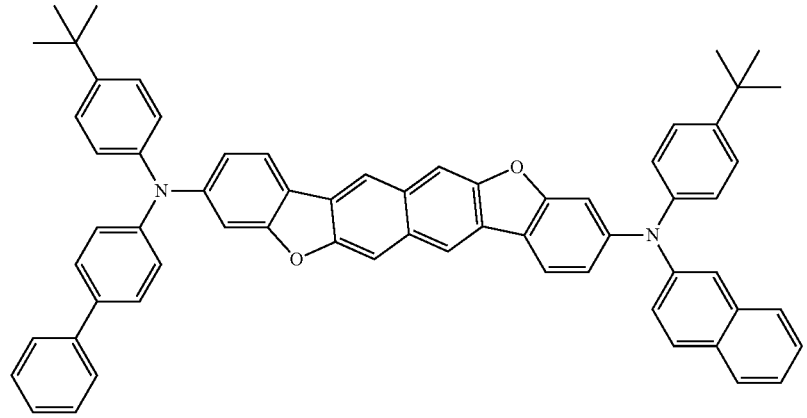
Compound IA-22
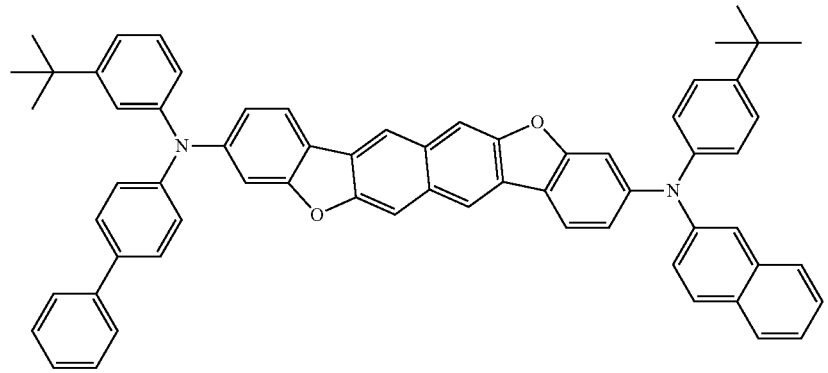

-continued
Compound IA-23
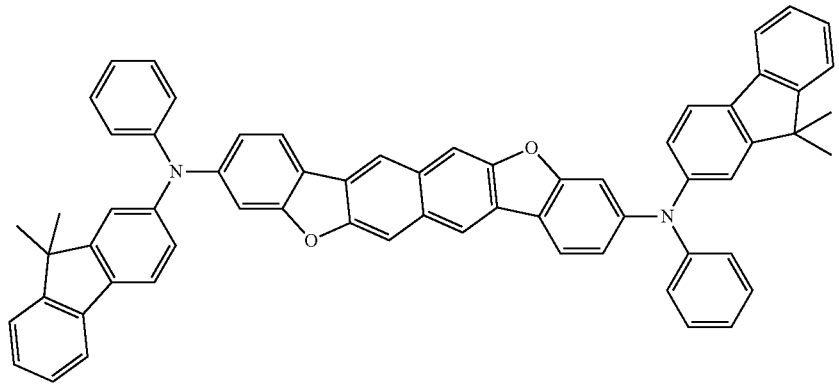
Compound IA-24
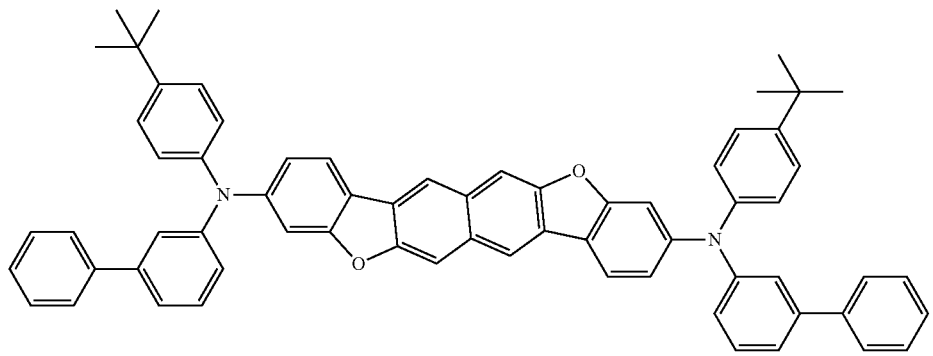
Compound IA-25
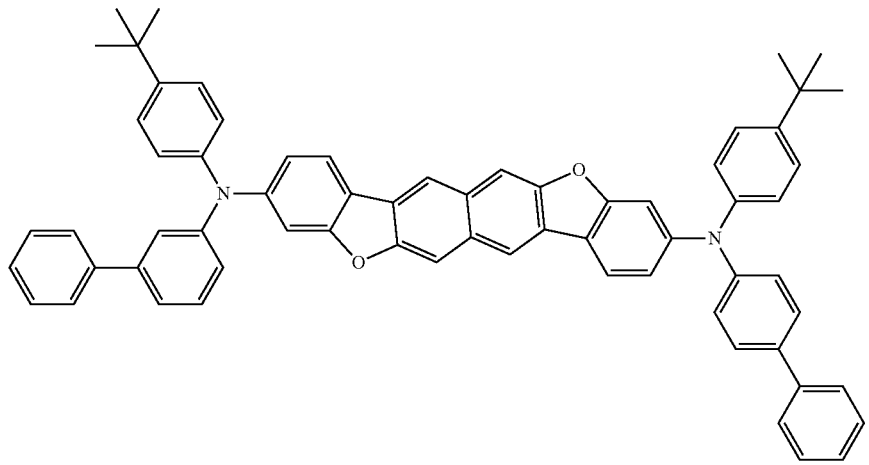
Compound IA-26
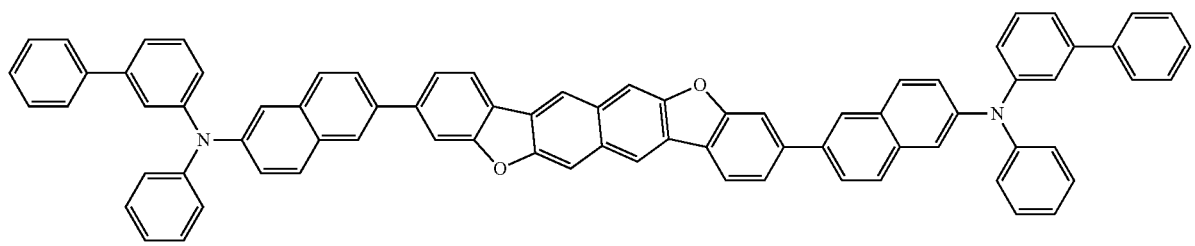

-continued
Compound IA-27
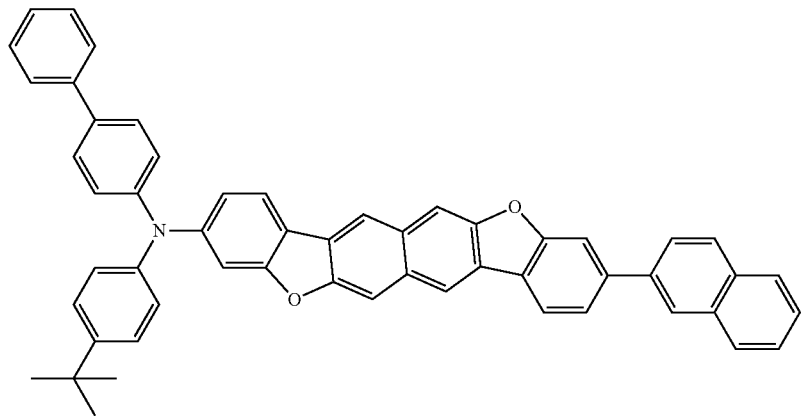
Compound IA-28
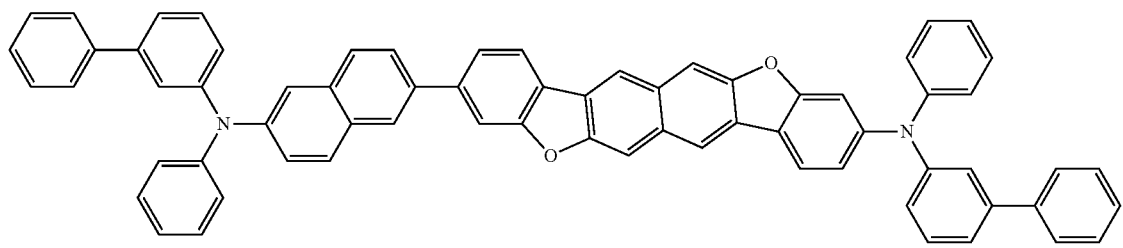
Compound IA-29
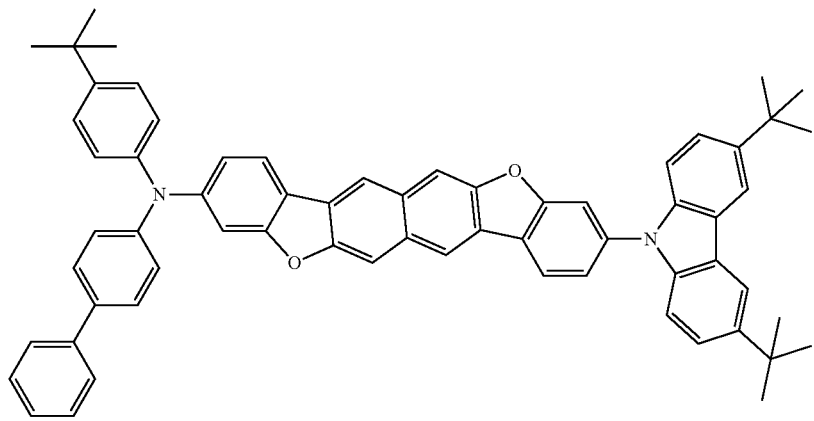

-continued
Compound IA-30
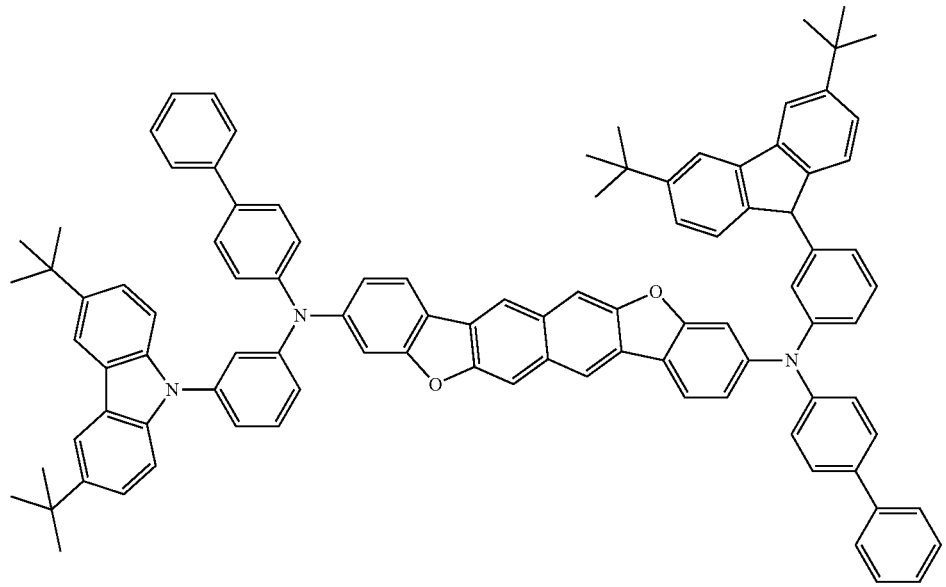
Compound IA-31
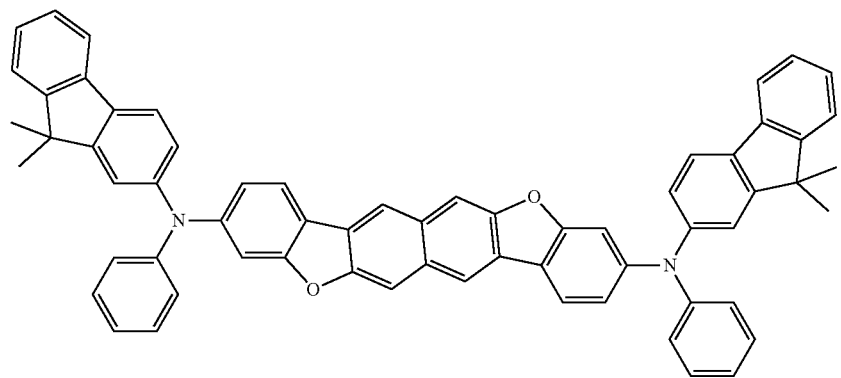
Compound IA-32
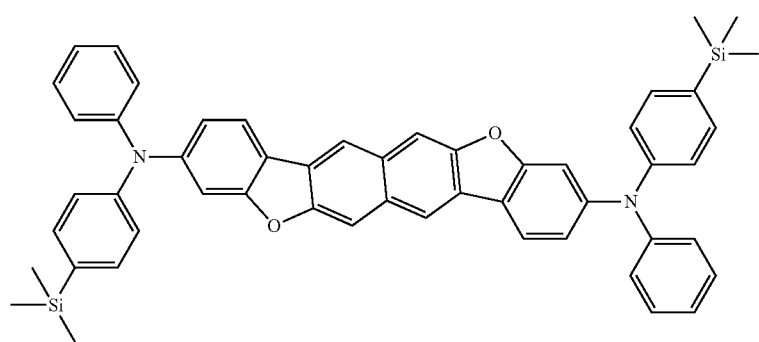

-continued
Compound IA-33
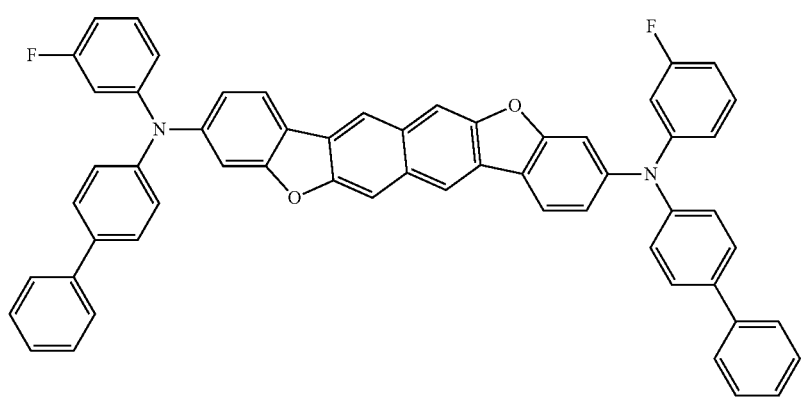
Compound IA-34
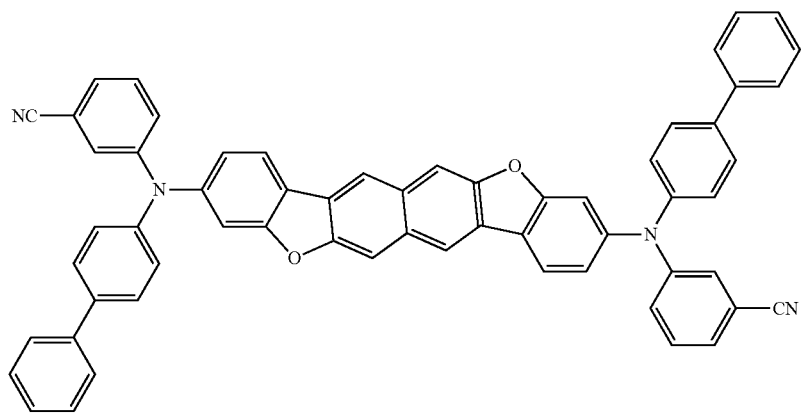
Compound IA-35
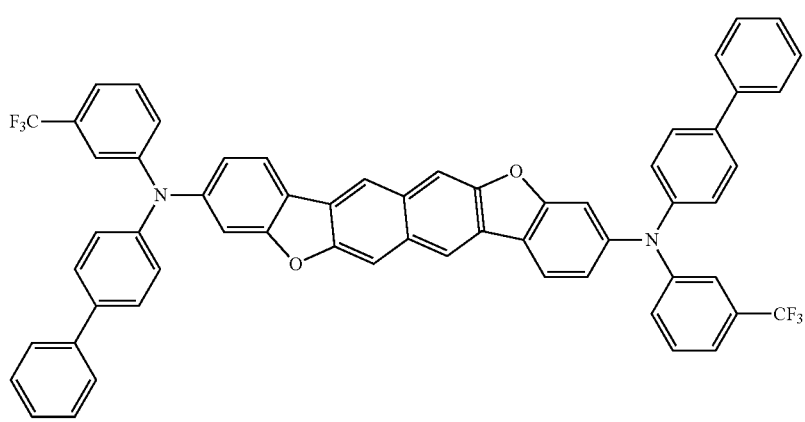
[Compound IA-36 and Compound IA-37 deleted.]
Compound IA-38
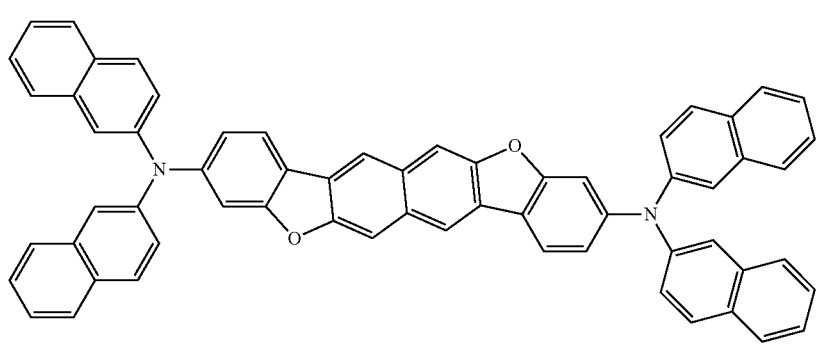

Compound IA-39
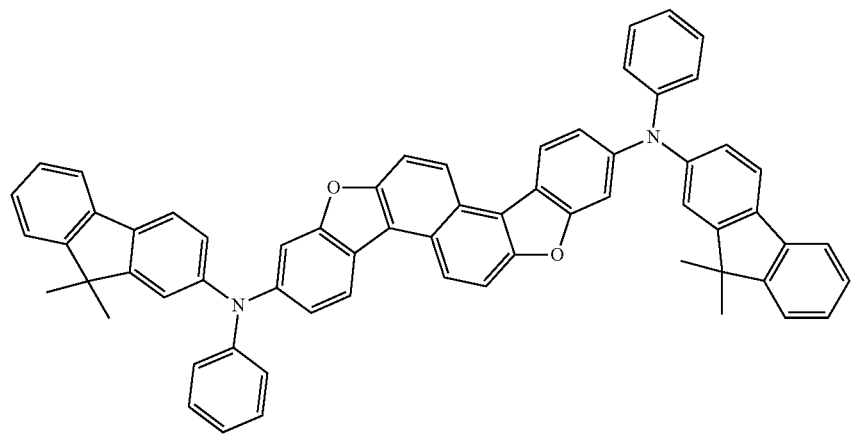
[Compound IA-40 and Compound IA-41 deleted.]
Compound IA-42
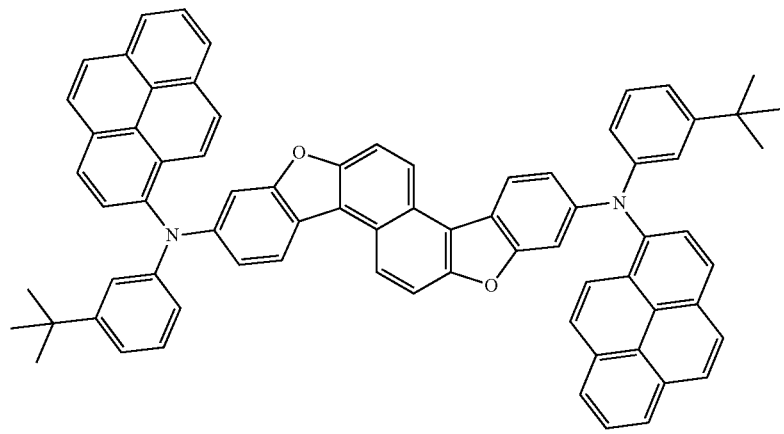
Compound IA-43
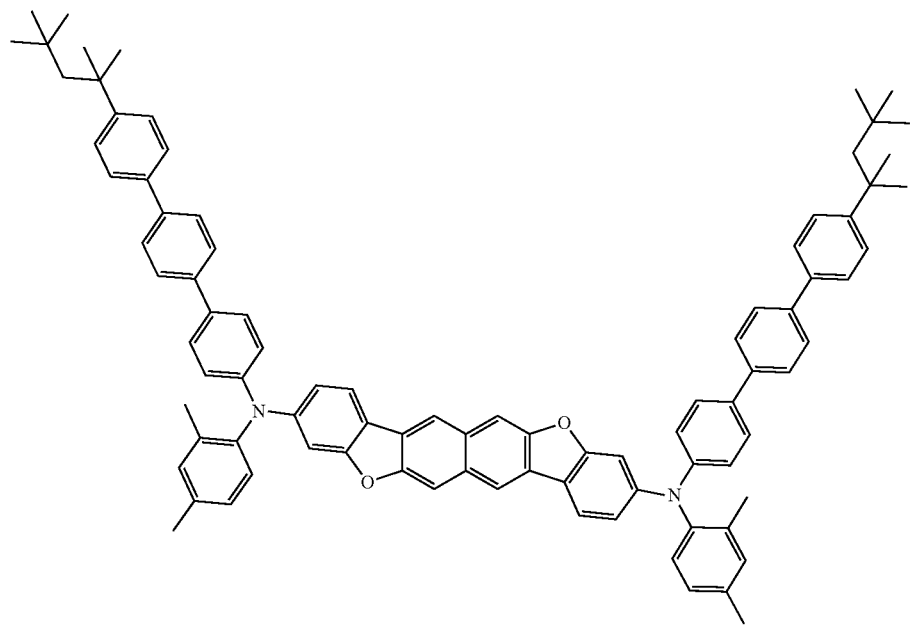

Compound IA-44
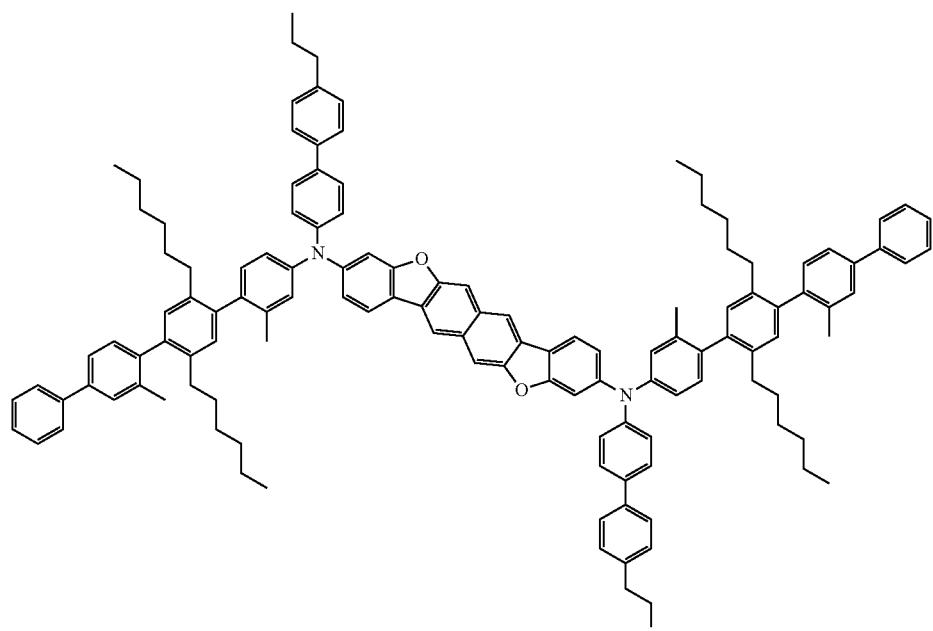
Compound IA-45
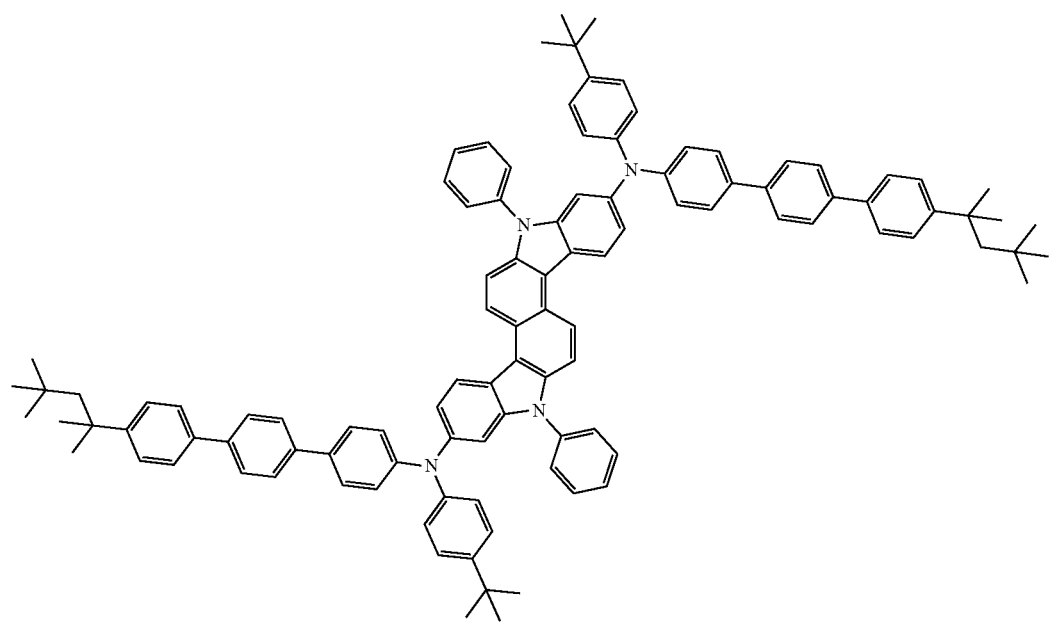

Compound IA-46
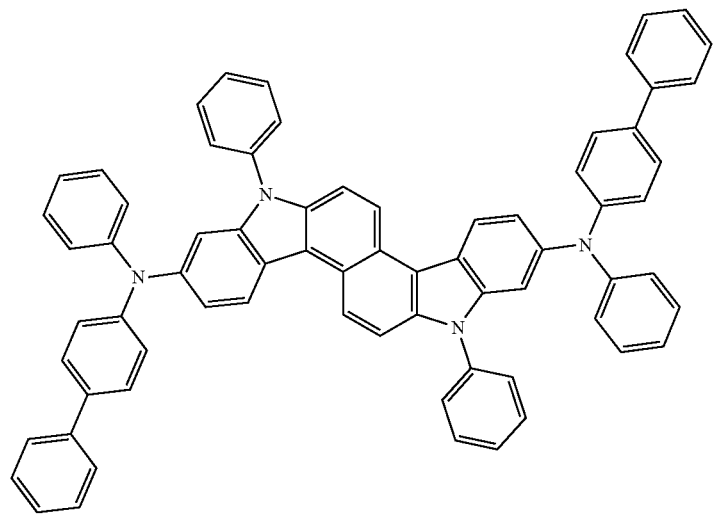
Compound IA-47
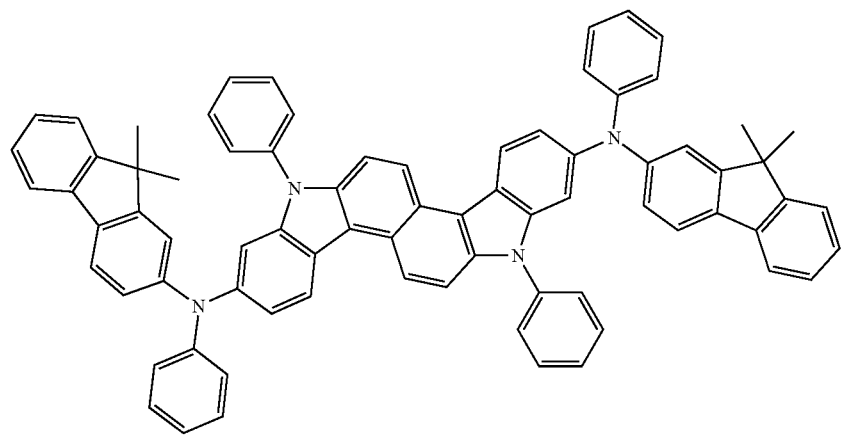
Compound IA-48
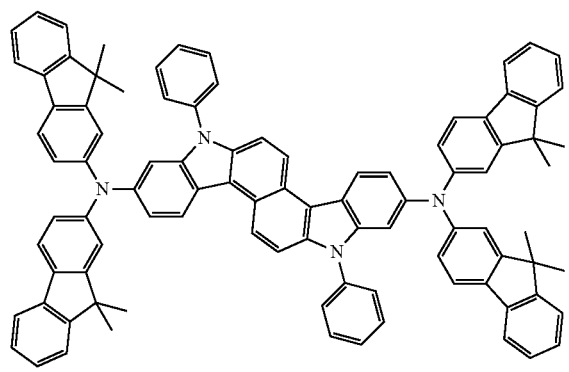
Compound IA-49
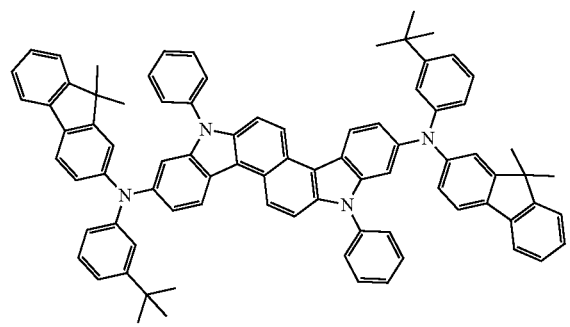

Compound IA-50
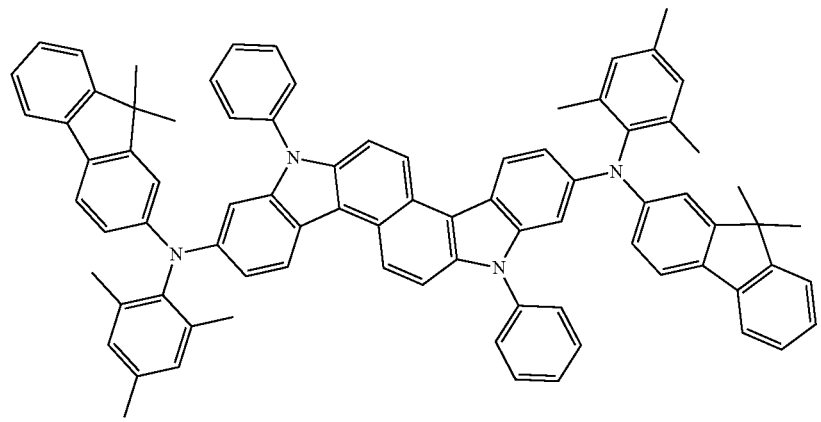
Compound IB-1
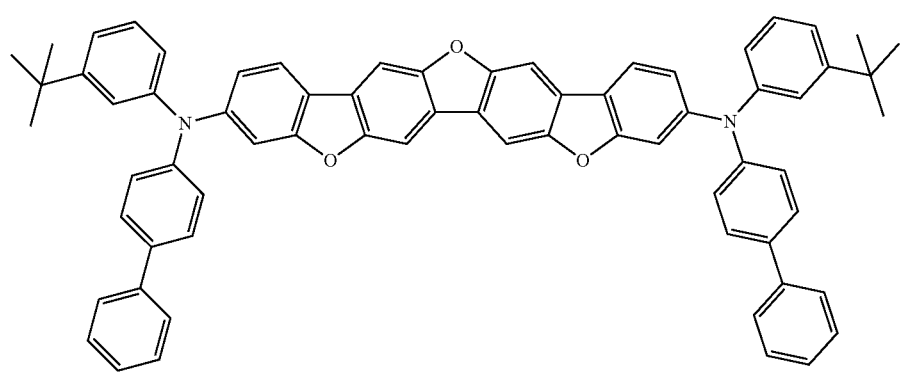
Compound IB-2
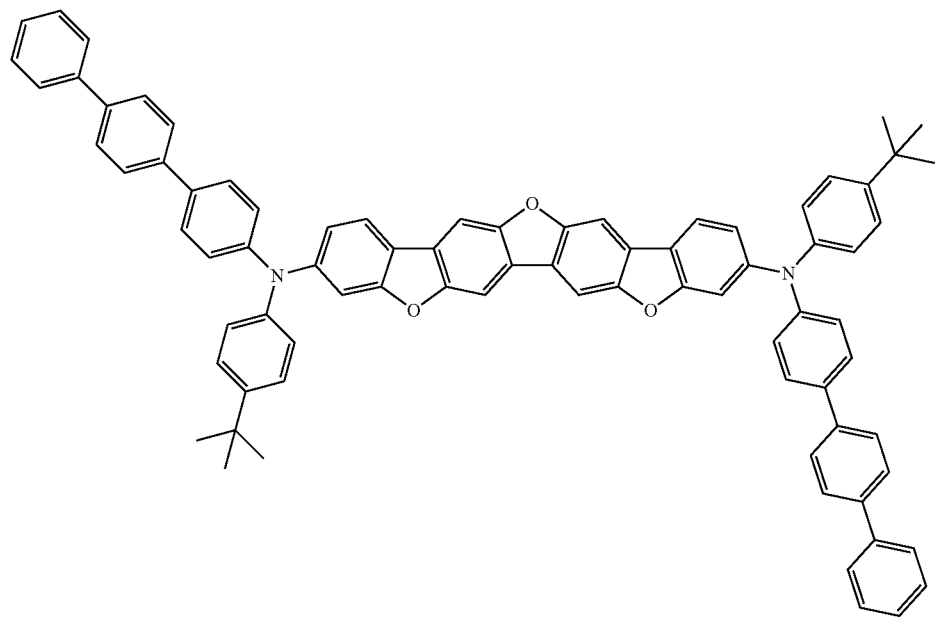

Compound IB-3
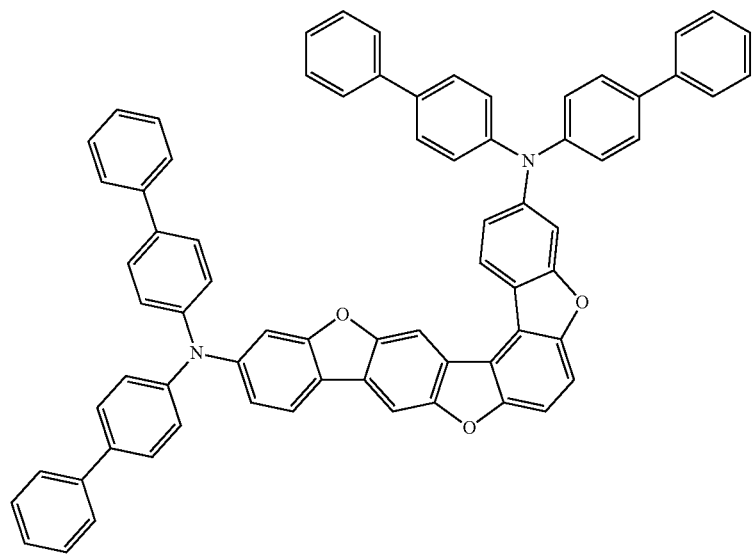
Compound IB-4
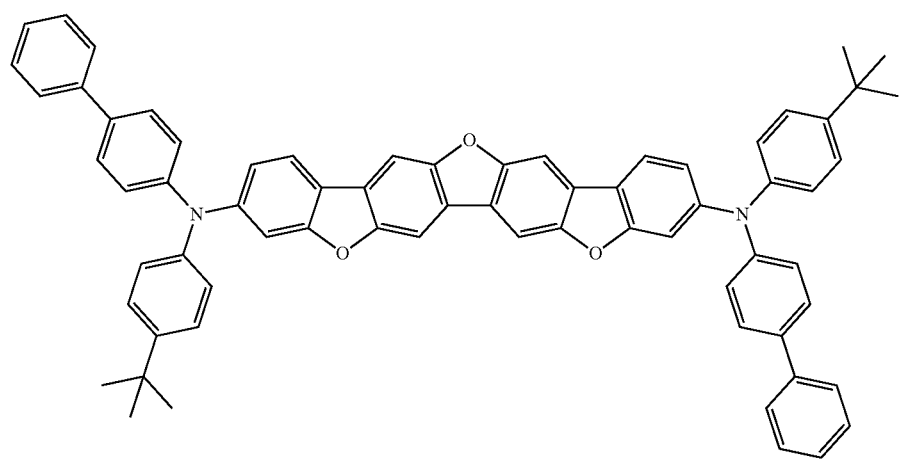
Compound IB-5
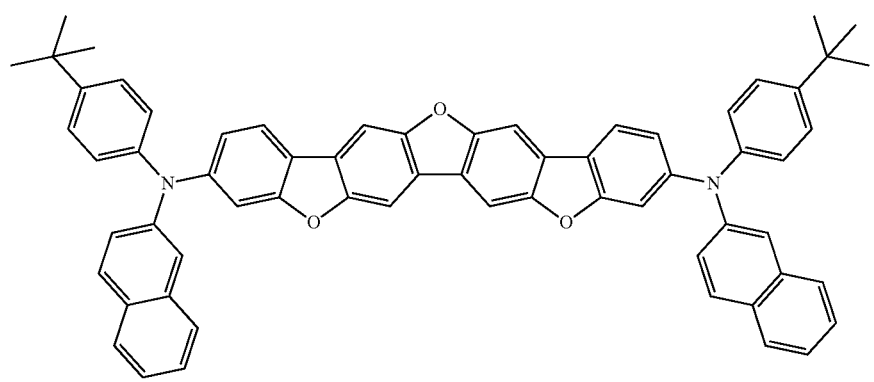

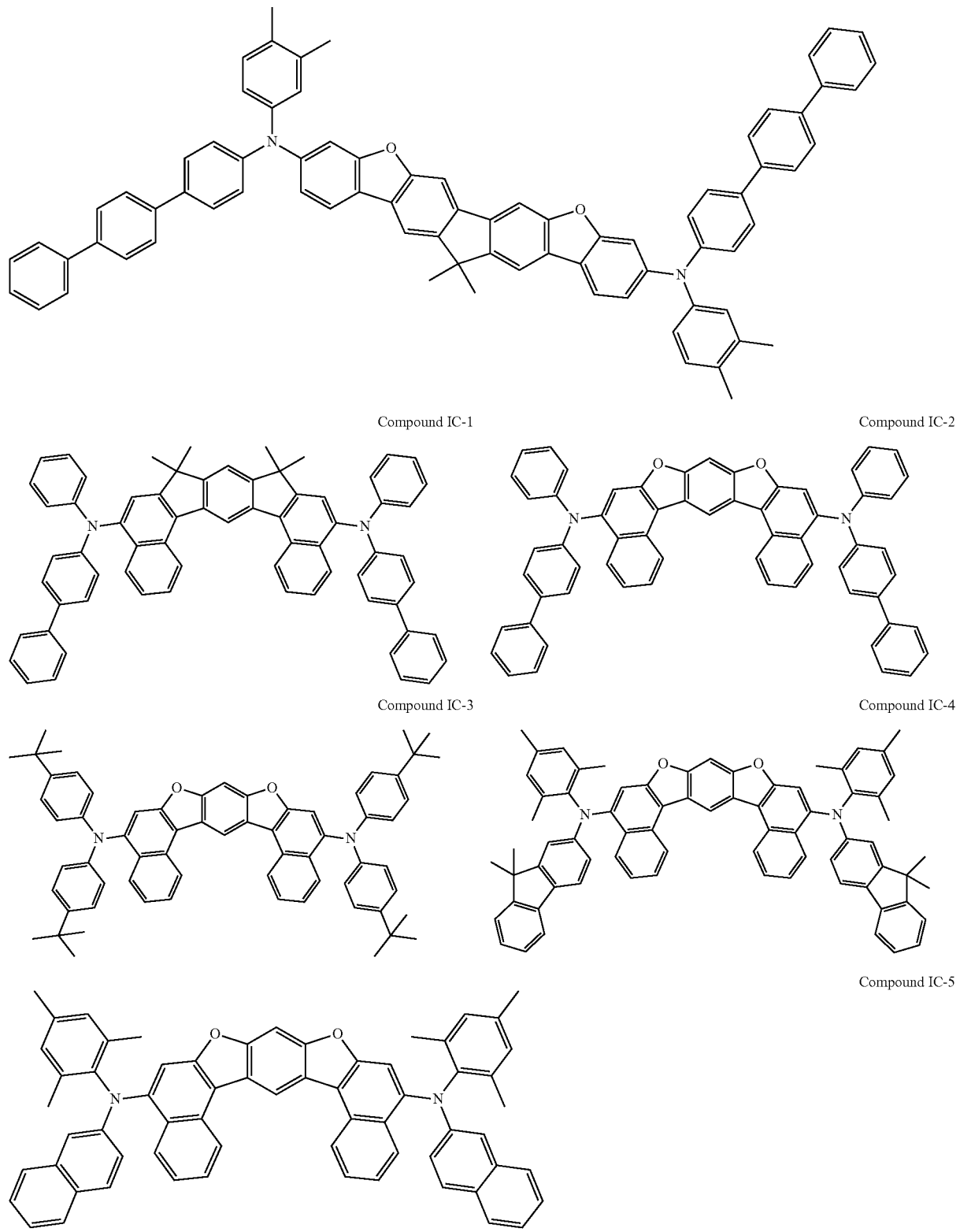

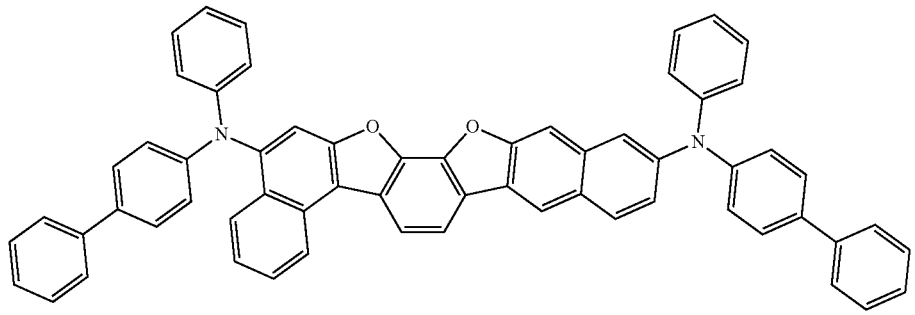

Compound IC-6

3. Compounds Having Formula II or Formula III

In some embodiments, the compounds having Formula II or Formula III are useful as emissive materials. In some embodiments, the compounds are blue emissive materials. They can be used alone or as a dopant in a host material.

In some embodiments, the compounds having Formula II or Formula III have deep blue color. As used herein, the term "deep blue color" refers to a C.I.E. y-coordinate of less than 0.10, according to the C.I.E. chromaticity scale (Commission Internationale de L'Eclairage, 1931). In some embodiments, the y-coordinate is less than 0.090; in some embodiments, the y-coordinate is less than 0.080; in some embodiments, the y-coordinate is less than 0.070; in some embodiments, the y-coordinate is less than 0.060.

In some embodiments, the compounds having Formula II or Formula III have a photoluminescence y-coordinate of less than 0.10; in some embodiments, less than 0.090.

In some embodiments, the compounds having Formula II or Formula III have a solubility in toluene of at least 10 mg/mL; in some embodiments, at least 15 mg/mL; in some embodiments, at least 20 mg/mL. This is advantageous for purification and for solution processing for optimal device performance.

In some embodiments, the compounds having Formula II or Formula III have sublimation temperatures less than 750° C. at 10 torr; in some embodiments, less than 600° C. at 10 torr; in some embodiments, less than 500° C. at 10 torr. This is advantageous for purification.

In some embodiments, the compounds having Formula II or Formula III have a high PLQY. Increased PLQY can contribute to increased efficiency in devices. In some embodiments, the compounds of Formula II or Formula II have a solution PLQY which is at least 90% vs. a standard of quinine bisulfate in 1 N sulfuric acid.

In some embodiments, devices including the compounds of Formula II or Formula III have improved efficiencies. In some embodiments, the current efficiency of a device including Formula II or Formula III is greater than 4.5 cd/A at 1000 nits; in some embodiments, greater than 5.0 cd/A at 1000 nits.

In some embodiments, devices including the compounds of Formula II or Formula III have increased lifetime at an initial luminance of 1000 nits. In some embodiments, devices including the compounds of Formula II or Formula III have a T70 greater than 1000 hours at 50° C. As used herein, T70 refers to the time to reach 70% of initial luminance. In some embodiments, devices including the compounds of Formula II or Formula III have a T70 greater than 1500 hours at 50° C.

In some embodiments, electroluminescent devices including the compounds of Formula II or Formula III as emissive materials have deep blue color. In some embodiments, the x-coordinate is less than 0.15 and the y-coordinate is less than 0.10. In some embodiments, the y-coordinate is less than 0.090; in some embodiments, the y-coordinate is less than 0.080; in some embodiments, the y-coordinate is less than 0.070; in some embodiments, the y-coordinate is less than 0.060.

In some embodiments, the compounds having Formula II or Formula III have a very narrow emission profile. In some embodiments, the FWHM is less than 75 nm; in some embodiments, less than 60 nm; in some embodiments, less than 50 nm; in some embodiments, less than 40 nm; in some embodiments, less than 30 nm. This is advantageous for display devices for producing more saturated color.

In some embodiments, the compounds of Formula II or Formula III have a high degree of horizontal alignment in when doped in films. "Horizontal alignment" and "horizontal orientation" are intended to mean that the emissive dipoles lie parallel to the substrate. Increased horizontal alignment can contribute to higher efficiency in devices. In some embodiments, the compounds of Formula II or Formula III have a horizontal orientation greater than 90%.

In some embodiments of Formula II or Formula III, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula II or Formula III, deuteration is present on the Q group.

In some embodiments of Formula II or Formula III, deuteration is present on one or more aryl groups bonded to Q.

In some embodiments of Formula II or Formula III, deuteration is present on one or more amino groups.

In some embodiments of Formula II or Formula III, deuteration is present on two or more of the Q group, an aryl group bonded to Q, and an amino group.

In some embodiments, the compounds described herein have Formula II

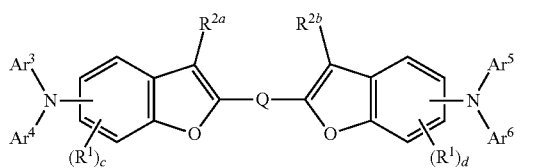

(II)

wherein:
Ar³-Ar⁶ are the same or different and are selected from hydrocarbon aryl groups, heteroaryl groups, and substituted derivatives thereof;
$R^1$ is the same or different at each occurrence and is selected from the group consisting of D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl deuterated silyl, deuterated siloxane, deuterated siloxy, and deuterated germyl;
$R^{2a}$ and $R^{2b}$ are the same or different and are selected from the group consisting of H, D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl deuterated silyl, deuterated siloxane, deuterated siloxy, and deuterated germyl;
Q is selected from the group consisting of a hydrocarbon aryl having 2 or more fused rings, a heteroaryl having 2 or more fused rings, and a substituted derivative thereof; and
c and d are the same or different and are an integer of 0-3.
In Formula II, the two groups

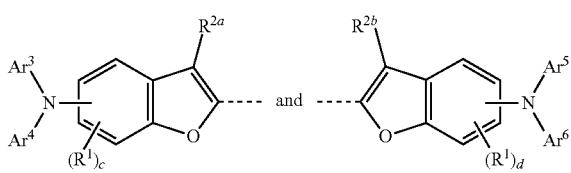

can be bonded to Q at any available bonding position and in any orientation, where the dashed line represents the point of attachment to Q.

In some embodiments of Formula II, there are no amino groups other that those explicitly shown in Formula II.

In some embodiments of Formula II, there are no more than 2 amino groups present.

In some embodiments of Formula II, $R^{2a}=R^{2b}$.

In some embodiments of Formula II, $R^{2a}\neq R^{2b}$.

In some embodiments of Formula II, $R^{2a}=H$.

In some embodiments of Formula II, $R^{2a}=D$.

In some embodiments of Formula II, $R^{2a}$ is an alkyl or deuterated alkyl having 1-12 carbons; in some embodiments 1-8 carbons.

In some embodiments of Formula II, $R^{2a}$ is a trialkylsilyl or deuterated trialkylsilyl. In some embodiments, the alkyl moiety in the trialkyl silyl group has 1-8 carbons; in some embodiments, 1-3 carbons.

In some embodiments of Formula II, $R^{2a}$ is an unsubstituted hydrocarbon aryl having 6-24 ring carbons.

In some embodiments of Formula II, $R^{2a}$ is a hydrocarbon aryl having 6-24 ring carbons and having at least one substituent selected from the group consisting of D, alkyl, silyl, deuterated alkyl, deuterated silyl, and combinations thereof.

In some embodiments of Formula II, $R^{2a}$ is selected from the group consisting of D, alkyl having 1-8 carbons, trialkylsilyl, phenyl, substituted phenyl, naphthyl, substituted naphthyl, biphenyl, substituted biphenyl, terphenyl, and substituted terphenyl, wherein the substituted groups have at least one substituent selected from the group consisting of D, alkyl, silyl, deuterated alkyl, deuterated silyl, and combinations thereof.

All of the above-described embodiments for $R^{2a}$ in Formula II, apply equally to $R^{2b}$ in Formula II.

All of the above-described embodiments for Ar³, Ar⁴, Ar⁵, and Ar⁶, in Formula I, apply equally to Ar³, Ar⁴, Ar⁵, and Ar⁶, in Formula II.

All of the above-described embodiments for $R^1$, c, and d in Formula IA-a, apply equally to $R^1$, c, and d in Formula II.

All of the above-described embodiments for Y in Formula IA, apply equally to Y in Formula II.

In some embodiments of Formula II, Q is selected from the group consisting of a hydrocarbon aryl having 2 or more fused rings, a heteroaryl having 2 or more fused rings, and a substituted derivative thereof, where the substituted derivative has at least one substituent selected from the group consisting of D, alkyl, hydrocarbon aryl, heteroaryl, alkylaryl, deuterated alkyl, deuterated hydrocarbon aryl, deuterated heteroaryl, and deuterated alkylaryl.

In some embodiments of Formula II, Q has at least three fused rings.

In some embodiments of Formula II, Q has at least four fused rings.

In some embodiments of Formula II, Q has at least five fused rings.

In some embodiments of Formula II, Q has at least six fused rings.

In some embodiments of Formula II, exclusive of Q, there are no groups having more than 2 fused rings. In some embodiments, there are also no substituents on Q having more than 2 fused rings.

In some embodiments of Formula II, there are no pyrene groups.

In some embodiments of Formula II, exclusive of Q, there are no fluorene groups. In some embodiments, there are also no fluorene substituents on Q.

In some embodiments of Formula II, exclusive of Q, there are no carbazole groups. In some embodiments, there are also no carbazole substituents on Q.

In some embodiments of Formula II, there are no spiro groups. In some embodiments, there are also no spiro substituents on Q.

In some embodiments of Formula II, Q includes at least one heteroatom.

In some embodiments of Formula II, Q is an unsubstituted hydrocarbon aryl.

In some embodiments of Formula II, Q is a substituted hydrocarbon aryl, where the substituent is selected from the group consisting of D, alkyl, hydrocarbon aryl, heteroaryl, alkylaryl, deuterated alkyl, deuterated hydrocarbon aryl, deuterated heteroaryl, and deuterated alkylaryl.

In some embodiments of Formula II, Q is an aryl group derived from a compound selected from the group consisting of naphthalene, anthracene, chrysene, pyrene, triphenylene, fluoranthene, phenanthrene and substituted derivatives thereof.

In some embodiments of Formula II, Q is an unsubstituted heteroaryl.

In some embodiments of Formula II, Q is an unsubstituted N,O,S-heteroaryl.

In some embodiments of Formula II, Q is a substituted heteroaryl, where the substituent is selected from the group consisting of D, alkyl, hydrocarbon aryl, heteroaryl, alkylaryl, deuterated alkyl, deuterated hydrocarbon aryl, deuterated heteroaryl, and deuterated alkylaryl.

In some embodiments of Formula II, Q is an unsubstituted or substituted N-heteroaryl.

In some embodiments, the N-heteroaryl is derived from a compound selected from the group consisting of carbazole, carbazolocarbazole, indolocarbazole, indoloindole, and substituted derivatives thereof.

In some embodiments of Formula II, Q is an unsubstituted or substituted O-heteroaryl.

In some embodiments, the O-heteroaryl is derived from a compound having multiple fused furan, isobenzofuran or benzofuran groups.

In some embodiments, the O-heteroaryl is derived from a compound selected from the group consisting of naphthodifuran, naphthobisbenzofuran, dibenzofuranbis(benzofuran), and substituted derivatives thereof.

In some embodiments of Formula II, Q is an unsubstituted or substituted S-heteroaryl.

In some embodiments, the S-heteroaryl is derived from a compound having multiple fused thiophene or benzothiophene groups.

In some embodiments, the S-heteroaryl is derived from a compound selected from the group consisting of naphthodithiophene, naphthobisbenzothiophene, dibenzothiophenebis(benzothiophene), and substituted derivatives thereof.

In some embodiments of Formula II, Q is an unsubstituted or substituted N,O,S-heteroaryl having two different heteroatoms.

In some embodiments of Formula II, Q is selected from the groups Formula IA, Formula IB, and Formula IC, as described above. In Formula IB, there are two terminal benzo groups. The Q group having Formula IB is attached to Formula II from the terminal benzo groups.

All of the above-described embodiments for Formula IA in Formula I, apply equally to Formula IA in Formula II.

All of the above-described embodiments for Formula IB in Formula I, apply equally to Formula IB in Formula II.

All of the above-described embodiments for Formula IA in Formula I, apply equally to Formula IA in Formula II.

In some embodiments of Formula II, Q is selected from the group consisting of Formulas IA-a through IA-t, described above. All of the above-described embodiments for Formula IA-a through IA-t for Formula I, apply equally to Formula IA-a through IA-t in Formula II.

In some embodiments of Formula II, Q is selected from the group consisting of Formulas IA-a1, IA-a2, IA-b1, IA-b2, IA-c1, and IA-c2, as described above. All of the above-described embodiments for Formulas IA-a1, IA-a2, IA-b1, IA-b2, IA-c1, and IA-c2 for Formula I, apply equally to Formulas IA-a1, IA-a2, IA-b1, IA-b2, IA-c1, and IA-c2 in Formula II.

In some embodiments of Formula II, Q is selected from the group consisting of Formulas IB-a through IB-m, as described above. All of the above-described embodiments for Formulas IB-a through IB-m for Formula I, apply equally to Formula IB-a through IB-m in Formula II.

In some embodiments of Formula II, Q is selected from the group consisting of Formulas IB-aa through IB-mm, as described above. All of the above-described embodiments for Formulas IB-aa through IB-mm for Formula I, apply equally to Formulas IB-aa through IB-mm in Formula II.

In some embodiments of Formula II, Q is selected from the group consisting of Formulas IC-a through IC-p, as described above. All the above-described embodiments of Formulas IC-a through IC-p for Formula I, apply equally to Formulas IC-a through IC-p in Formula II.

In some embodiments of Formula II, Q is selected from the group consisting of Formulas IC-a1 and IC-a2, described above. All the above-described embodiments of Formulas IC-a1 and IC-a2 in Formula I, apply equally to Formulas IC-a1 and IC-a2 in Formula II.

In some embodiments of Formula II, Q is selected from the group consisting of Formulas II-a through II-d

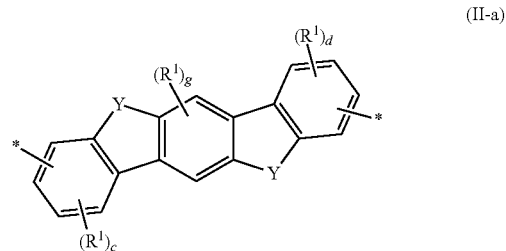

(II-a)

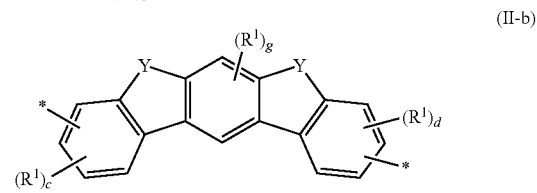

(II-b)

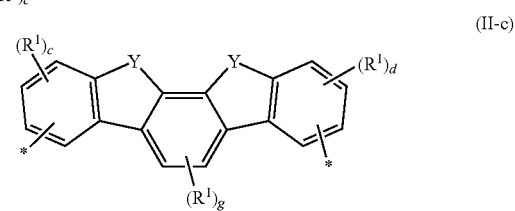

(II-c)

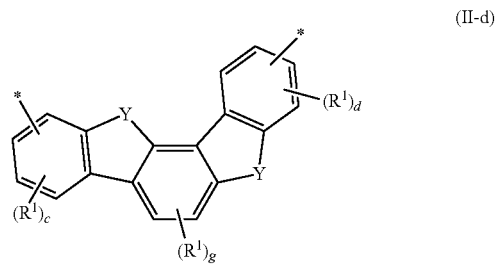

(II-d)

where:
Y is the same or different at each occurrence and is selected from the group consisting of O, S, Se, Te, $NR^2$, $CR^3R^4$, and $SiR^5R^6$;

$R^1$ is the same or different at each occurrence and is selected from the group consisting of D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl, deuterated silyl, deuterated siloxane, deuterated siloxy, and deuterated germyl;

$R^2$ is the same or different at each occurrence and is selected from the group consisting of alkyl, hydrocarbon aryl, heteroaryl, and substituted derivatives thereof;

$R^3$-$R^6$ are the same or different at each occurrence and are selected from the group consisting of alkyl, silyl, germyl, hydrocarbon aryl, heteroaryl, and substituted derivatives thereof, where $R^3$ and $R^4$ and/or $R^5$ and $R^6$ can be joined to form a cyclic group selected from the group consisting of cycloalkyl, silacycloalkyl, spirofluorenyl, silaspirofluorenyl, or a substituted derivative thereof;

c and d are the same or different and are an integer of 0-3;

g is an integer of 0-2; and

* indicates a point of attachment in the identified formula.

All of the above-described embodiments for c, d, g, and $R^1$ in Formula IA-a, apply equally to c, d, g, and $R^1$ in Formulas II-a through II-d.

All of the above-described embodiments for Y in Formula IA, apply equally to Y in Formulas II-a through II-d.

All of the above described embodiments for $R^2$-$R^6$ in Formula IA, apply equally to $R^2$-$R^6$ in Formulas II-a through II-d.

In some embodiments of Formula II, Q is selected from the group consisting of Formulas II-a1, II-a2, II-b1, II-b2, II-c1, II-c2, II-d1, and II-d2.

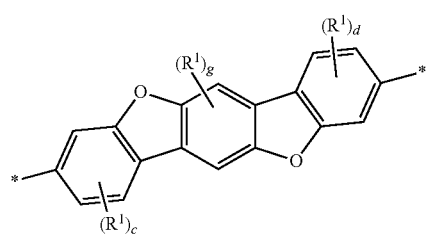

(II-a1)

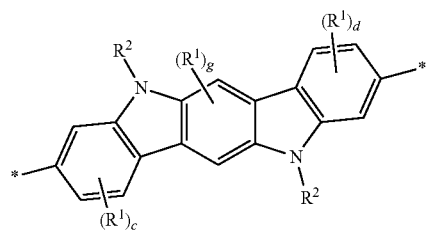

(II-a2)

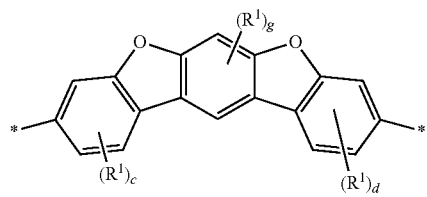

(II-b1)

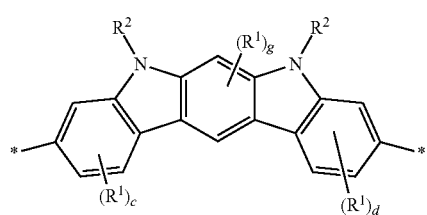

(II-b2)

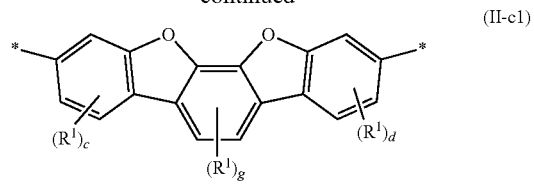

(II-c1)

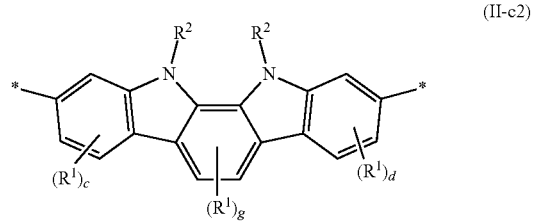

(II-c2)

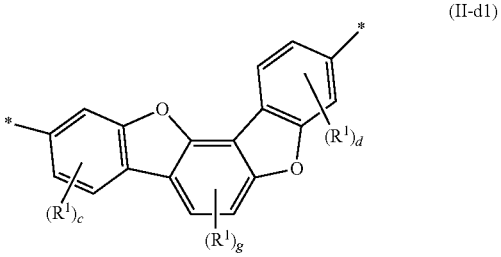

(II-d1)

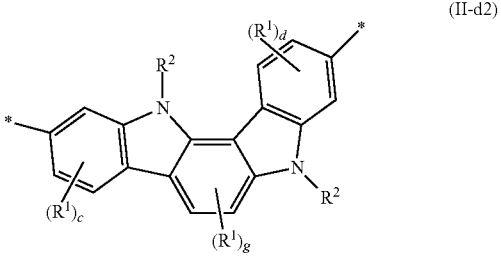

(II-d2)

where $R^1$, $R^2$, c, d, g, and * are as defined above.

All of the above-described embodiments for c, d, g, and $R^1$ in Formula IA-a, apply equally to c, d, g, and $R^1$ in Formulas II-a1, II-a2, II-b1, II-b2, II-c1, II-c2, II-d1, and II-d2.

All of the above described embodiments for $R^2$ in Formula IA, apply equally to $R^2$ in Formulas II-a1, II-a2, II-b1, II-b2, II-c1, II-c2, II-d1, and II-d2.

In some embodiments of Formula II, Q is selected from the group consisting of Formula II-a and Formula II-b.

In some embodiments of Formula II, Q is selected from the group consisting of Formula II-a1, Formula II-a2, Formula II-b1, and Formula II-b2.

In some embodiments, the compounds described herein have Formula III

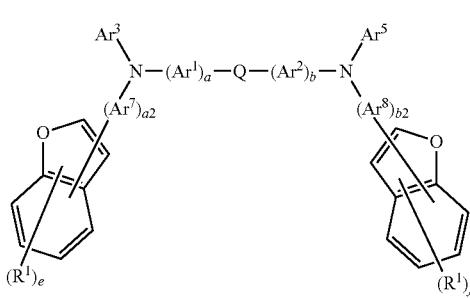

(III)

wherein:

Ar$^1$, Ar$^2$, Ar$^3$, Ar$^5$, Ar$^7$, and Ar$^8$ are the same or different and are selected from hydrocarbon aryl groups, heteroaryl groups, and substituted derivatives thereof;

R$^1$ is the same or different at each occurrence and is selected from the group consisting of D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl deuterated silyl, deuterated siloxane, deuterated siloxy, and deuterated germyl;

R$^{2a}$ and R$^{2b}$ are the same or different and are selected from the group consisting of H, D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl deuterated silyl, deuterated siloxane, deuterated siloxy, and deuterated germyl;

Q is selected from the group consisting of a hydrocarbon aryl having 2 or more fused rings, a heteroaryl having 2 or more fused rings, and a substituted derivative thereof;

a, a2, b, and b2 are the same or different and are 0 or 1; and e and f are the same or different and are an integer of 0-5.

In some embodiments of Formula III, there are no amino groups other that those explicitly shown in Formula III.

In some embodiments of Formula III, there are no more than 2 amino groups present.

In some embodiments of Formula III, a2=0.
In some embodiments of Formula III, a2=1.
In some embodiments of Formula III, b2=0.
In some embodiments of Formula III, b2=1.
In some embodiments of Formula III, e=0.
In some embodiments of Formula III, e=1.
In some embodiments of Formula III, e=2.
In some embodiments of Formula III, e=3.
In some embodiments of Formula III, e=4.
In some embodiments of Formula III, e=5.
In some embodiments of Formula III, e>0.
In some embodiments of Formula III, f=0.
In some embodiments of Formula III, f=1.
In some embodiments of Formula III, f=2.
In some embodiments of Formula III, f=3.
In some embodiments of Formula III, f=4.
In some embodiments of Formula III, f=5.
In some embodiments of Formula III, f>0.
In some embodiments of Formula III, e=f.
In some embodiments of Formula III, e≠f.

All of the above-described embodiments for Q in Formula II, apply equally to Q in Formula III.

In some embodiments of Formula III, Q has at least three fused rings.

In some embodiments of Formula III, Q has at least four fused rings.

In some embodiments of Formula III, Q has at least five fused rings.

In some embodiments of Formula III, Q has at least six fused rings.

In some embodiments of Formula III, exclusive of Q, there are no groups having more than 2 fused rings. In some embodiments, there are also no substituents on Q having more than 2 fused rings.

In some embodiments of Formula III, there are no pyrene groups.

In some embodiments of Formula III, exclusive of Q, there are no fluorene groups. In some embodiments, there are also no fluorene substituents on Q.

In some embodiments of Formula III, exclusive of Q, there are no carbazole groups. In some embodiments, there are also no carbazole substituents on Q.

In some embodiments of Formula III, there are no spiro groups. In some embodiments, there are also no spiro substituents on Q.

In some embodiments of Formula III, Q includes at least one heteroatom.

In some embodiments of Formula III, Q is selected from the group consisting of Formula II-a and Formula II-b, described above.

In some embodiments of Formula III, Q is selected from the group consisting of Formula II-a1, Formula II-a2, Formula II-b1, and Formula II-b2, described above.

All of the above-described embodiments for Ar$^1$ in Formula I, apply equally to Ar$^7$ and Ar$^8$ in Formula III.

In some embodiments of Formula III, Ar$^7$ and Ar$^8$ are selected from the group consisting of phenyl, biphenyl, naphthyl, and substituted derivatives thereof. In some embodiments, the substituent is selected from the group consisting of D, alkyl, silyl, deuterated alkyl, and deuterated silyl.

In some embodiments of Formula III, Ar$^7$ and Ar$^8$ are selected from the group consisting of phenyl, biphenyl, naphthyl, and deuterated analogs thereof.

All of the above-described embodiments for Ar$^1$, Ar$^2$, Ar$^3$, Ar$^5$, a, and b in Formula I, apply equally to Ar$^1$, Ar$^2$, Ar$^3$, and Ar$^5$, in Formula III.

All of the above-described embodiments for R$^1$ in Formula IA-a, apply equally to R$^1$ in Formula III.

In some embodiments of Formula III, the compound has Formula III-a

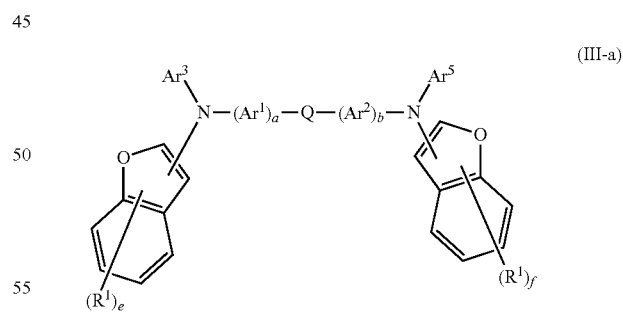

where Q, Ar$^1$, Ar$^2$, Ar$^3$, Ar$^5$, R$^1$, a, b, e, and f are as defined above. All of the above-described embodiments for Q, Ar$^1$, Ar$^2$, Ar$^3$, Ar$^5$, R$^1$, a, b, e, and f in Formula III, apply equally to Q, Ar$^1$, Ar$^2$, Ar$^3$, Ar$^5$, R$^1$, a, b, e, and f in Formula III-a.

In some embodiments of Formula III, the compound has Formula III-b

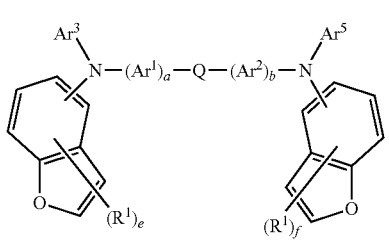
(III-b)

where Q, Ar$^1$, Ar$^2$, Ar$^3$, Ar$^5$, R$^1$, a, b, e, and f are as defined above. All of the above-described embodiments for Q, Ar$^1$, Ar$^2$, Ar$^3$, Ar$^5$, R$^1$, a, b, e, and f in Formula III, apply equally to Q, Ar$^1$, Ar$^2$, Ar$^3$, Ar$^5$, R$^1$, a, b, e, and f in Formula III-b.

In some embodiments of Formula III, the compound is selected from the group consisting of Formula III-a1, Formula III-a2, and Formula III-a3

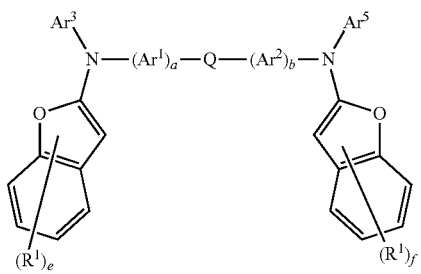
(III-a1)

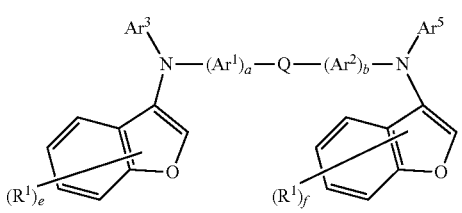
(III-a2)

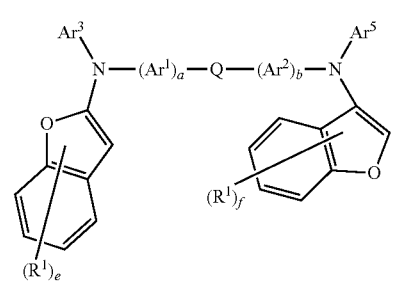
(III-a3)

where Q, Ar$^1$, Ar$^2$, Ar$^3$, Ar$^5$, R$^1$, a, b, e, and f are as defined above. All of the above-described embodiments for Q, Ar$^1$, Ar$^2$, Ar$^3$, Ar$^5$, R$^1$, a, b, e, and f in Formula III, apply equally to Q, Ar$^1$, Ar$^2$, Ar$^3$, Ar$^5$, R$^1$, a, b, e, and f in Formula III-a1, Formula III-a2, and Formula III-a3.

In some embodiments of Formula III, the compound is selected from the group consisting of Formula III-b1, Formula III-b2, and Formula III-b3.

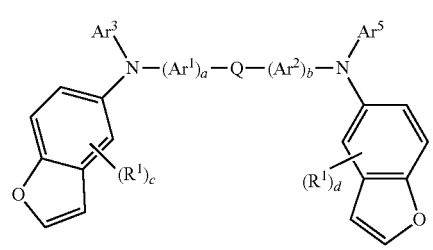
(III-b1)

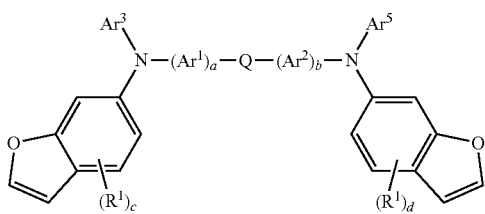
(III-b2)

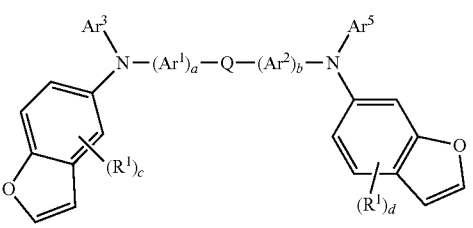
(III-b3)

where Q, Ar$^1$, Ar$^2$, Ar$^3$, Ar$^5$, R$^1$, a, b, c, and d are as defined above. All of the above-described embodiments for Q, Ar$^1$, Ar$^2$, Ar$^3$, Ar$^5$, R$^1$, a, and b in Formula III, and the embodiments for c and d in Formula II, apply equally to Q, Ar$^1$, Ar$^2$, Ar$^3$, Ar$^5$, R$^1$, a, b, c, and d in Formula III-b1, Formula III-b2, and Formula III-b3.

In some embodiments of Formula III, the compound is selected from the group consisting of Formula III-c1, Formula III-c2, and Formula III-c3

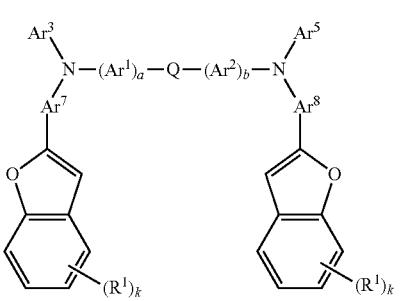
(III-c1)

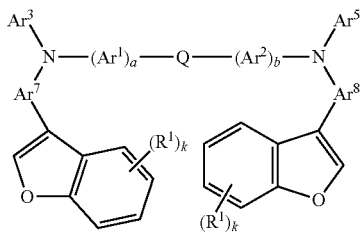
(III-c2)

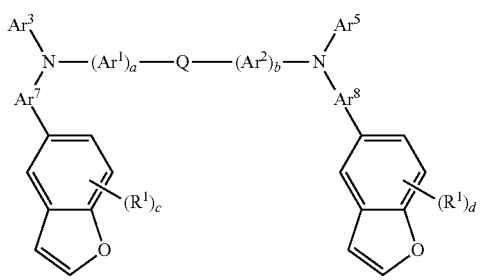
(III-d2)

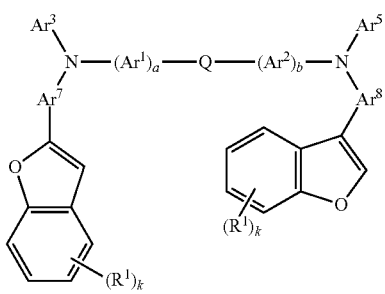
(III-c3)

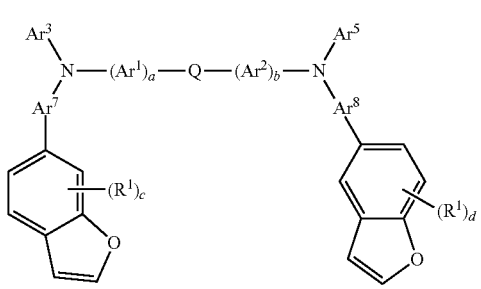
(III-d3)

where k1 is an integer from 0-4, and Q, $Ar^1$, $Ar^2$, $Ar^3$, $Ar^5$, $R^1$, a, b, and k are as defined above. All of the above described embodiments for k in Formula IA-q apply equally to k1 in Formula III-c1, Formula III-c2, and Formula III-c3. All of the above-described embodiments for Q, $Ar^1$, $Ar^2$, $Ar^3$, $Ar^5$, $R^1$, a, and b in Formula III, and the embodiments for k in Formula IA-q, apply equally to Q, $Ar^1$, $Ar^2$, $Ar^3$, $Ar^5$, $R^1$, a, b, and k in Formula III-c1, Formula III-c2, and Formula III-c3.

In some embodiments of Formula III, the compound is selected from the group consisting of Formula III-d1, Formula III-d2, and Formula III-d3

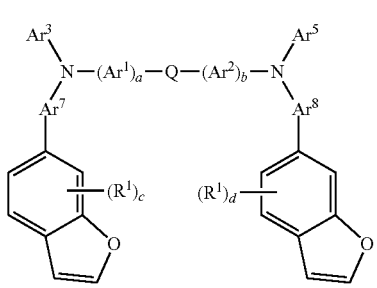
(III-d1)

where Q, $Ar^1$, $Ar^2$, $Ar^3$, $Ar^5$, $Ar^7$, $Ar^8$, $R^1$, a, b, c, and d are as defined above. All of the above-described embodiments for Q, $Ar^1$, $Ar^2$, $Ar^3$, $Ar^5$, $Ar^7$, $Ar^8$, $R^1$, a, and b in Formula III, and the embodiments for c and d in Formula II, apply equally to Q, $Ar^1$, $Ar^2$, $Ar^3$, $Ar^5$, $Ar^7$, $Ar^8$, $R^1$, a, b, c, and d in Formula III-d1, Formula III-d2, and Formula III-d3.

Any of the above embodiments of the above formulas can be combined with one or more of the other embodiments, so long as they are not mutually exclusive.

The compounds of Formula II and Formula III can be made using any technique that will yield a C—C, C—N, C—O, C—S, or C—Si bond. A variety of such techniques are known, such as Suzuki, Yamamoto, Stille, Negishi, and metal-catalyzed C—N couplings as well as metal catalyzed and oxidative direct arylation.

Deuterated compounds can be prepared in a similar manner using deuterated precursor materials or, more generally, by treating the non-deuterated compound with deuterated solvent, such as benzene-d6, in the presence of a Bronsted or Lewis acid H/D exchange catalyst, such as trifluoromethanesulfonic acid, aluminum trichloride or ethyl aluminum dichloride. Deuteration reactions have also been described in published PCT application WO2011/053334.

Exemplary preparations are given in the Examples.

Examples of compounds having Formula II and Formula III include, but are not limited to, the compounds shown below.

Compound II-1
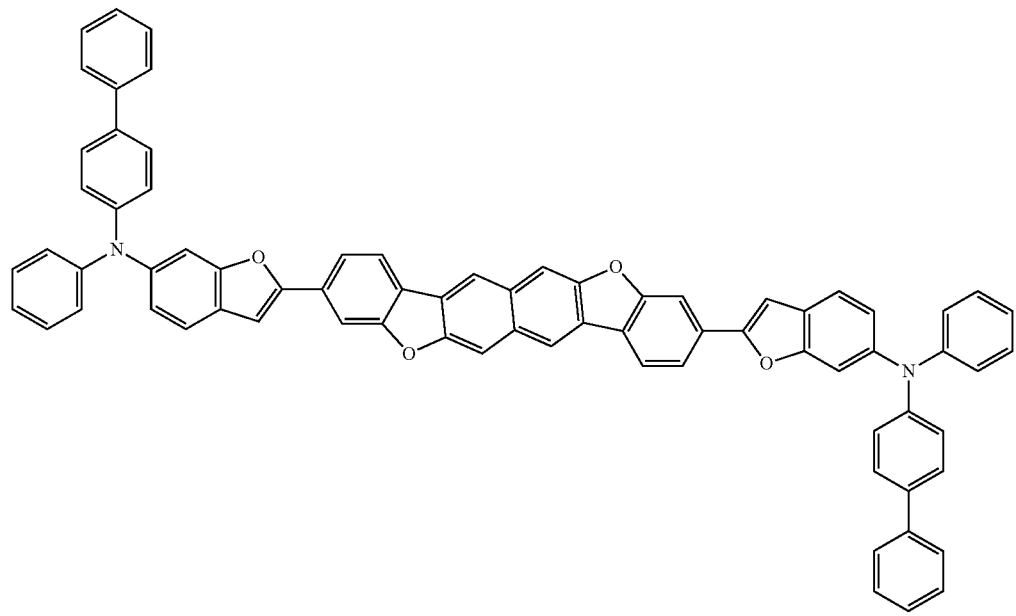
[Compound II-2 deleted.]
Compound II-3
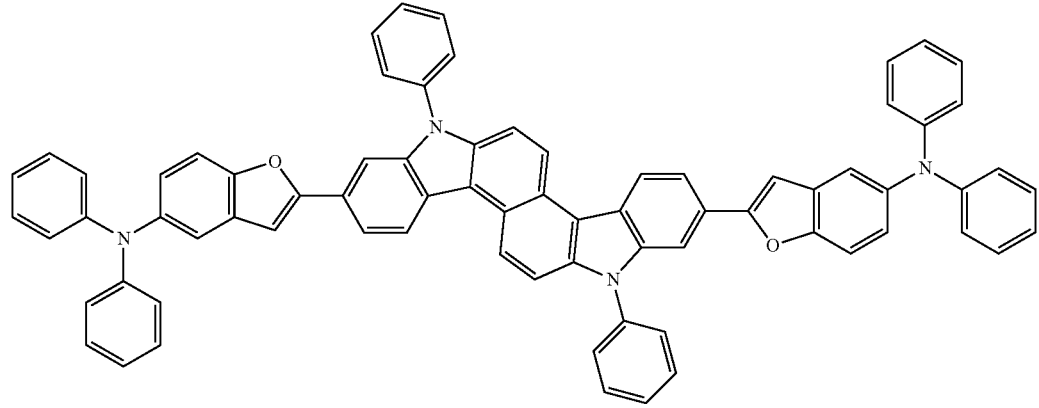
[Compounds II-4 through II-10 deleted.]
Compound II-11
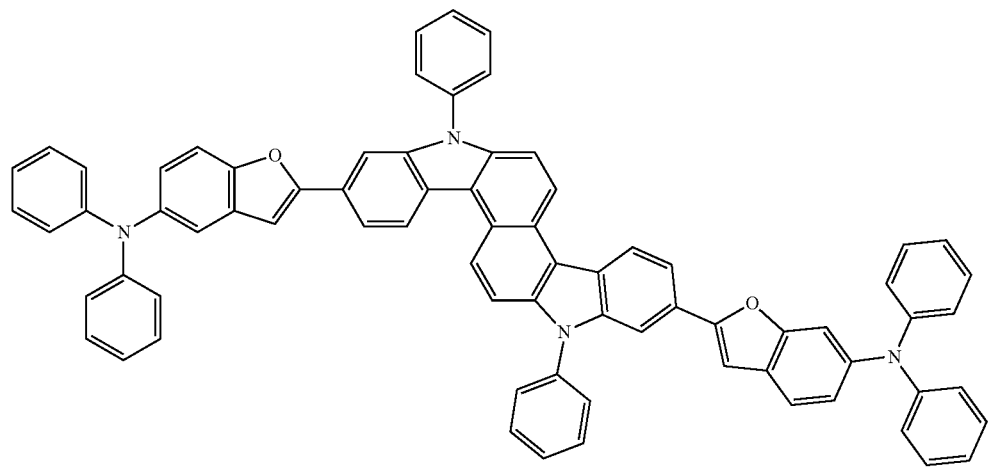

Compound II-13
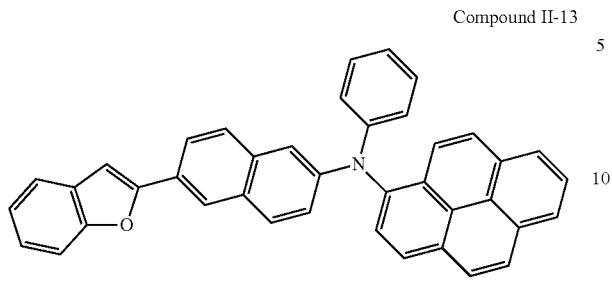
Compound II-13
[Compound II-14 is deleted.]
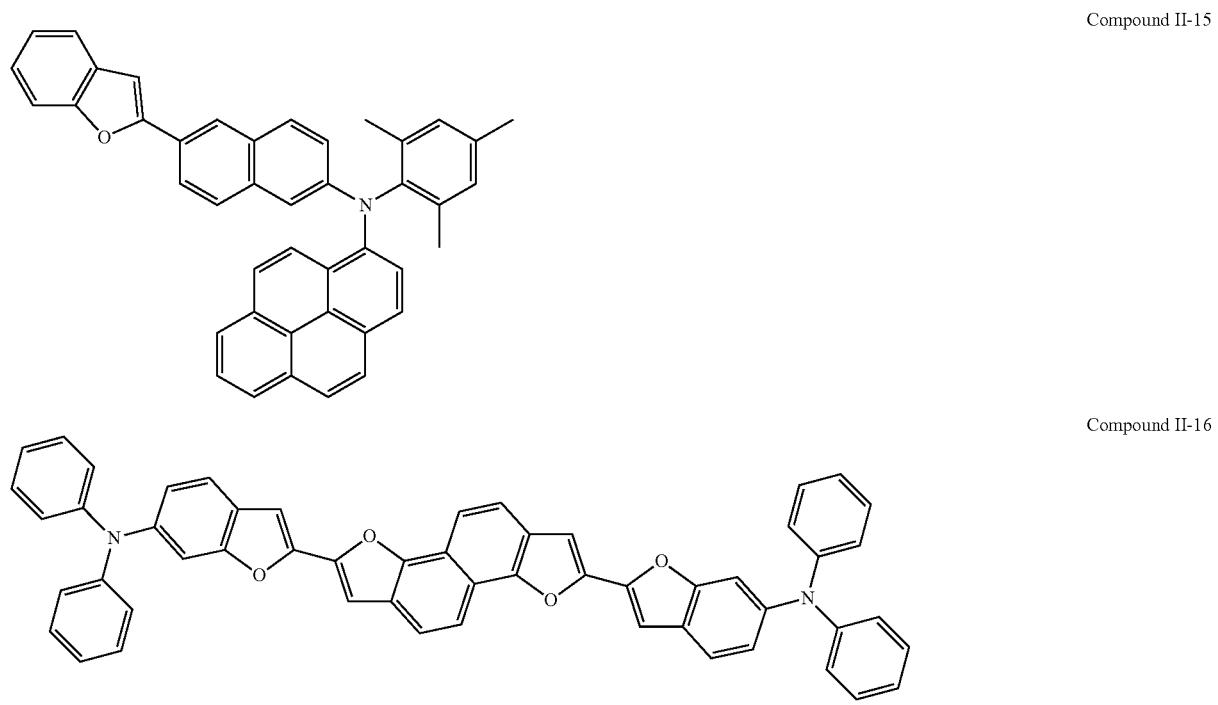
Compound II-15
Compound II-16
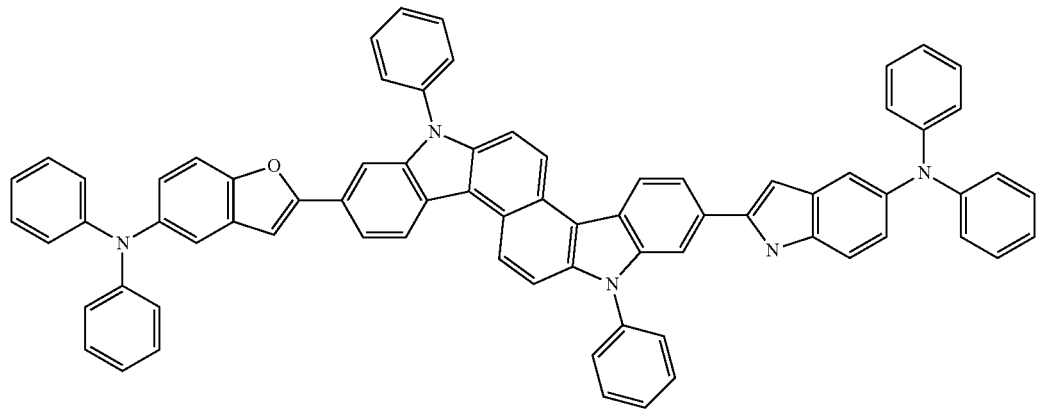
Compound II-17

-continued
Compound III-1
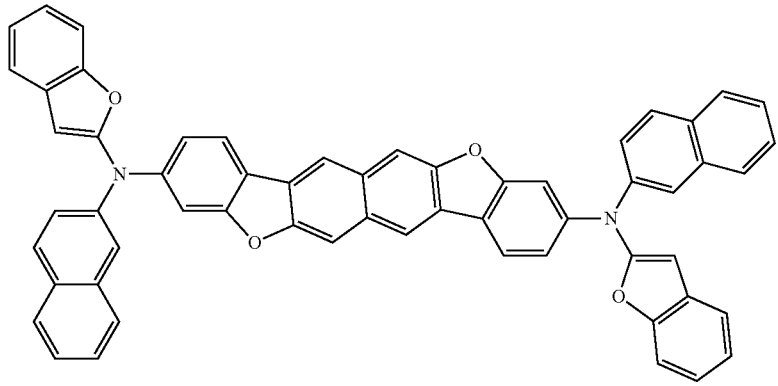
Compound III-2
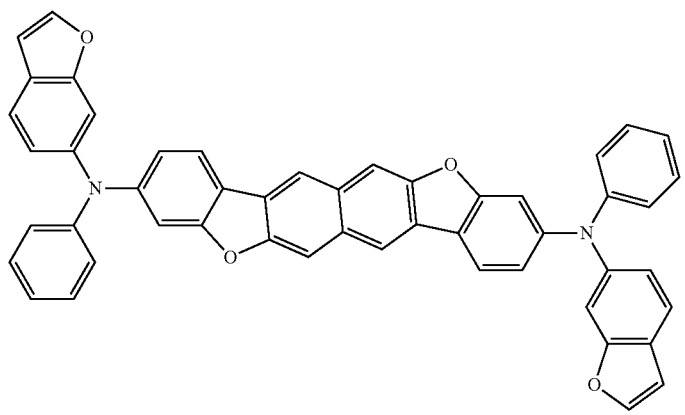
Compound III-3
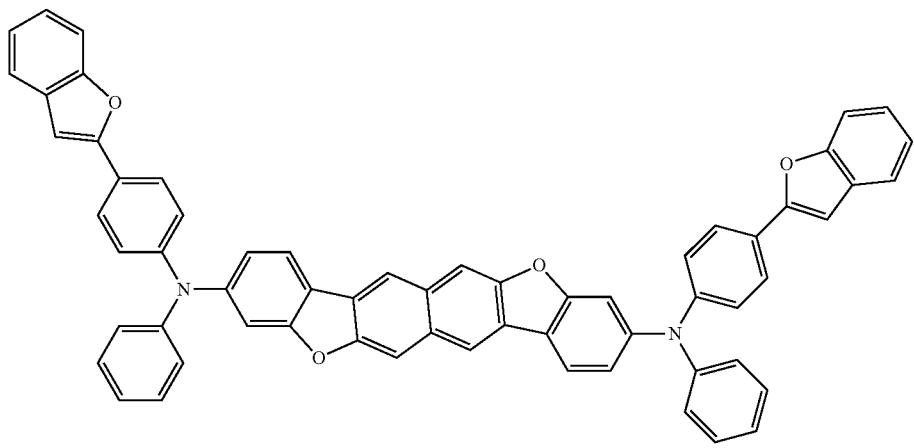

Compound III-4
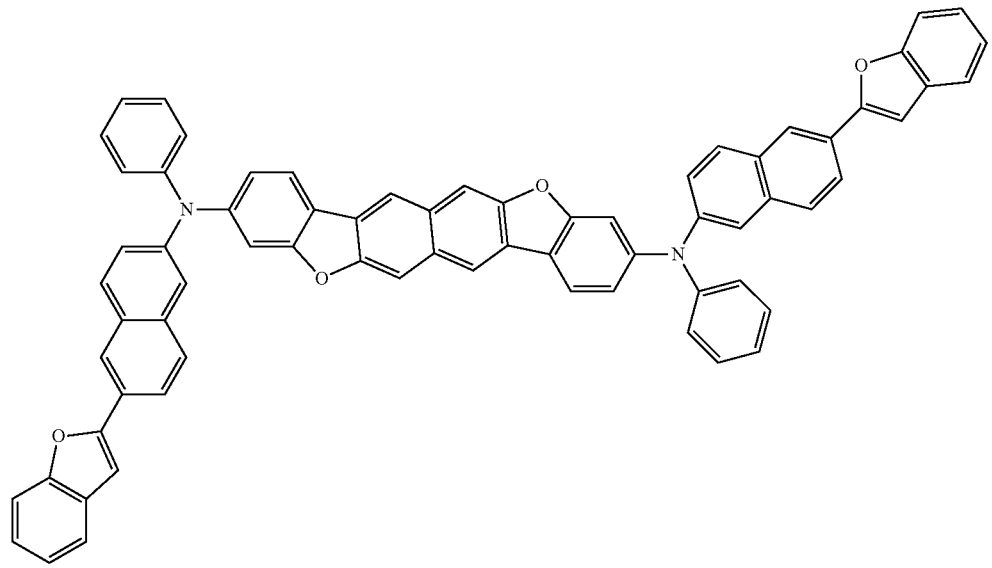
Compound III-5
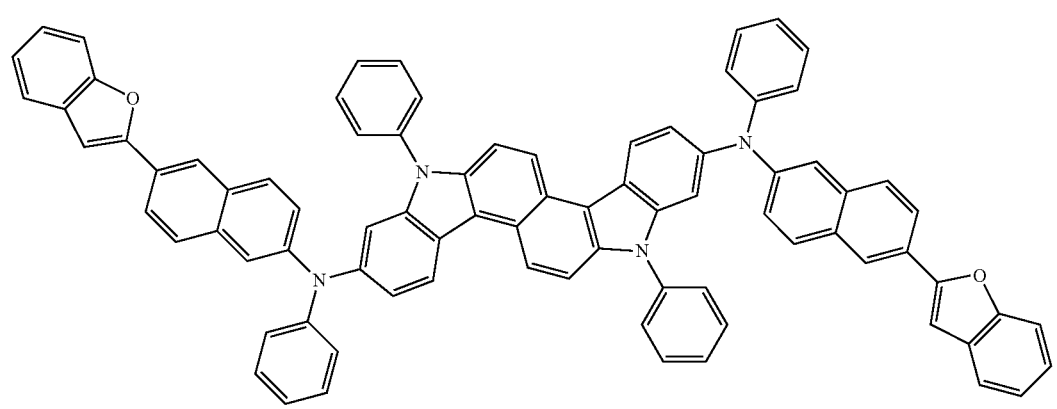
Compound III-6
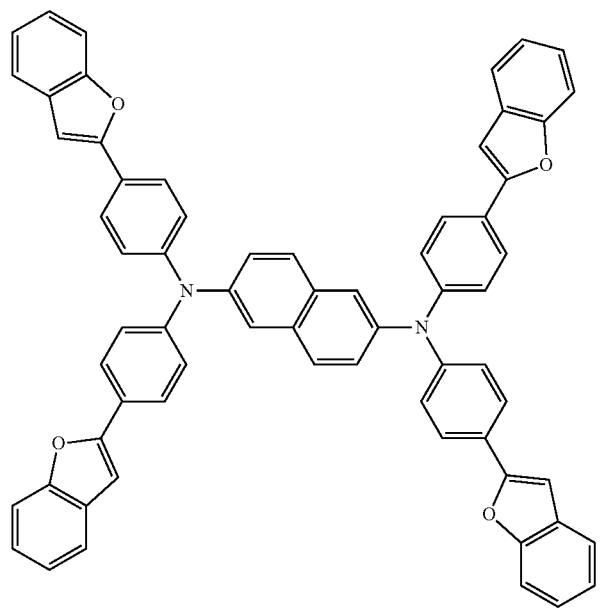

Compound III-7
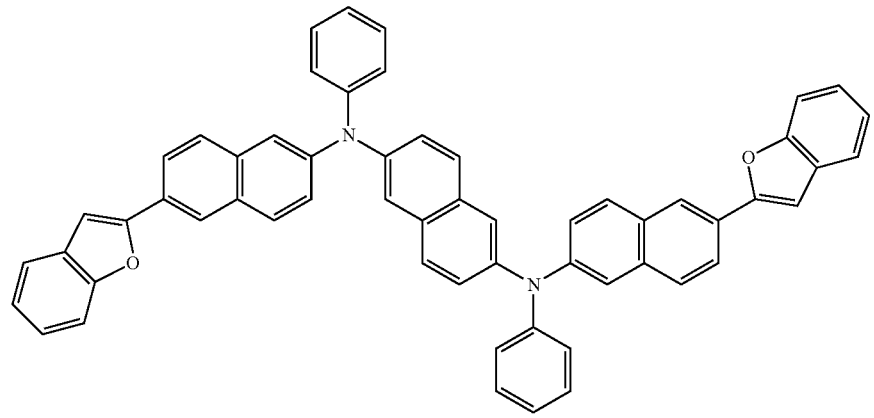
Compound III-8
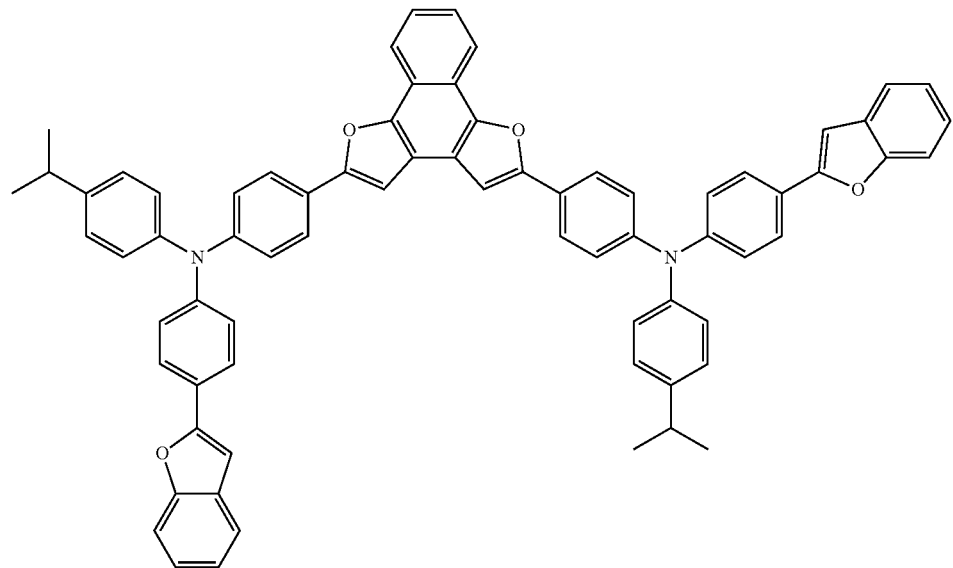
Compound III-9
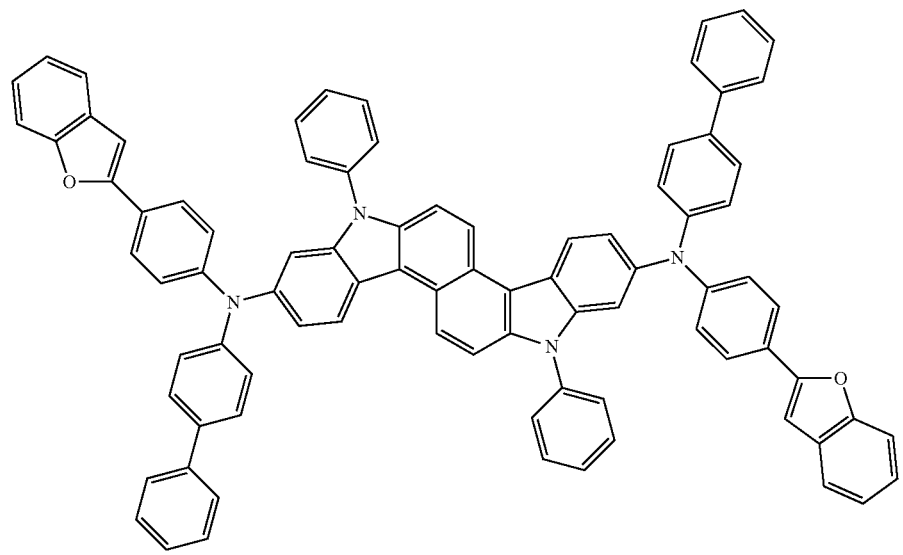

Compound III-10
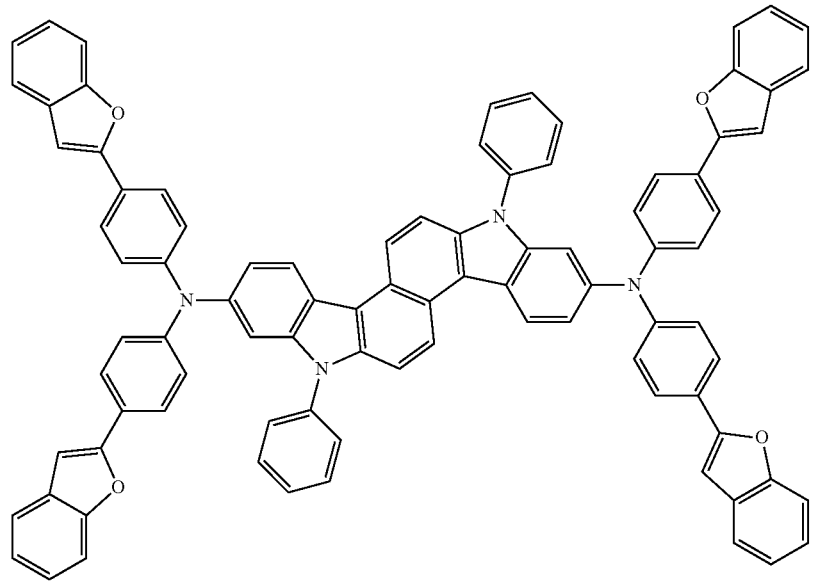
Compound III-11
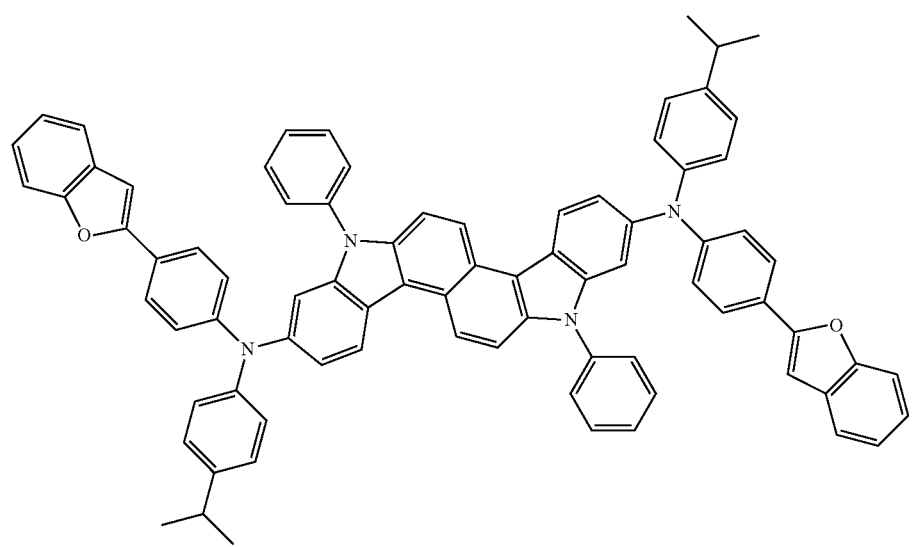

-continued
Compound III-12
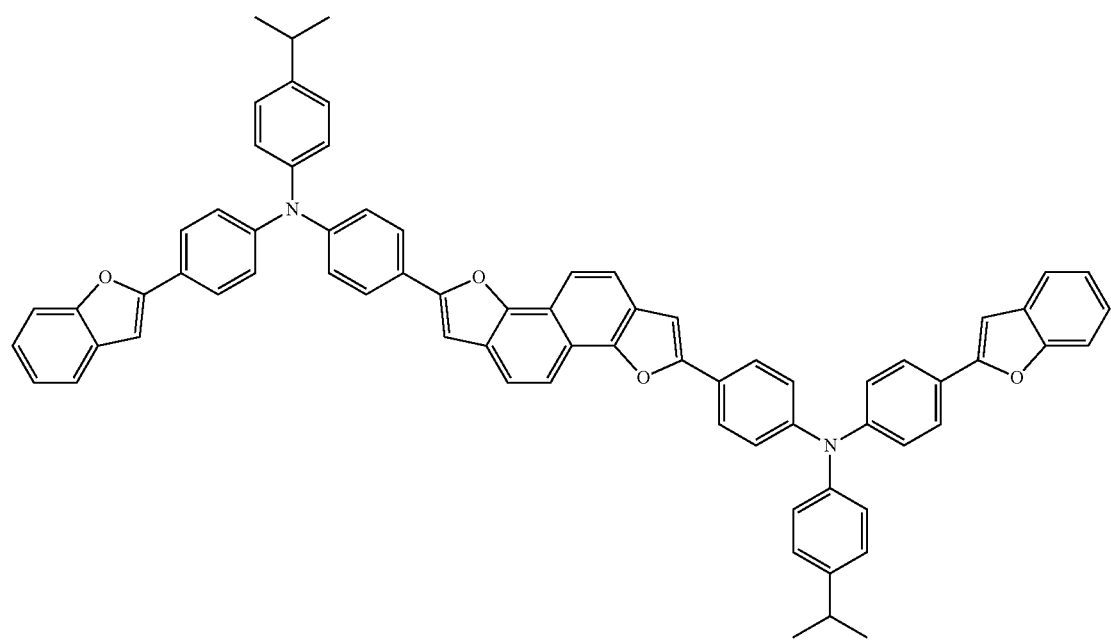
Compound III-13
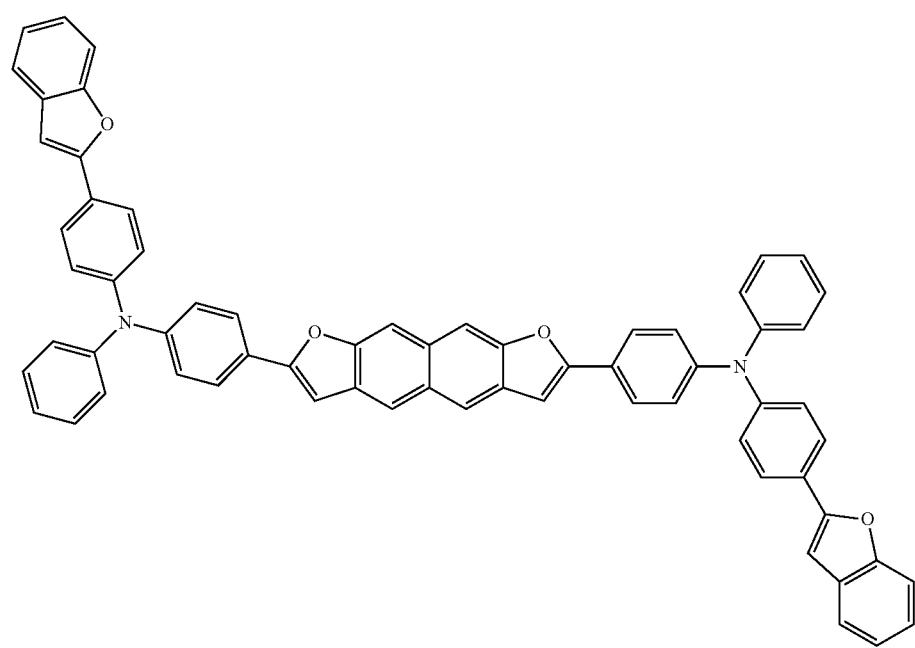

Compound III-14
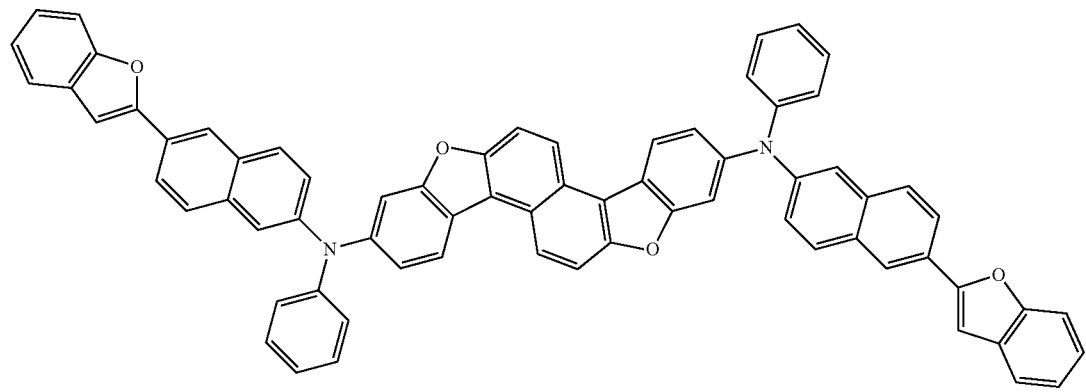
Compound III-15
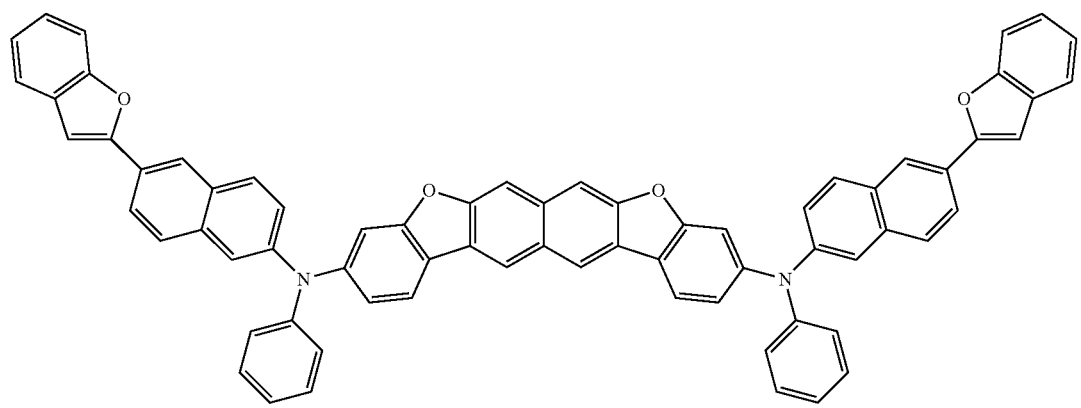
Compound III-16
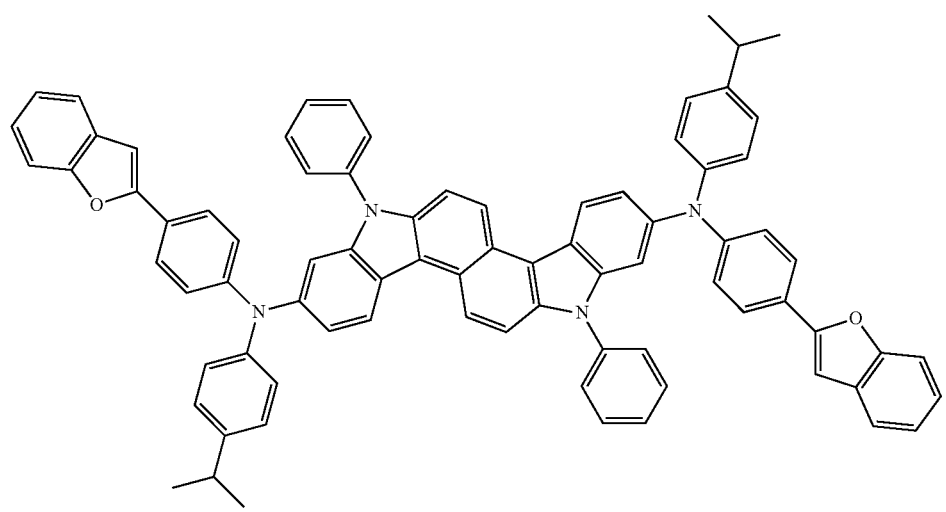

Compound III-17
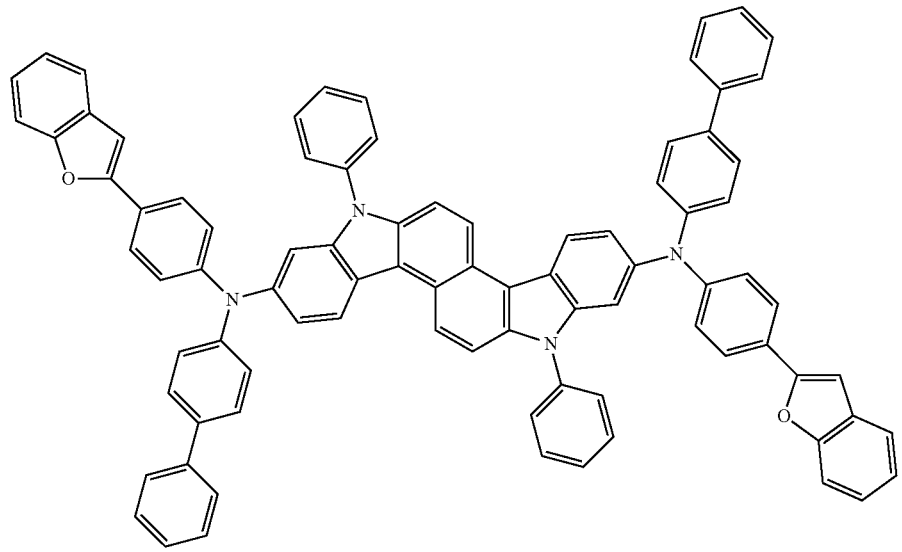
Compound III-18
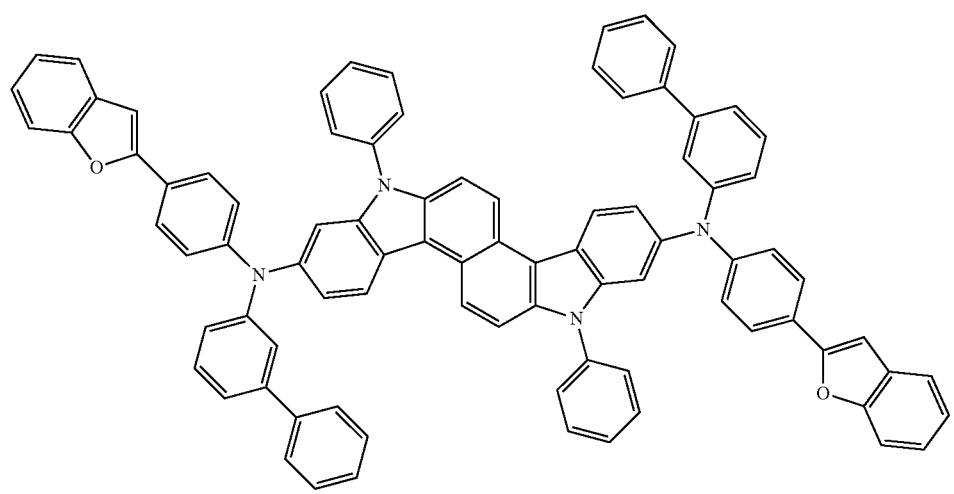

-continued
Compound III-19
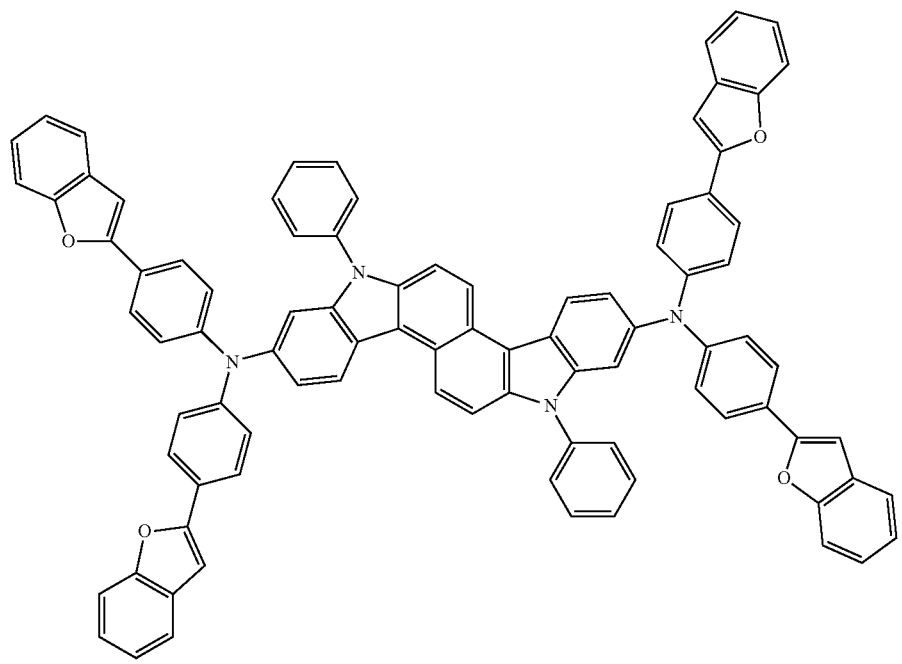
Compound III-20
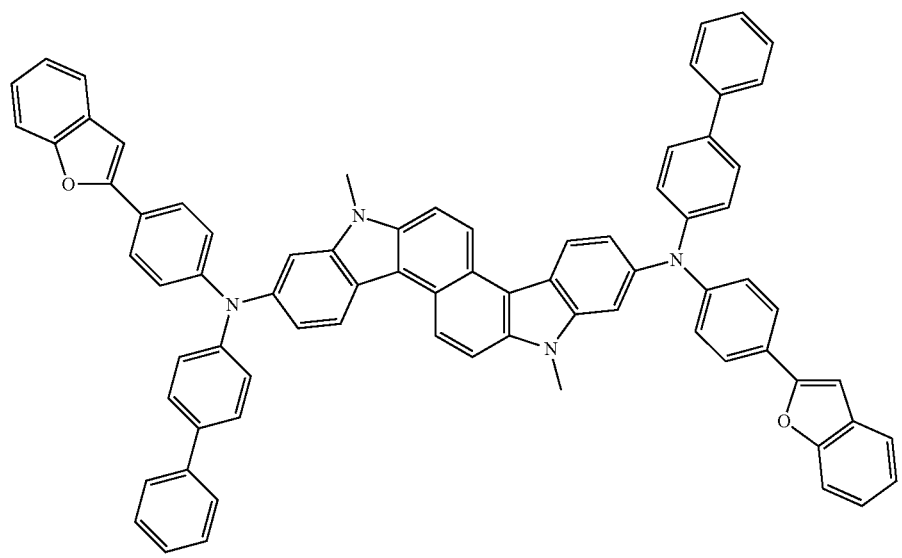
Compound III-21
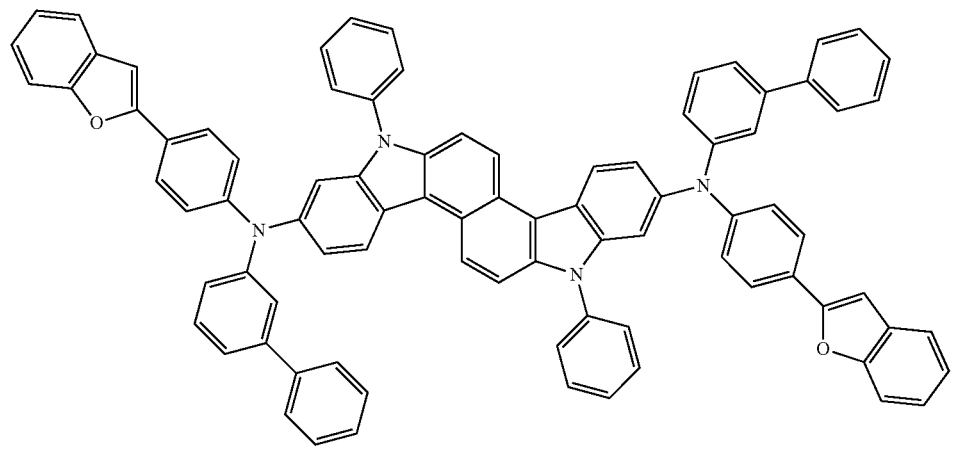

Compound III-22

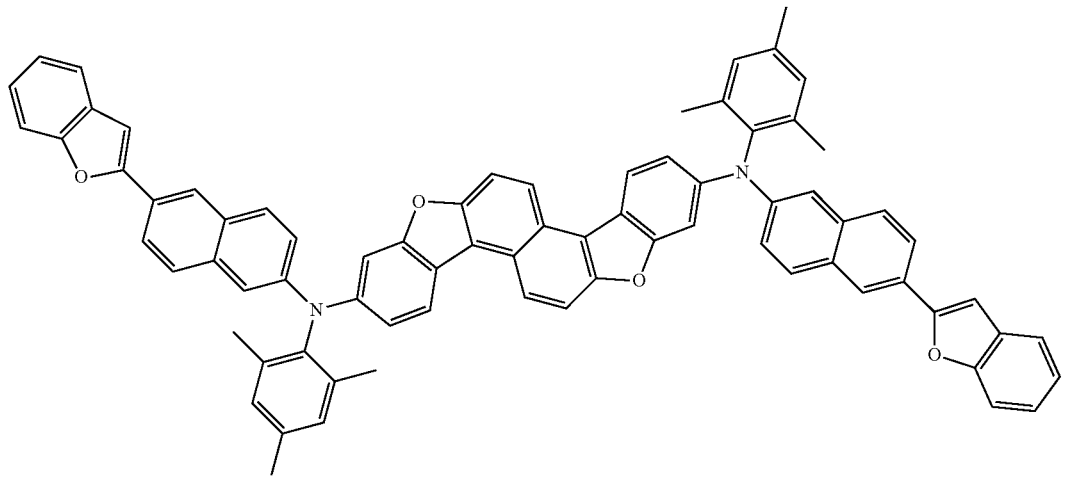

Compound III-23

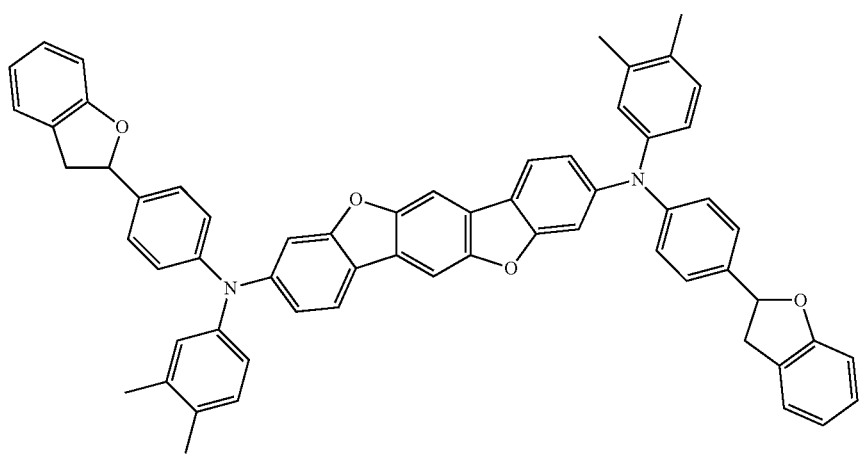

4. Devices

Organic electronic devices that may benefit from having one or more layers comprising the compounds having Formula I, Formula II, or Formula III described herein include, but are not limited to, (1) devices that convert electrical energy into radiation (e.g., a light-emitting diode, light emitting diode display, diode laser, or lighting panel), (2) devices that detect a signal using an electronic process (e.g., a photodetector, a photoconductive cell, a photoresistor, a photoswitch, a phototransistor, a phototube, an infrared ("IR") detector, or a biosensors), (3) devices that convert radiation into electrical energy (e.g., a photovoltaic device or solar cell), (4) devices that convert light of one wavelength to light of a longer wavelength, (e.g., a down-converting phosphor device); (5) devices that include one or more electronic components that include one or more organic semiconductor layers (e.g., a transistor or diode), or any combination of devices in items (1) through (5).

In some embodiments, the device includes a photoactive layer having a compound of Formula I.

In some embodiments, the device includes a photoactive layer having a compound of Formula II.

In some embodiments, the device includes a photoactive layer having a compound of Formula III.

In some embodiments, the device includes an anode and a cathode with a photoactive layer therebetween, where the photoactive layer includes a compound having Formula I.

In some embodiments, the device includes an anode and a cathode with a photoactive layer therebetween, where the photoactive layer includes a compound having Formula II.

In some embodiments, the device includes an anode and a cathode with a photoactive layer therebetween, where the photoactive layer includes a compound having Formula III.

One illustration of an organic electronic device structure is shown in FIG. 1. The device 100 has a first electrical contact layer, an anode layer 110 and a second electrical contact layer, a cathode layer 160, and a photoactive layer ("EML") 140 between them. Adjacent to the anode is a hole injection layer ("HIL") 120. Adjacent to the hole injection layer is a hole transport layer ("HTL") 130, comprising hole transport material. Adjacent to the cathode may be an electron transport layer ("ETL") 150, comprising an electron transport material. As an option, devices may use one or more additional hole injection or hole transport layers (not shown) next to the anode 110 and/or one or more additional electron injection layer ("EIL") or electron transport layer (not shown) next to the cathode 160. As a further option, devices may have an anti-quenching layer (not shown) between the photoactive layer 140 and the electron transport layer 150.

Layers 120 through 150, and any additional layers between them, are individually and collectively referred to as the active layers.

Figure 2:
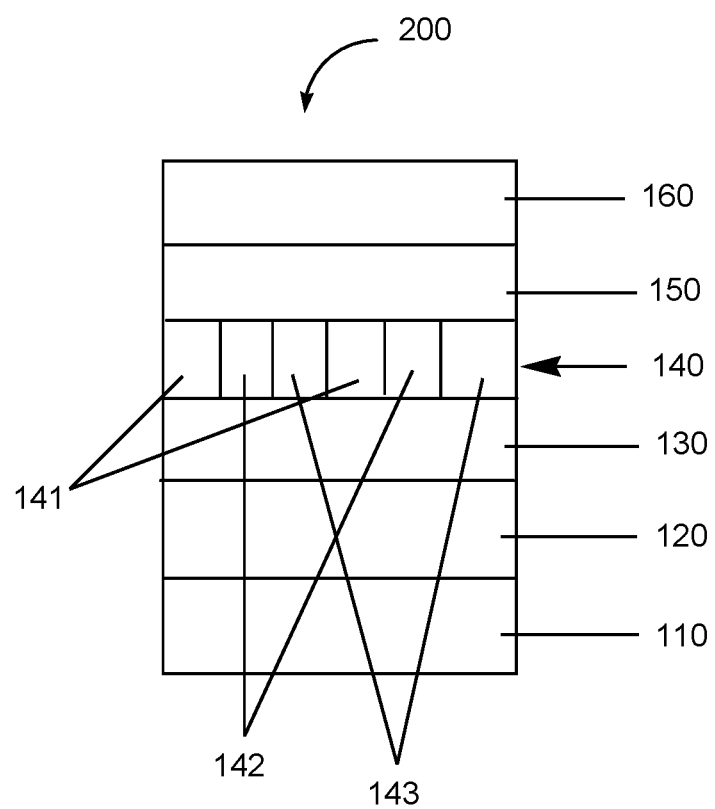
FIG. 2 includes an illustration of another example of an organic electronic device including a new compound described herein.

In some embodiments, the photoactive layer is pixellated, as shown in FIG. 2. In device 200, layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In some embodiments, the different layers have the following range of thicknesses: anode 110, 500-5000 Å, in some embodiments, 1000-2000 Å; hole injection layer 120, 50-2000 Å, in some embodiments, 200-1000 Å; hole transport layer 130, 50-2000 Å, in some embodiments, 200-1000 Å; photoactive layer 140, 10-2000 Å, in some embodiments, 100-1000 Å; electron transport layer 150, 50-2000 Å, in some embodiments, 100-1000 Å; cathode 160, 200-10000 Å, in some embodiments, 300-5000 Å. The location of the electron-hole recombination zone in the device, and thus the emission spectrum of the device, can be affected by the relative thickness of each layer. The desired ratio of layer thicknesses will depend on the exact nature of the materials used.

In some embodiments, the compounds having Formula I, Formula II, or Formula III are useful as the emissive material in photoactive layer 140, having blue emission color. They can be used alone or as a dopant in a host material.

In some embodiments, the compounds having Formula I, Formula II, or Formula III are useful as the host material in photoactive layer 140.

a. Photoactive Layer

In some embodiments, the photoactive layer includes a host material and a compound having Formula I, Formula II, or Formula III as a dopant. In some embodiments, a second host material is present.

In some embodiments, the photoactive layer includes only a host material and a compound having Formula I, Formula II, or Formula III as a dopant. In some embodiments, minor amounts of other materials, are present so long as they do not significantly change the function of the layer.

In some embodiments, the photoactive layer includes only a first host material, a second host material, and a compound having Formula I, Formula II, or Formula III as a dopant. In some embodiments, minor amounts of other materials, are present so long as they do not significantly change the function of the layer.

The weight ratio of dopant to total host material is in the range of 2:98 to 70:30; in some embodiments, 5:95 to 70:30; in some embodiments, 10:90 to 20:80.

In some embodiments, the host material is selected from the group consisting of anthracenes, chrysenes, pyrenes, phenanthrenes, triphenylenes, phenanthrolines, naphthalenes, triazines, quinolines, isoquinolines, quinoxalines, phenylpyridines, benzodifurans, metal quinolinate complexes, indolocarbazoles, substituted derivatives thereof, and combinations thereof.

In some embodiments, the host material is a 9,10-diaryl anthracene compound or deuterated analog thereof.

In some embodiments, the host material is a chrysene derivative having one or two diarylamino substituents, or a deuterated analog thereof Any of the compounds of Formula I, Formula II, or Formula III represented by the embodiments, specific embodiments, specific examples, and combination of embodiments discussed above can be used in the photoactive layer.

b. Other Device Layers

The other layers in the device can be made of any materials which are known to be useful in such layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also be made of an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

The hole injection layer 120 includes hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can include charge transfer compounds, and the like, such as copper phthalocyanine and the tetrathiafulvalene-tetracyanoquinodimethane system (TTF-TCNQ).

In some embodiments, the hole injection layer includes at least one electrically conductive polymer and at least one fluorinated acid polymer.

In some embodiments, the hole injection layer is made from an aqueous dispersion of an electrically conducting polymer doped with a colloid-forming polymeric acid. Such materials have been described in, for example, published U.S. patent applications US 2004/0102577, US 2004/0127637, US 2005/0205860, and published PCT application WO 2009/018009.

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'- bis-(phenyl)benzidine (α-NPB), and porphyrinic compounds, such as copper phthalocyanine. In some embodiments, the hole transport layer includes a hole transport polymer. In some embodiments, the hole transport polymer is a distyrylaryl compound. In some embodiments, the aryl group has two or more fused aromatic rings. In some embodiments, the aryl group is an acene. The term "acene" as used herein refers to a hydrocarbon parent component that contains two or more ortho-fused benzene rings in a straight linear arrangement. Other commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

In some embodiments, the hole transport layer further includes a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

In some embodiments, more than one hole transport layer is present (not shown).

Examples of electron transport materials which can be used for layer 150 include, but are not limited to, metal chelated oxinoid compounds, including metal quinolate derivatives such as tris(8-hydroxyquinolato)aluminum (AlQ), bis(2-methyl-8-quinolinolato)(p-phenylphenolato)aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; fluoranthene derivatives, such as 3-(4-(4-methylstyryl)phenyl-p-tolylamino)fluoranthene; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

In some embodiments, an anti-quenching layer may be present between the photoactive layer and the electron transport layer to prevent quenching of blue luminance by the electron transport layer. To prevent energy transfer quenching, the singlet energy of the anti-quenching material has to be higher than the singlet energy of the blue emitter. To prevent electron transfer quenching, the LUMO level of the anti-quenching material has to be shallow enough (with respect to the vacuum level) such that electron transfer between the emitter exciton and the anti-quenching material is endothermic. Furthermore, the HOMO level of the anti-quenching material has to be deep enough (with respect to the vacuum level) such that electron transfer between the emitter exciton and the anti-quenching material is endothermic. In general, anti-quenching material is a large band-gap material with high singlet and triplet energies.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

Alkali metal-containing inorganic compounds, such as LiF, CsF, $Cs_2O$ and $Li_2O$, or Li-containing organometallic compounds can also be deposited between the organic layer 150 and the cathode layer 160 to lower the operating voltage. This layer, not shown, may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

c. Device Fabrication

The device layers can be formed by any deposition technique, or combinations of techniques, including vapor deposition, liquid deposition, and thermal transfer.

In some embodiments, the device is fabricated by liquid deposition of the hole injection layer, the hole transport layer, and the photoactive layer, and by vapor deposition of the anode, the electron transport layer, an electron injection layer and the cathode.

The hole injection layer can be deposited from any liquid medium in which it is dissolved or dispersed and from which it will form a film. In some embodiments, the liquid medium includes only one or more organic solvents. In some embodiments, minor amounts of other materials are present, so long as they do not substantially affect the liquid medium.

In some embodiments, the liquid medium includes only water or includes only water and an organic solvent. In some embodiments, minor amounts of other materials are present, so long as they do not substantially affect the liquid medium.

The hole injection material is present in the liquid medium in an amount from 0.5 to 10 percent by weight.

In some embodiments, the hole injection layer is formed by any continuous or discontinuous liquid deposition technique. In some embodiments, the hole injection layer is applied by spin coating. In some embodiments, the hole injection layer is applied by ink jet printing. In some embodiments, the hole injection layer is applied by continuous nozzle printing. In some embodiments, the hole injection layer is applied by slot-die coating. After liquid deposition, the liquid medium can be removed in air, in an inert atmosphere, or by vacuum, at room temperature or with heating.

In some embodiments, the hole transport layer is formed by liquid deposition of hole transport material in a liquid medium. The liquid medium is one in which the hole transport material is dissolved or dispersed and from which it will form a film. In some embodiments, the liquid medium includes one or more organic solvents. In some embodiments, the liquid medium includes water or water and an organic solvent. In some embodiments, the organic solvent is an aromatic solvent. In some embodiments, the organic liquid is selected from chloroform, dichloromethane, chlorobenzene, dichlorobenzene, toluene, xylene, mesitylene, anisole, and mixtures thereof. The hole transport material can be present in the liquid medium in a concentration of 0.2 to 2 percent by weight. The hole transport layer can be applied by any continuous or discontinuous liquid deposition technique. In some embodiments, the hole transport layer is applied by spin coating. In some embodiments, the hole transport layer is applied by ink jet printing. In some embodiments, the hole transport layer is applied by continuous nozzle printing. In some embodiments, the hole transport layer is applied by slot-die coating. After liquid deposition, the liquid medium can be removed in air, in an inert atmosphere, or by vacuum, at room temperature or with heating.

In some embodiments, the photoactive layer is formed by vapor deposition. Such techniques are well known in the art.

In some embodiments, the photoactive layer is formed by liquid deposition of the photoactive material and one or more host materials in a liquid medium. The liquid medium is one in which the materials of the photoactive layer are dissolved or dispersed and from which it will form a film. In some embodiments, the liquid medium includes one or more organic solvents. In some embodiments, minor amounts of additional materials are present so long as they do not substantially affect the function of the photoactive layer.

Suitable classes of solvents include, but are not limited to, aliphatic hydrocarbons (such as decane and hexadecane), halogenated hydrocarbons (such as methylene chloride, chloroform, chlorobenzene, and perfluoroheptane), aromatic hydrocarbons (such as non-substituted and alkyl- and alkoxy-substituted toluenes and xylenes), aromatic ethers (such as anisole and dibenzyl ether), heteroaromatics (such as pyridine) polar solvents (such as tetrahydropyran ("THP"), dimethylacetamide ("DMAC") and N-methyl pyrrolidone ("NMP")), esters (such as ethylacetate, propylene carbonate, methyl benzoate), alcohols and glycols (such as isopropanol and ethylene glycol), glycol ethers and derivatives (such as propylene glycol methyl ether and propylene glycol methyl ether acetate), and ketones (such as cyclopentanone and diisobutyl ketone).

The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In some embodiments, the photoactive layer is applied by spin coating. In some embodiments, the photoactive layer is applied by ink jet printing. In some embodiments, the photoactive layer is applied by continuous nozzle printing. In some embodiments, the photoactive layer is applied by slot-die coating. After liquid deposition, the liquid medium can be removed in air, in an inert atmosphere, or by vacuum, at room temperature or with heating.

The electron transport layer can be deposited by any vapor deposition method. In some embodiments, it is deposited by thermal evaporation under vacuum.

The electron injection layer can be deposited by any vapor deposition method. In some embodiments, it is deposited by thermal evaporation under vacuum.

The cathode can be deposited by any vapor deposition method. In some embodiments, it is deposited by thermal evaporation under vacuum.

EXAMPLES

The concepts described herein will be further described in the following examples, which do not limit the scope of the invention described in the claims.

Synthesis Examples

These examples illustrate the preparation of compounds having Formula I, Formula II, or Formula III, as described above.

Synthesis Example 1

This example illustrates the preparation of a compound having Formula I, Compound IA-7.

(a) 3,7-dibromonaphthalene-2,6-diol

The compound was synthesized according the procedures reported in Takimiya, K. Compound, method of producing the compound, organic semiconductor material and organic semiconductor device, U.S. Pat. No. 8,816,100 B2, 2014.

(b) 3,7-bis(4-chloro-2-fluorophenyl)naphthalene-2,6-diol

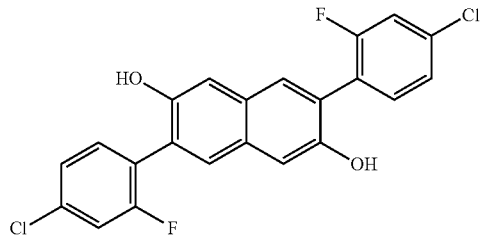 [SMILES: Oc1cc2cc(-c3ccc(Cl)cc3F)c(O)cc2cc1-c1ccc(Cl)cc1F]

Inside a fume hood, an oven-dried 500-mL 2-neck round-bottom flask containing a stir bar was charged with 3,7-dibromonaphthalene-2,6-diol (5.06 g, 15.9 mmol), (4-chloro-2-fluorophenyl)boronic acid (6.06 g, 34.8 mmol), sodium carbonate (6.68 g, 63.0 mmol), toluene (268 mL), ethanol (48 mL) and water (32 mL). The flask was fitted with a reflux condenser that was connected to a nitrogen manifold equipped with a bubbler. The side arm of the flask was seal with a septum. The mixture was sparged with nitrogen for 15 min. Inside a glovebox, tetrakis(triphenylphosphine)palladium (0.91 g, 0.79 mmol) was added to a 20-mL pear-shape flask, and toluene (10 mL) was added. The flask was sealed with a rubber septum, and brought out of the glovebox, and the catalyst solution was transferred to the reaction flask via a cannula, a light yellow cloudy solution. The reaction mixture was heated at 110° C. and stirred for 37 h. After about 14 h, (4-chloro-2-fluorophenyl)boronic acid (3.0 g, 17 mmol) was added, and the mixture was sparged with nitrogen for 10 min. Then another batch of tetrakis(triphenylphosphine)palladium (0.91 g, 0.79 mmol) in toluene (10 mL) was added via cannula. After 37 h, the reaction mixture was allowed to cool to room temperature, diluted with ethylacetate (200 mL) and filtered through a plug of Celite® diatomaceous earth, available from Sigma Aldrich. The cake was washed with ethyl acetate (100 mL). The collected filtrate was washed with water (200 mL). The organic layer was separated, and the aqueous layer washed with ethyl acetate (150 mL). The organic layers were combined were combined and washed with brine (100 mL), separated and dried over anhydrous $MgSO_4$. The solvent was removed under reduced pressure to yield a crude brown solid (12.08 g). The brown solid purified by automated column chromatography to give an off-white solid (3.3 g, 50%). $^1$H NMR ($CD_2Cl_2$, 499.8 MHz) δ 7.63 (s, 1H), δ 7.44 (m, 2H), δ 7.31-7.26 (m, 6H), δ 5.13 (br, 2H, OH). $^{19}$F NMR ($CD_2Cl_2$, 470.3 MHz) δ 111.8. In this the following examples the "δ" is only shown once and refers to all of the chemical shift values that follow in the $^1$H and $^{19}$F NMR data. UPLC-MS APCl$^+$ (m/z) Calcd for $C_{22}H_{12}Cl_2F_2O_2$ ([M+H]$^+$) 417.02. Found 417.10.

(c) 3,10-dichlorodibenzo[d,d']naphtho[2,3-b:6,7-b']difuran

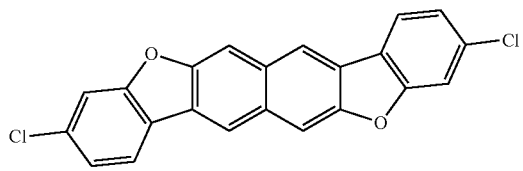 [SMILES: Clc1ccc2c(c1)oc1cc3cc4c(cc3cc12)oc1cc(Cl)ccc14]

Inside a fume hood, an oven-dried 100-mL 2-neck round-bottom flask containing a stir bar was charged with 3,7-bis (4-chloro-2-fluorophenyl)naphthalene-2,6-diol (3.0 g, 7.2 mmol), potassium carbonate (2.2 g, 16 mmol) and N-Methyl-2-pyrrolidinone (NMP) (40 mL). The flask was fitted with a reflux condenser that was connected to a nitrogen manifold equipped with a bubbler. The side arm of the flask was seal with a septum. The resulting mixture was sparged with nitrogen for 10 min, then heated to 120° C. and stirred at this temperature for about 7 h. The reaction mixture was then allowed to cool to room temperature. The reaction mixture and filtered through a medium fritted funnel. The filter cake was washed with acetonitrile (300 mL), followed by deionized water (300 mL) then acetonitrile (100 mL). This cake was dried under reduced pressure to constant weight to yield of an off-white solid (2.24 g, 83%).

(d) N,N'-di(biphenyl-4-yl)-N,N'-bis(4-tert-butylphenyl)dibenzo[d,d']naphtho[2,3-b:6,7-b']difuran-3,10-diamine, Compound IA-7

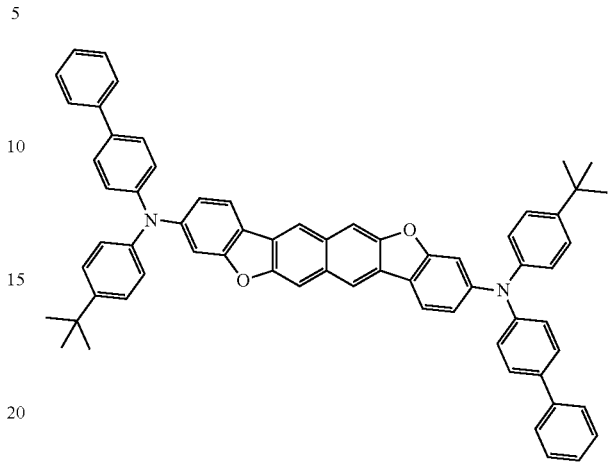

Inside a glovebox, a 2-neck 100-mL round-bottom flask containing a stir bar was charged with $Pd_2(dba)_3$ (0.125 g, 0.137 mmol), tri-tert-butyl-phosphine (0.056 g, 0.28 mmol) and toluene (10 mL). The mixture was stirred for 10 minutes. Sodium tert-butoxide (0.300 g, 3.12 mmol) was charged, followed by N-(4-(tert-butyl)phenyl)-[1,1'-biphenyl]-4-amine (0.920 g, 3005 mmol) and toluene (40 mL). The mixture was stirred for about 1 minute. 3,10-dichlorodibenzo[d,d']naphtho[2,3-b:6,7-b']difuran (0.500 g, 1.33 mmol) was added. The reaction mixture was stirred with the heating block set at 100° C. for 16 h. The product was purified by silica flash column chromatography followed by recrystallization to yield a yellow powder (643 mg, 53%). $^1$H NMR ($CD_2C_{12}$, 499.8 MHz) δ 8.37 (s, 2H), 7.98 (s, 2H), 7.91 (d, J=8.4 Hz, 2H), 7.61 (m, 4H), 7.55 (m, 4H), 7.44 (m, 4H), 7.38 (m, 4H), 7.33 (m, 2H), 7.24-7.22 (m, 6H), 7.16 (m, 4H), 7.11 (dd, J=8.4, 1.9 Hz, 2H), 1.35 (s, 18H). $^{13}$C NMR ($CD_2Cl_2$, 125.69 MHz) δ 159.4, 155.1, 149.5, 147.6, 147.4, 145.0, 140.9, 136.1, 129.9, 129.2, 128.2, 127.3, 127.0, 126.9, 125.9, 125.5, 124.9, 121.8, 118.7, 118.2, 117.7, 106.8, 105.8, 34.7, 31.6. UPLC-MS 99.99% purity. APCl$^+$ (m/z) Calcd for $C_{66}H_{54}N_2O_2$ ([M+H]$^+$) 907.43. Found 907.78.

Synthesis Example 2

This example illustrates the preparation of a compound having Formula I, Compound IA-6.

A procedure analogous to Synthesis Example 1 was used to produce N,N'-di(biphenyl-4-yl)-N,N'-bis(3-tert-butylphenyl)dibenzo[d,d']naphtho[2,3-b:6,7-b']difuran-3,10-diamine, Compound IA-6. $^1$H NMR ($CD_2Cl_2$, 499.8 MHz) δ 8.38 (s, 2H), 7.99 (s, 2H), 7.92 (d, J=8.4 Hz, 2H), 7.62 (m, 4H), 7.56 (m, 4H), 7.44 (t, J=7.6 Hz, 4H), 7.34-7.23 (m, 12H), 7.19 (m, 2H), 7.12 (dd, J=8.4, 1.6 Hz, 2H), 7.01 (m, 2H), 1.29 (s, 18H). $^{13}$C NMR ($CD_2Cl_2$, 125.69 MHz) δ 159.4, 155.1, 153.3, 149.5, 147.5, 140.9, 136.1, 129.9, 129.5, 129.2, 128.2, 127.3, 127.0, 125.9, 124.9, 123.3, 123.1, 121.8, 121.5, 118.9, 118.3, 117.8, 106.9, 106.0, 35.1, 31.4. UPLC-MS APCl$^+$ (m/z) Calcd for $C_{66}H_{54}N_2O_2$ ([M+H]$^+$) 907.43. Found 907.66.

Synthesis Example 3

This example illustrates the preparation of a compound having Formula I, N,N'-di(biphenyl-4-yl)-N,N'-bis(3-tertbutylphenyl)benzo[2,3][1]benzofuro[5,6-b][1]benzofuro[2,3-f][1]benzofuran-3,10-diamine, Compound IB-1.

(a)
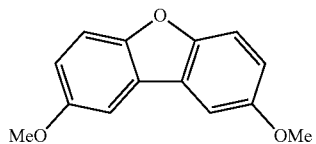
MeO OMe 2,8-dimethoxydibenzo[b,d]furan was synthesized according to procedures published in Yempala, T.; Cassels, B. K., Simple and efficient synthesis of various dibenzofuran carbaldehydes. *Synthetic Communications* 2016, 46 (23), 1909-1915.

(b)
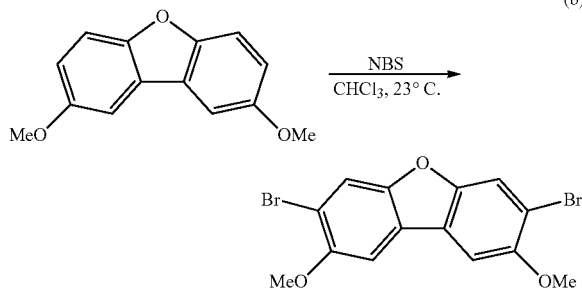

3,7-dibromo-2,8-dimethoxydibenzo[b,d]furan. A 1-L flask was charged with 2,8-dimethoxydibenzo[b,d]furan (27 g) and chloroform (675 mL). The mixture was cooled to 0° C. Then N-bromosuccinimide ("NBS") (2 equiv) was added slowly. The reaction mixture was allowed to warm to room temperature and stirred for about 8 h. The crude product was purified by flash column chromatography to give an off-white solid (16 g, 35%). $^1$H NMR (CDCl$_3$, 400 MHz) δ 7.76 (s, 2H), 7.37 (s, 2H), 4.02 (s, 6H). LC-MS APCl$^+$ (m/z) Calcd for C$_{14}$H$_{10}$Br$_2$O$_3$ ([M]$^+$) 385.90. Found 386.05.

(c)
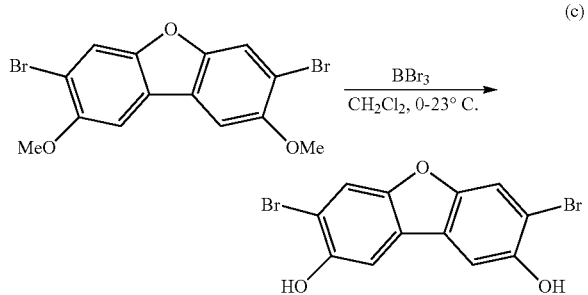

3,7-dibromo-2,8-dihydroxydibenzo[b, d]furan. 3,7-dibromo-2,8-dimethoxydibenzo[b,d]furan (16 g) was treated with a BBr3 solution (3 equiv) dichloromethane (160 mL) at 0° C. Then the mixture was allowed to warm to room temperature and stirred for 16 h. The product was purified by washing with hexanes to give 11.7 g of an off-white powder. $^1$H NMR (DMSO-d$_6$, 499.8 MHz) δ 10.29 (b, 2H), 7.85 (s, 2H), 7.47 (s, 2H).

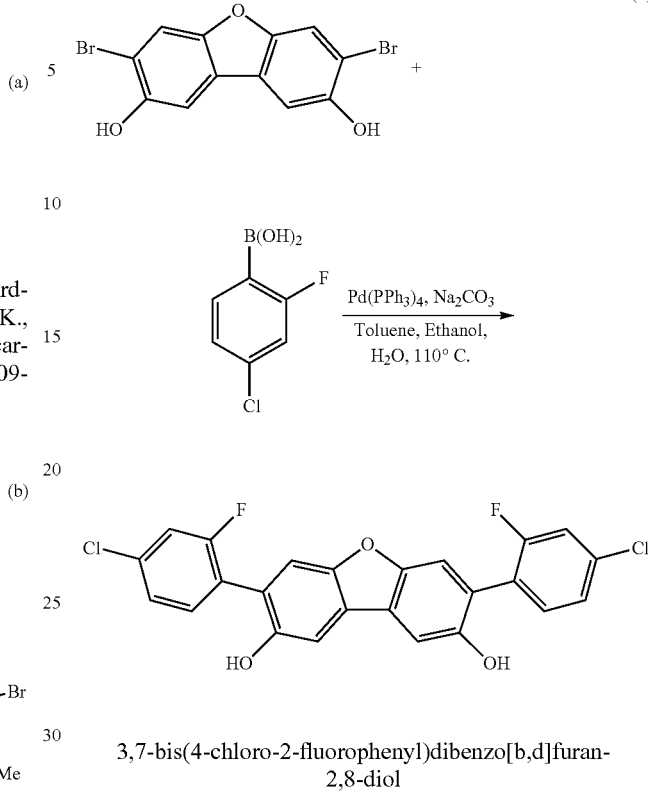

3,7-bis(4-chloro-2-fluorophenyl)dibenzo[b,d]furan-2,8-diol

Inside a fume hood, an oven-dried 300-mL 2-neck round-bottom flask containing a stir bar was charged with 3,7-dibromodibenzo[b,d]furan-2,8-diol (0.760 g, 2.12 mmol), (4-chloro-2-fluorophenyl)boronic acid (0.820 g, 4.7 mmol), sodium carbonate (0.900 g, 8.49 mmol), toluene (37 mL), ethanol (18 mL) and water (10 mL). The flask was fitted with a reflux condenser that was connected to a nitrogen manifold equipped with a bubbler. The side arm of the flask was seal with a septum. The mixture was sparged with nitrogen for 25 min. Inside a glovebox, tetrakis(triphenylphosphine)palladium (0.130 g, 0.113 mmol) was added to a 20-mL pear-shape flask, and toluene (10 mL) was added. The flask was sealed with a rubber septum, and brought out of the glovebox, and the catalyst solution was transferred to the reaction flask via a cannula. The reaction mixture was heated at 110° C. and stirred for 15 h. The reaction mixture was allowed to cool to room temperature, and filtered through a plug of Celite®. The plug was washed with ethyl acetate (200 mL). The collected filtrate was washed with water (100 mL). The organic layer was separated, and the aqueous layer washed with ethyl acetate (150 mL). The organic layers were combined were combined and washed with brine (150 mL), separated and dried over anhydrous MgSO$_4$. The solvent was removed under reduced pressure to yield a crude brown solid (1.2 g). The brown solid purified by automated column chromatography to give an off-white solid (0.48 g, 50%). $^1$H NMR (DMSO-d$_6$, 499.8 MHz) δ 9.79 (br, 2H), 7.50-7.44 (m, 8H), 7.34 (m, 2H). $^{13}$C NMR (DMSO-d$_6$, 125.69 MHz) δ 159.6 (d, J=249.7 Hz), 150.9, 150.1, 133.5 (d, J=4.3 Hz), 133.0 (d, J=10.5 Hz), 125.4 (d, J=16.0 Hz), 124.5 (d, J=3.6 Hz), 124.4, 122.1, 116.1 (d, J=26.4 Hz), 113.4, 106.1. UPLC-MS APCl$^+$ (m/z) Calcd for C$_{24}$H$_{12}$Cl$_2$F$_2$O$_3$ ([M+H]$^+$) 457.02. Found 457.01.

(e)

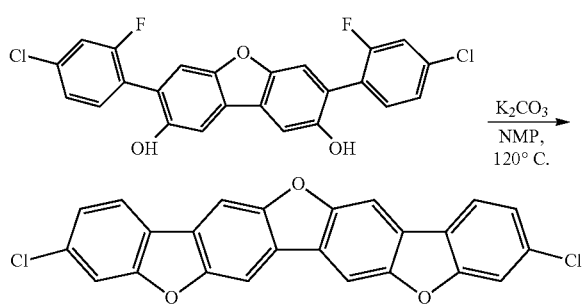

3,10-dichlorobenzo[2,3][1]benzofuro[5,6-b][1]benzofuro[2,3-f][1]benzofuran. An oven-dried 100-mL 2-neck round-bottom flask was charged with 3,7-bis(4-chloro-2-fluorophenyl)dibenzo[b,d]furan-2,8-diol (0.480 g, 1.05 mmol), and $K_2CO_3$ (0.322 g, 2.32 mmol) and 1-methyl-2-pyrrolidinone (NMP) (18 mL). The flask was fitted with a reflux head connected to a nitrogen line. The resulting mixture was degassed with nitrogen for 20 minutes. It was stirred at 120° C. for 3 h. After it was cooled to room temperature, the gray suspension was filtered through a medium fritted funnel. The cake was washed with acetonitrile (100 mL), followed by deionized water (100 mL) and finally acetonitrile (150 mL). The sample was dried under reduced pressure to constant weight of 0.302 g, 83% yield.

(f) N,N'-di(biphenyl-4-yl)-N,N'-bis(3-tert-butylphenyl)benzo[2,3][1]benzofuro[5,6-b][1]benzofuro[2,3-f][1]benzofuran-3,10-diamine, Compound 1B-1

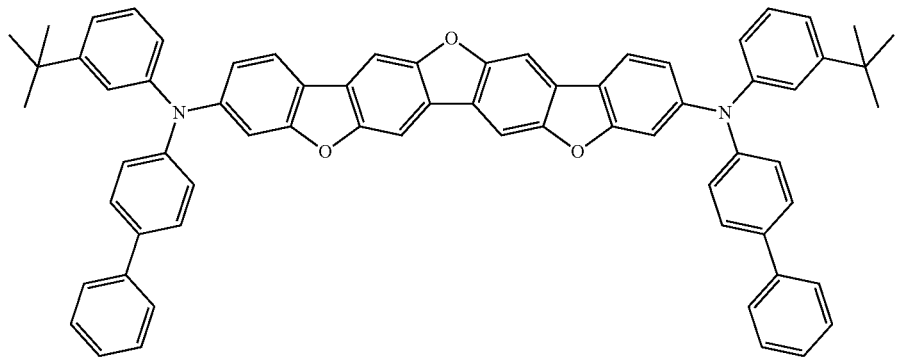 [SMILES: CC(C)(C)c1cccc(N(c2ccc(-c3ccccc3)cc2)c2ccc3c(c2)oc2cc4c(cc23)oc2cc3c(cc24)oc2cc(N(c4ccc(-c5ccccc5)cc4)c4cccc(C(C)(C)C)c4)ccc23)c1]

Inside a glovebox, a 25-mL tube containing a stir bar was charged with $Pd_2(dba)_3$ (0.028 g, 0.031 mmol), tri-tert-butylphosphine (0.014 g, 0.069 mmol) and toluene (5 mL). The mixture was stirred for 10 minutes. Sodium tert-butoxide (0.108 g, 1.12 mmol) was charged, followed by N-(3-(t-butyl)phenyl)-[1,1'-biphenyl]-4-amine hydrochloride (0.164 g, 0.485 mmol). The mixture was stirred for about 1 minute. 3,10-Dichlorobenzo[b][1]benzofuro[2',3':5,6][1]benzofuro[2,3-f][1]benzofuran (0.09 g, 0.21 mmol) was added followed by toluene (5 mL). The reaction mixture was stirred with the heating block set at 110° C. for 15 h. The reaction mixture was lifted from the heating block and allowed to cool to room temperature. The reaction mixture purified by silica flash column chromatography to yield of a canary yellow powder (150 mg, 74%). $^1$H NMR ($CD_2Cl_2$, 499.8 MHz) δ 8.04 (s, 2H), 7.99 (s, 2H), 7.87 (d, J=8.4 Hz, 2H), 7.62 (m, 4H), 7.55 (m, 4H), 7.44 (m, 4H), 7.34-7.25 (m, 8H), 7.23-7.21 (m, 4H), 7.19-7.13 (m, 4H), 7.00 (m, 2H), 1.28 (s, 18H). $^{13}$C NMR ($CD_2Cl_2$, 125.69 MHz) δ 158.9, 154.3, 153.5, 153.3, 148.7, 147.5(6), 147.5(5), 140.9, 135.9, 129.5, 129.2, 128.2, 127.3, 127.0, 124.9, 124.7, 123.7, 123.1, 122.9, 121.4, 121.3, 119.4, 119.3, 106.5, 102.5, 102.1, 35.1, 31.4. UPLC-MS 99.42% purity. APCl$^+$ (m/z) Calcd for $C_{68}H_{54}N_2O_3$ ([M+H]$^+$) 947.42. Found 947.54.

Synthesis Example 4

This example illustrates the preparation of a compound having Formula I, Compound IA-11.

(a) 6-methyl-N-(naphthalen-2-yl)biphenyl-3-amine

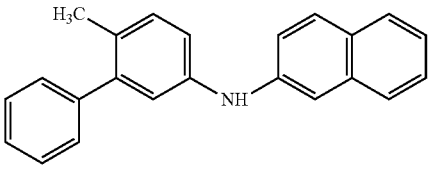 [SMILES: Cc1ccc(Nc2ccc3ccccc3c2)cc1-c1ccccc1]

Inside a glovebox, a 250-mL round-bottom flask containing a stir bar was charged with 2-bromonaphthalene (2.34 g, 11.3 mmol), $Pd_2(dba)_3$ (0.330 g, 0.36 mmol), tri-tert-butylphosphine (0.138 g, 0.68 mmol) and toluene (45 mL) followed by 6-methyl-biphenyl-3-amine hydrochloride salt (2.48 g, 11.3 mmol), sodium tert-butoxide (2.17 g, 22.6 mmol) and toluene (45 mL). The reaction mixture was stirred at room temperature overnight. The reaction was removed from the glove box. Water and brine were added and the contents extracted with dichloromethane. The combined extracts were dried over anhydrous sodium sulfate, filtered, and the solvent was removed under reduced pressure. Purification by silica flash column chromatography (hexanes/dichloromethane) provided the product as a burnt-orange oil (2.32 g, 66%). NMR ($CD_2Cl_2$, 499.8 MHz) δ 7.75 (dd, J=4.9, 8.64 Hz, 2H), 7.65 (d, J=8.2 Hz, 1H) 7.46-7.34 (m, 7H), 7.31-7.27 (m, 1H), 7.26-7.23 (m, 2H), 7.15 (dd, J=8.1, 2.4, 1H), 7.08 (d, J=2.4, 1H), 5.97 (s, 1H), 2.25 (s, 3H). UPLC-MS 99.69% purity. APCl$^+$ (m/z) Calcd for $C_{23}H_{19}N$ ([M+H]+) 309.40. Found 310.53.

(b) 3,10-Bis[6-methyl-N-(naphthalen-2-yl)biphenyl-3-amino]naphtho[2,3-b:6,7-b']bisbenzofuran, Compound IA-11

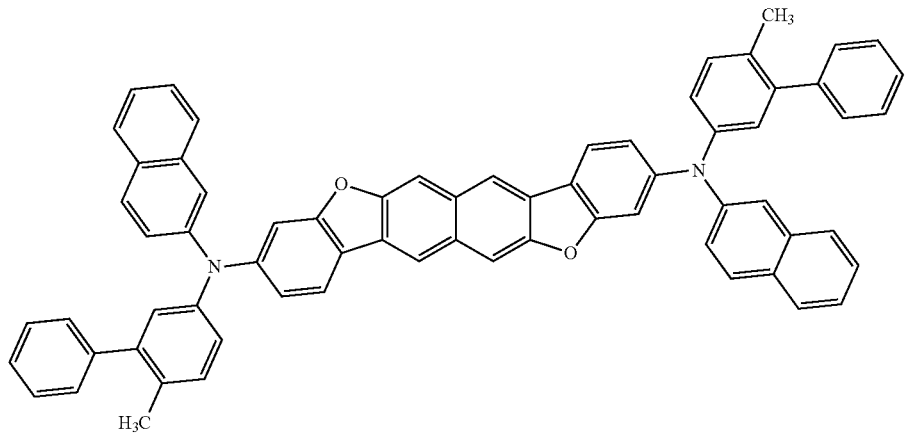 [SMILES: Cc1ccc(N(c2ccc3ccccc3c2)c2ccc3c(c2)oc2cc4cc5c(cc4cc23)oc2cc(N(c3ccc(C)c(-c4ccccc4)c3)c3ccc4ccccc4c3)ccc25)cc1-c1ccccc1]

Inside a glovebox, a 250-mL round-bottom flask containing a stir bar was charged with 3,10-dichlorodibenzo[d,d']naphtho[2,3-b:6,7-b']difuran (0.50 g, 1.33 mmol), Pd$_2$(dba)$_3$ (0.122 g, 0.13 mmol), tri-tert-butyl-phosphine (0.053 g, 0.26 mmol) and toluene (15 mL) followed by 6-methyl-N-(naphthalen-2-yl)biphenyl-3-amine, (0.902 g, 2.92 mmol), sodium tert-butoxide (0.281 g, 2.92 mmol) and toluene (10 mL). The reaction mixture was stirred with the heating block set at 100° C. After 18.5 h, the reaction mixture was allowed to cool to room temperature. The reaction was removed from the glove box, filtered through a plug of Celite®, washing the Celite® with dichloromethane. The solvent was removed under reduced pressure, and the product was purified by successive silica flash column chromatography (hexanes/chloroform) then hexanes/dichloromethane followed by recrystallization from dichloromethane/acetonitrile to yield a yellow powder (280 mg, 23%). 1H NMR (CD$_2$Cl$_2$, 499.8 MHz) δ 8.39 (s, 2H), 8.00 (s, 2H), 7.94 (d, J=8.4 Hz, 2H), 7.83-7.79 (m, 4H), 7.65 (d, J=7.8 Hz, 2H), 7.60 (d, J=1.8 Hz, 2H), 7.46-7.26 (m, 20H), 7.18 (d, J=1.9 Hz, 1H), 7.16 (d, J=2.1 Hz, 2H), 7.15 (br s, 3H), 2.31 (s, 6H). UPLC-MS 99.92% purity. APCl$^+$ (m/z) Calcd for C$_{68}$H$_{46}$N$_2$O$_4$ ([M+H]$^+$) 923.11. Found 924.07.

Synthesis Example 5

This example illustrates the preparation of a compound having Formula I, N,N'-di(biphenyl-4-yl)-N,N'-bis(4-tert-butylphenyl)benzo[b][1]benzofuro[2',3':5,6][1]benzofuro[2,3-f][1]benzofuran-3,10-diamine, Compound IB-4.

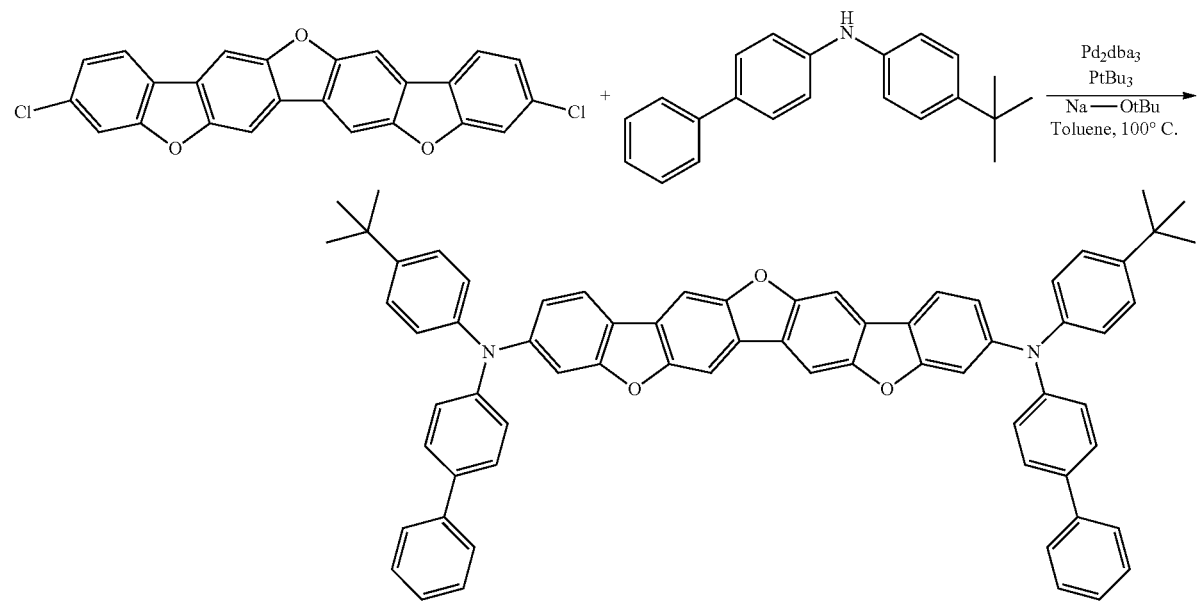

Inside a glovebox, a 50-mL 2-neck round-bottom flask containing a stir bar was charged with Pd$_2$(dba)$_3$ (0.034 g, 0.037 mmol), tri-tert-butyl-phosphine (0.015 g, 0.074 mmol) and toluene (8 mL). The mixture was stirred for 10 minutes. Sodium tert-butoxide (0.160 g, 1.64 mmol) was charged, followed by N-(4-(tert-butyl)phenyl)-[1,1'-biphenyl]-4-amine (0.485 g, 1.61 mmol) and 3,10-dichlorobenzo[b][1]benzofuro[2',3':5,6][1]benzofuro[2,3-f][1]benzofuran, made as in Synthesis Example 3, (0.302 g, 0.724 mmol) were added followed by toluene (22 mL). The reaction mixture was stirred with the heating block set at 100° C. for 18 h. The reaction mixture was purified by silica flash column chromatography to yield of a canary yellow powder (0.446 g, 65%). $^1$H NMR (CD$_2$Cl$_2$, 499.8 MHz) δ 7.99 (s, 2H), 7.94 (s, 2H), 7.83 (d, J=8.4 Hz, 2H), 7.60 (d, J=7.5 Hz, 4H), 7.54 (d, J=8.3 Hz, 4H), 7.43 (t, J=7.5 Hz, 4H), 7.37 (d, J=8.4 Hz, 4H), 7.32 (t, J=7.3 Hz, 2H), 7.26 (s, 2H), 7.21 (d, J=8.3 Hz, 4H), 7.15-7.10 (m, 6H), 1.35 (s, 18H). $^{13}$C NMR (CD$_2$Cl$_2$, 125.69 MHz) δ 158.9, 154.2, 153.4, 148.7, 147.5, 147.4, 145.1, 140.9, 135.9, 129.2, 128.2, 127.3, 127.0, 126.8, 125.4, 124.8, 124.7, 123.7, 121.3, 119.2, 119.1, 106.2, 102.5, 102.1, 34.7, 31.6. APCI$^+$ (m/z) Calcd for C$_{68}$H$_{54}$N$_2$O$_3$ ([M+H]$^+$) 947.42. Found 947.57.

Synthesis Example 6

This example illustrates the preparation of a compound having Formula I, N,N'-bis(4-tert-butylphenyl)-N,N'-di(naphthalen-2-yl)benzo[2,3][1]benzofuro[5,6-b][1]benzofuro[2,3-f][1]benzofuran-3,10-diamine, Compound IB-5.

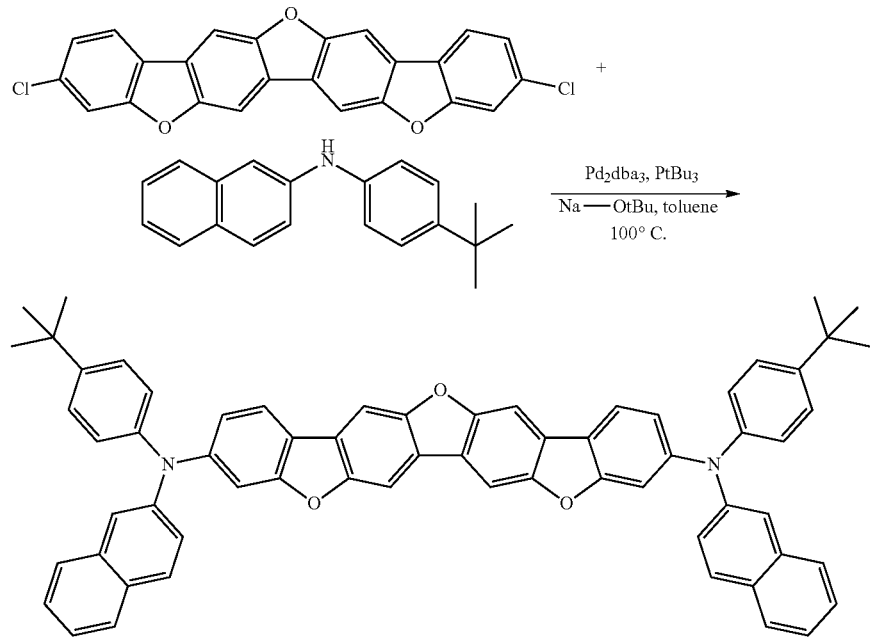

Inside a glovebox, a 100-mL 2-neck round-bottom flask containing a stir bar was charged with Pd$_2$(dba)$_3$ (0.052 g, 0.057 mmol), tri-tert-butyl-phosphine (0.023 g, 0.11 mmol) and toluene (10 mL). The mixture was stirred for 10 minutes. Sodium tert-butoxide (0.232 g, 2.41 mmol) was charged, followed by N-(4-(tert-butyl)phenyl)naphthalen-2-amine (0.630 g, 2.28 mmol) and 3,10-dichlorobenzo[b][1]benzofuro[2',3':5,6][1]benzofuro[2,3-f][1]benzofuran, made as in Synthesis Example 3, (0.430 g, 1.03 mmol) were added followed by toluene (24 mL). The reaction mixture was stirred with the heating block set at 110° C. for 24 h. The reaction mixture was purified by silica flash column chromatography to yield of a canary yellow powder (0.550 g, 60%). $^1$H NMR (CD$_2$C1$_2$, 499.8 MHz) δ 8.00 (m, 2H), 7.96 (m, 2H), 7.84 (d, J=8.4 Hz, 2H), 7.80-7.75 (m, 4H), 7.62 (d, J=8.0 Hz, 2H), 7.51 (d, J=8.0 Hz, 2H), 7.42-7.33 (m, 10H), 7.27 (d, J=1.7 Hz, 2H), 7.15-7.11 (m, 6H), 1.35 (s, 18H). $^{13}$C NMR (CD$_2$Cl$_2$, 125.69 MHz) δ 158.5, 153.8, 153.0, 148.4, 147.0, 145.4, 144.8, 134.5, 130.2, 128.9, 127.5, 126.9, 126.4, 126.3, 124.8, 124.6, 124.4, 124.3(8), 123.2, 120.8, 120.5, 118.9, 118.8, 106.0, 102.0, 101.6, 34.3, 31.2. APCI$^+$ (m/z) Calcd for C$_{64}$H$_{50}$N$_2$O$_3$ ([M+H]$^+$) 895.34. Found 895.97.

Synthesis Example 7

This example illustrates the preparation of a compound having Formula I, Compound IB-7.

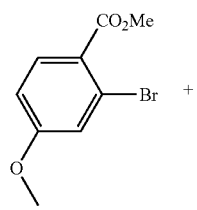

-continued

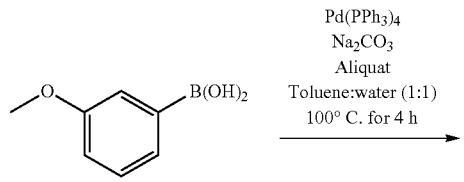

-continued

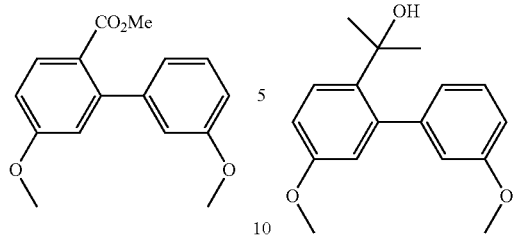

(a) Methyl 3',5-dimethoxybiphenyl-2-carboxylate

A dried 100-mL two-neck round-bottom flask was charged with methyl-2-bromo-4-methoxybenzoate (2.0 g, 8.2 mmol), 3-methoxyphenylboronic acid (1.86 g, 12.3 mmol), sodium carbonate (2.60 g, 24.6 mmol), toluene (20 mL) and water (20 mL) under argon atmosphere at room temperature. The resulting mixture was stirred and purged with argon for 10 minutes. Then Pd(PPh$_3$)$_4$ (0.47 g, 0.40 mmol) was added, and the reaction mixture was stirred at 100° C. for 4 h. After 4 h, the reaction mixture was cooled to room temperature, diluted with EtOAc (50 mL), organic layer was washed with water, brine, dried over Na$_2$SO$_4$ and concentrated under vacuum to afford 1.8 g of a crude compound. The crude compound was purified by column chromatography (100-200 silica gel) using 5% EtOAc in petroleum ether to afford a colorless gummy compound (1.56 g, 70%). APCl$^+$ (m/z) Calcd for C$_{16}$H$_{16}$O$_4$ ([M+H]$^+$) 273.11. Found 273.09.

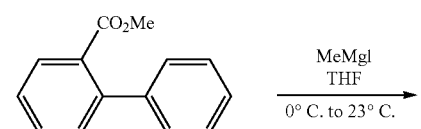

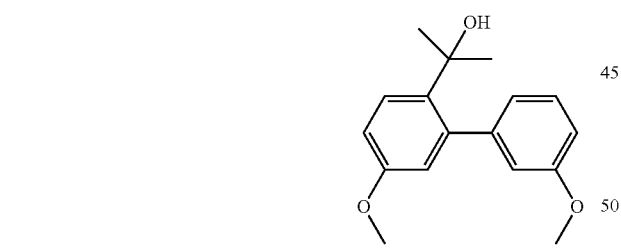

(b) 2-(3',5-dimethoxybiphenyl-2-yl)propan-2-ol

To a stirred solution of methyl 3',5-dimethoxy biphenyl-2-carboxylate (3.0 g, 12.3 mmol) in anhydrous THF (60 mL), was added MeMgI (19.0 mL of 1.4 M in diethyl ether, 56.6 mmol) drop-wise at 0° C. under argon atmosphere. After that reaction mixture was stirred at 23° C. After 24 h, the reaction mixture was cooled to 0° C., quenched with saturated NH$_4$Cl solution, and diluted with ethyl acetate (50 mL). The organic layer was washed with water, brine, dried over Na$_2$SO$_4$ and concentrated under vacuum to afford a crude compound as a yellow liquid (3.5 g).

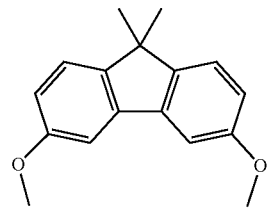

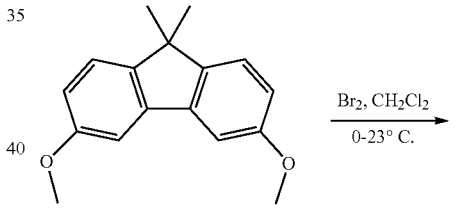

(c) 3,6-dimethoxy-9,9-dimethyl-9H-fluorene

To a stirred solution of 2-(3',5-dimethoxybiphenyl-2-yl)propan-2-ol (1.6 g, 5.9 mmol) in CH$_2$Cl$_2$ (48 mL) under argon atmosphere at 0° C. was added trifluoro acetic acid (6.4 mL) drop-wise. After that reaction mixture was stirred at 23° C. After 1 h, the reaction mixture cooled to 0° C., quenched with saturated sodium carbonate solution and extracted with dichloromethane (100 mL), organic layer was washed with brine, dried over Na$_2$SO$_4$ and concentrated under vacuum. The crude compound was purified by flash chromatography to afford as colorless oil (1.56 g).

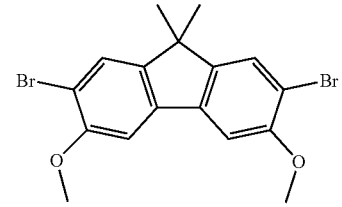

(d) 2,7-dibromo-3,6-dimethoxy-9,9-dimethyl-9H-fluorene

To a stirred solution of 3,6-dimethoxy-9,9-dimethyl-9H-fluorene (0.3 g, 1.2 mmol) in CH$_2$Cl$_2$ (10 mL) under argon atmosphere at 0° C. was added bromine (0.12 g, 2.45 mmol) in CH$_2$Cl$_2$ drop-wise. After that reaction mixture was stirred at 0° C. After 2 h, the reaction mixture was quenched with sodium thiosulfate solution and extracted with dichloromethane (50 mL), organic layer was washed with water, brine, dried over Na$_2$SO$_4$ and concentrated under vacuum to afford 0.4 g of off-white solid compound (crude). The crude compound purified by flash chromatography to afford 2,7-dibromo-3,6-dimethoxy-9,9-dimethyl-9H-fluorene (0.33 g, 70%).

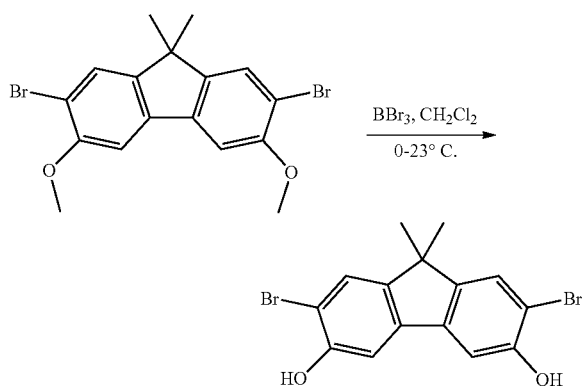

(e) 2,7-dibromo-9,9-dimethyl-9H-fluorene-3,6-diol

To a stirred solution of 2,7-dibromo-3,6-dimethoxy-9,9-dimethyl-9H-fluorene (0.3 g, 0.73 mmol) in CH$_2$Cl$_2$ (10 mL) under argon atmosphere at 0° C. was added BBr$_3$ in CH$_2$O$_{12}$ (2.19 mL, 2.19 mmol) drop-wise. After that reaction mixture was stirred at 23° C. After 16 h, the reaction mixture was quenched with MeOH, diluted with dichloromethane (20 mL), organic layer was washed with water, brine, dried over Na$_2$SO$_4$ and concentrated under vacuum to afford crude solid. The crude compound was purified by flash chromatography to afford an off-white solid (190 mg, 70%). $^1$H NMR (DMSO-d$_6$, 400 MHz) δ 10.70 (s, 2H), 7.62 (s, 2H), 7.20 (s, 2H), 1.37 (s, 6H). GC/MS Calcd for C$_{15}$H$_{12}$Br$_2$O$_2$ ([M]$^+$) 383.92 (100.0%), 381.92 (51.4%), 385.92 (48.6%). Found 383.8 (100.0%), 381.8 (~50%), 385.8 (~50%).

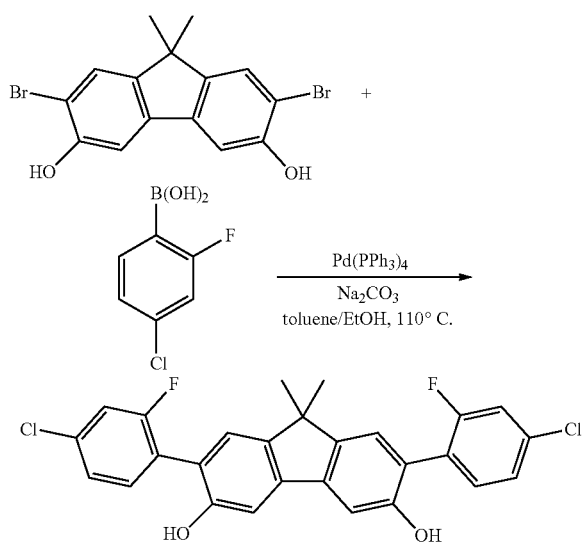

(f) 2,7-bis(4-chloro-2-fluorophenyl)-9,9-dimethyl-9H-fluorene-3,6-diol

Inside a fume hood, an oven-dried 500-mL 2-neck round-bottom flask containing a stir bar was charged with 2,7-dibromo-9,9-dimethyl-9H-fluorene-3,6-diol (5.0 g, 13.02 mmol), (4-chloro-2-fluorophenyl)boronic acid (4.55 g, 26.1 mmol), sodium carbonate (5.59 g, 52.7 mmol), toluene (187 mL), ethanol (38 mL) and water (25 mL). The flask was fitted with a reflux condenser that was connected to a nitrogen manifold equipped with a bubbler. The side arm of the flask was seal with a septum. The mixture was sparged with nitrogen for 25 min. Inside a glovebox, tetrakis(triphenylphosphine)palladium (0.760 g, 0.651 mmol) was added to a 100-mL pear-shape flask, and toluene (62 mL) was added. The flask was sealed with a rubber septum, and brought out of the glovebox, and the catalyst solution was transferred to the reaction flask via a cannula. The reaction mixture was heated at 110° C. and stirred for 15 h. The reaction mixture was allowed to cool to room temperature, and purified by automated column chromatography to give an off-white solid (4.43 g, 70%). $^1$H NMR (CD$_2$Cl$_2$, 499.8 MHz) δ 7.44-7.41 (m, 2H), 7.30-7.25 (m, 8H), 5.45 (s, 2H), 1.48 (s, 6H). $^{13}$C NMR (CD$_2$Cl$_2$, 125.69 MHz) δ 160.3 (d, J=250.1), 153.0, 147.4, 140.7, 134.80 (d, J=10.1 Hz), 133.3 (d, J=4.3 Hz), 125.4 (d, J=1.3 Hz), 125.3 (d, J=3.6 Hz), 124.7 (d, J=16.1 Hz), 121.4, 117.1 (d, J=26.2 Hz), 108.0, 46.5, 21.2. APCI$^+$ (m/z) Calcd for C$_{27}$H$_{18}$Cl$_2$F$_2$O$_2$ ([M+H]$^+$) 483.07. Found 483.41.

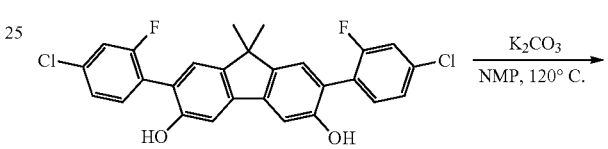

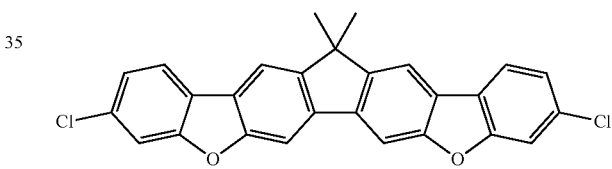

(g) 3,10-dichloro-14,14-dimethyl-14H-dibenzo[d,d'] fluoreno[3,2-b:6,7-b]difuran

An oven-dried 200-mL 2-neck round-bottom flask was charged with 2,7-bis(4-chloro-2-fluorophenyl)-9,9-dimethyl-9H-fluorene-3,6-diol (4.4 g, 9.10 mmol), and K$_2$CO$_3$ (2.80 g, 20.3 mmol) and 1-methyl-2-pyrrolidinone (155 mL). The flask was fitted with a reflux head connected to a nitrogen line. The resulting mixture was degassed with nitrogen for 20 minutes. It was stirred at 120° C. for 15 h. After it was cooled to room temperature, the gray suspension was filtered through a medium fritted funnel. The cake was washed with acetonitrile (300 mL), followed by deionized water (250 mL) and finally acetonitrile (100 mL). The sample was dried under reduced pressure to constant weight of 2.52 g, 62% yield. $^1$H NMR (CD$_2$Cl$_2$, 499.8 MHz) δ 8.14 (s, 2H), 8.09 (s, 2H), 8.02 (d, J=8.2 Hz, 2H), 7.67 (d, J=1.6 Hz, 2H), 7.38 (dd, J=1.7, 8.2 Hz), 1.67 (s, 6H). $^{13}$C NMR (CD$_2$Cl$_2$, 125.69 MHz) δ 157.9, 157.6, 150.8, 140.1, 133.0, 124.2, 124.1(5), 124.0(5), 121.9, 115.4, 112.8, 104.1, 46.7, 28.3. APCI$^+$ (m/z) Calcd for C$_{27}$H$_{16}$Cl$_2$O$_2$ ([M+H]$^+$) 443.06. Found 444.30.

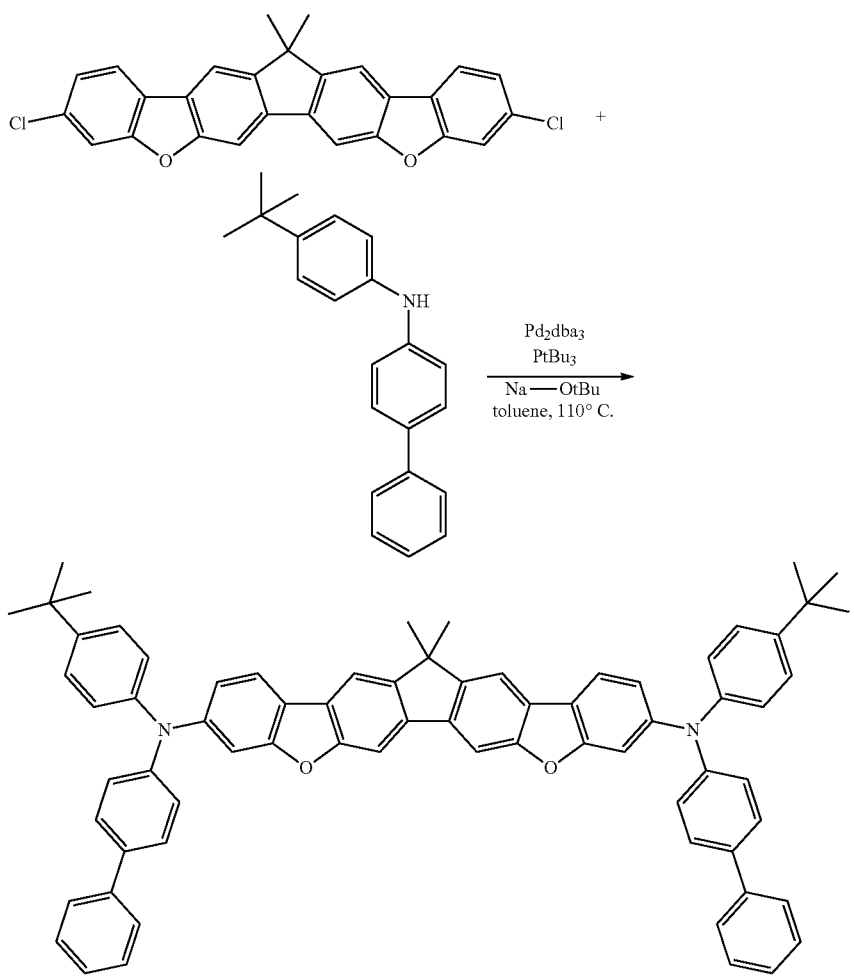

(h) N,N'-di(biphenyl-4-yl)-N,N'-bis(4-tert-butylphenyl)-14,14-dimethyl-14H-dibenzo[d,d']fluoreno[3,2-b:6,7-b']difuran-3,10-diamine, Compound IB-7

Inside a glovebox, a 100-mL 2-neck round-bottom flask containing a stir bar was charged with Pd$_2$(dba)$_3$ (0.032 g, 0.035 mmol), tri-tert-butyl-phosphine (0.014 g, 0.069 mmol) and toluene (5 mL). The mixture was stirred for 10 minutes. Sodium tert-butoxide (0.139 g, 1.45 mmol), N-[4-(1,1-dimethylethyl)phenyl]-[1,1'-biphenyl]-3-amine (0.425 g, 1.41 mmol) and 3,10-dichloro-14,14-dimethyl-14H-dibenzo[d,d]fluoreno[3,2-b:6,7-b]difuran (0.270 g, 0.609 mmol) were added followed by toluene (20 mL). The reaction mixture was stirred with the heating block set at 110° C. for 16 h. The reaction mixture was purified by silica flash column chromatography to yield of a canary yellow powder (0.330 g, 59%). $^1$H NMR (CD$_2$Cl$_2$, 499.8 MHz) δ 7.93 (s, 2H), 7.84 (s, 3H), 7.82 (s, 1H), 7.61 (m, 4H), 7.54 (m, 4H), 7.43 (m, 4H), 7.36 (m, 4H), 7.32 (m, 2H), 7.26 (d, J=1.7 Hz, 2H), 7.20 (m, 4H), 7.15-7.11 (m, 6H), 1.66 (s, 6H), 1.35 (s, 18H). $^{13}$C NMR (CD$_2$Cl$_2$, 125.69 MHz) δ 158.4, 157.0, 150.1, 148.0, 147.7, 147.3, 145.2, 141.0, 138.4, 135.7, 129.2, 128.2, 127.3, 127.0, 126.8, 125.2, 124.5, 124.4, 120.9, 119.6, 119.5, 114.2, 106.7, 103.0, 46.4, 34.7, 31.6, 28.5. APCI$^+$ (m/z) Calcd for C$_{71}$H$_{60}$N$_2$O$_2$ ([M+H]$^+$) 973.4728. Found 973.4703.

Synthesis Example 8

This example illustrates the preparation of a compound having Formula I, N,N'-di(biphenyl-4-yl)-14,14-dimethyl-N,N'-bis(3,4,5-trimethylphenyl)-14H-dibenzo[d,d']fluoreno[3,2-b:6,7-b']difuran-3,10-diamine, Compound IB-8.

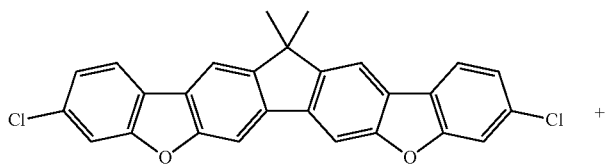

-continued

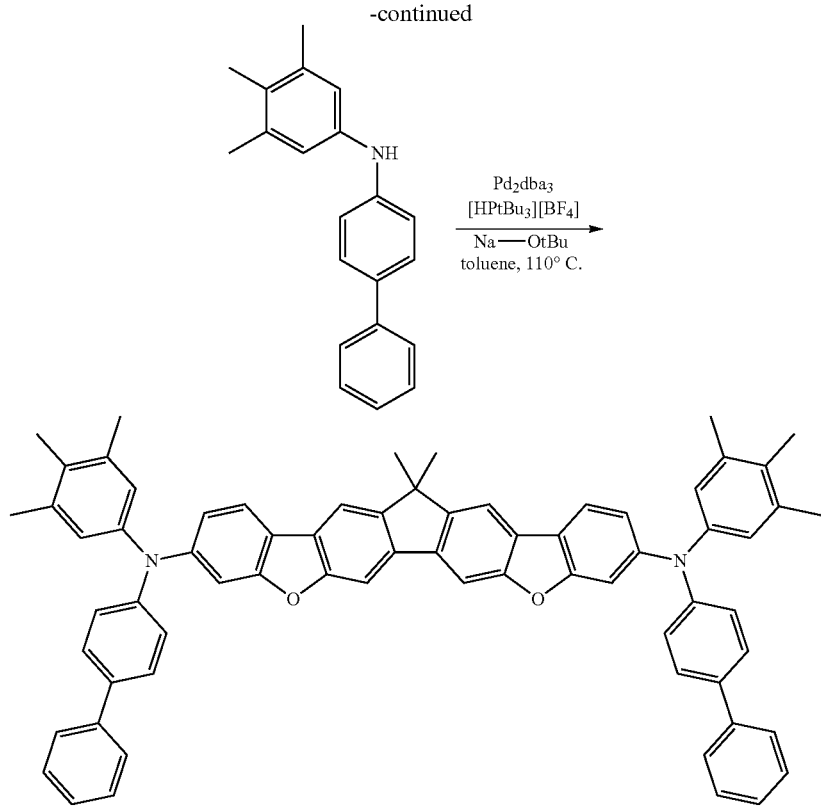

Inside a glovebox, a 100-mL 2-neck round-bottom flask containing a stir bar was charged with Pd$_2$(dba)$_3$ (0.017 g, 0.019 mmol), tri-t-butylphosphonium tetrafluoroborate (0.010 g, 0.034 mmol) and toluene (5 mL). The mixture was stirred for 10 minutes. Sodium tert-butoxide (0.145 g, 1.51 mmol), N-(3,4,5-trimethylphenyl)biphenyl-4-amine (0.390 g, 1.36 mmol) and 3,10-dichloro-14,14-dimethyl-14H-dibenzo[d,d']fluoreno[3,2-b:6,7-b]difuran (0.280 g, 0.632 mmol) were added followed by toluene (17 mL). The reaction mixture was stirred with the heating block set at 110° C. for 17.5 h. The reaction mixture was purified by silica flash column chromatography to yield of a canary yellow powder (0.238 g, 40%). $^1$H NMR (CD$_2$Cl$_2$, 499.8 MHz) δ 7.91 (s, 2H), 7.84 (s, 2H), 7.81 (d, J=8.4 Hz, 2H), 7.61 (d, J=7.4 Hz, 4H), 7.52 (d, J=8.4 Hz, 4H), 7.43 (t, J=7.6 Hz, 4H), 7.32 (m, 2H), 7.24 (br, 2H), 7.19-7.16 (m, 4H), 7.11-7.07 (m, 2H), 6.88 (s, 4H), 2.24 (s, 12H), 2.19 (s, 6H), 1.65 (s, 6H). APCl$^+$ (m/z) Calcd for C$_{69}$H$_{56}$N$_2$O$_2$ ([M+H]$^+$) 945.44. Found 946.24.

Synthesis Example 9

This example illustrates the preparation of a compound having Formula I, N,N'-di(biphenyl-4-yl)-N,N'-bis(3,4-dimethylphenyl)-14,14-dimethyl-14H-dibenzo[d,d']fluoreno[3,2-b:6,7-b]difuran-3,10-diamine, Compound IB-9.

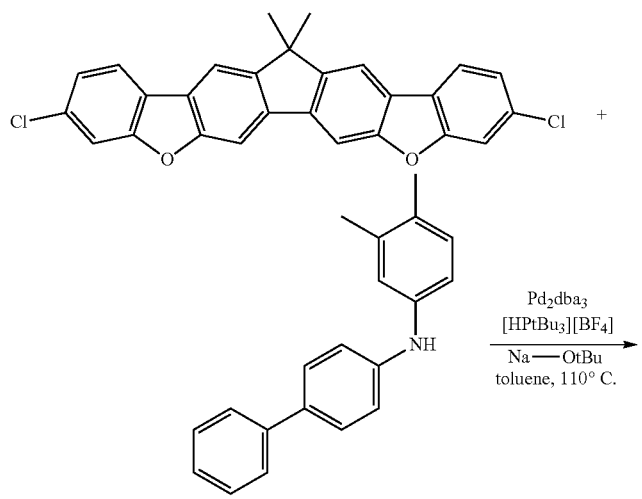

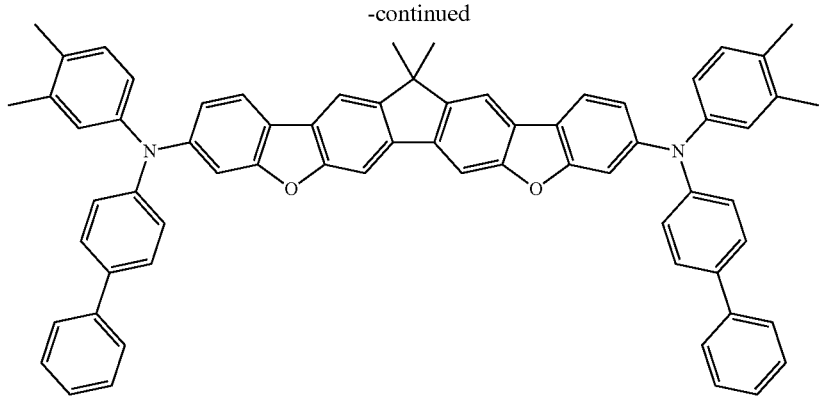

Inside a glovebox, a 100-mL 2-neck round-bottom flask containing a stir bar was charged with Pd₂(dba)₃ (0.052 g, 0.057 mmol), tri-t-butylphosphonium tetrafluoroborate (0.034 g, 0.12 mmol), toluene (10 mL) and sodium tert-butoxide (0.060 g, 0.62 mmol). The mixture was stirred for 10 minutes. Sodium tert-butoxide (0.180 g, 1.87 mmol), N-(3,4-dimethylphenyl)-[1,1'-biphenyl]-4-amine (0.680 g, 2.48 mmol) and 3,10-dichloro-14,14-dimethyl-14H-dibenzo[d,d']fluoreno[3,2-b:6,7-b']difuran (0.508 g, 1.15 mmol) were added followed by toluene (41 mL). The reaction mixture was stirred with the heating block set at 110° C. for 16 h. The reaction mixture was purified by silica flash column chromatography to yield of a canary yellow powder (0.690 g, 67%). ¹H NMR (CD₂Cl₂, 499.8 MHz) δ 7.92 (s, 2H), 7.84 (s, 2H), 7.82 (d, J=8.4 Hz, 2H), 7.60 (m, 4H), 7.53 (d, J=8.4 Hz, 4H), 7.43 (t, J=7.7 Hz, 4H), 7.32 (m, 2H), 7.25 (d, J=1.7 Hz, 2H), 7.18 (d, J=8.4 Hz, 4H), 7.12-7.09 (m, 4H), 7.02 (m, 2H), 6.95 (m, 2H), 2.28 (s, 6H), 2.22 (s, 6H), 1.66 (s, 6H). ¹³C NMR (CD₂Cl₂, 125.69 MHz) δ 158.4, 157.0, 150.1, 148.1, 147.8, 145.6, 141.0, 138.4, 138.3(9), 135.4, 133.0, 131.0, 129.2, 128.1, 127.3, 127.2, 126.9, 124.4, 124.2, 123.6, 120.8, 119.4, 119.3, 114.2, 106.5, 102.9, 46.4, 28.5, 20.0, 19.3. APCI⁺ (m/z) Calcd for $C_{67}H_{52}N_2O_2$ ([M+H]⁺) 917.41. Found 917.17.

Synthesis Example 10

This example illustrates the preparation of a compound having Formula I, N,N'-bis(3,4-dimethylphenyl)-14,14-dimethyl-N,N'-di(1,1':4',1''-terphenyl-4-yl)-14H-dibenzo[d,d']fluoreno[3,2-b:6,7-b']difuran-3,10-diamine, Compound IB-6.

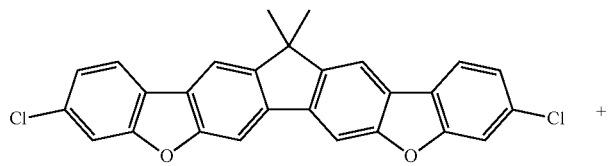

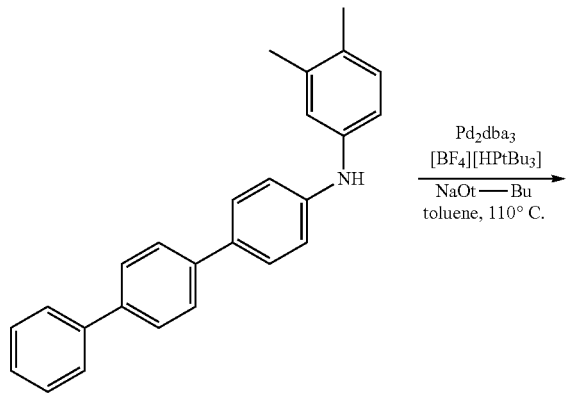

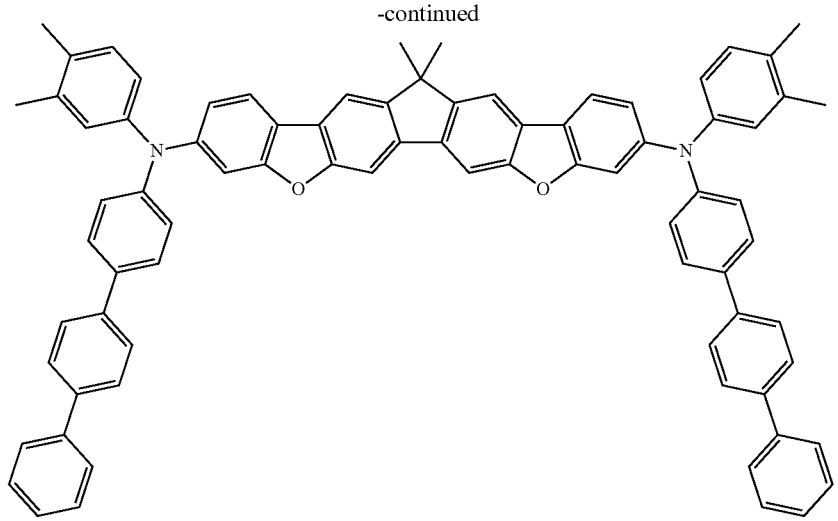

Inside a glovebox, a 100-mL 2-neck round-bottom flask containing a stir bar was charged with Pd$_2$(dba)$_3$ (0.052 g, 0.057 mmol), tri-t-butylphosphonium tetrafluoroborate (0.033 g, 0.113 mmol), toluene (10 mL) and sodium tert-butoxide (0.060 g, 0.62 mmol). The mixture was stirred for 10 minutes. Sodium tert-butoxide (0.180 g, 1.87 mmol), N-(3,4-dimethylphenyl)-[1,1':4',1''-terphenyl]-4-amine (0.868 g, 2.48 mmol) and 3,10-dichloro-14,14-dimethyl-14H-dibenzo[d,d']fluoreno[3,2-b:6,7-b']difuran (0.500 g, 1.13 mmol) were added followed by toluene (42 mL). The reaction mixture was stirred with the heating block set at 110° C. for 15.5 h. The reaction mixture was purified by silica flash column chromatography to yield of a canary yellow powder (0.689 g, 57%). $^1$H NMR (CD$_2$Cl$_2$, 499.8 MHz) δ 7.92 (s, 2H), 7.84 (s, 2H), 7.82 (d, J=8.4 Hz, 2H), 7.68-7.65 (m, 12H), 7.56 (d, J=8.6 Hz, 4H), 7.46 (t, J=7.7 Hz, 4H), 7.36 (m, 2H), 7.27 (d, J=1.7 Hz, 2H), 7.19 (d, J=8.6 Hz, 4H), 7.13-7.10 (m, 4H), 7.04 (m, 2H), 6.96 (m, 2H), 2.29 (s, 6H), 2.23 (s, 6H), 1.66 (s, 6H). $^{13}$C NMR (CD$_2$Cl$_2$, 125.69 MHz) δ 158.4, 157.0, 150.1, 148.1, 147.9, 145.6, 141.0, 139.9, 139.8, 138.4(3), 138.4(2), 134.7, 133.1, 131.0, 129.2, 128.0, 127.8, 127.7, 127.3, 127.2(5), 127.2(4), 124.5, 124.2, 123.6, 120.8, 119.4, 119.4(0), 114.2, 106.6, 103.0, 46.4, 28.5, 20.0, 19.4. APCl$^+$ (m/z) Calcd for C$_{79}$H$_{60}$N$_2$O$_2$ ([M+H]$^+$) 1069.47. Found 1069.38.

Synthesis Example 11

This example illustrates the preparation of a compound having Formula I, N,N'-bis(2',5'-dihexyl-2,2''-dimethyl-1,1':4',1'':4'',1'''-quaterphenyl-4-yl)-N,N'-bis(4'-propylbiphenyl-4-yl)dibenzo[d,d']naphtho[2,3-b:6,7-b']difuran-3,10-diamine, Compound IA-44.

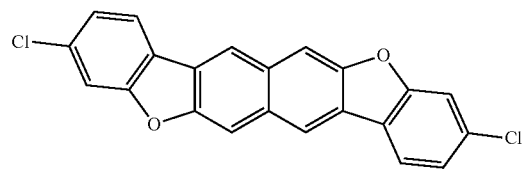

-continued

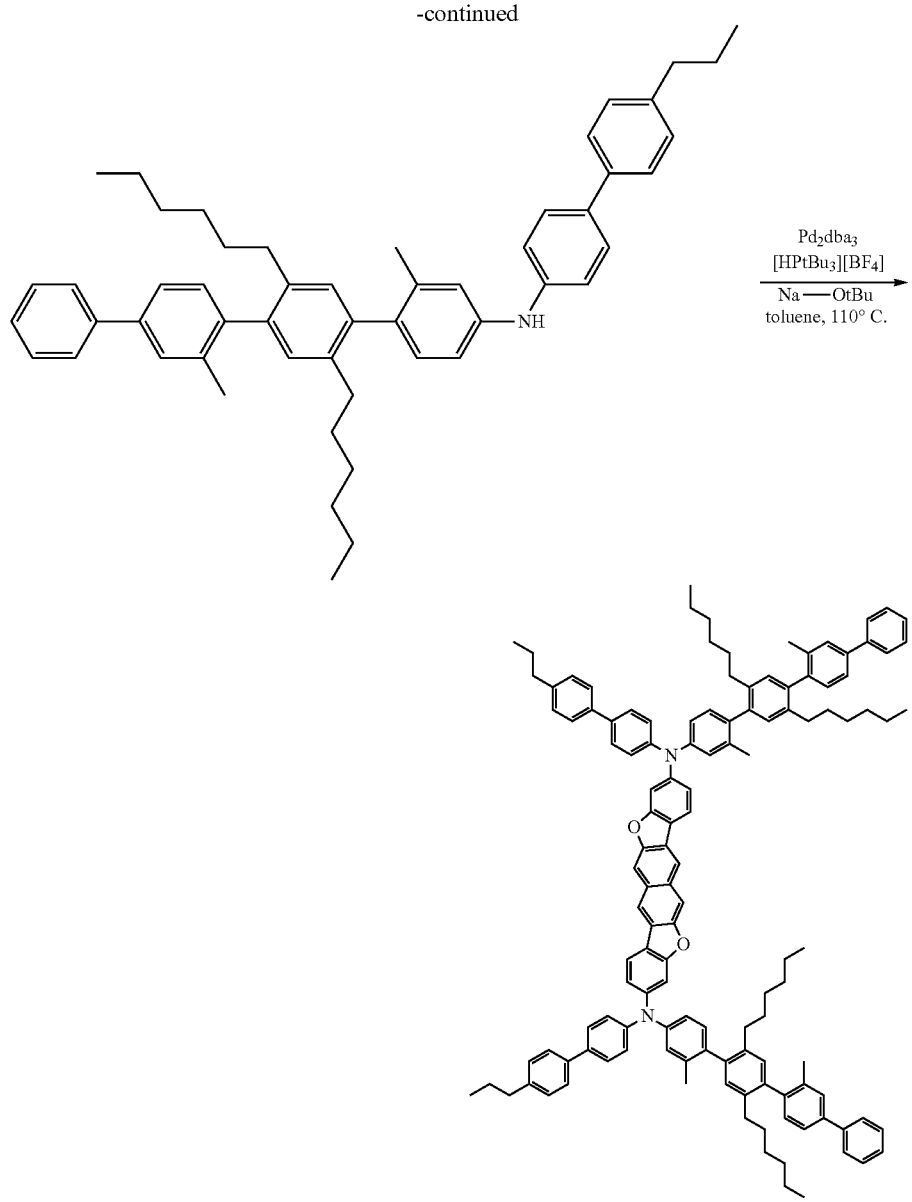

Inside a glovebox, a 100-mL 2-neck round-bottom flask containing a stir bar was charged with $Pd_2(dba)_3$ (0.010 g, 0.011 mmol), tri-t-butylphosphonium tetrafluoroborate (0.0063 g, 0.0217 mmol), toluene (2 mL) and sodium tert-butoxide (0.042 g, 0.44 mmol). The mixture was stirred for 10 minutes. 2',5'-dihexyl-2,2''-dimethyl-N-(4'-propyl-[1,1'-biphenyl]-4-yl)-[1,1':4',1'':4'',1'''-quaterphenyl]-4-amine (0.310 g, 0.435 mmol) and 3,10-dichlorodibenzo[d,d']naphtho[2,3-b:6,7-b']difuran (0.076 g, 0.20 mmol) were added followed by toluene (8 mL). The reaction mixture was stirred with the heating block set at 110° C. for 16 h. The reaction mixture was purified by silica flash column chromatography to yield of a canary yellow powder (0.190 g, 56%). $^1$H NMR ($CD_2Cl_2$, 499.8 MHz) δ 8.40 (s, 2H), 8.01 (s, 2H), 7.95 (d, J=8.4 Hz, 2H), 7.70 (d, J=7.9 Hz, 4H), 7.60-7.54 (m, 10H), 7.51-7.46 (m, 6H), 7.37 (m, 2H), 7.34-7.27 (m, 12H), 7.21-7.19 (m, 6H), 7.12 (m, 4H), 7.06 (d, J=2.2 Hz, 2H), 2.65 (t, J=7.6 Hz, 4H), 2.52 (m, 4H), 2.41 (m, 4H), 2.21 (s, 3H), 2.20 (s, 3H), 2.11 (s, 3H), 2.10 (s, 3H), 1.70 (sextet, J=7.5 Hz, 4H), 1.52-1.44 (m, 8H), 1.33-1.18 (m, 24H), 0.99 (t, J=7.4 Hz, 6H), 0.90 (t, J=7.1 Hz, 6H), 0.82 (t, J=6.9 Hz, 6H). $^{13}$C NMR ($CD_2Cl_2$, 125.69 MHz) δ 159.5, 155.2, 149.6, 147.2, 146.6, 142.2, 141.5, 141.3, 141.2, 140.1, 140.0, 138.3, 138.2(9), 138.2, 138.1, 138.0, 137.9, 137.1, 137.0, 136.4, 131.4, 131.3, 130.8(4), 130.8(1), 130.7 (5), 130.7(0), 130.6, 129.9, 129.4, 129.2, 128.8, 128.1, 127.6, 127.4, 126.9, 125.9, 125.3, 124.3, 122.7, 121.9, 118.9, 118.4, 117.8, 106.9, 106.1, 38.1, 33.1(8), 33.1(7), 33.0(5), 33.0(4), 32.0, 31.3, 31.2(6), 31.1(9), 29.5(5), 29.5 (1), 29.4(5), 29.4(2), 25.1, 23.0, 22.9, 20.5, 20.4, 14.3, 14.2, 14.1. APCl$^+$ (m/z) Calcd for $C_{128}H_{130}N_2O_2$ ([M+H]$^+$) 1728.0205. Found 1729.0955.

Synthesis Example 12

This example illustrates the preparation of a compound having Formula I, N,N'-bis(4-tert-butylphenyl)-1,8-diphenyl-N,N'-bis[4"-(2,4,4-trimethylpentan-2-yl)-1,1':4',1"-terphenyl-4-yl]-1,8-dihydrocarbazolo[4,3-c]carbazole-3,10-diamine, Compound IA-45.

purified by silica flash column chromatography to yield of a canary yellow powder (0.410 g, 42%). $^1$H NMR (CD$_2$Cl$_2$, 499.8 MHz) δ 8.83 (s, 1H), 8.58 (d, J=8.7 Hz, 2H), 7.80 (d, J=8.9 Hz, 2H), 7.70-7.65 (d, J=7.6 Hz, 8H), 7.61-7.54 (m, 17H), 7.49-7.47 (m, 6H), 7.35-7.31 (m, 6H), 7.24-7.18 (m, 6H), 7.14 (m, 4H), 1.83 (s, 4H), 1.43 (s, 12H), 1.36 (s, 18H), 0.79 (s, 18H). APCl$^+$ (m/z) Calcd for C$_{106}$H$_{104}$N$_4$ ([M+H]$^+$) 1433.83. Found 1433.92.

Synthesis Example 13

This example illustrates the preparation of a compound having Formula I, N,N'-bis[6-(1-benzofuran-2-yl)naphthalen-2-yl]-14,14-dimethyl-N,N'-diphenyl-14H-dibenzo[d,d']fluoreno[3,2-b:6,7-b']difuran-3,10-diamine, Compound IB-10.

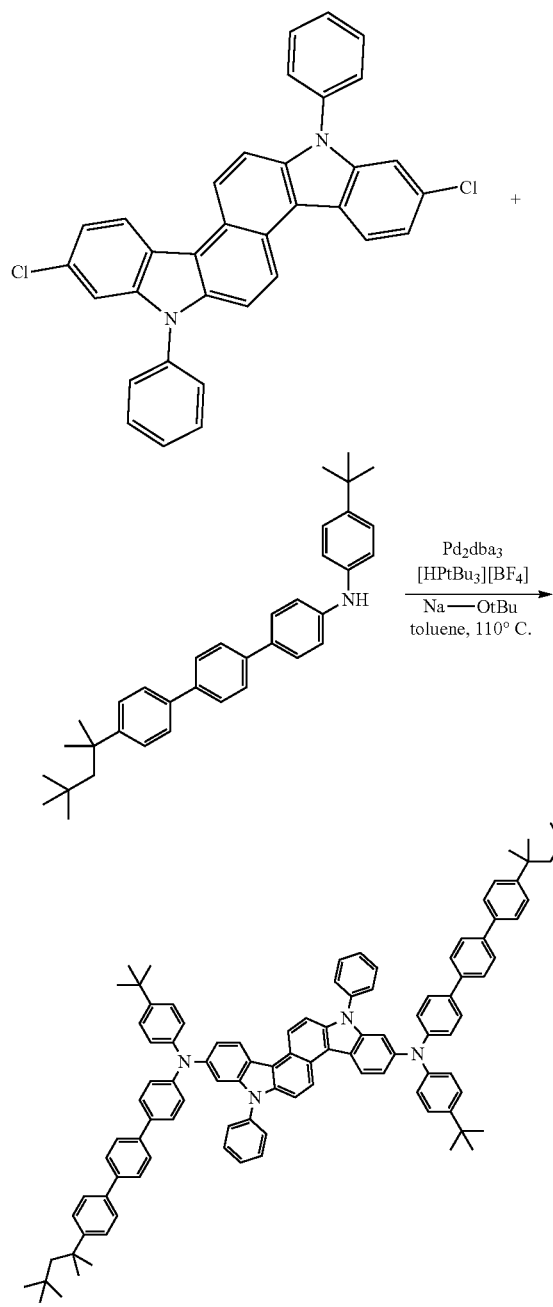

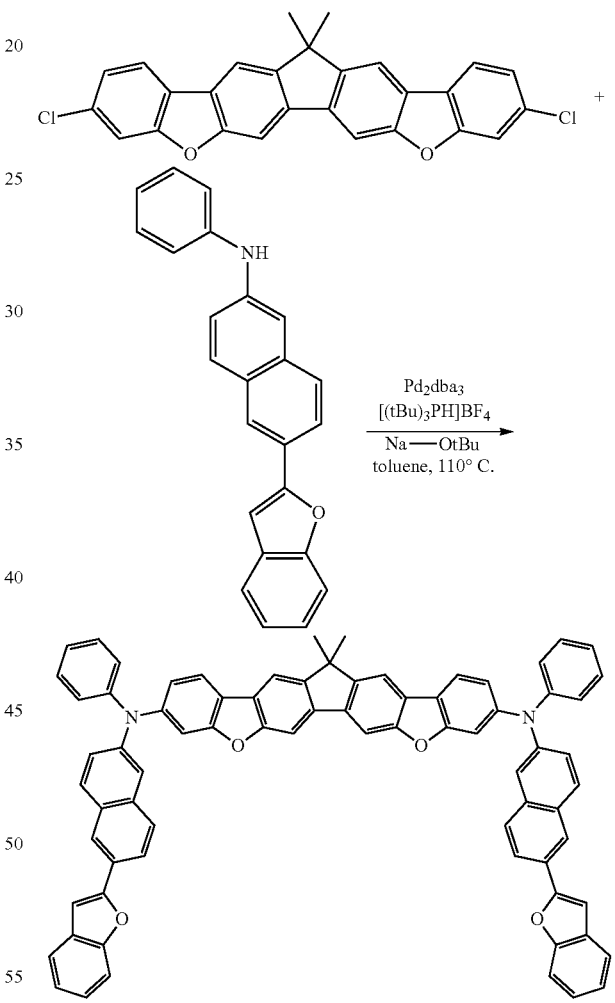

Inside a glovebox, a 100-mL 2-neck round-bottom flask containing a stir bar was charged with Pd$_2$(dba)$_3$ (0.019 g, 0.020 mmol), tri-t-butylphosphonium tetrafluoroborate (0.013 g, 0.045 mmol), toluene (5 mL) and sodium tert-butoxide (0.026 g, 0.27 mmol). The mixture was stirred for 10 minutes. Sodium tert-butoxide (0.118 g, 1.23 mmol), N-(4-(tert-butyl)phenyl)-4"-(2,4,4-trimethylpentan-2-yl)-[1,1':4',1"-terphenyl]-4-amine (0.9 g, 1.8 mmol) and 3,10-dichloro-1,8-diphenyl-1,8-dihydrocarbazolo[4,3-c]carbazole (0.363 g, 0.688 mmol) were added followed by toluene (25 mL). The reaction mixture was stirred with the heating block set at 110° C. for 15 h. The reaction mixture was Inside a glovebox, a 100-mL 2-neck round-bottom flask containing a stir bar was charged with Pd$_2$(dba)$_3$ (0.030 g, 0.033 mmol), tri-t-butylphosphonium tetrafluoroborate (0.0175 g, 0.0603 mmol), toluene (10 mL) and sodium tert-butoxide (0.010 g, 0.10 mmol). The mixture was stirred for 10 minutes. Sodium tert-butoxide (0.243 g, 2.53 mmol), 6-(1-benzofuran-2-yl)-N-phenylnaphthalen-2-amine (0.740 g, 2.21 mmol) and 3,10-dichloro-14,14-dimethyl-14H-dibenzo[d,d']fluoreno[3,2-b:6,7-b]difuran (0.440 g, 0.993 mmol) were added followed by toluene (50 mL). The reaction mixture was stirred with the heating block set at 110° C. for 15 h. The reaction mixture was purified by silica flash column chromatography to yield of a canary yellow powder (0.740 g, 63%). $^1$H NMR (CD$_2$Cl$_2$, 499.8 MHz) δ 8.31 (s, 2H), 7.95 (s, 2H), 7.87-7.82 (m, 8H), 7.65-7.61 (m, 4H), 7.56 (d, J=8.0 Hz, 2H), 7.48 (m, 2H), 7.38-7.22 (m, 16H), 7.18-7.12 (m, 6H), 1.67 (s, 6H). $^{13}$C NMR (CD$_2$Cl$_2$, 125.69 MHz) δ 158.4, 157.1, 126.5, 155.3, 150.2, 147.9, 147.6, 146.6, 138.6, 134.8, 130.3, 129.9, 129.8, 129.7(8), 127.8, 126.7, 125.5, 125.1, 124.7, 124.3, 124.2, 123.8, 123.6, 123.4, 121.2, 121.1, 120.3, 120.1, 114.3, 111.4, 107.7, 103.1, 101.8, 46.4, 28.5. APCl$^+$ (m/z) Calcd for C$_{75}$H$_{48}$N$_2$O$_4$ ([M+H]$^+$) 1041.3686. Found 1041.3706.

Synthesis Example 14

This example illustrates the preparation of a compound having Formula II, Compound II-16.

(a) bromo-2-(2,2-dichlorovinyl)phenol

Ref. Newman, Stephen G. et al., Synthesis, (2), 342-346; 2011

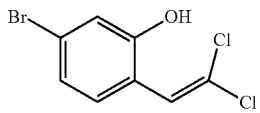 [SMILES: Oc1cc(Br)ccc1C=C(Cl)Cl]

4-bromo-2-hydroxybenzaldehyde (1.0 g, 4.98 mmol), MeCN (41 mL), and triphenylphosphane (3.91 g, 14.92) were added to a flask equipped with a magnetic stir bar. The mixture was stirred for 5 min, after which bromotrichloromethane (1.78 g, 8.96 mmol) was added in one portion. The reaction mixture was stirred at ambient temperature for 4 h, by which time the aldehyde and triphenylphosphane had been consumed as shown by TLC analysis. The mixture was diluted with a Et$_2$O-pentane mixture (3:1) until solid Ph$_3$PO began to precipitate. The heterogeneous mixture was then filtered through a pad of silica gel, which was rinsed with a Et$_2$O-pentane mixture (3:1). The solvent was evaporated and the product was purified by flash column chromatography (silica gel, EtOAc-pentane, 5:95) to give a colorless oil, yield 105 mg, 79%. 1H NMR (CDCl$_3$): δ=7.49 (d, 1H), 7.11 (d, 1H), 7.02 (s, 1H), 6.95 (s, 1H), 5.32 (s, b, 1H). 13C NMR (100 MHz, CDCl$_3$): δ=118.89, 119.91, 122.54, 122.82, 123.07, 123.99, 130.40, 153.47.

(b) 6-bromo-2-chlorobenzofuran

Ref. Ji, Yong; Li, Pinhua; Zhang, Xiuli; Wang, Lei. Organic & Biomolecular Chemistry, 11(24), 4095-4101, 2013

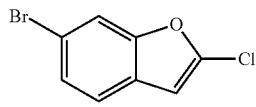 [SMILES: Clc1cc2ccc(Br)cc2o1]

To a solution of 5-bromo-2-(2,2-dichlorovinyl)phenol (0.22 g, 0.82 mmol) in ethanol (2 mL), was added cesium carbonate (1.34 g, 0.41 mmol). The reaction was stirred and heated at 80° C. for 2 hours, UPLC analysis showed the reaction was completed. After cooling, ethyl acetate (50 mL) was added and the solution was washed with water, saturated brine and dry over MgSO$_4$. The solvent was evaporated and the product was purified by flash column chromatography to give a white solid, yield 154 mg, 81%. LC/MS analysis, M+H 232, and NMR spectra are in consistence with the structure of the product.

(c) 2-chloro-N,N-diphenylbenzofuran-6-amine

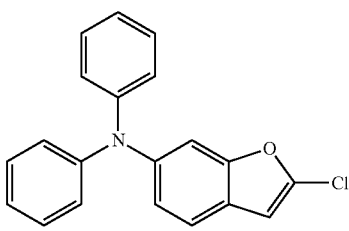 [SMILES: Clc1cc2ccc(N(c3ccccc3)c3ccccc3)cc2o1]

Inside a glovebox, 6-bromo-2-chlorobenzofuran (694 mg, 3.00 mmol), diphenylamine (592 mg, 3.50 mmol), sodium t-butoxide (692 g, 7.20 mmol), tri-t-butylphosphine (61 mg, 0.30 mmol), and tris(dibenzylideneacetone) dipalladium(0) (137 mg, 0.15 mmol) were mixed with dry toluene (50 mL). The reaction mixture was stirred at room temperature for 3 hours, filtered through a Celite® plug, and concentrated under reduced pressure. The crude product obtained was purified by silica gel column chromatography (Combi-Flash® purification system available from Teledyne Isco) eluted with dichloromethane/hexane gradient. The product was obtained as a clear liquid (748 mg, 78%). MS analysis, M+H 320, 1 H-NMR spectrum is in consistence with the structure of the product.

(d) N,N-diphenyl-2-(4,4,5,5-tetramethyl-1,3,2-dioxaborolan-2-yl)benzofuran-6-amine

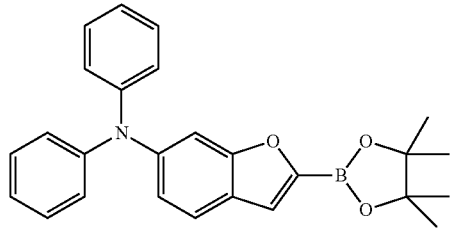 [SMILES: CC1(C)OB(c2cc3ccc(N(c4ccccc4)c4ccccc4)cc3o2)OC1(C)C]

In dry box, a 250 mL 3-neck round-bottom flask was charged with 2-chloro-N,N-diphenylbenzofuran-6-amine (748 g, 2.40 mmol), 4,4,4',4',5,5,5',5'-octamethyl-2,2'-bi(1,3,2-dioxaborolane) (731 mg, 2.88 mmol), potassium acetate (942 mg, 9.60 mmol), Pd$_2$(dba)$_3$ (44 mg, 0.04 mmol), X-Phos™ (38 mg, 0.08 mmol) and 1,4-Dioxane (50 mL). The reaction was stirred at 80° C. for 16 hours. After cooling, the mixture was filtered through a Celite® plug eluted with DCM. The solvent was evaporated and the crude product was subjected to column separation (CombiFlash®) using chloroform/hexane gradient. The product containing fractions were identified by UPLC analysis and combined to give a white powder (681 g, 69%). NMR spectra are in consistence with the structure of the product.

(e) 2,2'-(naphtho[1,2-b:5,6-b']difuran-2,7-diyl)bis(N,N-diphenylbenzofuran-6-amine), Compound II-16

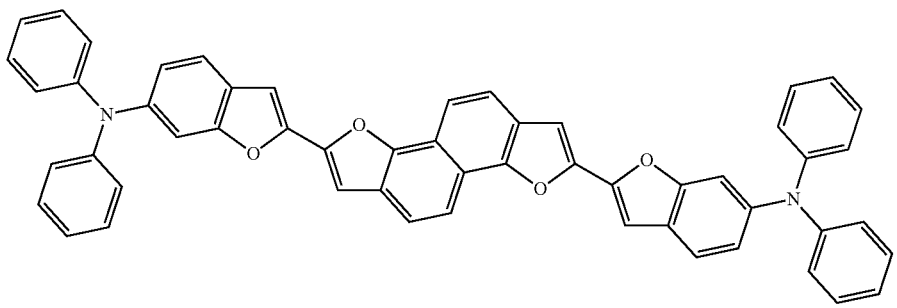 [SMILES: c1ccc(N(c2ccccc2)c2ccc3cc(-c4cc5ccc6c(ccc7cc(-c8cc9ccc(N(c%10ccccc%10)c%10ccccc%10)cc9o8)oc76)c5o4)oc3c2)cc1]

A 100 mL 3-neck round-bottom flask was charged with 2,7-dibromonaphtho[1,2-b:5,6-b']difuran (0.55 g, 1.50 mmol), N,N-diphenyl-2-(4,4,5,5-tetramethyl-1,3,2-dioxaborolan-2-yl)benzofuran-6-amine (1.30 g, 3.15 mmol), aqueous sodium carbonate (2M, 29 mL), Aliquat™ 336 (13 mg, 0.03 mmol) and toluene (116 mL). The system was purged with nitrogen for 15 minutes. After which, tetrakis(triphenylphosphine)palladium(0) (70 mg, 0.06 mmol) was added and the system was purged for another 5 min. The reaction was stirred with refluxing for 16 hours. UPLC analysis indicated that all, 7-dibromonaphtho[1,2-b:5,6-b']difuran had been consumed and the product formed as the major component. The organic phase was separated, washed with diluted HCl (10%, 50 ml) and saturated brine (50 mL), and dried over magnesium sulfate. The solution was passed through a short alumina (basic) column eluted with toluene. The solvent was evaporated and the crude product was purified by preparative chromatography (CombiFlash®) using hexane/DCM gradient to give a pale yellow powder (335 mg, yield 29% in 99.4% purity).

Synthesis Example 15

This example illustrates the preparation of a compound having Formula I, N,N'-bis(3'-tert-butylphenyl-4-yl)-N,N'-di(naphthalen-2-yl)-dibenzo[d,d']naphtho[2,3-b:6,7-b']difuran-3,10-diamine, Compound IA-17.

In drybox, 3,10-dichlorodibenzo[d,d']naphtho[2,3-b:6,7-b']difuran (2.64 g, 7.00 mmol), 3 N-(4-(tert-butyl)phenyl)naphthalen-2-amine (4.05 g, 14.70 mmol), Pd$_2$(DBA)$_3$ (321 mg, 0.35 mmol) and anhydrous toluene (300 ml) were taken in a 1000 mL flask under nitrogen and stirred for 5 min. NaOtBu (1.61 g, 16.80 mmol) was added in small portions in 10 min. The reaction was stirred at 80° C. for 16 hours. After cooling, the reaction was removed from the drybox, and passed through a Celite® plug to remove the insoluble materials. The solvent was removed by rotary evaporation and the residue was separated by the preparative chromatography (CombiFlash®) eluted with DCM/hexanes gradient. The product containing fractions were identified by UPLC analysis and collected. The solvent was evaporated and the product was crystallized from toluene/acetonitrile to give 4.2 g pale yellow material in >99.9% purity by UPLC analysis. LC/MS analysis, M+H 855, and NMR spectra are in consistence with the structure of the product.

Synthesis Example 16

This example illustrates the preparation of a compound having Formula I, N,N'-di(2,4-dimethylphenyl)-N,N'-di(4'-tert-octylterphenyl-4-yl)-Naphtho[2,3-b:6,7-b']bisbenzofuran-3,10-diamine, Compound IA-43.

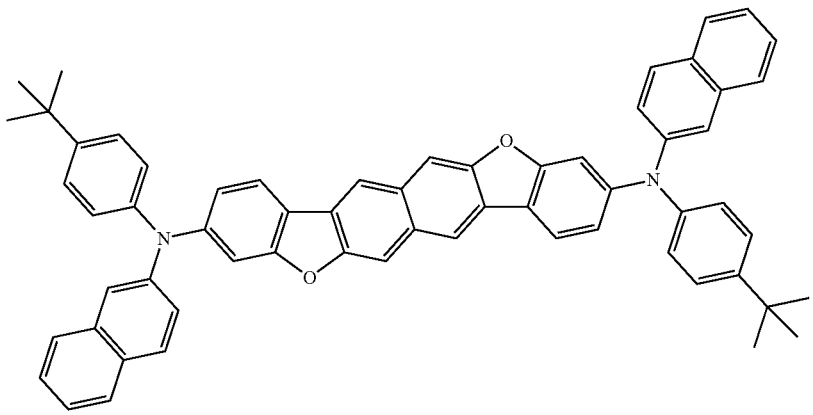 [SMILES: CC(C)(C)c1ccc(N(c2ccc3ccccc3c2)c2ccc3c(c2)oc2cc4cc5c(cc4cc23)oc2cc(N(c3ccc(C(C)(C)C)cc3)c3ccc4ccccc4c3)ccc25)cc1]

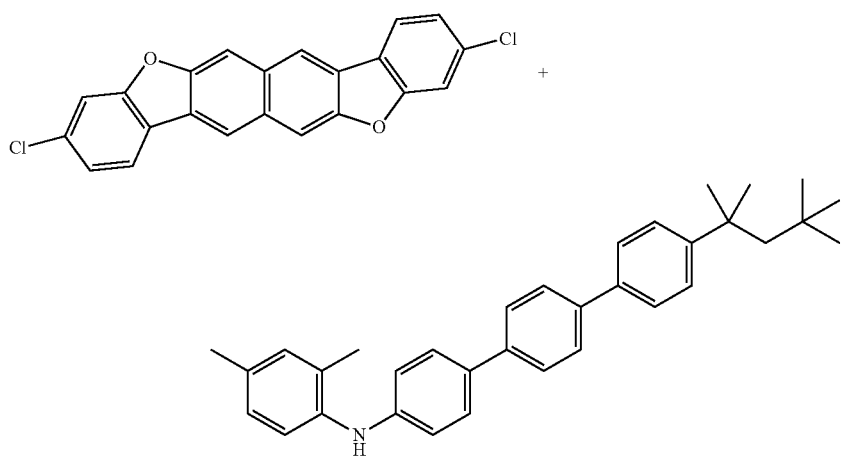

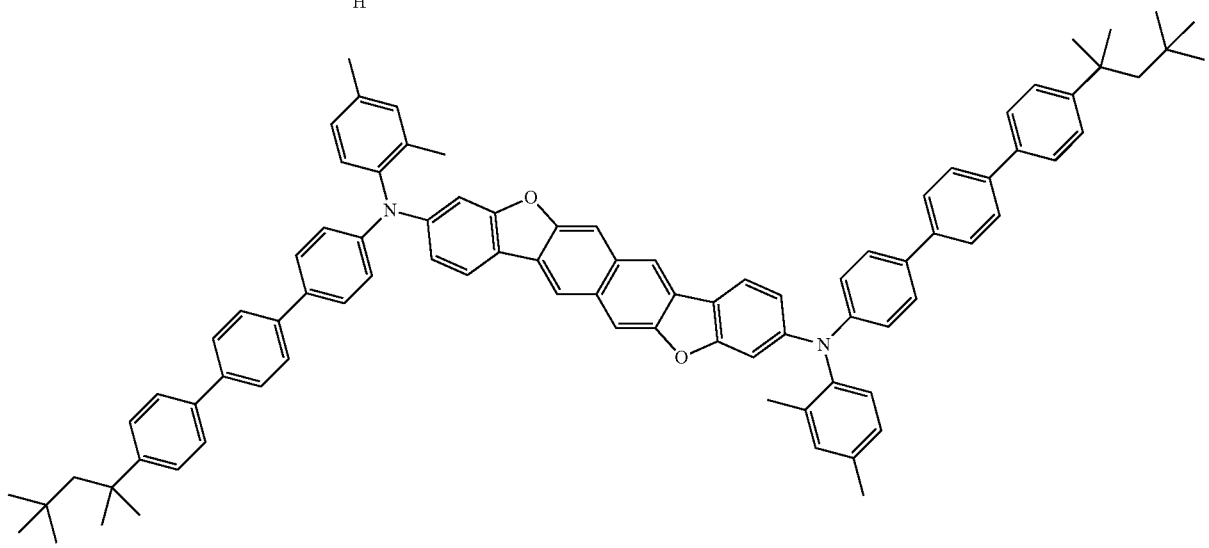

Naphtho[2,3-b:6,7-b']bisbenzofuran-3,10-dichloride (1.03 g, 2.7 mmol), [1,1':4',1"-Terphenyl]-4-amine N-(2,4-dimethylphenyl)-4"'-(1,1,3,3-tetramethylbutyl)-(2.6 g, 5.6 mmol), Tris(dibenzylideneacetone)dipalladium(0) (52 mg, 0.06 mmol), tri-tert-butyl-phosphine (23 mg, 0.011 mmol), sodium t-butoxide (0.57 g, 5.9 mmol) and 55 ml sparged anhydrous toluene were taken in the 100 ml round bottom flask in the glove box and the resulting slurry heated to 80° C. till the reaction was deemed complete. The reaction mixture was cooled and quenched with water. The brown organic layer was separated, passed through alumina and concentrated to yield crude product. The product was further purified via Toluene-Methanol crystallization and a short plug through alumina and Florisil® magnesium silicate (available from Sigma-Aldrich) to yield 3.36 g of desired product.

Synthesis Example 17

This example illustrates the preparation of a compound having Formula III, Compound III-12.

(a) Preparation of difuran core 2,7-bis(4-bromophenyl)naphtho[1,2-b:5,6-b']difuran (Product 1)

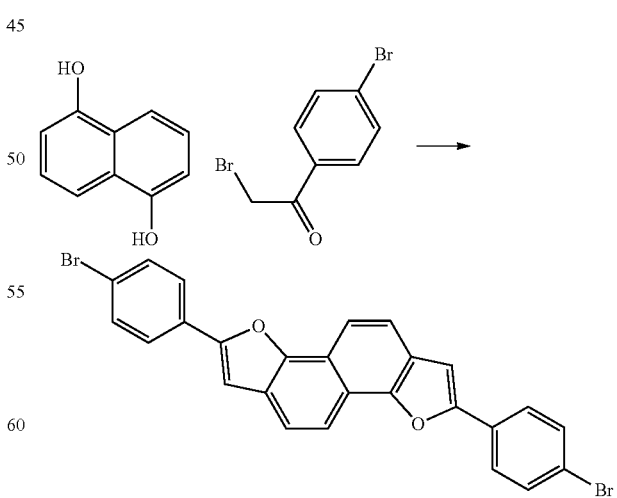

product 1

1,5-Naphthalenediol (7.2 g, 0.0450 mol), 4-bromophenacyl bromide (35.01 g, 0.1260 mol), basic alumina (60 g, 0.5885 mol) slurried into 210 mL xylenes were refluxed overnight then cooled and filtered yielding the original filtrate and a filter cake. The filter cake was extracted with THF and m-xylene and refluxing m-xylene. This filtrate was concentrated, filtered, and the solids triturated in THF to yield 50 mg of product 1. The original filtrate was concentrated, filtered for a cake that was triturated with xylenes to yield 70 mg of product 1 and the filtrate was concentrated and recrystallized from THF for 20 mg of product 1. A further crop of product was also extracted from the original filter cake by soxhlet extraction with THF. Total yield 0.25 g.

(b) Preparation of N,N'-[naphtho[1,2-b:5,6-b']difuran-2,7-diyldi(4,1-phenylene)]bis{N-[4-(1-benzofuran-2-yl)phenyl]-4-(propan-2-yl)aniline}

In a nitrogen filled drybox, $Pd_2DBA_3$ (0.0090 g, 0.0098 mmol), tri-t-butylphosphine (0.0045 g, 0.0222 mmol), sodium-t-butoxide (0.18 g, 1.873 mmol), product 1 (0.23 g, 0.444 mmol), secondary amine (0.31 g, 0.954 mmol) and 10 mL of o-xylene were combined and heated to 90° C. Silica chromatography with toluene/hexanes followed by toluene/acetonitrile recrystallization yielded 165 mg Compound III-12, identified by UPLC/MS and 1H-nmr spectroscopy.

Synthesis Example 18

This example illustrates the preparation of a compound having Formula III, Compound III-13.

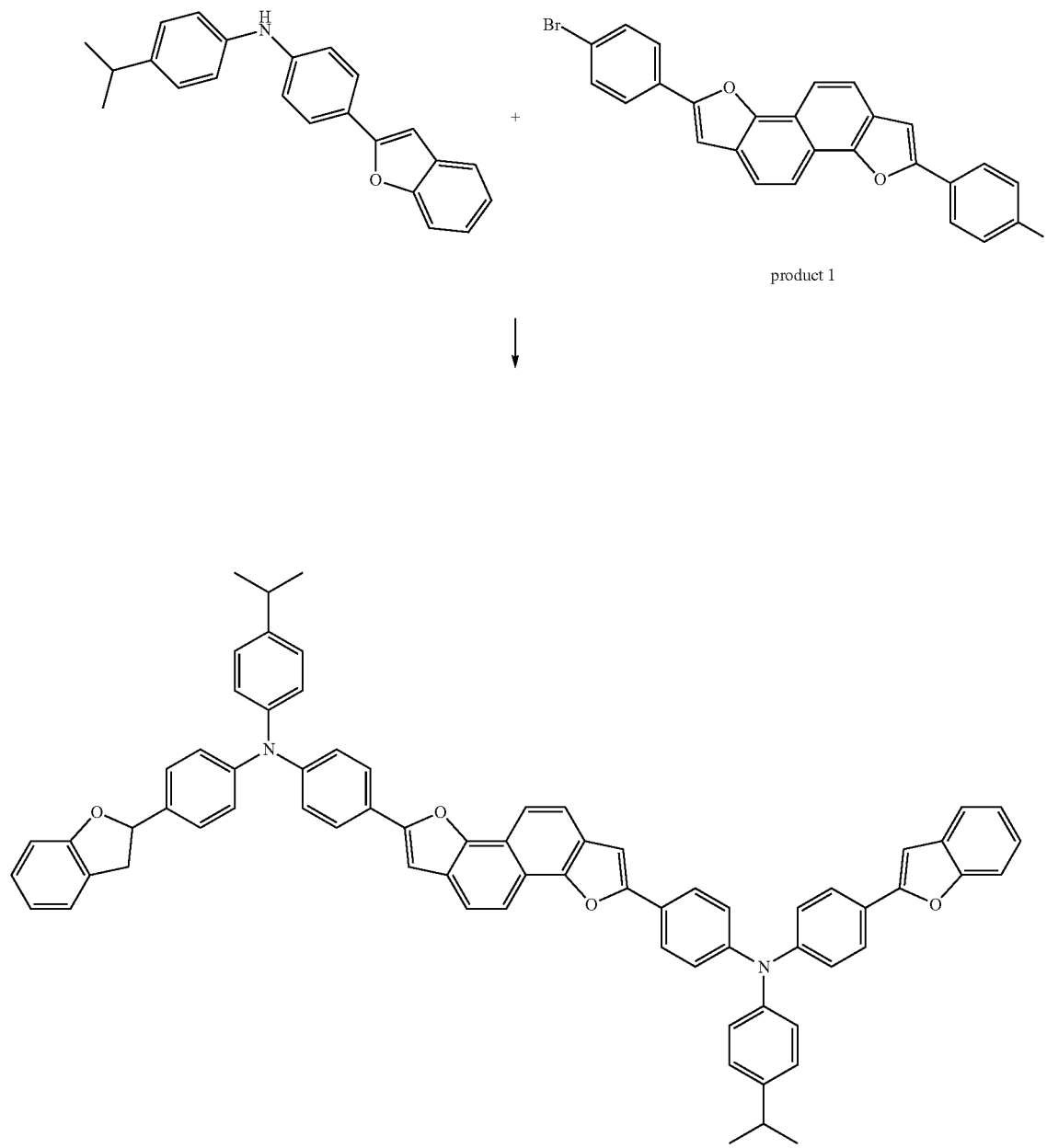

(a) Preparation of difuran core 2,7-dibromonaphtho[2,3-b:7,6-b']difuran (Product 2a)

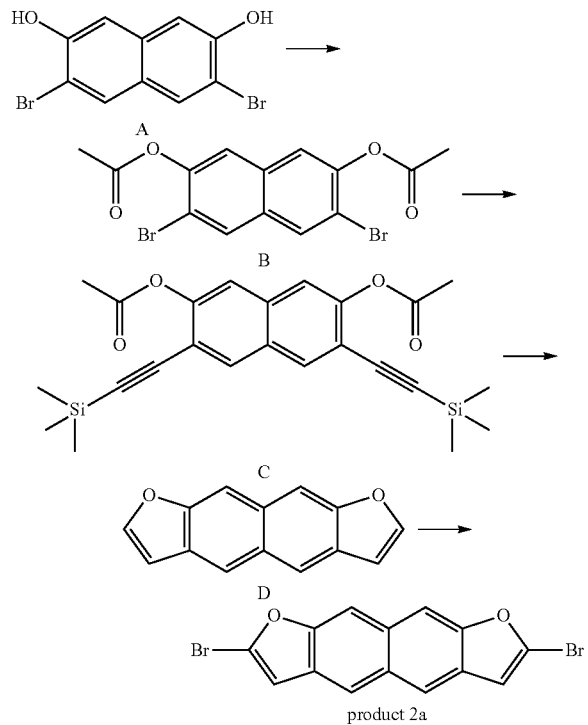

Commercially available 3,6-dibromonaphthalene-2,7-diol (A) was converted to its di-acetate ester with acetic anhydride (6 eq) in pyridine (3 eq) at room temperature for 16 hrs. Addition of water and filtration of the resulting solid gave 3,6-dibromonaphthalene-2,7-diyl diacetate (B) in 59% yield. 12 g of this product were reacted with TMS acetylene (10.0 eq), $Cs_2CO_3$ (4 eq), $Pd(CH_3CN)_2Cl_2$ (0.05 eq), X-phos (0.12 eq), 1,4-dioxane (6 vol), THF (6 vol), at 60° C. for 45 min. The crude compound was purified by column chromatography using 10% EtOAc in pet-ether as eluent and followed by leaching with n-pentane to give 21% yield of 3,6-bis[(trimethylsilyl)ethynyl]naphthalene-2,7-diyl diacetate (C). This material was treated with tetra-n-butylammonium fluoride (3.2 eq), in THF (20 vol), at 60° C. for 16 h. resulting in isolation of 74% yield of a poorly soluble solid, naphtho[2,3-b:7,6-b']difuran (D), which was purified by leaching with pentane. This solid was brominated using 1.0 M n-BuLi (3 eq), dibromotetrachloroethane (3 eq), in THF (15 vol), beginning at −78° C. then warming slowly to room temperature for 16 h. The crude product was purified by column chromatography, then recrystallized from EtOH and followed by co-precipitation using THF/hexane to give the dibromo difuran product 2a in 34% yield identified by UPLC/MS and 1H-nmr spectroscopy.

(b) Preparation of difuran core 2,7-bis(4-chlorophenyl)naphtho[2,3-b:7,6-b']difuran (Product 2b)

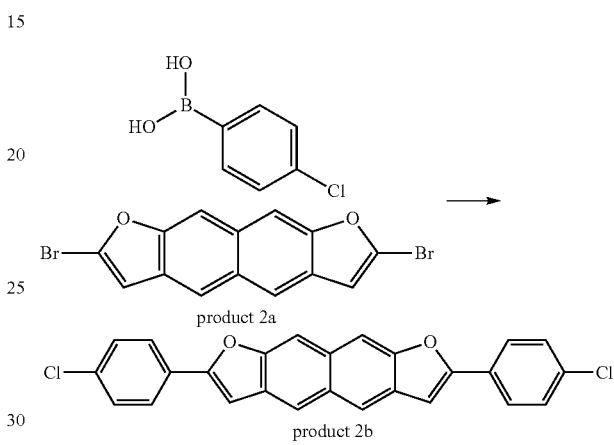

Product 2a (0.468 g, 1.3 mmol), 4-chlorophenylboronic acid (0.497 g, 3.2 mmol), 7.2 ml water, 21.6 mL monoglyme and potassium carbonate (2.02 g, 1.4 mmol) were sparged with nitrogen for 40 minutes. Tetrakistriphenylphosphinepalladium(0) (0.065 g, 0.0561 mmol) was quickly added and the mixture refluxed overnight. The reaction was cooled and diluted with water, filtered, and the cake was washed with acetone and dichloromethane giving 320 mg of product 2b. 58% yield.

(c) Preparation of emitter material N,N'-[naphtho[2,3-b:7,6-b']difuran-2,7-diyldi(4,1-phenylene)]bis{N-[4-(1-benzofuran-2-yl)phenyl]aniline}, Compound III-13

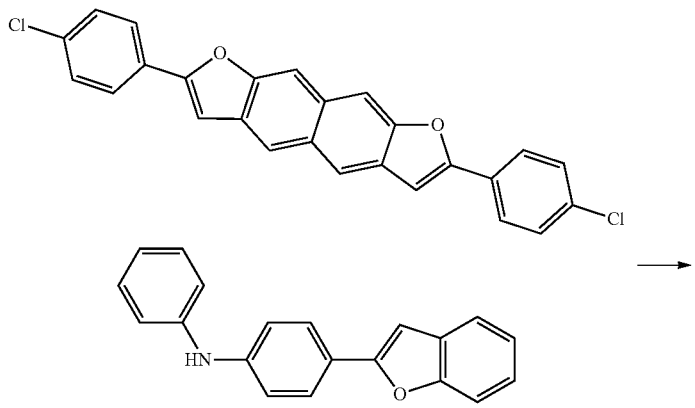

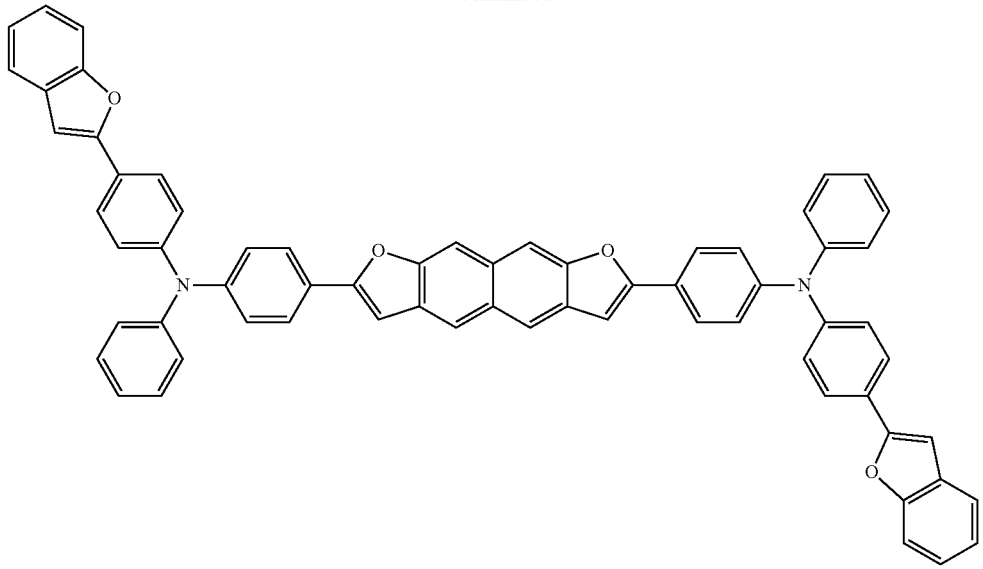

In a nitrogen filled drybox Pd₂DBA₃ (0.0600 g, 0.0655 mmol), tri-t-butylphosphine (0.0300 g, 0.1483 mmol), sodium-t-butoxide (0.162 g, 1.686 mmol), product 2b from above (0.207 g, 0.482 mmol), secondary amine (0.306 g, 1.072 mmol) and 9 mL of o-xylene were combined and heated to 100° C. for 4 hrs. Silica chromatography with dichloromethane/hexanes followed by toluene/acetonitrile recrystallization, o-xylene recrystallization and dichloromethane/acetonitrile recrystallization yielded 70 mg product Compound III-13, identified by UPLC/MS and 1H-nmr spectroscopy.

Synthesis Example 19

This example illustrates the preparation of a compound having Formula III, Compound III-8.

(a) Preparation of difuran core 2,5-bis(4-bromophenyl)naphtho[1,2-b:4,3-b']difuran (Product 3)

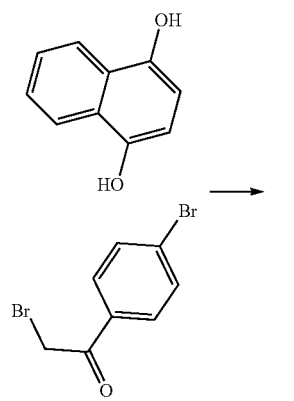

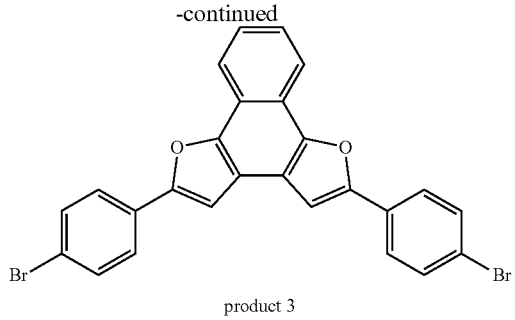

product 3

1,4-Naphthalenediol (14.4 g, 0.0899 mol), 4-bromophenacyl bromide (70.02 g, 0.2519 mol), basic alumina (150 g, 1.4712 mol) and 420 mL xylenes were refluxed overnight. The slurry was hot filtered through a medium glass frit and allowed to cool. The generated solids were filtered from the cooled filtrate, washed with toluene and methanol to yield a grey solid that was triturated with THF for 1.7 g of product 3. 3% yield (b) Preparation of emitter material N,N'-[naphtho[1,2-b:4,3-b]difuran-2,5-diyldi(4,1-phenylene)]bis{N-[4-(1-benzofuran-2-yl)phenyl]-4-(propan-2-yl)aniline}, Compound III-8.

151 152

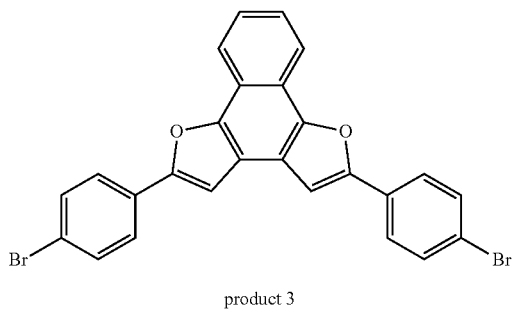

product 3

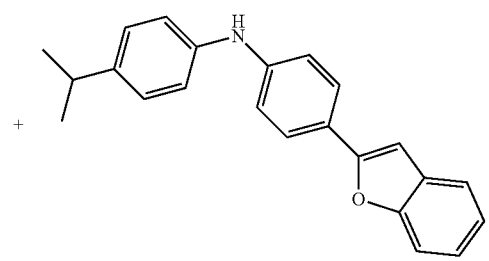

↓

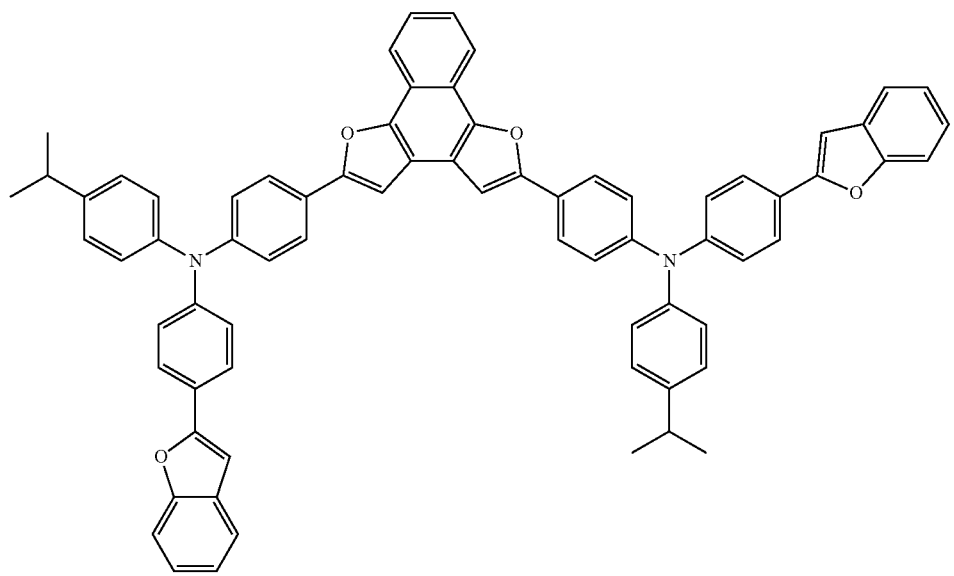

In a nitrogen filled drybox Pd$_2$DBA$_3$ (0.0900 g, 0.0098 mmol), tri-t-butylphosphine (0.0045 g, 0.0222 mmol), sodium-t-butoxide (0.1800 g, 1.873 mmol), product 3 from above (0.230 g, 0.4440 mmol), secondary amine (0.3080 g, 0.9410 mmol) and 10 mL o-xylene were combined and heated to 100° C. The cooled reaction solution was filtered through Florisil®. Silica chromatography with toluene/hexanes eluent followed by toluene/acetonitrile/methanol recrystallization, o-xylene recrystallization and dichloromethane/acetonitrile recrystallization yielded 210 mg product Compound III-8, identified by UPLC/MS and 1H-nmr spectroscopy.

Synthesis Example 20

This example illustrates the preparation of a compound having Formula I, Compound IB-3.

(a) Preparation of core precursor material 1,7-bis(4-chloro-2-fluorophenyl)dibenzo[b,d]furan-2,8-diol (Product 4a)

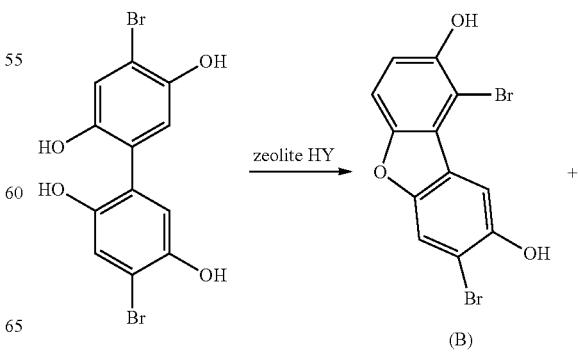

-continued

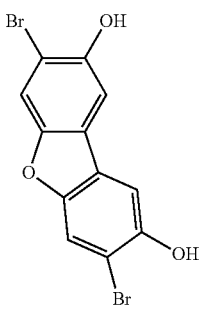

(S)

4,4'-dibromo[1,1'-biphenyl]-2,2',5,5'-tetrol (50.29 grams, 0.1337 mol) was slurried in 1340 mL of o-dichlorobenzene and Zeolite HY (52.73 grams) in a nitrogen filled drybox and was warmed to 140° C. for about 8 hours and then cooled overnight with stirring. Most of the ODCB was stripped away and 500 mL EtAc was added. The resulting solution was sparged with nitrogen and filtered through a bed of Celite®. ~710 ml hexanes was added and the solution was allowed to stand overnight, 2.9 grams of initial solids were filtered and discarded. The filtrate was concentrated down to yield 37 grams of orange solid. The orange solid was recrystallized from EtAc/Heptane to yield 3 successive crops of solids varying in ratios of straight (S) and bent (B) product. 61% mixed yield.

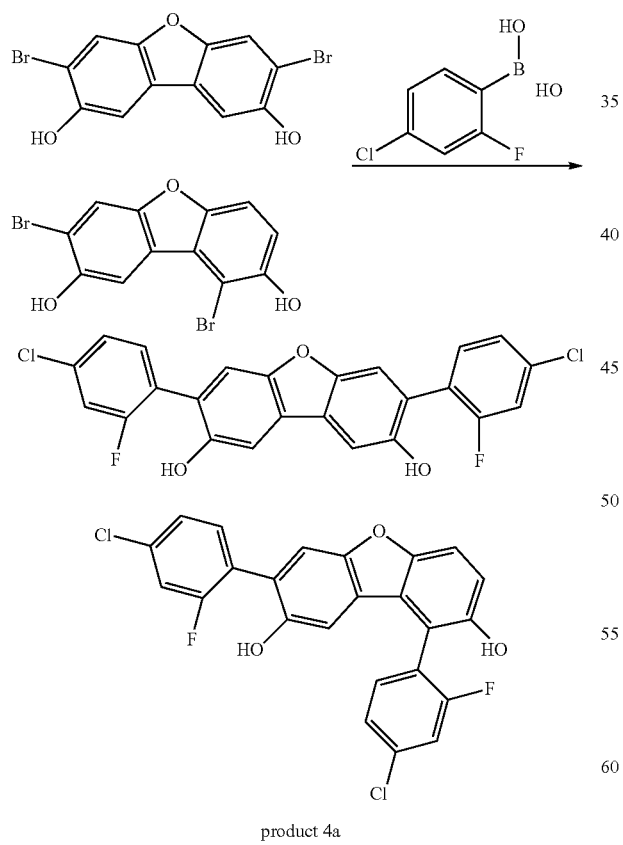

product 4a

Mixed B and S material from the above recrystallization (~75% B, ~25% S) (6.498 g, 18.2 mmol), 4-chloro-2-fluorophenylboronic acid (6.960 g, 39.9 mmol), 77 mL water, 1060 mL toluene, 145 mL ethanol and potassium carbonate (14.535 g, 105.2 mmol) are sparged with nitrogen for 40 minutes. Tetrakistriphenylphosphinepalladium(0) (1.00 g, 0.895 mmol) is quickly added and the mixture heated to 66° C. overnight. The temperature of the reaction is increased to 96° C. for 2 hours then cooled, partitioned with water washes, then the organic layer is preabsorbed to 86 g of Celite® for EtAc/hexanes chromatography on silica. The product 4b is separated as the leading band in the chromatography and is identified by UPLC/MS and 1H-nmr spectroscopy. Yield 1.8 grams, 21%.

(b) Preparation of core trifuran 3,12-dichlorobenzo[2,3][1]benzofuro[5,6-b][1]benzofuro[3,2-e][1]benzofuran (Product 4b)

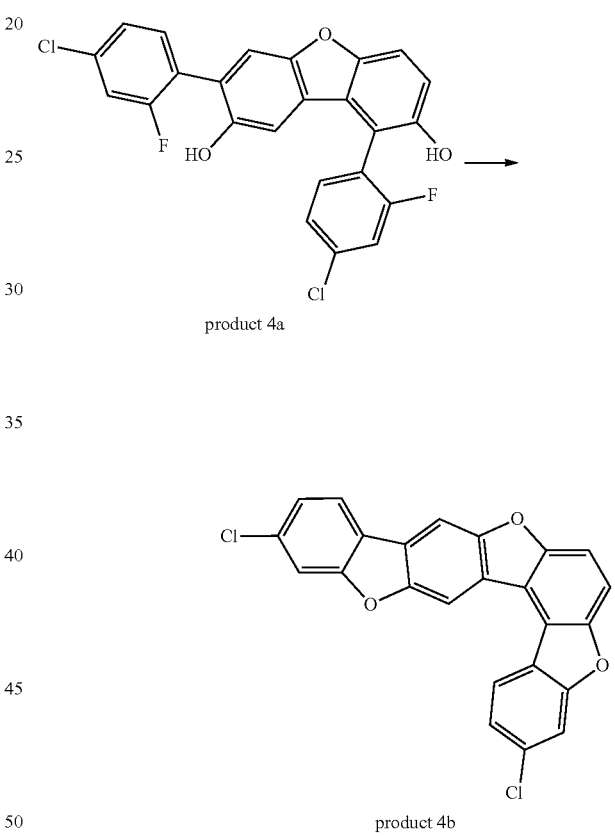

product 4b

Product 4a from above (1.78 g, 0.0039 mol), potassium carbonate (1.18 g, 0.0086 mol) and 45 mL 1-methyl-2-pyrrolidinone were combined in a nitrogen filled drybox and heated to 120° C. for 2 hours, cooled, diluted with water and the resultant solid filtered. The recovered filter cake was washed with acetonitrile and water and dried to give 1.39 g of poorly soluble product 4b. 85% yield.

(c) Preparation of emitter material N³,N³,N¹²,N¹²-tetra([1,1'-biphenyl]-4-yl)benzo[2,3][1]benzofuro[5,6-b][1]benzofuro[3,2-e][1]benzofuran-3,12-diamine, Compound IB-3

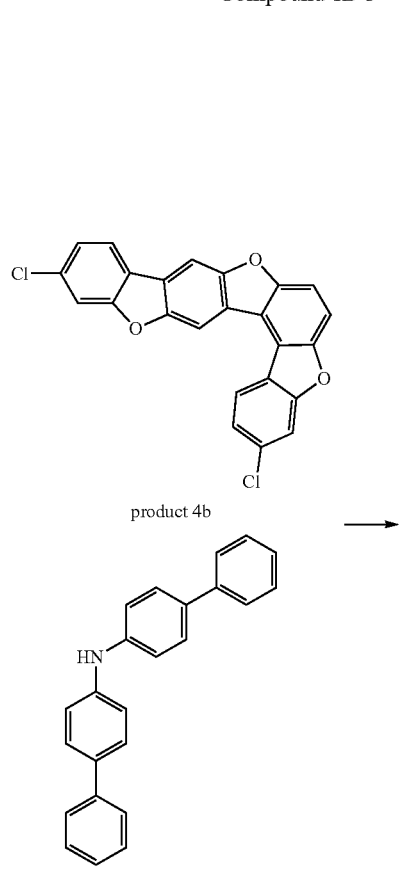

product 4b

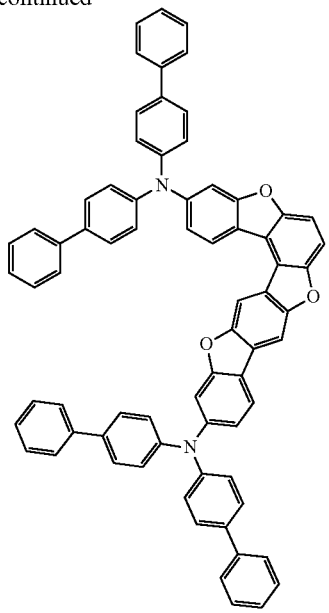

In a nitrogen filled drybox Pd$_2$DBA$_3$ (0.0630 g, 0.0688 mmol), tri-t-butylphosphine (0.0322 g, 0.1592 mmol), sodium-t-butoxide (0.3150 g, 3.277 mmol), product 4b from above (0.40.5 g, 0.965 mmol), secondary amine (0.6790 g, 2.113 mmol) and 17.5 mL toluene were combined and heated to 90° C. for 4 hrs. The reaction mixture was eluted through basic alumina and Florisil® with toluene. Silica column chromatography eluting with toluene/hexanes, and recrystallization from toluene/n-propanol gave 280 mg of product Compound IB-3. 29% yield identified by UPLC/MS and 1H-nmr spectroscopy.

Synthesis Example 21

This example illustrates the preparation of a compound having Formula I, N³,N¹⁰-bis(4-tert-butylphenyl)-N³,N¹⁰-di([1¹,2¹:2⁴,3¹-terphenyl]-1⁴-yl)benzo[2,3][1]benzofuro[5,6-b][1]benzofuro[2,3-f][1]benzofuran-3,10-diamine, Compound IB-2.

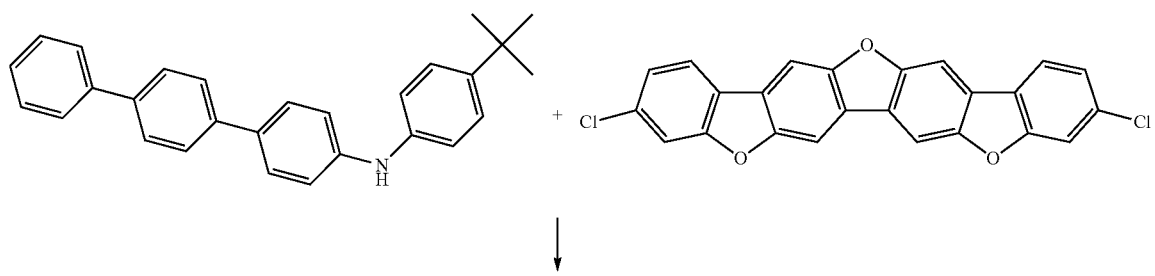

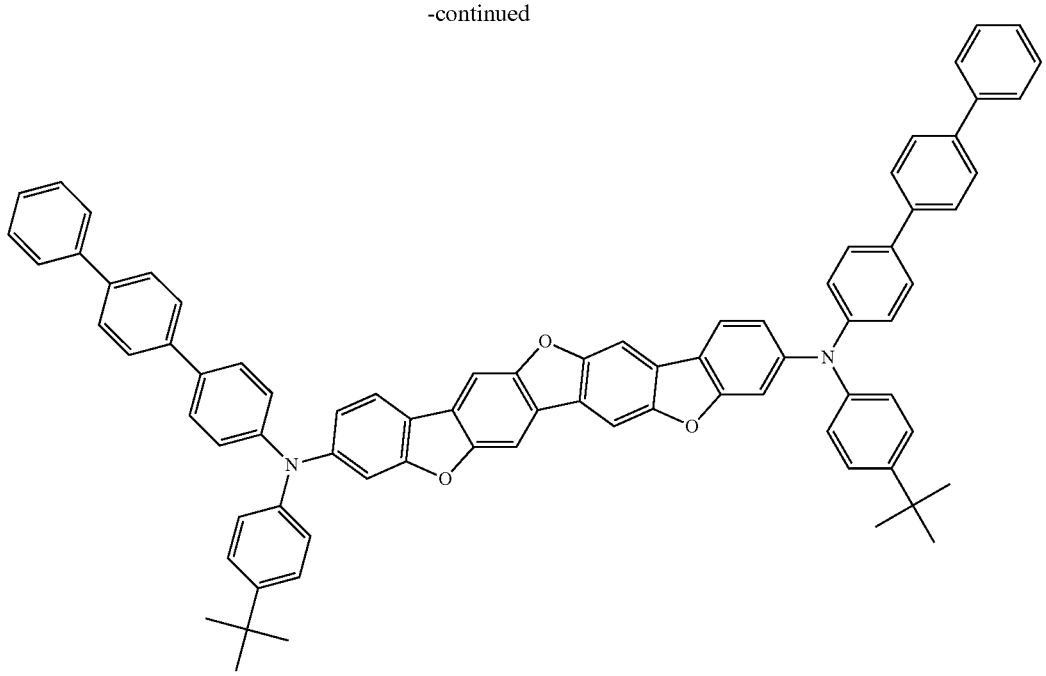

0.42 g of trifuran core dichloride 3,10-dichlorobenzo[2,3][1]benzofuro[5,6-b][1]benzofuro[2,3-f][1]benzofuran, 0.76 g of sec. amine are mixed as solids in a nitrogen filled glove box. 0.2 g Pd$_2$DBA$_3$ 0.09 g P(t-Bu)3 and 0.25 g t-BuONa are also added and all slurried into 100 mL toluene. The mixture is heated at 90° C. under nitrogen overnight. Cool the solution and then evaporate down and load onto a stacked basic-alumina/acidic-alumina/Florisil® plug and elute with DCM to a bright blue PL soln. Evaporate down to low volume then add toluene and warm and let stand to generate a poorly soluble pale yellow solid. Filter the yellow solid and pump dry. Final recrystallization from hot toluene and suction drying gives 0.75 g pale yellow crystalline material Compound IB-2, identified by UPLC/MS and 1H-nmr spectroscopy.

Synthesis Example 22

This example illustrates the preparation of a compound having Formula I, Compound IA-46.

Part 1: Synthesis of Dichlorocarbazolocarbazole Precursor 5

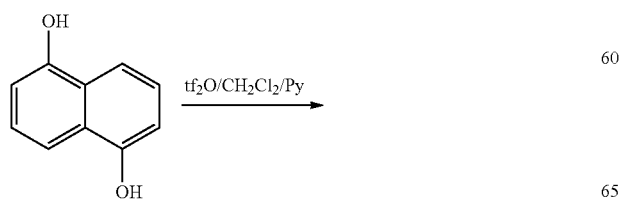

-continued

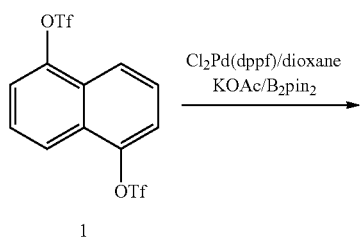

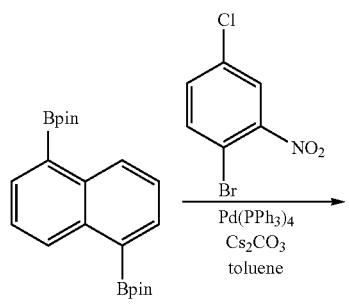

-continued

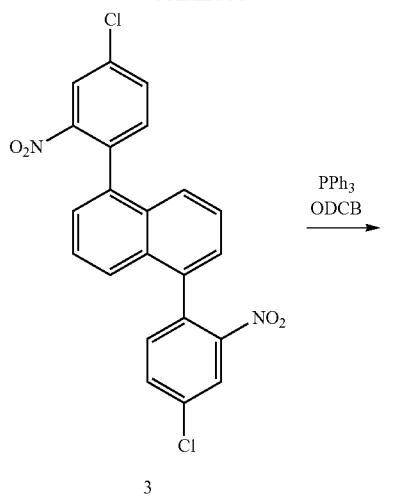

3

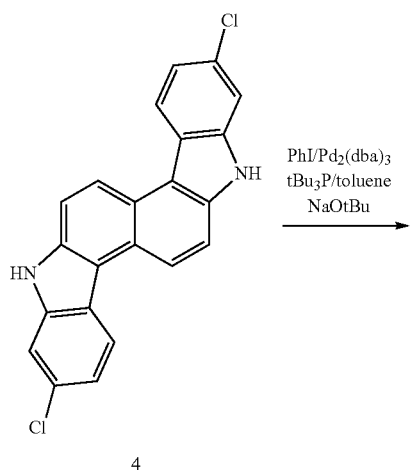

4

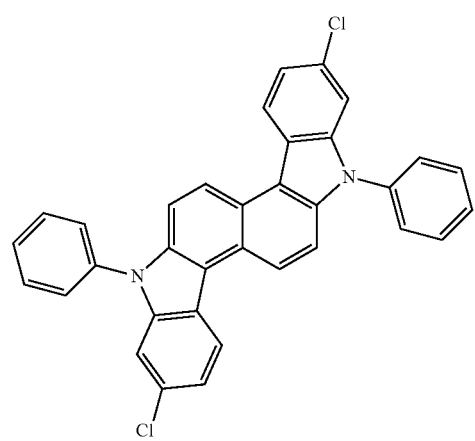

5

(a) 1,5-Bis(trifluoromethanesulfonyloxy)naphthalene (1)

Pyridine (28 g, 28.5 ml, 354.5 mmole) was added to a stirred suspension of 1,5-dihydroxynapthalene (11.35 g, 70.89 mmole) in 500 ml of dichloromethane in 3-neck 1 L under nitrogen atmosphere. After that triflic anhydride (50 g, 177 mmole) was added dropwise to a mixture cooled with water/ice bath and the resulting suspension allowed to warm gradually to ambient temperature under nitrogen atmosphere. The mixture was poured into 200 ml of water and stirred at ambient temperature for 10 min. Organic phase separated, aqueous layer extracted with dichloromethane. Combined organic layers washed with diluted aqueous hydrochloric acid followed by aqueous sodium bicarbonate. Organic layer was passed through a filter filled with silica gel eluting with dichloromethane. Solvent was evaporated using rotary evaporator to a volume approximately 30 ml and the formed precipitate filtered and dried in vacuum to give 20.5 g (41.17 mmole, 68%) of 1,5-bis(trifluoromethanesulfonyloxy)naphthalene 1. $^1$H-NMR (CDCl$_3$, 500 MHz): 7.63 (d, 2H, J=8 Hz), 7.71 (t, 2H, J=8 Hz), 8.15 (d, 2H, J=8 Hz). MS: MH+=425.

(b) 1,5-Naphthalenediboronic Acid Pinacol Ester (2)

A mixture of 1,5-bis(trifluoromethanesulfonyloxy)naphthalene 1 (7 g, 16.5 mmole), bis(pinacolato)diboron (12.57 g, 49.5 mmole), Cl$_2$Pd(dppf) (603 mg, 0.825 mmole, 5 mol %), anhydrous potassium acetate (9.7 g, 99 mmole) in dry 1,4-dioxane (200 ml) was stirred at 100° C. for 3.5 hours. After that reaction mixture was cooled down and passed through a short plug of Celite® eluting with toluene. Solvents evaporated using rotary evaporator to a volume approximately 15 ml, precipitate collected by filtration and dried in vacuum to give 1,5-naphthalenediboronic acid pinacol ester 2 (5.92 g, 15.6 mmole, 94%). $^1$H-NMR (CDCl$_3$, 500 MHz): 1.44 (s, 24H), 7.52 (dd, 2H, J1=7 Hz, J2=8 Hz), 8.08 (dd, 2H, J1=7 Hz, J2=1 Hz), 8.90 (d, 2H, J=8 Hz). MS: MH+=391.

(c) 1,5-Bis(4-chloro-2-nitro)-naphthalene (3)

A mixture of 1,5-naphthalenediboronic acid pinacol ester 2 (2.55 g, 6.71 mmole totally), 1-bromo-4-chloro-2-nitrobenzene (6.25 g, 26.4 mmole totally), cesium carbonate (8.75 g, 26.86 mmole totally), Pd(PPh$_3$)$_4$ (0.819 g, 0.709 mmole totally) in toluene (130 ml totally) was stirred under nitrogen atmosphere at 110° C. until consumption of starting materials by TLC/HPLC. After that reaction mixture was cooled down, passed through a filter filled with silica gel and Celite® eluting with dichloromethane. Crude product was purified by chromatography on silica gel column using gradient elution with mixtures of hexanes and dichloromethane. Fractions containing the desired product combined, eluent evaporated to volume approximately 10 ml, precipitate collected by filtration, dried in vacuum to afford 1,5-bis(4-chloro-2-nitro)-naphthalene 3 as a mixture of atropoisomers (1.928 g, 4.39 mmole, 65%). $^1$H-NMR (CDCl$_3$, 500 MHz): 7.35 (m, 2H), 7.43-7.54 (m, 6H), 7.71 and 7.74 (atropoisomers, dd, 2H, J1=8 Hz, J2=2 Hz), 8.11 and 8.14 (d, 2H, J=2 Hz). MS: MH+=439.

(d) 3,10-dichloro-5,12-H-carbazolo[4,3-c]carbazole (4)

A mixture of 1,5-bis(4-chloro-2-nitro)-naphthalene 3 (3.322 g, 7.57 mmole), triphenylphosphine (9.9 g, 37.8 mmole) in 1,2-dichlorobenzene (100 ml) was heated at 180° C. under nitrogen atmosphere until consumption of starting material for 8 hours. After that reaction mixture was cooled down, diluted with hexanes (approximately 200 ml) and loaded on silica gel column eluting with hexanes to remove excess of triphenylphosphine followed by elution with tetrahydrofuran. Tetrahydrofuran was evaporated using rotary evaporator to residual volume approximately 20 ml, precipitate collected by filtration, washed with small amount of tetrahydrofuran, dried in vacuum to give a mixture of 3,10-dichloro-5,12-H-carbazolo[4,3-c]carbazole 4 with triphenylphosphine oxide (3.15 g, ratio 1:1.46 by NMR) that was used for the next step without further purification. $^1$H-NMR (DMSO-$d_6$, 500 MHz): 7.32 (dd, 2H, J1=8 Hz, J2=2 Hz), 7.70 (d, 2H, J=2 Hz), 7.96 (d, 2H, J=8 Hz), 8.67 (d, 2H, J=8 Hz), 8.86 (d, 2H, J=8 Hz), 11.85 (s, 2H). MS: MH+=375.

(e) 3,10-Dichloro-5,12-diphenyl-5,12-H-carbazolo [4,3-c]carbazole (5)

A mixture of crude 3,10-dichloro-5,12-H-carbazolo[4,3-c]carbazole 4 (3.15 g, 1:1.46 mixture with triphenylphosphineoxide), iodobenzene (7.72 g, 37.85 mmole), Pd$_2$(dba)$_3$ (0.693 g, 0.757 mmole), tri-tert-butyl-phosphine (0.306 g, 1.1514 mmole) and sodium tert-butoxide (3.63 g, 38 mmole) in dry toluene (200 ml) was stirred with heating at 110° C. under nitrogen atmosphere for 2 hours. After that the mixture was cooled down, additional amount of iodobenzene (3 g), Pd$_2$(dba)$_3$ (0.2 g) and tri-tert-butyl-phosphine (0.1 g) added and stirring with heating at 110° C. continued under nitrogen atmosphere for additional 40 minutes until nearly complete consumption of starting material by HPLC. After that reaction mixture was cooled down, filtered, precipitate was washed consecutively with toluene, methanol, water, methanol and dried in vacuum to give 3,10-dichloro-5,12-diphenyl-5,12-H-carbazolo[4,3-c]carbazole (1.3 g, purity 99.93% by HPLC). Toluene filtrate was partially evaporated using rotary evaporator and additional amount of the product (0.176 g) collected by filtration. Yield—1.394 g (2.64 mmole, 35% over two steps). $^1$H-NMR (CD$_2$Cl$_2$, 500 MHz): 7.43 (dd, 2H, J1=9 Hz, J2=2 Hz), 7.55 (s, 2H, J=2 Hz), 7.63 (t, 2H, J=7 Hz), 7.68 (d, 4H, J=7.5 Hz), 7.75 (t, 4H, J=6 Hz), 7.85 (d, 2H, J=9 Hz), 8.63 (d, 2H, J=8 Hz), 8.92 (d, 2H, J=9 Hz). MS: MH+=527.

Part 2: Synthesis of 7,14-dihydro-N2,N9-bis([1,1'-biphenyl]-4-yl-)-N2,N9-7,14-tetraphenylcarbazolo [4,3-c]carbazole-2,9-diamine, Compound IA-46

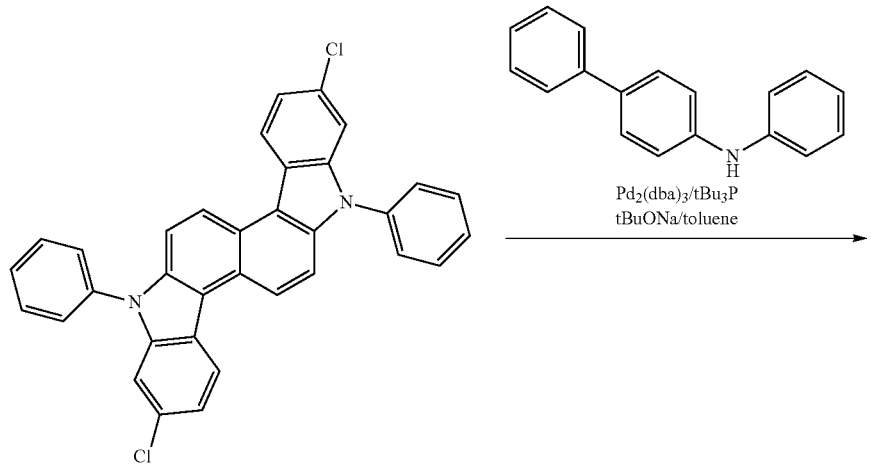

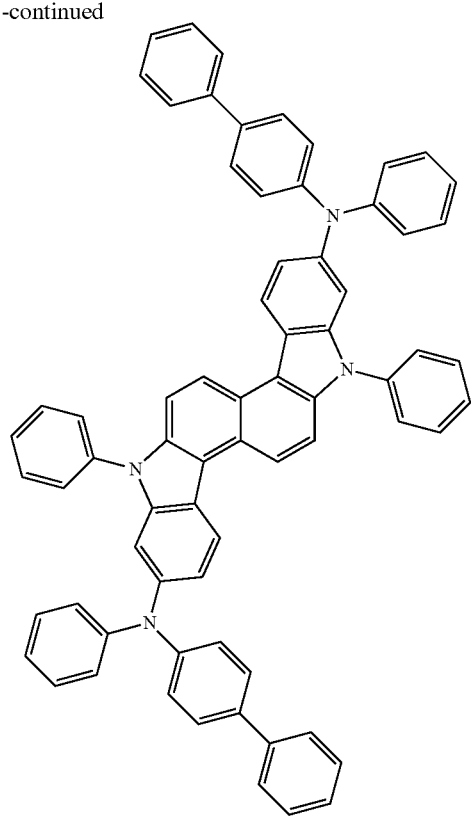

To a mixture of dichlorodiphenylcarbazolocarbazole 5 (0.4 g, 0.758 mmole) N-phenyl-[1,1'-biphenyl]-4-amine (0.557 g, 2.274 mmole) in toluene (40 ml) was added a mixture of Pd$_2$(dba)$_3$ (0.069 g, 0.0758 mmole) and tri-tert-butyl-phosphine (0.031 g, 0.1516 mmole) in dry toluene (20 ml) followed by addition of sodium tert-butoxide (0.33 g, 3.44 mmole). Resulting mixture was stirred with heating at 110° C. under nitrogen atmosphere for 2 hours. After that the mixture was cooled down, water (100 ml) added and the mixture stirred in the air for 20 min. Organic phase separated, passed through a filter filled with basic alumina, Florisil®, silica gel and Celite® eluting with toluene. The residue after evaporation of solvents was redissolved in dichloromethane, absorbed on Celite® and subjected to chromatography on silica gel column using gradient elution with mixtures of hexanes and dichloromethane. Fraction containing the product were combined, eluent evaporated to minimal volume, precipitate collected by filtration and dried. The product was further purified by chromatography on basic alumina column using dichloromethane as an eluent followed by precipitation of dichloromethane solution (30 ml) with methanol (200 ml), collecting precipitate, drying in vacuum. Yield—246 mg. $^1$H-NMR (toluene-d$_8$, 500 MHz): 6.89 (t, 2H, J=8 Hz), 7.10-7.14 (m, 12H), 7.23 (t, 4H, J=8 Hz), 7.27-7.29 (m, 10H), 7.38-7.41 (m, 5H), 7.46 (d, 4H, J=8 Hz), 7.55 (d, 2H, J=2 Hz), 7.71 (d, 2H, J=9 Hz), 8.62 (d, 2H, J=9 Hz), 8.91 (d, 2H, J=9 Hz). MS: MH+=945. UV-vis in toluene ($\lambda_{max}$, nm, ε): 425 (51800), 403 (42600), 386 (56300). Emission (toluene): 436 nm.

Synthesis Example 23

This example illustrates the preparation of a compound having Formula I, 7,14-dihydro-N2,N9-bis(9,9-dimethyl-9H-fluoren-2-yl)-N2,N9-7,14-tetraphenyl-carbazolo[4,3-c]carbazole-2,9-diamine, Compound IA-47.

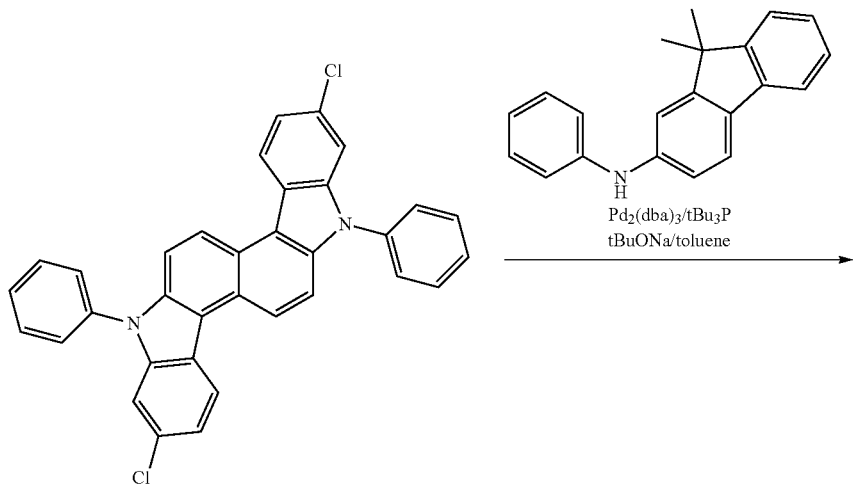

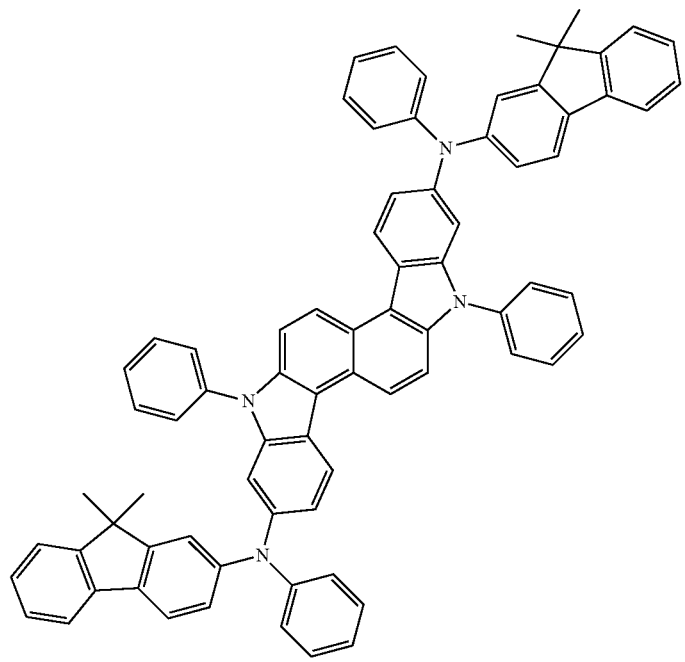

To a mixture of dichlorodiphenylcarbazolocarbazole 5 (made as in Synthesis Example 22) (0.5 g, 0.948 mmole) 9,9-dimethyl-N-phenyl-9H-fluoren-2-amine (0.811 g, 2.84 mmole) in toluene (50 ml) was added a mixture of $Pd_2(dba)_3$ (0.087 g, 0.095 mmole) and tri-tert-butyl-phosphine (0.038 g, 0.19 mmole) in dry toluene (20 ml) followed by addition of sodium tert-butoxide (0.43 g, 4.27 mmole). Resulting mixture was stirred with heating at 110° C. under nitrogen atmosphere for 18 hours. After that the mixture was cooled down, water (30 ml) and dichloromethane (100 ml) added and the mixture stirred in the air for 10-15 min. Organic phase separated, water phase extracted with dichloromethane (2 times-50 ml) and combined organic phase passed through a filter filled with basic alumina, silica gel and Celite® eluting with dichloromethane. The residue after evaporation of solvents was redissolved in dichloromethane, absorbed on Celite® and subjected to chromatography on silica gel column (2 times consecutively) using gradient elution with mixtures of hexanes and dichloromethane to dichloromethane. Fraction containing the desired product were combined, eluent evaporated to minimal volume, precipitate collected by filtration and dried. Yield after first column—532 mg, yield of recovered product after second column—220 mg. $^1$H-NMR (toluene-d$_8$, 500 MHz): 1.28 (s, 12H), 6.90 (t, 2H, J=8 Hz), 6.95 (t, 2H, J=8 Hz), 7.08 (t, 4H, J=8 Hz), 7.12-7.22 (m, 12H), 7.27 (d, 4H, J=8 Hz), 7.33 (d, 4H, J=8 Hz), 7.44 (d, 4H, J=8 Hz), 7.49 (d, 2H, J=8 Hz), 7.51 (d, 2H, J=2 Hz), 7.58 (d, 2H, J=2 Hz), 7.69 (d, 2H, J=9 Hz), 8.61 (d, 2H, J=9 Hz), 8.88 (d, 2H, J=9 Hz). MS: MH+=1026. UV-vis in toluene ($\lambda_{max}$, nm, ε): 430 (52100), 407 (37600), 389 (48500), 351 (46900). Emission (toluene): 441 nm.

Synthesis Example 24

This example illustrates the preparation of a compound having Formula I, 7,14-dihydro-N2,N2,N9,N9-tetra(9,9-dimethyl-9H-fluoren-2-yl)-7,14-diphenyl-carbazolo[4,3-c]carbazole-2,9-diamine, Compound IA-48.

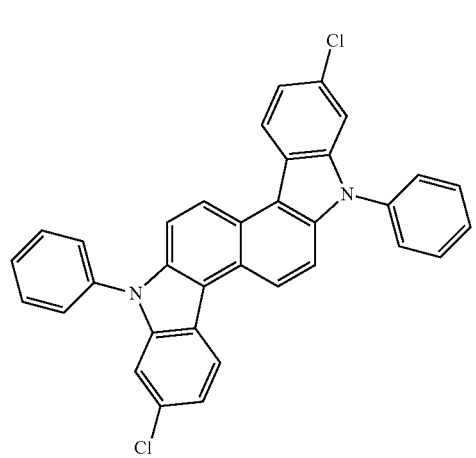
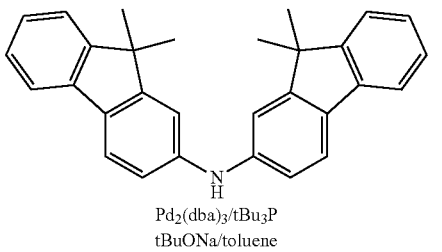

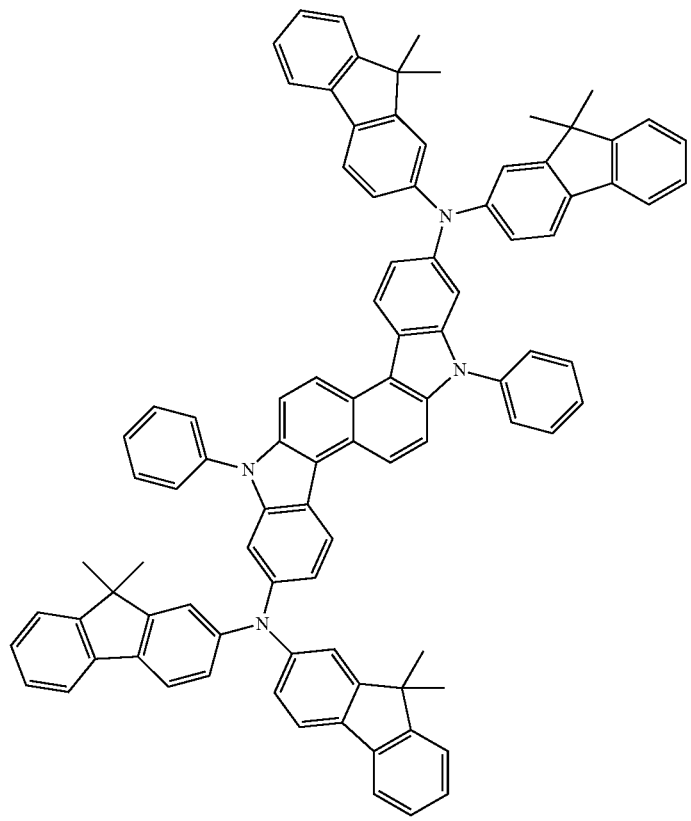

To a mixture of dichlorodiphenylcarbazolocarbazole 5 (made as in Synthesis Example 22) (0.2 g, 0.379 mmole) N-(9,9-dimethyl-9H-fluoren-2-yl)-9,9-dimethyl-9H-fluoren-2-amine (0.457 g, 1.138 mmole) in toluene (50 ml) was added a mixture of $Pd_2(dba)_3$ (0.035 g, 0.038 mmole) and tri-tert-butyl-phosphine (0.015 g, 0.074 mmole) in dry toluene (20 ml) followed by addition of sodium tert-butoxide (0.164 g, 1.706 mmole). Resulting mixture was stirred with heating at 110° C. under nitrogen atmosphere for 17 hours. After that the mixture was cooled down, filtered, precipitate was washed with water, methanol and dried in the air to give 309 mg of crude product. The product was dissolved in 140 ml of 1,2-dichlorobenzene under nitrogen atmosphere at 180 C and hot solution was passed through a filter filled with basic alumina, Florisil® and silica gel eluting with hot 1,2-dichlorobenzene. 1,2-Dichlorobenzene was removed in vacuum using rotary evaporator to a volume of ca 2 ml, 30 ml of toluene added and the product filtered to give 208 mg of the desired compound after drying in vacuum at 60° C. MS: MH+=1258. UV-vis in toluene ($\lambda_{max}$, nm, ε): 436 (33400), 412 (22300), 376 (39800). Emission (toluene): 447 nm.

Synthesis Example 25

This example illustrates the preparation of a compound having Formula I, 7,14-dihydro-N2,N9-bis(9,9-dimethyl- 9H-fluoren-2-yl)-N2,N9-bis(3-tert-butylphenyl)-7,14-diphenyl-carbazolo[4,3-c]carbazole-2,9-diamine, Compound IA-49.

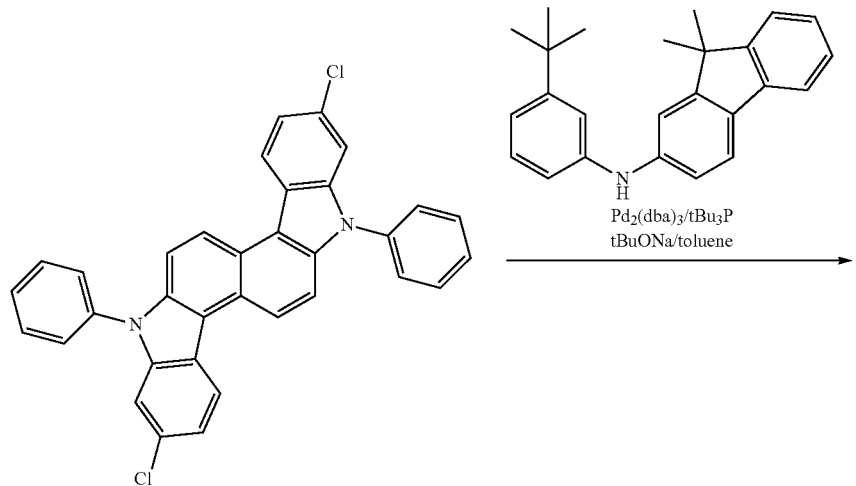

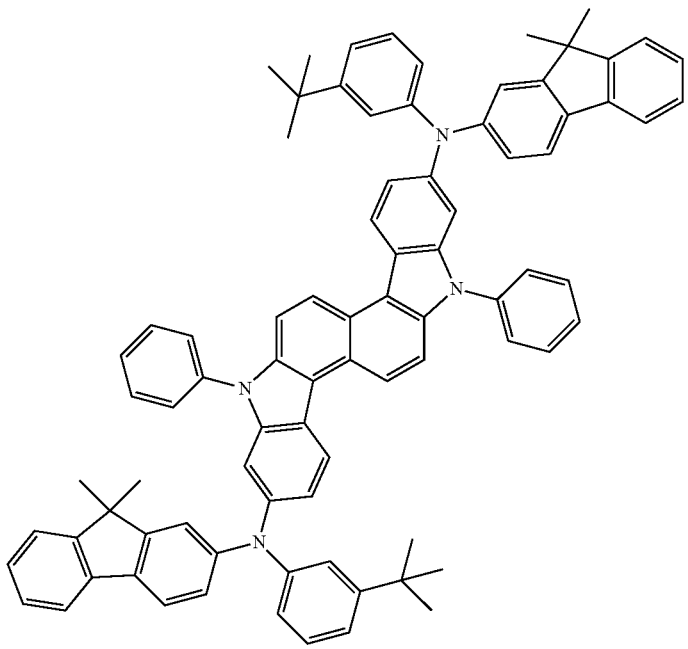

To a mixture of dichlorodiphenylcarbazolocarbazole 5 (made as in Synthesis Example 22) (0.2 g, 0.379 mmole) N-(3-tert-butylphenyl)-9,9-dimethyl-9H-fluoren-2-amine (0.39 g, 1.14 mmole) in toluene (20 ml) was added a mixture of Pd$_2$(dba)$_3$ (0.035 g, 0.038 mmole) and tri-tert-butylphosphine (0.015 g, 0.074 mmole) in dry toluene (20 ml) followed by addition of sodium tert-butoxide (0.16 g, 1.7 mmole). Resulting mixture was stirred with heating at 110° C. under nitrogen atmosphere overnight. After that the mixture was cooled down, water added and the mixture stirred in the air for 30 min. Crude mixture was filtered through a filter filled with silica gel, Florisil®, basic alumina and Celite® eluting with dichloromethane. Fractions containing the product were collected, eluent evaporated. The product was precipitated into methanol and dried in vacuum to give 143 mg of the product. $^1$H-NMR (toluene-d$_8$, 500 MHz): 1.21 (s, 18H), 1.29 (s, 12H), 6.96 (t, 2H, J=8 Hz), 7.01-7.03 (m, 2H), 7.14-7.22 (m, 10H), 7.24-7.29 (m, 6H), 7.45-7.50 (m, 6H), 7.56 (d, 2H, J=2 Hz), 7.63-7.67 (m, 6H), 8.62 (d, 2H, J=9 Hz), 8.86 (d, 2H, J=9 Hz). MS: MH+=1138. UV-vis in toluene ($\lambda_{max}$, nm, ε): 432 (67400), 409 (48000), 389 (58300), 354 (53300). Emission (toluene): 442 nm.

Synthesis Example 26

This example illustrates the preparation of a compound having Formula III, 7,14-dihydro-N2,N9-bis(4-(2-benzofuranyl)benzene)-N2,N9-bis(4-isopropylphenyl)-7,14-diphenyl-carbazolo[4,3-c]carbazole-2,9-diamine, Compound III-11.

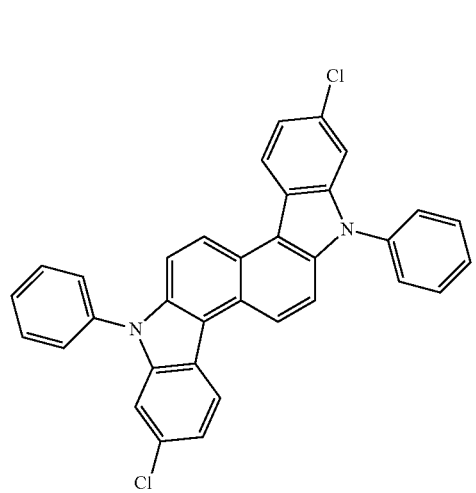
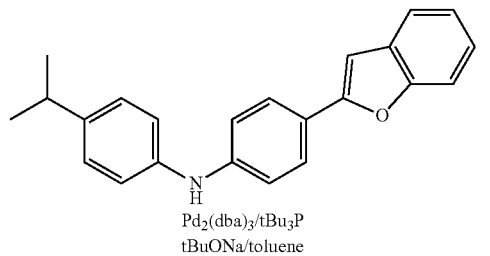

5

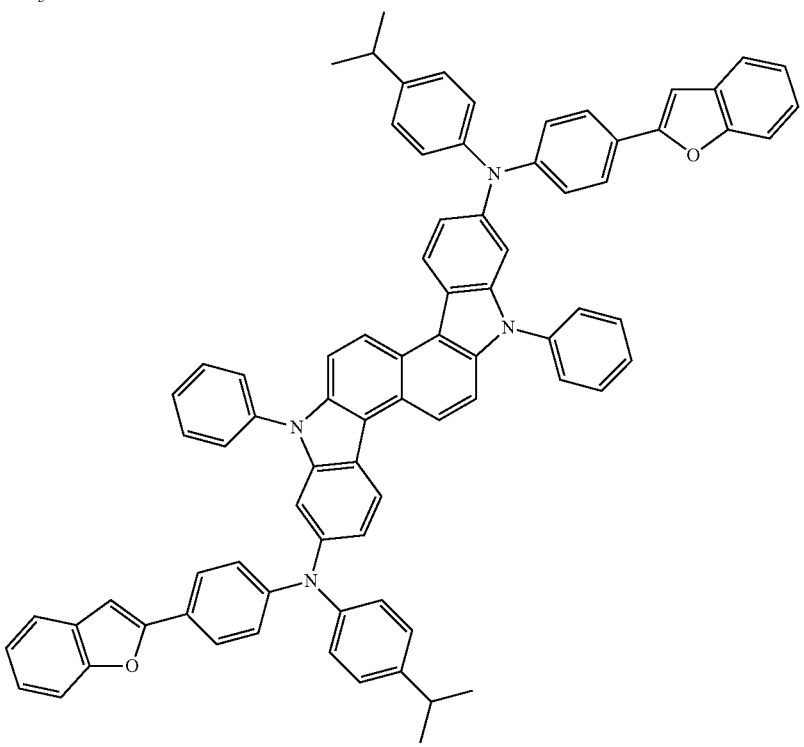

A mixture of dichlorodiphenylcarbazolocarbazole 5 (made as in Synthesis Example 22) (0.119 g, 0.225 mmole) N-(4-isopropylphenyl)-4-(2-benzofuranyl)benzeneamine (0.162 g, 0.495 mmole), tert-butoxide (0.065 g, 0.675 mmole), Pd$_2$(dba)$_3$ (0.021 g, 0.023 mmole) and tri-tert-butyl-phosphine (0.009 g, 0.045 mmole) in dry toluene (25 ml) was stirred with heating at 110° C. under nitrogen atmosphere for 16 hours. After that the mixture was cooled down and filtered through a filter filled with silica gel eluting with dichloromethane. The residue after evaporation of solvents was absorbed on Celite® and subjected to chromatography on silica gel column using gradient elution with mixtures of hexanes and dichlromethane to dichlorometh-ane. Fractions containing the product combined, eluent evaporated to minimal volume, precipitate collected by filtration, dried in vacuum to give 120-140 mg of the product. The product was additionally purified by chromatography on column filled with basic alumina eluting with dichloromethane. Fractions containing pure product by HPLC were combined, eluent evaporated to minimal volume, precipitate collected by filtration and dried in vacuum to give 42 mg of the product. MS: MH+=1110. UV-vis in toluene ($\lambda_{max}$, nm, ε): 429 (69300), 407 (48000), 390 (59300), 371 (74600). Emission (toluene): 442 nm.

Synthesis Example 27

This example illustrates the preparation of a compound having Formula III, Compound III-9.

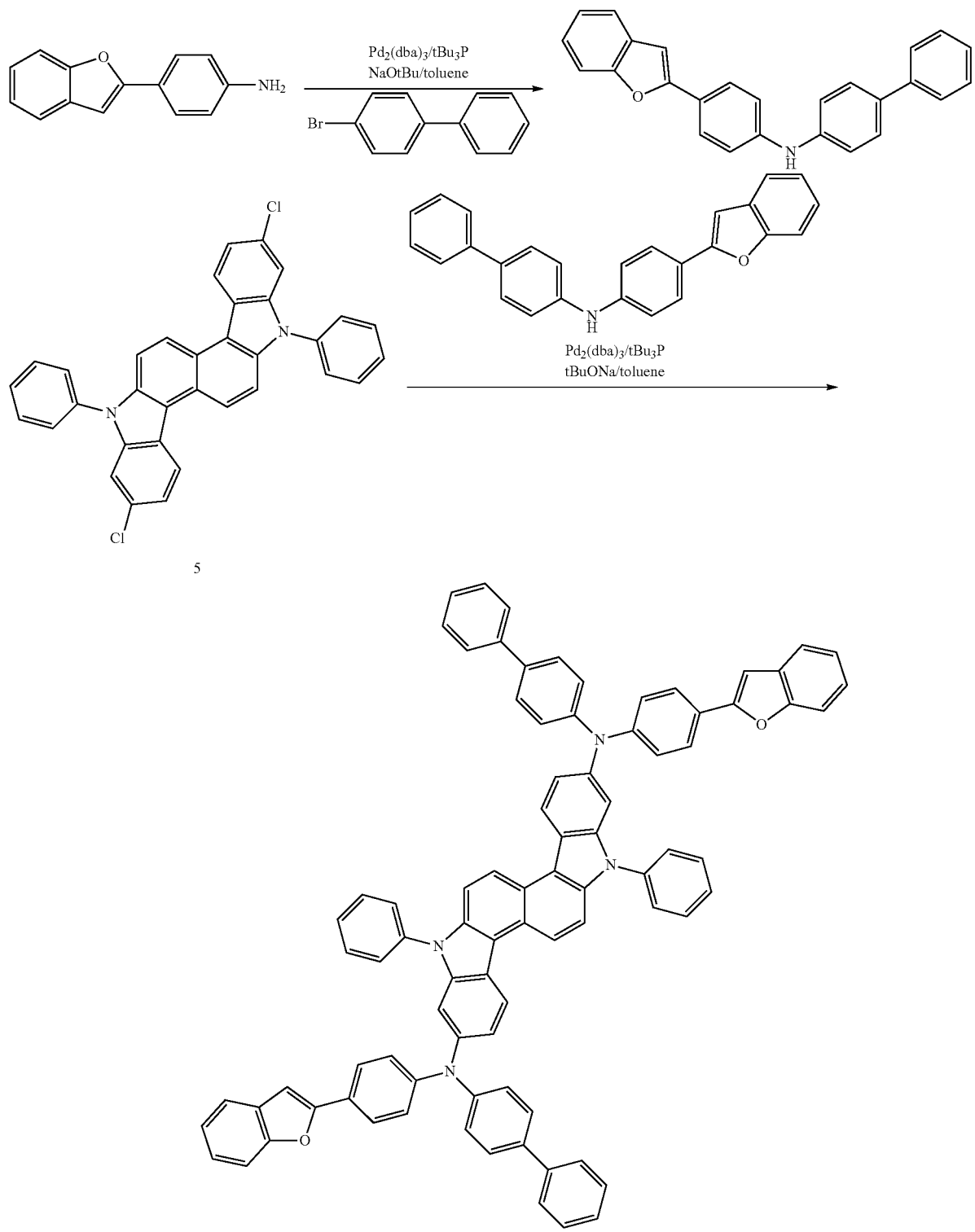

(a) N-([1,1'-Biphenyl]-4-yl-)-4-(benzofuranyl)benzeneamine

To a mixture of 4-(2-benzofuranyl)-benzenamine (0.67 g, 3.202 mmole), 4-bromobiphenyl (0.746 g, 3.202 mmole) in dry toluene (100 ml) a mixture of $Pd_2(dba)_3$ (0.153 g, 0.167 mmole) and tri-tert-butyl-phosphine (0.070 g, 0.347 mmole) in toluene was added followed by sodium tert-butoxide (0.369 g, 3.84 mmole). The mixture was stirred at 33° C. for overnight followed by addition of water (20 ml). Precipitate was filtered, washed with water, methanol and dried in vacuum to give 0.875 g of N-([1,1'-biphenyl]-4-yl-)-4-(benzofuranyl)benzeneamine with purity 99.81% by HPLC. $^1$H-NMR (toluene-$d_8$, 500 MHz): 5.18 (s, 1H), 6.61 (s, 1H), 6.86 (d, 2H, J=9 Hz), 6.93 (d, 2H, J=9 Hz), 7.08-7.11 (m, 1H), 7.14-7.17 (m, 2H), 7.27 (t, 2H, J=8 Hz), 7.40-7.45 (m, 4H), 7.50 (d, 2H, J=8 Hz), 7.71 (d, 2H, J=9H). MS: MH+=362.

(b) 7,14-dihydro-N2,N9-bis(4-(2-benzofuranyl)benzene)-N2,N9-bis([1,1'-biphenyl]-4-yl-)-7,14-diphenyl-carbazolo[4,3-c]carbazole-2,9-diamine, Compound III-9

To a mixture of dichlorodiphenylcarbazolocarbazole 5 (made as in Synthesis Example 22) (0.3 g, 0.569 mmole) N-([1,1'-biphenyl]-4-yl-)-4-(benzofuranyl)benzeneamine (0.452 g, 1.25 mmole) and sodium tert-butoxide (0.17 g, 1.77 mmole) in toluene (50 ml) was added a mixture of Pd$_2$(dba)$_3$ (0.032 g, 0.028 mmole) and tri-tert-butyl-phosphine (0.015 g, 0.074 mmole) in dry toluene (10 ml). Resulting mixture was stirred with heating at 110° C. under nitrogen atmosphere for 17 hours. After that the mixture was cooled down, filtered, precipitate was washed consecutively with toluene, methanol, water, methanol and dried in vacuum to give 0.582 g of crude product. Crude product was dissolved in 30 ml of 1,2-dichlorobenzene at 180° C. under nitrogen atmosphere, hot solution passed through a filter filled with basic alumina, Florisil®, silica gel and Celite® eluting with toluene to give 0.334 g of the product after cooling solution and collecting precipitate by filtration and then with dichloromethane. Dichloromethane was further diluted with methanol and the formed precipitate collected by filtration to give 87 mg of the product. Total yield—0.421 g. MS: MH+=1178. UV-vis in toluene ($\lambda_{max}$, nm, ε): 430 (70900), 389 (109000), 309 (55500). Emission (toluene): 441 nm.

Synthesis Example 28

This example illustrates the preparation of a compound having Formula III, Compound III-21.

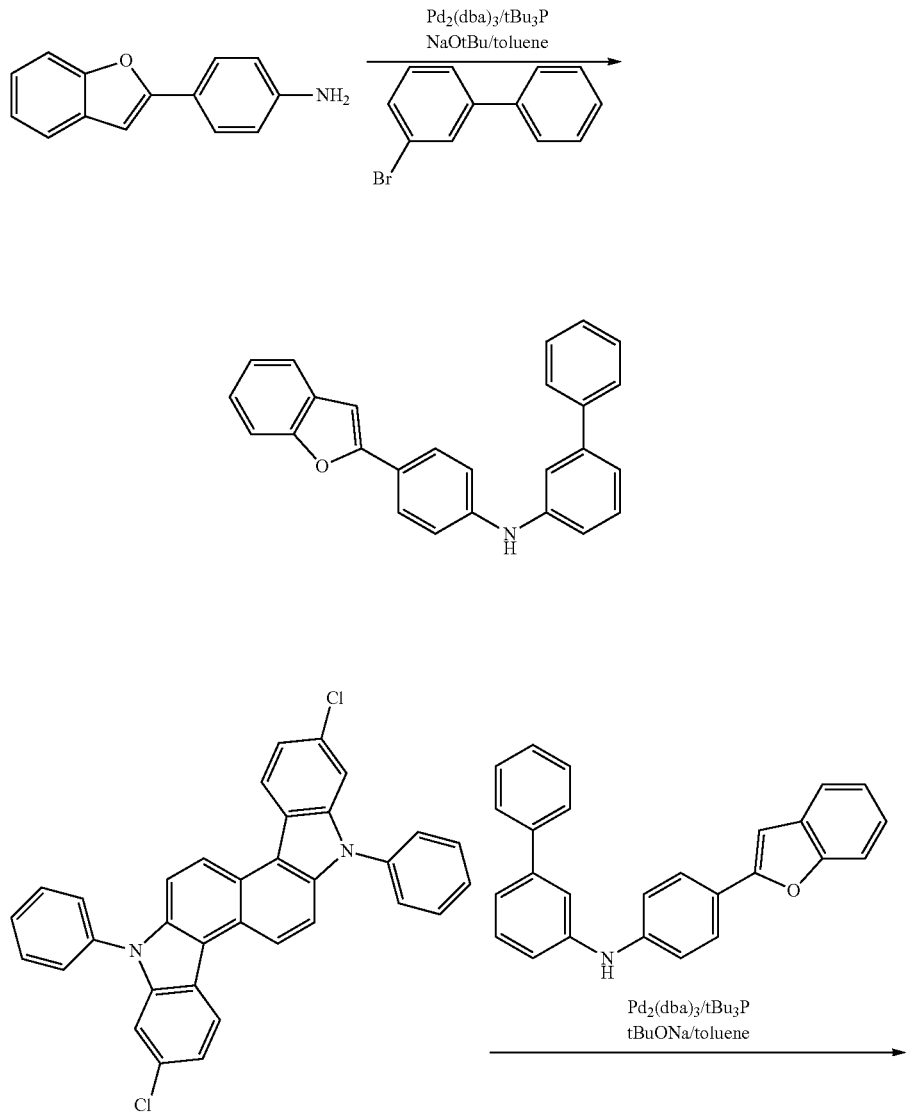

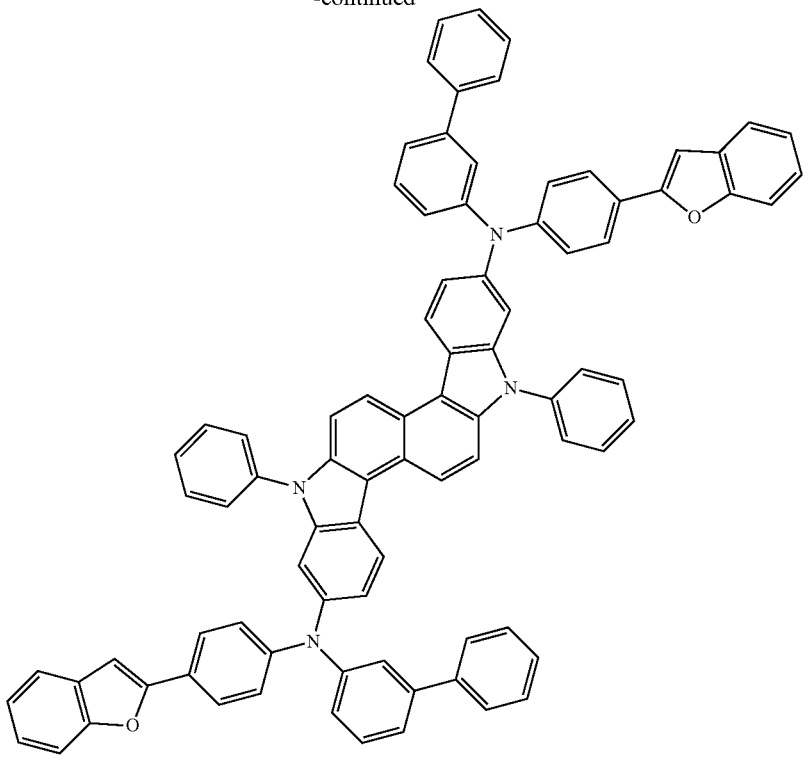

(a) N-([1,1'-Biphenyl]-3-yl-)-4-(benzofuranyl)benzeneamine

To a mixture of 4-(2-benzofuranyl)-benzenamine (0.67 g, 3.202 mmole), 3-bromobiphenyl (0.746 g, 3.202 mmole) in dry toluene (50 ml) a mixture of $Pd_2(dba)_3$ (0.153 g, 0.167 mmole) and tri-tert-butyl-phosphine (0.070 g, 0.347 mmole) in toluene was added followed by sodium tert-butoxide (0.369 g, 3.84 mmole). The mixture was stirred at 33° C. for 16 hours, precipitate filtered, washed with toluene, methanol, water, methanol and dried in vacuum to give 0.668 g of N-([1,1'-biphenyl]-4-yl-)-4-(benzofuranyl)benzeneamine with purity 99.7% by HPLC. $^1$H-NMR (toluene-$d_8$, 500 MHz): 5.20 (s, 1H), 6.59 (s, 1H), 6.87-6.91 (m, 3H), 7.08-7.20 (m, 6H), 7.25 (t, 2H, J=8 Hz), 7.42 (t, 2H, J=8 Hz), 7.50 (d, 2H, J=7 Hz), 7.68 (d, 2H, J=9 Hz). MS: MH+=362.

(b) 7,14-dihydro-N2,N9-bis(4-(2-benzofuranyl)benzene)-N2,N9-bis([1,1'-biphenyl]-3-yl-)-7,14-diphenyl-carbazolo[4,3-c]carbazole-2,9-diamine, Compound III-21

To a mixture of dichlorodiphenylcarbazolocarbazole 5 (made as in Synthesis Example 22) (0.3 g, 0.569 mmole) N-([1,1'-biphenyl]-3-yl-)-4-(benzofuranyl)benzeneamine (0.452 g, 1.25 mmole) and sodium tert-butoxide (0.164 g, 1.708 mmole) in toluene (50 ml) was added a mixture of $Pd_2(dba)_3$ (0.026 g, 0.028 mmole) and tri-tert-butyl-phosphine (0.011 g, 0.054 mmole) in dry toluene (10 ml).

Resulting mixture was stirred with heating at 110° C. under nitrogen atmosphere for 16 hours. After that the mixture was cooled down and stirred at ambient temperature overnight to complete precipitation of the product. Precipitate was collected by filtration, washed consecutively with toluene, methanol, water, methanol and dried in vacuum to give 0.62 g of crude product. Crude product was dissolved in 10 ml of 1,2-dichlorobenzene at 180° C. under nitrogen atmosphere, hot solution was diluted with toluene (20 ml) and passed through a filter filled with basic alumina, Florisil®, silica gel and Celite® eluting with toluene and then with dichloromethane. Toluene and dichloromethane filtrates were diluted with methanol and resulting precipitate collected by filtration to give 0.392 g and 0.079 g of the product correspondingly. Total yield—0.471 g. $^1$H-NMR (toluene-$d_8$, 500 MHz): 6.56 (s, 2H), 6.96-7.23 (m, 33H), 7.27-7.32 (m, 4H), 7.37-7.45 (m, 6H), 7.63 (d, 2H, J=2 Hz), 7.67-7.74 (m, 5H), 8.64 (d, 2H, J=10 Hz), 8.91 (d, 2H, J=10). MS: MH+=1178. UV-vis in toluene ($\lambda_{max}$, nm, ε): 428 (40900), 406 (35300), 389 (51900), 371 (49000). Emission (toluene): 439 nm.

Synthesis Example 29

This example illustrates the preparation of a compound having Formula III, Compound III-10.

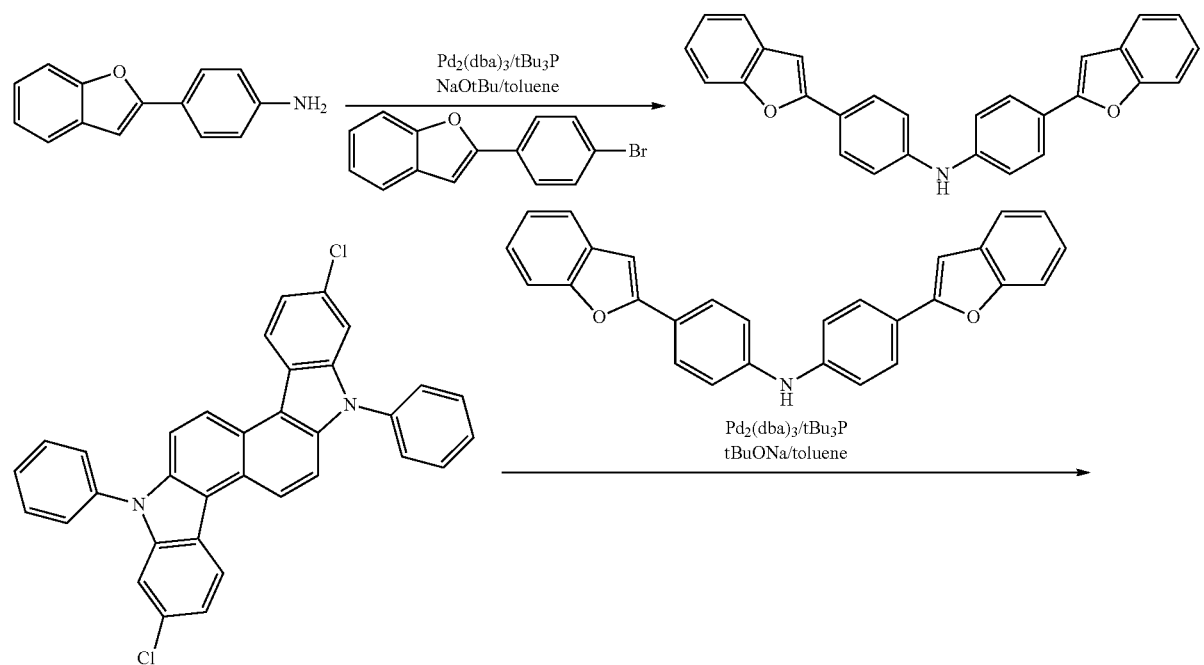
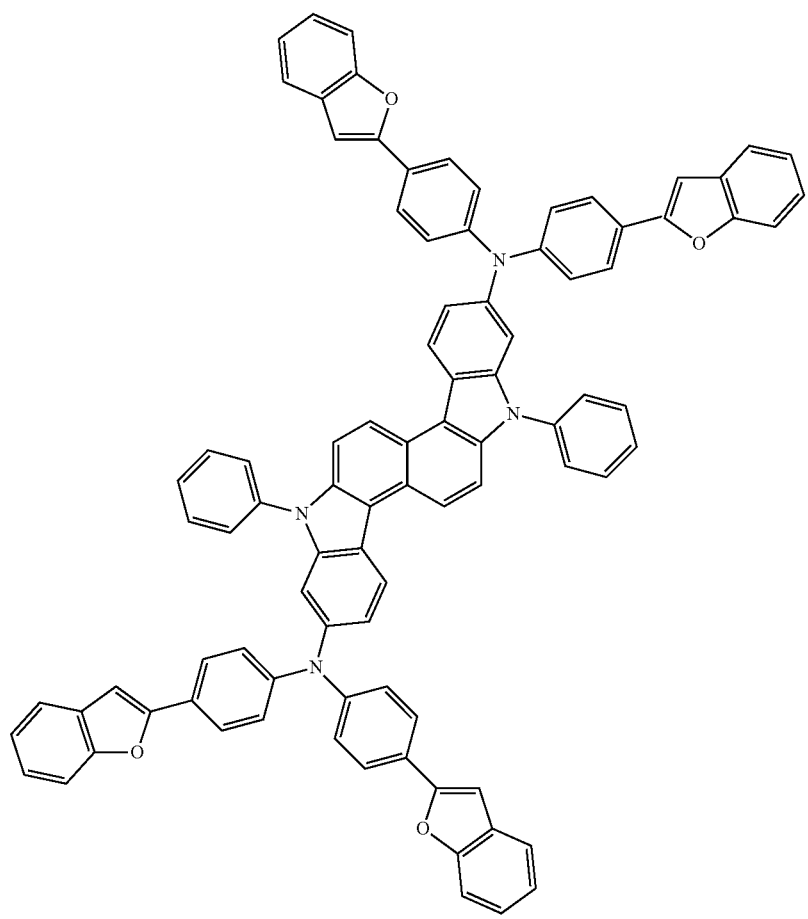

(a) N,N-bis(4-(benzofuranyl)benzene)amine

To a mixture of 4-(2-benzofuranyl)-benzenamine (0.69 g, 3.3 mmole), 2-(4-bromophenyl)benzofuran (0.746 g, 3.87 mmole) in dry toluene (50 ml) a mixture of Pd$_2$(dba)$_3$ (0.151 g, 0.165 mmole) and tri-tert-butyl-phosphine (0.14 g, 0.693 mmole) in toluene was added followed by sodium tert-butoxide (0.59 g, 6.15 mmole). The mixture was stirred at ambient temperature for 2 days, precipitate filtered, washed with toluene, methanol, water, methanol and dried in vacuum to give 0.911 g of crude N,N-bis(4-(benzofuranyl)benzene)amine. Crude material was dissolved in a mixture of toluene and 1,2-dichlorobenzene at elevated temperature under nitrogen atmosphere. Hot solution filtered, crystallized product in 30 min collected by filtration, washed with methanol and dried in vacuum to give 0.624 g of the product. MS: MH+=402.

(b) 7,14-dihydro-N2,N2,N9,N9-tetra(4-(2-benzofuranyl)benzene)-7,14-diphenyl-carbazolo[4,3-c]carbazole-2,9-diamine, Compound III-10

To a mixture of dichlorodiphenylcarbazolocarbazole 5 (made as in Synthesis Example 22) (0.3 g, 0.569 mmole) bis(4-2-benzofuranyl)benzene)amine (0.562 g, 1.4 mmole) in toluene (50 ml) was added a mixture of Pd$_2$(dba)$_3$ (0.032 g, 0.035 mmole) and tri-tert-butyl-phosphine (0.015 g, 0.074 mmole) in dry toluene (10 ml) followed by addition of sodium tert-butoxide (0.17 g, 1.77 mmole). Resulting mixture was stirred with heating at 110° C. under nitrogen atmosphere for 16 hours. After that the mixture was cooled down, filtered, precipitate was washed consecutively with toluene, methanol, water, methanol and dried to give 537 mg of crude product. The product was dissolved in 20 ml of 1,2-dichlorobenzene under nitrogen atmosphere at 180° C., diluted with toluene (30-40 ml) and hot solution was passed through a filter filled with basic alumina, Florisil®, silica gel and Celite® eluting with toluene and then with dichloromethane. Partially eluted product was precipitated by addition of methanol to give 154 mg of solids after drying in vacuum. MS: MH+=1258. UV-vis in toluene ($\lambda_{max}$, nm, ε): 433 (66400), 394 (141000). Emission (toluene): 451 nm.

Synthesis Example 30

This example illustrates the preparation of a compound having Formula III, Compound III-5.

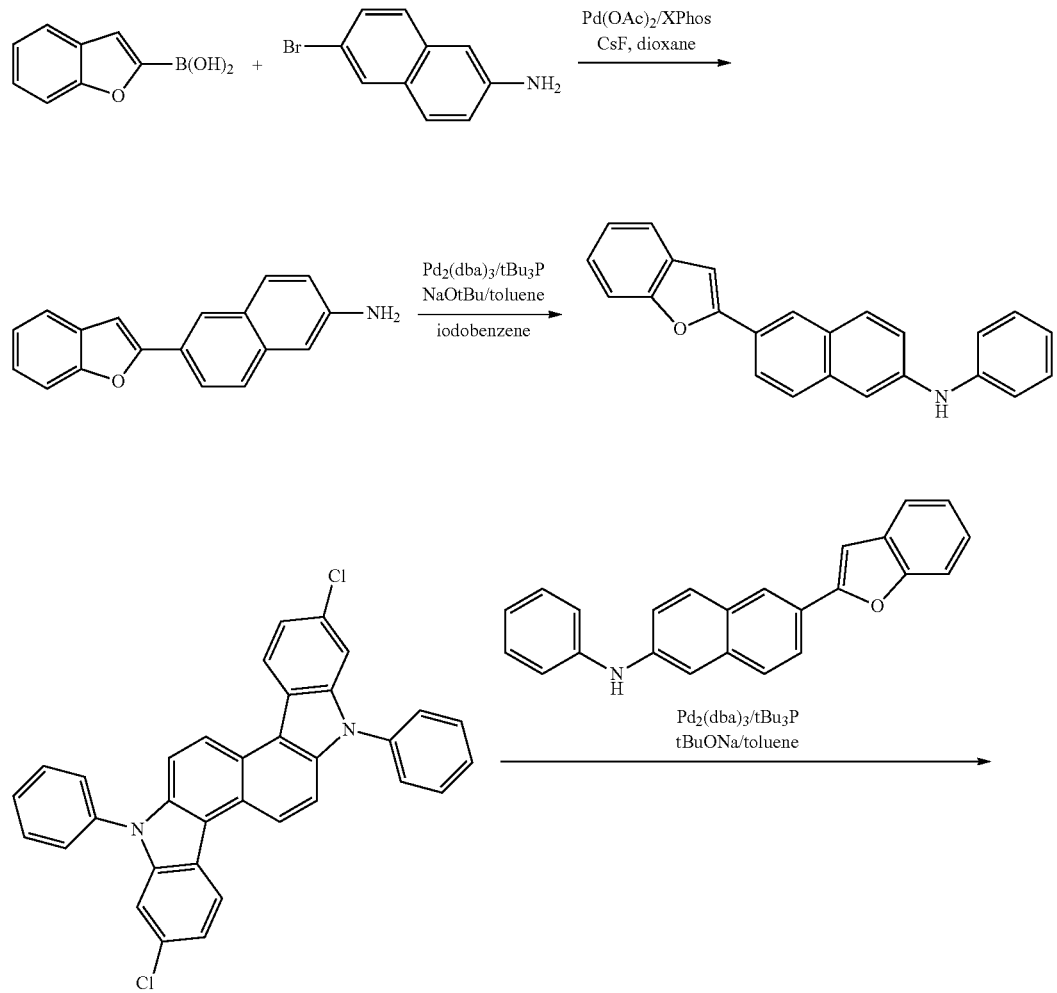

-continued

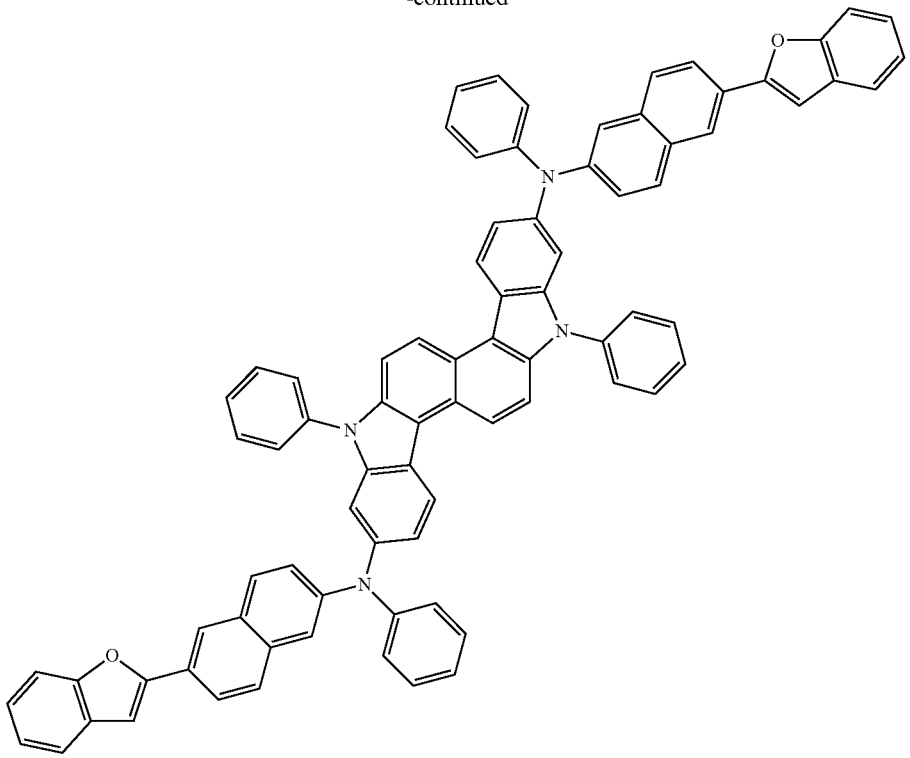

(a) 6-(2-Benzofuranyl)naphthylamine

A mixture of benzofuran-2-boronic acid (2.19 g, 13.51 mmole), 6-bromo-2-naphthaleneamine (3 g, 13.51 mmole), cesium fluoride (6.45 g, 42.46 mmole), Pd(OAc)$_2$ (0.1517 g, 0.678 mmole), XPhos (0.676 g, 1.42 mmole) in 1,4-dioxane (60 ml) was stirred at 100° C. for 2 hours totally. After that the mixture was cooled down, passed thorugh a filter filled with silica gel and Celite® eluting with dichloromethane. The residue after evaporation of solvent was absorbed on Celite® and subjected to chromatography purification on silica gel using gradient elution with mixtures of hexanes and dichloromethane to dichloromethane. Fractions containing product collected, eluent evaporated using rotary evaporator to minimal volume, diluted with hexanes. Precipitates formed upon dilution with hexanes and by partial evaporation of filtrates were collected, dried in vacuum to give 1.67 g of the product. $^1$H-NMR (toluene-d$_8$, 500 MHz): 3.01 (s, 2H), 6.47-76.50 (m, 2H), 6.71 (s, 1H), 7.09-7.15 (m, 3H), 7.44-7.46 (d, 2H, J=9 Hz), 7.48 (d, 1H, J=9 Hz), 7.76 (dd, 1H, J1=2 Hz, J2=9 Hz), 8.24 (s, 1H). MS: MH+=260.

(b) N-Phenyl-6-(2-benzofuranyl)naphthylamine

To a mixture of 6-(2-benzofuranyl)naphthylamine (0.829 g, 3.202 mmole), iodobenzene (0.653 g, 3.202 mmole) in toluene (50 ml) was added a mixture of Pd$_2$(dba)$_3$ (0.153 g, 0.167 mmole) and tri-tert-butyl-phosphine (0.070 g, 0.347 mmole) in dry toluene followed by addition of sodium tert-butoxide (0.369 g, 3.84 mmole). Resulting mixture was stirred with heating at ambient temperature under nitrogen atmosphere for 20 hours. After that precipitate was collected by filtration, washed with toluene, methanol, water, methanol, dried in vacuum to give 0.615 g of the product with purity 99.4% by HPLC. $^1$H-NMR (toluene-d$_8$, 500 MHz): 5.21 (s, 1H), 6.72 (s, 1H), 6.88-6.91 (m, 2H), 6.96 (d, 2H, J=8 Hz), 7.13-7.19 (m, 5H), 7.45-7.47 (m, 3H), 7.54 (d, 1H, J=9 Hz), 7.75 (dd, 1H, J1=2 Hz, J2=9 Hz), 8.27 (s, 1H). MS: MH+=336.

(c) 7,14-dihydro-N2,N9-bis((6-(2-benzofuranyl)-2-naphthalenyl))-N2,N9,7,14-diphenyl-carbazolo[4,3-c]carbazole-2,9-diamine, Compound III-5

To a mixture of dichlorodiphenylcarbazolocarbazole 5 (made as in Synthesis Example 22) (0.346 g, 0.656 mmole) N-phenyl-6-(2-benzofuranyl)-2-naphthalenylamine (0.55 g, 1.64 mmole) in toluene (100 ml) was added a mixture of Pd$_2$(dba)$_3$ (0.060 g, 0.0656 mmole) and tri-tert-butyl-phosphine (0.0265 g, 0.1312 mmole) in dry toluene (10 ml) followed by addition of sodium tert-butoxide (0.189 g, 1.967 mmole). Resulting mixture was stirred with heating at 110° C. under nitrogen atmosphere for 23 hours. After that the mixture was cooled down and allowed to stand at ambient temperature overnight for slow product precipitation. Precipitate formed was filtered, washed consecutively with toluene, methanol, water, methanol to give crude product. The product was dissolved in 20 ml of 1,2-dichlorobenzene under nitrogen atmosphere at 180° C. and hot solution was passed through a filter filled with basic alumina, Florisil®, silica gel and Celite® eluting with toluene (100 ml). The product was precipitated from toluene filtrate by addition of methanol (100 ml), collecting precipitate, drying in vacuum to afford 0.282 g of product. $^1$H-NMR (toluene-d$_8$, 500 MHz): 6.56-6.58 (m, 2H), 6.69 (s, 2H), 6.84-7.17 (m, 22H), 7.27-7.30 (m, 5H), 7.34 (d, 2H, J=9 Hz), 7.41-7.46 (m, 5H), 7.56 (d, 2H, J=9 Hz), 7.58 (d, 2H, J=1 Hz), 7.68 (dd, 2H, J1=2 Hz, J2=9 Hz), 7.73 (d, 2H, J=9 Hz), 8.25 (s, 2H), 8.65 (d, 2H, J=9 Hz), 8.93 (d, 2H, J=9 Hz). MS: MH+=1126.

UV-vis in toluene ($\lambda_{max}$, nm, ε): 429 (73000), 407 s (72000), 390 (83100), 369 (66600), 310 (50100). Emission (toluene): 444 nm.

Synthesis Example 31

This example illustrates the preparation of a compound having Formula I, Compound IA-50.

(a) 9,9-Dimethyl-N-(2,4,6-trimethylphenyl)-9H-fluoren-2-amine

To a mixture of 2,4,6-trimethylaniline (8.11 g, 60 mmole), 2-bromo-9,9-dimethylfluorene (15 g, 55 mmole) in toluene (200 ml) was added a mixture of Pd$_2$(dba)$_3$ (0.81 g, 0.88 mmole) and tri-tert-butyl-phosphine (0.36 g, 1.76 mmole) and sodium tert-butoxide (6.34 g, 66 mmole) in dry toluene.

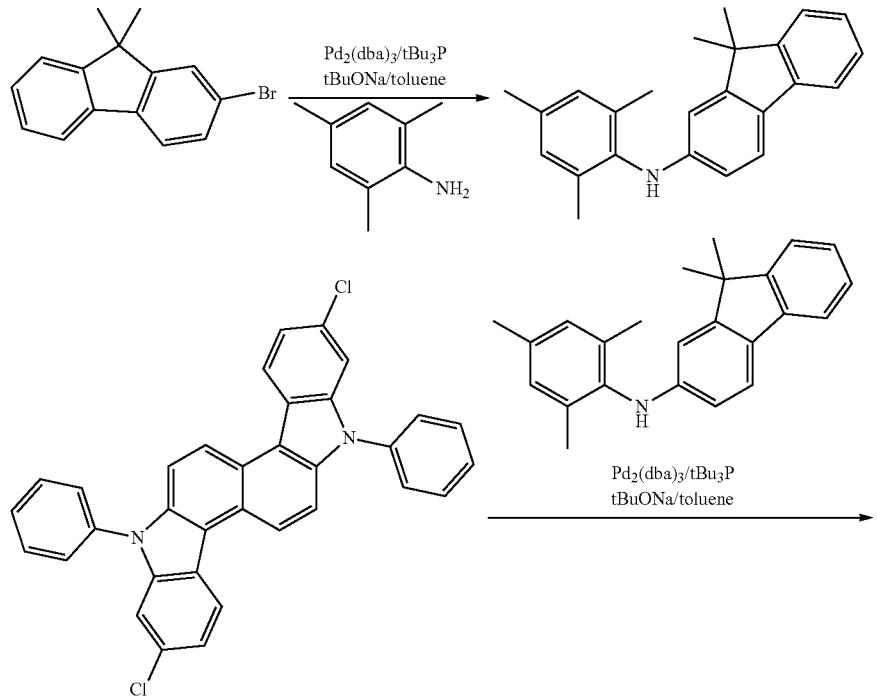

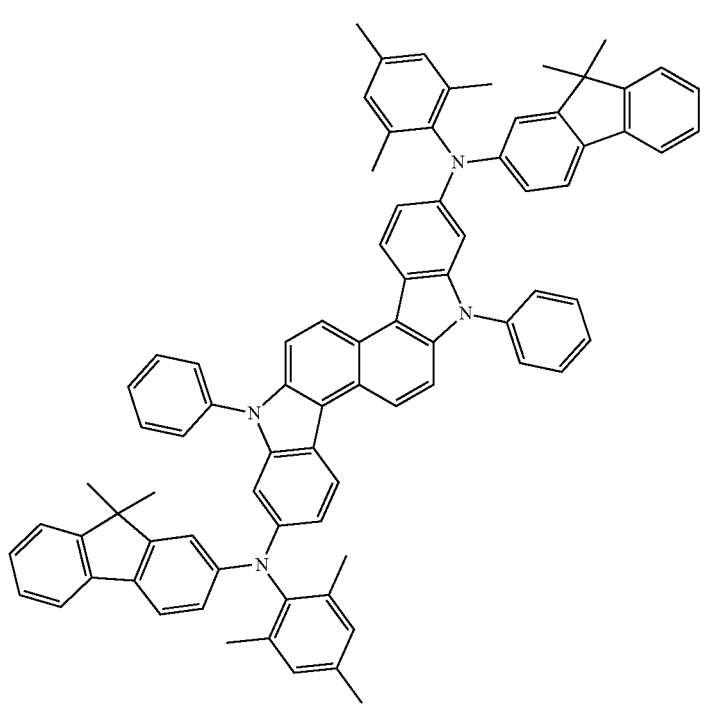

Resulting mixture was stirred under nitrogen atmosphere at ambient temperature overnight. After that the mixture was passed through a filter fileld with silica gel, Florisil®, silica gel and Celite® eluting with toluene. Toluene evaporated using rotary evaporator, the residue dissolved in hexanes and precipitate collected after 1 day to give 11.7 g of the product after drying in vacuum. $^1$H-NMR (toluene-d$_8$, 500 MHz): 1.31 (s, 6H), 2.13 (s, 6H), 2.20 (s, 3H), 4.66 (s, 1H), 6.36 (dd, 1, J1=2 Hz, J2=9 Hz), 6.48 (d, 1H, J=2 Hz), 6.84 (s, 2H), 7.10-7.11 (m, 1H), 7.18-7.22 (m, 2H), 7.41 (d, 1H, J=8 Hz), 7.49 (d, 1H, J=8 Hz). MS: MH+=328.

(b) 7,14-dihydro-N2,N9-bis(9,9-dimethyl-9H-fluoren-2-yl)-N2,N9-bis(2,4,6-trimethylphenyl)-7,14-diphenyl-carbazolo[4,3-c]carbazole-2,9-diamine, Compound IA-50

To a mixture of dichlorodiphenylcarbazolocarbazole 5 (made as in Synthesis Example 22) (0.55 g, 1.04 mmole), 9,9-dimethyl-N-(2,4,6-trimethylphenyl)-9H-fluoren-2-amine (0.75 g, 2.3 mmole) and sodium tert-butoxide (0.3 g, 3.12 mmole) in toluene (80 ml) was added a mixture of Pd$_2$(dba)$_3$ (0.092 g, 0.1 mmole) and tri-tert-butyl-phosphine (0.04 g, 0.2 mmole) in dry toluene. Resulting mixture was stirred with heating at 110° C. under nitrogen atmosphere overnight. After that the mixture was cooled down, water added and the mixture stirred in the air for 30 min. The mixture was filtered through a filter filled with silica gel, Florisil®, basic alumina and Celite® eluting with toluene. The residue after evaporation of toluene using rotary evaporator was purified by consecutive chromatography on silica gel columns using gradient elution with mixtures hexanes and dichloromethane to dichloromethane to give 0.218 g of the desired product. To remove small impurities of competitive coupling with tert-butoxide the product was additionally purified by column chromatography on silica gel followed by crystallization. MS: MH+=1110. UV-vis in toluene ($\lambda_{max}$, nm, ε): 438 (66700), 415 (43000), 390 (54000), 372 (36700), 350 (39300), 322 (41300). Emission (toluene): 454 nm.

Synthesis Example 32

This example illustrates the preparation of a compound having Formula III, Compound III-20.

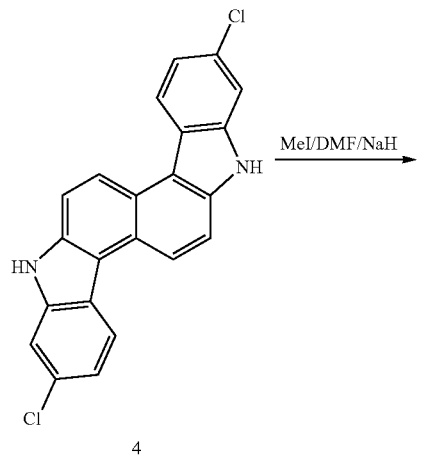

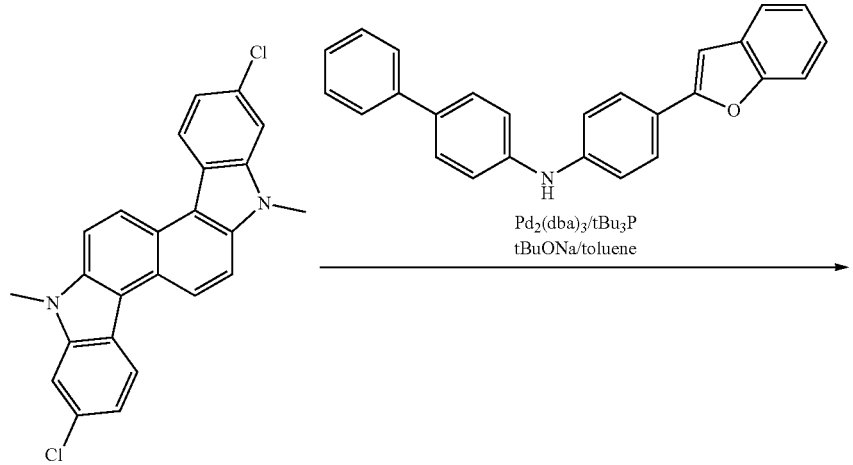

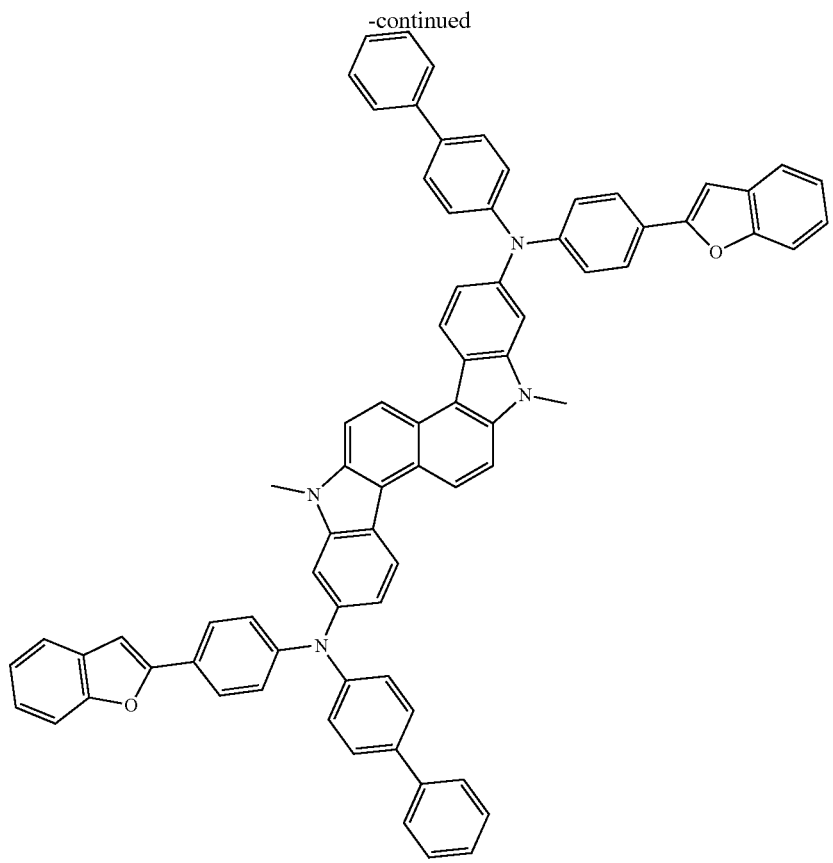

(a) 7,14-dihydro-2,9-dichloro-carbazolo[4,3-c]carbazole-(15)

3,10-Dichloro-5,12-H-carbazolo[4,3-c]carbazole 4 (0.5 g, 1.33 mmole) was dissolved in dimethylformamide (25 ml) under nitrogen atmosphere followed by addition of 60% suspension of sodium hydride in mineral oil (194 mg, 4.85 mmole) at once at ambient temperature and after stirring for 2-5 minutes iodomethane (1.89 g, 13.3 mmole) at once. The mixture was stirred for 4 hours at ambient temperature, quenched with minimal amount of methanol, product filtered, washed carefully with methanol, water, methanol and dried in vacuum to give 0.375 g of crude product that was subjected to complete methylation by adding sodium hydride (90 mg of 60% dispersion in mineral oil) and iodomethane (1 ml) to a suspension of partially alkylated product in dimethylformamide (25 ml) at 70° C. and stirring the reaction mixture at 100° C. for 16 hours followed by second addition of sodium hydride (100 mg) and iodomethane (1 ml) and heating the mixture further at for 100° C. 2 days totally. The mixture was cooled down, quenched with minimal amount of methanol, filtered, washed with methanol and dried to give 0.203 g of 15 that was used for the next step without further purification MS: MH+=403.

(b) 7,14-dihydro-N2,N9-bis(4-(2-benzofuranyl)benzene)-N2,N9-bis([1,1'-biphenyl]-4-yl-)-7,14-dimethyl-carbazolo[4,3-c]carbazole-2,9-diamine, Compound III-20

To a mixture of dichlorodimethylcarbazolocarbazole 15 (0.203 g, 0.503 mmole) N-([1,1'-biphenyl]-4-yl-)-4-(benzofuranyl)benzeneamine (0.4 g, 1.11 mmole) and sodium tert-butoxide (0.145 g, 1.509 mmole) in toluene (50 ml) was added a mixture of $Pd_2(dba)_3$ (0.023 g, 0.025 mmole) and tri-tert-butyl-phosphine (0.010 g, 0.05 mmole) in dry toluene (10 ml). Resulting mixture was stirred with heating at 110° C. under nitrogen atmosphere overnight. After that the mixture was cooled down and allowed to stand at ambient temperature for product crystallization. Precipitate was filtered, washed consecutively with toluene, methanol, water, methanol and dried in vacuum to give 0.195 g of crude product. Crude product was dissolved in 10 ml of 1,2-dichlorobenzene at elevated temperature under nitrogen atmosphere, hot solution passed through a filter filled with basic alumina, Florisil®, silica gel and Celite® eluting with toluene and dichloromethane. Filtrate was diluted with methanol, product collected by filtration, dried in vacuum to give 60 mg of product. $^1$H-NMR (toluene-$d_8$, 500 MHz): 3.14 (s, 6H), 6.55-6.57 (m, 2H), 6.66 (s, 2H), 6.98-7.17 (m, 15H), 7.27 (t, 4H, J=9 Hz), 7.40-7.44 (m, 13H), 7.48 (d, 2H, J=9 Hz), 7.54 (d, 2H, J=9 Hz), 7.55 (dd, 2H, J1=1 Hz, J2=8 Hz), 7.82 (d, 2H, J=9 Hz), 8.67 (d, 2H, J=8 Hz). MS: MH+=1054. UV-vis in toluene ($\lambda_{max}$, nm, ε): 433 (54300), 392 (94600). Emission (toluene): 444 nm.

Synthesis Example 33

This example illustrates the preparation of a compound having Formula II, 7,14-dihydro-2,9-bis(5-diphenylamino-2-benzofuranyl)-7,14-diphenyl-carbazolo[4,3-c]carbazole, Compound II-17.

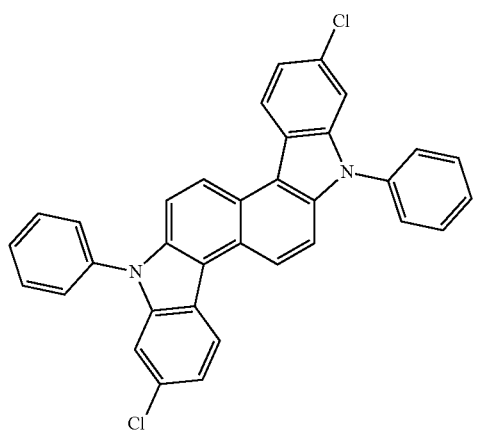
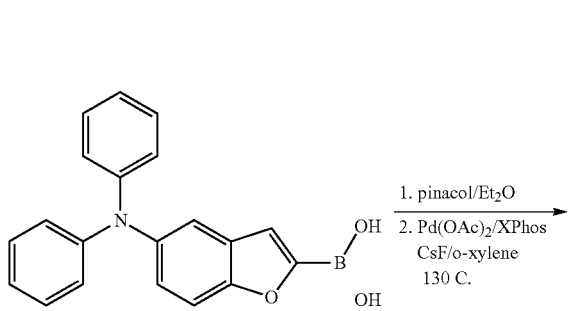

5

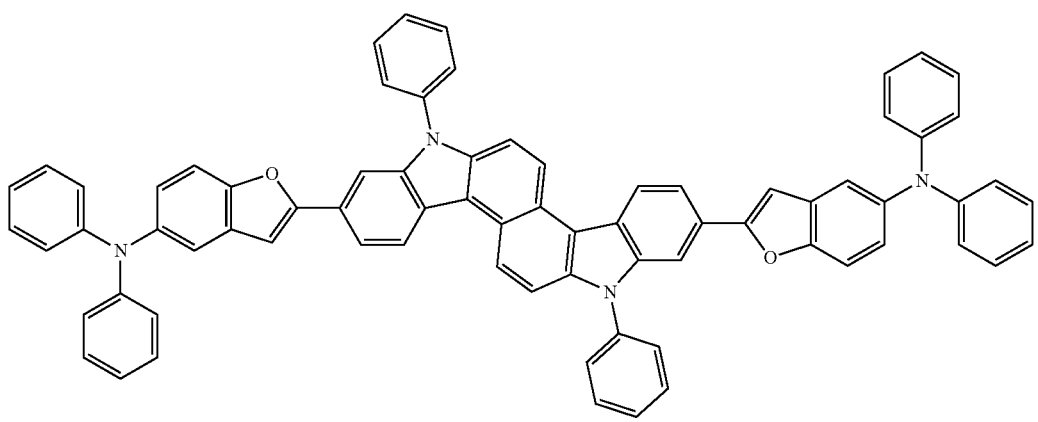

17

5-Diphenylaminobenzofuran-2-boronic acid (0.1 g, 0.3038 mmole) was stirred with pinacol (0.38 g, 0.319 mmole) in diethyl ether (10 ml) at ambient temperature overnight. The residue after evaporation of diethyl ether was transferred to a flask containing a mixture of dichlorodiphenylcarbazolocarbazole 5 (made as in Synthesis Example 22) (10 mg, 0.019 mmole), cesium fluoride (66 mg, 0.434 mmole), palladium acetate (2 mg, 0.009 mmole) and XPhos (9.5 mg, 0.02 mmole) in o-xylene (13 ml). Resulting mixture was stirred with heating at 130° C. under nitrogen atmosphere for 4 hours. After that the mixture was cooled down, precipitate filtered, washed consecutively with toluene, methanol, water and dried in vacuum to give crude product. Crude product was dissolved in 1,2-dichlorobenzene at 180° C. under nitrogen atmosphere, diluted with dichloromethane after cooling the mixture, and passed through a filter filed with silica gel and Celite® eluting with dichloromethane. Dichloromethane evaporated using rotary evaporator to volume approximately 3-4 ml, diluted with methanol, precipitate collected by filtration and dried in vacuum to give 1.5 mg of 17. MS: MH+=1026. UV-vis in toluene ($\lambda_{max}$, nm, ε): 433 (151000), 409 (122000), 395 (167000), 321 (160000), 309 (150000). Emission (toluene): 438 nm.

Synthesis Example 34

This example illustrates the preparation of a compound having Formula II, 7,14-dihydro-2,9-bis(6-diphenylamino-2-benzofuranyl)-7,14-diphenyl-carbazolo[4,3-c]carbazole, Compound II-11.

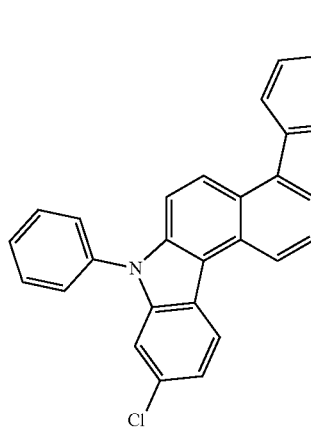

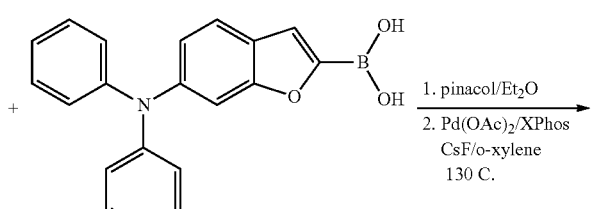

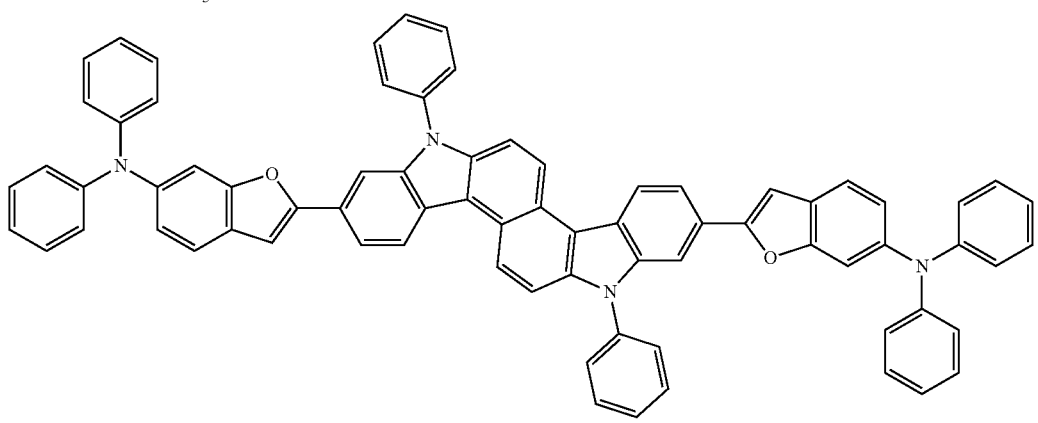

6-Diphenylaminobenzofuran-2-boronic acid (50 mg, 0.137 mmole), dichlorodiphenylcarbazolocarbazole 5 (made as in Synthesis Example 22) (27 mg, 0.019 mmole) and pinacol (1.1 equiv.) were stirred in diethyl ether at ambient temperature overnight. The residue after evaporation of diethyl ether was transferred to a flask containing a mixture of cesium fluoride (40 mg, 0.26 mmole) and o-xylene (40 ml) followed by addition of palladium acetate (1.5 mg, 0.007 mmole) and XPhos (13 mg, 0.064 mmole) in o-xylene (5 ml). Resulting mixture was stirred with heating at 130° C. under nitrogen atmosphere overnight. After that the mixture was cooled down, precipitate filtered, washed with toluene, hexanes, water, methanol and dried to give crude product. Crude product was dissolved in 1,2-dichlorobenzene at elevated temperature under nitrogen atmosphere and passed through a filter filed with silica gel, Florisil® and Celite® eluting with toluene. Precipitate formed upon standing at ambient temperature was collected by filtration and dried in vacuum to give 14 mg of product. MS: MH+=1026. UV-vis in toluene ($\lambda_{max}$, nm, ε): 440 (64800), 415 (44300), 401 (49700), 320 (26800). Emission (toluene): 448 nm.

Synthesis Example 35

This example illustrates the preparation of a compound having Formula I, N5,N11-di([1,1'-biphenyl]-4-yl)-7,7,9,9-tetramethyl-N5,N11-diphenyl-7,9-dihydrobenzo[g]benzo[6,7]indeno[2,1-b]fluorene-5,11-diamine, Compound IC-1.

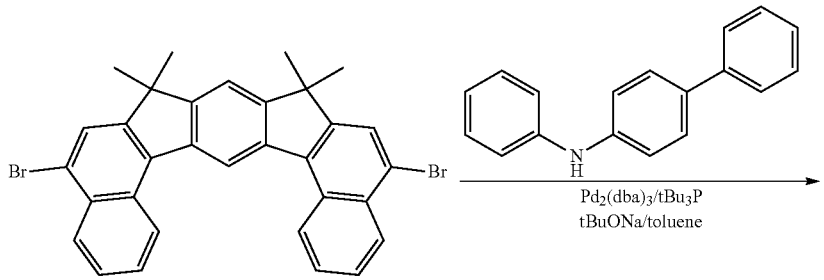

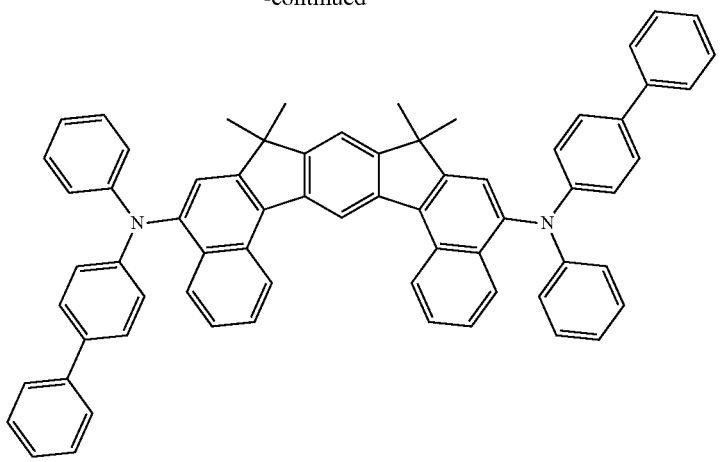

To a mixture of 5,11-dibromo-7,7,9,9-tetramethyl-7,9-dihydrobenzo[g]benzo[6,7]indeno[2,1-b]fluorene 19 (01.0 g, 1.76 mmole), N-phenyl-[1,1'-Biphenyl]-4-amine (1.079 g, 4.4 mmole) in toluene (50 ml) was added Pd$_2$(dba)$_3$ (0.081 g, 0.088 mmole) and tri-tert-butyl-phosphine (0.036 g, 0.176 mmole) followed by addition of sodium tert-butoxide (0.506 g, 5.28 mmole). Resulting mixture was stirred with heating at 80° C. under nitrogen atmosphere for 10 hours. After that the mixture was cooled down, water (50 ml) added and the mixture stirred in the air for 10 min. The residue after evaporation of solvents from organic phase was redissolved in dichloromethane, absorbed on Celite® and subjected to chromatography on silica gel column using gradient elution with mixtures of hexanes and dichloromethane. Fraction containing the product were combined, eluent evaporated to minimal volume, precipitate collected by filtration and dried to give 1.05 g of the product. The product (0.57 g) can be further purified by passing its toluene solution under nitrogen atmosphere through a filter filled basic alumina eluting with toluene followed by precipitation with methanol, evaporation of solvents to minimal amount, collecting precipitate, drying it in vacuum to afford 0.548 g of the finely purified product. $^1$H-NMR (toluene-d$_8$, 500 MHz): 1.44 (s, 12H), 6.86 (t, 2H, J=7 Hz), 7.07-7.27 (m, 20H), 7.34 (d, 4H, J=9 Hz), 7.44 (d, 4H, J=8 Hz), 7.53 (t, 2H, J=8 Hz), 7.55 (s, 1H), 7.69 (s, 2H), 8.39 (d, 2H, J=9 Hz), 9.24 (d, 2H, J=9 Hz), 9.62 (s, 1H). MS: MH+=898. UV-vis in toluene ($\lambda_{max}$, nm, ε): 411 (33800), 323 (42700). Emission (toluene): 446 nm.

Synthesis Example 36

This example illustrates the preparation of a compound having Formula I, Compound IC-2.

Part 1. Synthesis of Dinaphthobenzodifuran Precursor 24

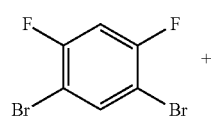

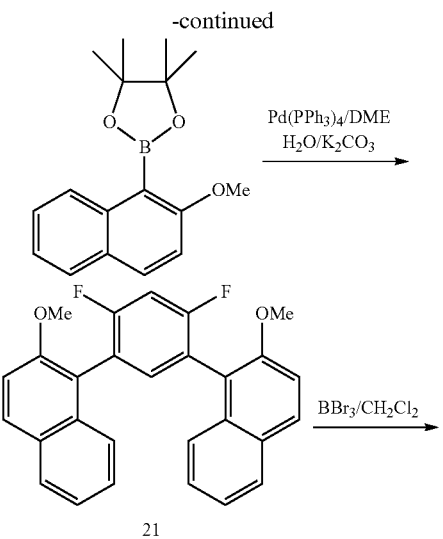

21

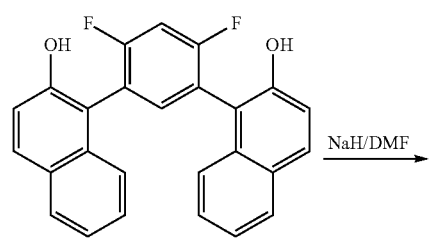

22

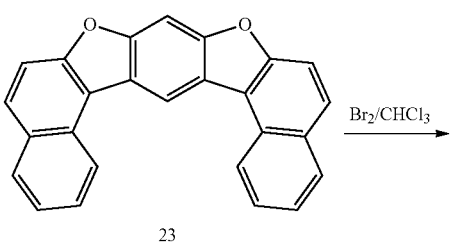

23

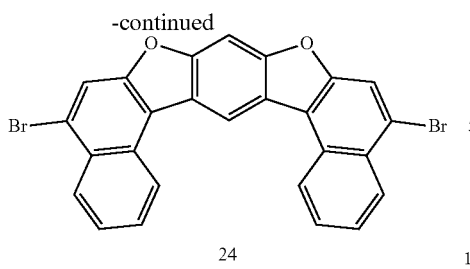

24

(a) 1,1'-(4,5-difluoro-1,3-phenylene)bis[2-methoxy-naphthalene] (21)

A mixture of 2-(2-methoxy-1-naphthalenyl)-boronic acid (3.24 g, 16 mmole), 1,5-dibromo-2,4-difluorobenzene (1.78 g, 6.55 mmole), Pd(PPh$_3$)$_4$ (0.33 g, 0.29 mmole) and potassium carbonate (4.53 g, 32.8 mmole) in 1,2-dimethoxyethane (120 ml) and water (30 ml) was stirred with heating at reflux temperature under nitrogen atmosphere for 4 hours. After that reaction mixture cooled down, precipitate collected by filtration to give 1.12 g of the product. Organic phase of the filtrate was evaporated further and the second precipitate collected by filtration, dried in vacuum to give 1.8 g of the product. Crude product as a mixture of diastereomers was used for the next step without further purification. Crude product can be purified by chromatography on silica gel column using gradient elution with mixtures of hexanes and dichlromethane to isolate pure isolated diastereomers. MS: MH+=427. $^1$H-NMR of diastereomer 1 (CDCl$_3$, 500 MHz): 3.95 (s, 6H), 7.14 (t, 1H, J=9 Hz), 7.34-7.37 (m, 3H), 7.38 (d, 2H, J=9 Hz), 7.43 (td, 2H, J1=1 Hz, J2=8 Hz), 7.68 (d, 2H, J=9 Hz), 7.83 (d, 2H, J=8 Hz), 7.92 (d, 2H, J=9 Hz). $^1$H-NMR of diastereomer 2 (CDCl$_3$, 500 MHz): 3.91 (s, 6H), 7.14 (t, 1H, J=9 Hz), 7.31-7.38 (m, 3H), 7.38 (d, 2H, J=9 Hz), 7.44 (td, 2H, J1=1 Hz, J2=8 Hz), 7.64 (d, 2H, J=9 Hz), 7.83 (d, 2H, J=9 Hz), 7.92 (d, 2H, J=9 Hz).

(b) 1,1'-(4,5-difluoro-1,3-phenylene)bis[2-naphthol] (22)

To a solution of 1,1'-(4,5-difluoro-1,3-phenylene)bis[2-methoxy-naphthalene] 21 (mixture of diastereomers, 0.57 g, 1.336 mmole) in dichloromethane (10 ml) 1M solution of boron tribromide in dichloromethane (6 ml) added carefully under nitrogen atmosphere and the mixture stirred at ambient temperature for overnight. After that the mixture was poured into water, stirred for 1 day, organic phase separated. The residue (0.51 g) after evaporation of dichloromethane was used for the next step without further purification. MS: MH+=399. $^1$H-NMR, mixture of diastereomers, (CDCl$_3$, 500 MHz): 7.21-7.26 (m, 4H), 7.28-7.33 (m, 1H), 7.36-7.39 (m, 2H), 7.44-7.53 (m, 5H), 7.82-7.86 (m, 4H). (c) Dinaphtho[1,2-d:1',2'-d']benzo[1,2-b:5,4-b']difuran (23). 1,1'-(4,5-Difluoro-1,3-phenylene)bis[2-naphthol] 22 (2.35 g, 5.90 mmole) was dissolved in dimethylformamide (30 ml) under nitrogen atmosphere followed by addition of sodium hydride (60% suspension in mineral oil, 0.95 g, 23.7 mmole) at once. Resulting mixture was stirred at 100° C. for overnight and at 142° C. for 35 hours with addition of the second portion of sodium hydride (60% suspension in mineral oil, 0.48 g, 11.9 mmole). After that the mixture was cooled down, diluted with water, precipitate collected by filtration, washed with water, methanol, dried in vacuum to give 1.44 g of dinaphtho[1,2-d:1',2'-d']benzo[1,2-b:5,4-b']difuran 23. $^1$H-NMR (CDCl$_3$, 500 MHz): 7.64 (t, 2H, J=8 Hz), 7.84 (d, 2H, J=9 Hz), 7.90 (t, 2H, J=8 Hz), 7.98 (d, 2H, J=9 Hz), 7.99 (s, 1H), 8.10 (d, 2H, J=9 Hz), 8.89 (d, 2H, J=9 Hz), 9.31 (s, 1H). MS: MH+=359. UV-vis in acetonitrile-water, $\lambda_{max}$, nm: 359, 261, 237. Emission in toluene: 368 nm.

(d) 5,11-Dibromo-dinaphtho[1,2-d:1',2'-d']benzo[1,2-b:5,4-b']difuran (24)

Bromine (0.2 g, 1.25 mmole) in chloroform (3 ml) was added at once to a stirring suspension of dinaphtho[1,2-d:1',2'-d']benzo[1,2-b:5,4-b']difuran 23 (127 mg, 0.354 mmole) in chloroform at ambient temperature. After that the reaction mixture was heated to reflux for 45 min. Reaction mixture cooled down, precipitate filtered, washed with chloroform, acetone and dried to give 156 mg of the product as a mixture of mono and 5,11-dibromo-dinaphtho[1,2-d:1',2'-d']benzo[1,2-b:5,4-b']difuran 24 (ratio mono:bis=0.3:1 by NMR) that was used for coupling reactions without further purification. $^1$H-NMR (CDCl$_3$, 500 MHz): 7.76 (t, 2H, J=8 Hz), 7.91 (t, 2H, J=8 Hz), 7.99 (s, 1H), 8.19 (s, 2H), 8.53 (d, 2H, J=9 Hz), 9.46 (d, 2H, J=9 Hz), 10.13 (s, 1H). MS: MH+=516. UV-vis in acetonitrile-water, $\lambda_{max}$, nm: 365, 262, 239.

Part 2. Synthesis of N5,N11-diphenyl-N5,N11-bis ([1,1'-biphenyl]-4-yl)-dinaphtho[1,2-d:1',2'-d']benzo [1,2-b:5,4-b']difuran-5,11-diamine, Compound IC-2

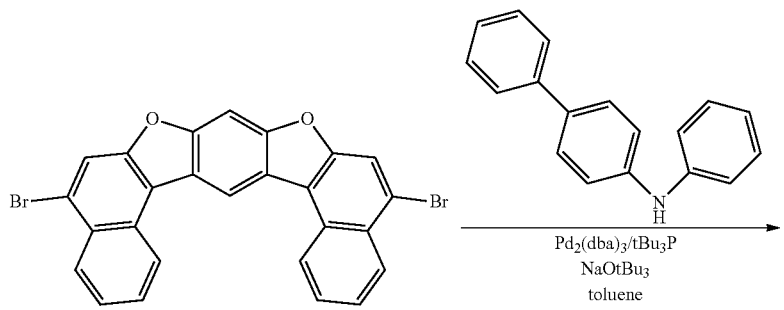

24

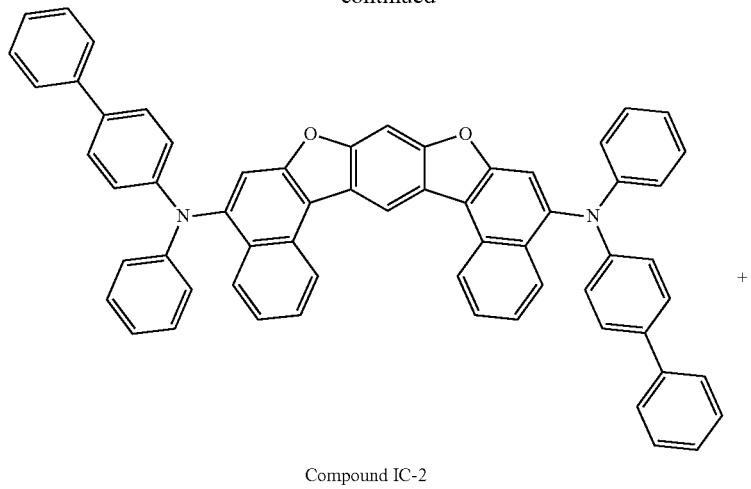

Compound IC-2

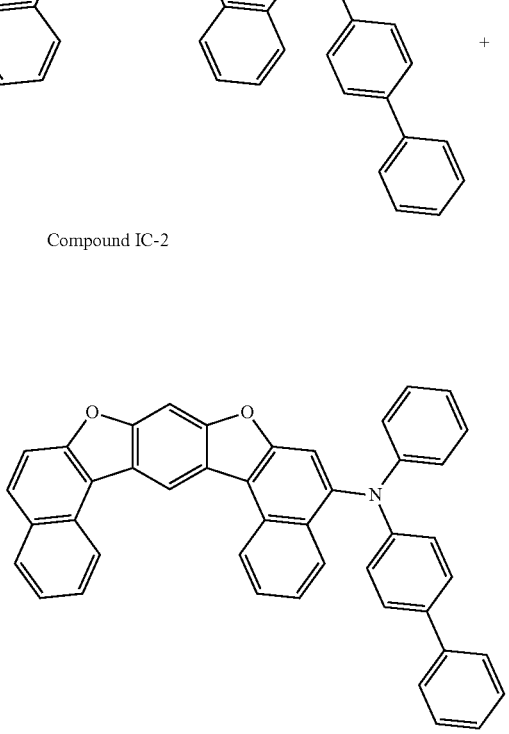

To a mixture of 5,11-dibromo-dinaphtho[1,2-d:1',2'-d']benzo[1,2-b:5,4-b']difuran 24 (75 mg, 0.145 mmole), N-phenyl-[1,1'-Biphenyl]-4-amine (89 mg, 0.363 mmole) in toluene (25 ml) was added $Pd_2(dba)_3$ (0.014 g, 0.015 mmole) and tri-tert-butyl-phosphine (0.08 g, 0.04 mmole) followed by addition of sodium tert-butoxide (0.05 g, 0.521 mmole). Resulting mixture was stirred with heating at 110° C. under nitrogen atmosphere for 2 hours. After that the mixture was cooled down, water (20 ml) added and the mixture stirred in the air. The mixture was diluted with toluene, organic phase passed through a filter filled with basic alumina, Florisil®, silica gel and Celite® eluting with toluene and dichloromethane. The residue after evaporation of solvents was redissolved in dichloromethane, absorbed on Celite® and subjected to chromatography on silica gel column using gradient elution with mixtures of hexanes and dichloromethane. Fraction containing first product were combined, eluent evaporated to minimal volume, precipitate collected by filtration and dried to give 12 mg of monocoupled product (N5-phenyl-N5-([1,1'-biphenyl]-4-yl)-dinaphtho[1,2-d:1',2'-d']benzo[1,2-b:5,4-b']difuran-5-amine). Fractions containing second product were combined, eluent evaporated to minimal volume, precipitate collected by filtration and dried in vacuum to give 32 mg of bis-coupled Compound IC-2.

Monoamine N5-phenyl-N5-([1,1'-biphenyl]-4-yl)-dinaphtho[1,2-d:1',2'-d']benzo[1,2-b:5,4-b']difuran-5-amine: $^1$H-NMR (toluene-$d_8$, 500 MHz): 6.84-6.89 (m, 2H), 7.04-7.15 (m, 5H), 7.19-7.27 (m, 4H), 7.33-7.38 (m, 3H), 7.44-7.45 (m, 2H), 7.49-7.62 (m, 4H), 7.71 (s, 1H), 7.79-7.80 (m, 2H), 8.42 (d, 1H, J=8 Hz), 8.83 (d, 1H, J=9 Hz), 8.91 (d, 1H, J=9 Hz), 9.33 (s, 1H). MS: MH+=602. UV-vis in acetonitrile-water, $\lambda_{max}$, nm: 389, 353, 325, 259, 237. Emission in toluene: 449 nm.

Diamine N5,N11-diphenyl-N5,N11-bis([1,1'-biphenyl]-4-yl)-dinaphtho[1,2-d:1',2'-d']benzo[1,2-b:5,4-b']difuran-5,11-diamine, Compound IC-2: $^1$H-NMR (toluene-$d_8$, 500 MHz): 6.86-6.89 (m, 2H), 7.07-7.15 (m, 14H), 7.19-7.27 (m, 6H), 7.34 (d, 2H, J=9 Hz), 7.44-7.46 (m, 4H), 7.51 (t, 2H, J=8 Hz), 7.72 (s, 2H), 7.81 (s, 1H), 8.42 (d, 2H, J=9 Hz), 8.94 (d, 2H, J=9 Hz), 9.41 (s, 1H). MS: MH+=845.5. UV-vis in toluene, $\lambda_{max}$, nm (ε): 417 (49200), 322 (49400). Emission in toluene: 449 nm.

Synthesis Example 37

This example illustrates the preparation of a compound having Formula I, N5,N11-bis(2,4,6-trimethylphenyl)-N5,N11-bis(9,9-dimethyl-9H-fluoren-2-yl)-dinaphtho[1,2-d:1',2'-d']benzo[1,2-b:5,4-b']difuran-5,11-diamine, Compound IC-3.

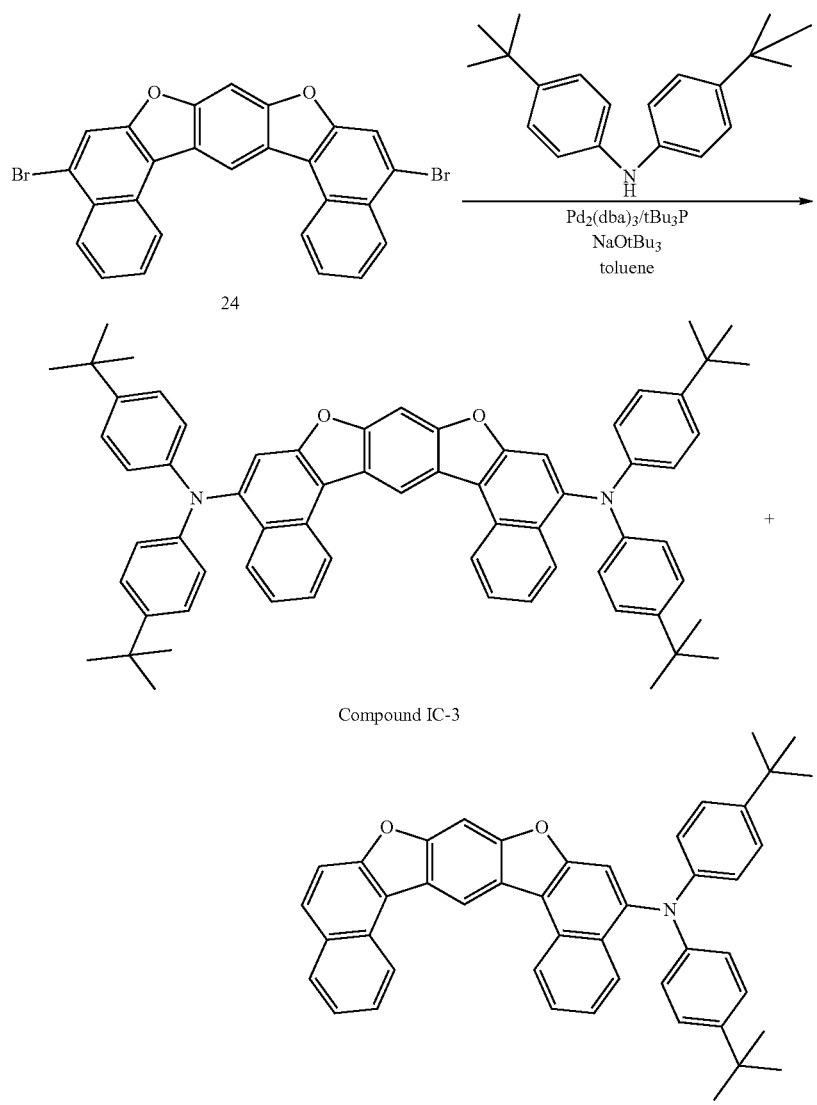

Compound IC-3

To a mixture of 5,11-dibromo-dinaphtho[1,2-d:1',2'-d']benzo[1,2-b:5,4-b']difuran 24 (made as in Synthesis Example 36) (75 mg, 0.145 mmole), bis(4-tert-butylphenyl)amine (102 mg, 0.363 mmole) in toluene (25 ml) was added Pd$_2$(dba)$_3$ (0.014 g, 0.015 mmole) and tri-tert-butyl-phosphine (0.08 g, 0.04 mmole) followed by addition of sodium tert-butoxide (0.05 g, 0.521 mmole). Resulting mixture was stirred with heating at 110° C. under nitrogen atmosphere for 1 hour. After that the mixture was cooled down, water (20 ml) added and the mixture stirred in the air. The mixture was diluted with toluene, organic phase passed through a filter filled with basic alumina, Florisil®, silica gel and Celite® eluting with toluene. The residue after evaporation of solvents was redissolved in dichloromethane, absorbed on Celite® and subjected to 2 consecutive chromatography purifications on silica gel columns using gradient elution with mixtures of hexanes and dichloromethane. Fraction containing monocoupled product were combined, eluent evaporated to minimal volume, precipitate collected by filtration and dried to give 1 mg of N5,N5-bis(4-tert-butylphenyl)-dinaphtho[1,2-d:1',2'-d']benzo[1,2-b:5,4-b']difuran-5-amine. Fractions containing biscoupled product were combined, eluent evaporated to minimal volume, precipitates collected by filtration and dried in vacuum to give 52 mg of bis-coupled Compound IC-3.

Monoamine N5,N5-bis(4-tert-butylphenyl)-dinaphtho[1,2-d:1',2'-d']benzo[1,2-b:5,4-b']difuran-5-amine: $^1$H-NMR (toluene-d$_8$, 500 MHz): 1.25 (s, 18H), 7.10 (d, 4H, J=9.5 Hz), 7.15 (d, 4H, J=9.5 Hz), 7.19 (t, 1H, J=9 Hz), 7.36 (t, 1H, J=8 Hz), 7.48 (t, 1H, J=8 Hz), 7.56-7.61 (m, 2H), 7.72 (s, 1H), 7.78 (s, 1H), 7.79 (d, 1H, J=8 Hz), 8.48 (d, 1H, J=9 Hz), 8.83 (d, 1H, J=8 Hz), 8.91 (d, 1H, J=8 Hz), 9.33 (s, 1H). MS: MH+=638.

Diamine N5,N5,N11,N11-tetra(4-tert-butylphenyl)-dinaphtho[1,2-d:1',2'-d']benzo[1,2-b:5,4-b']difuran-5,11-diamine, Compound IC-3: $^1$H-NMR (toluene-d$_8$, 500 MHz): 1.25 (s, 36H), 7.10 (d, 8H, J=9 Hz), 7.15 (d, 8H, J=9 Hz), 7.19 (t, 2H, J=8 Hz), 7.48 (t, 2H, J=8 Hz), 7.73 (s, 2H), 7.77 (s, 1H), 8.48 (d, 2H, J=8 Hz), 8.92 (d, 2H, J=8 Hz), 9.39 (s, 1H). MS: MH+=918. UV-vis in toluene, $\lambda_{max}$, nm (ε): 421 (49500). Emission in toluene: 455 nm.

Synthesis Example 38

This example illustrates the preparation of a compound having Formula I, N5,N11-bis(2,4,6-trimethylphenyl)-N5, N11-bis(9,9-dimethyl-9H-fluoren-2-yl)-dinaphtho[1,2-d:1',2'-d']benzo[1,2-b:5,4-b']difuran-5,11-diamine, Compound IC-4

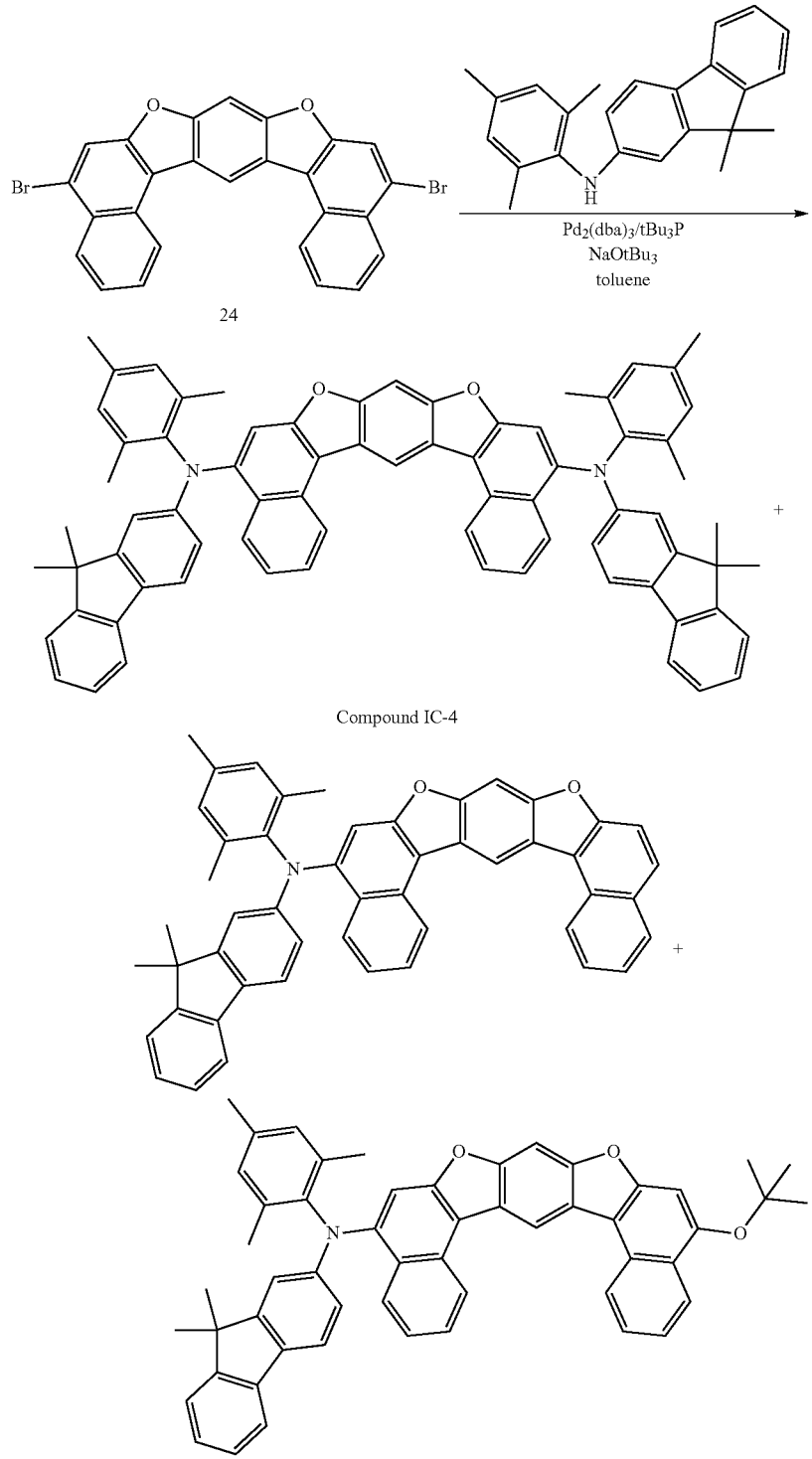

Compound IC-4

To a mixture of 5,11-dibromo-dinaphtho[1,2-d:1',2'-d']benzo[1,2-b:5,4-b']difuran 24 (made as in Synthesis Example 36) (0.4 g, 0.775 mmole), 9,9-dimethyl-N-(2,4,6-trimethylphenyl)-9H-fluoren-2-amine (0.56 g, 1.7 mmole) in toluene (80 ml) was added Pd$_2$(dba)$_3$ (0.071 g, 0.078 mmole) and tri-tert-butyl-phosphine (0.032 g, 0.158 mmole) followed by addition of sodium tert-butoxide (0.224 g, 2.33 mmole). Resulting mixture was stirred with heating at 110° C. under nitrogen atmosphere for 18 hours. After that the mixture was cooled down, water added and the mixture stirred in the air for 30 min. The mixture was passed through a filter filled with silica gel, Florisil®, basic alumina and Celite® eluting with toluene. The residue after evaporation of solvents was redissolved in dichloromethane, absorbed on Celite® and subjected to 2 consecutive chromatography purifications on silica gel columns using gradient elution with mixtures of hexanes and dichloromethane. Fractions containing monocoupled product combined, eluent evaporated, the residue was precipitated from toluene solution with methanol, precipitate collected, dried to give 35 mg of N5-(2,4,6-trimethylphenyl)-N5-(9,9-dimethyl-9H-fluoren-2-yl)-dinaphtho[1,2-d:1',2'-d']benzo[1,2-b:5,4-b']difuran-5-amine (MS: MH+=684. UV-vis in toluene, $\lambda_{max}$, nm (ε): 417 (31500), 332 (31500). Emission in toluene: 455 nm). Fractions containing monoamino-monotert-butoxy substituted product combined, eluent evaporated to give 0.151 g of N9-tert-butoxy-N5-(2,4,6-trimethylphenyl)-N5-(9,9-dimethyl-9H-fluoren-2-yl)-dinaphtho[1,2-d:1',2'-d']benzo[1,2-b:5,4-b']difuran-5-amine (MS: MH+=756. UV-vis in toluene, $\lambda_{max}$, nm (ε): 416 (68900), 333 (51700). Emission in toluene: 453 nm).

Fractions containing biscoupled product were combined, eluent evaporated to minimal volume, precipitates collected by filtration and dried in vacuum to give 0.159 g of biscoupled compound that was further purified by precipitation of toluene solution with methanol, collecting precipitate and drying in vacuum to give 0.105 g of N5,N11-bis(2,4,6-trimethylphenyl)-N5,N11-bis(9,9-dimethyl-9H-fluoren-2-yl)-dinaphtho[1,2-d:1',2'-d']benzo[1,2-b:5,4-b']difuran-5,11-diamine, Compound IC-4: $^1$H-NMR (toluene-d$_8$, 500 MHz): 1.16 (s, 6H), 1.20 (s, 6H), 2.16 (s, 6H), 2.21 (s, 6H), 2.22 (s, 6H), 6.77 (dd, 2H, J1=2 Hz, J2=9 Hz), 6.85 (s, 4H), 6.96 (s, 2H), 7.1-=7.21 (m, 8H), 7.38 (d, 2H, J=8 Hz), 7.46-7.49 (m, 4H), 7.59 (d, 2H), 7.72 (s, 1H), 8.44 (d, 2H, J=9 Hz), 8.94 (d, 2H, J=8 Hz), 9.30 (s, 1H). MS: MH+=1009. UV-vis in toluene, $\lambda_{max}$, nm (ε): 433 (84600), 321 (48600). Emission in toluene: 454 nm.

Synthesis Example 39

This example illustrates the preparation of a compound having Formula III, N3,N10-diphenyl-N3,N10-bis(6-(2-benzofuranyl)naphthyl)-naphtho[2,3-b;7,6-b']bisbenzofuran-3,10-diamine, Compound III-15.

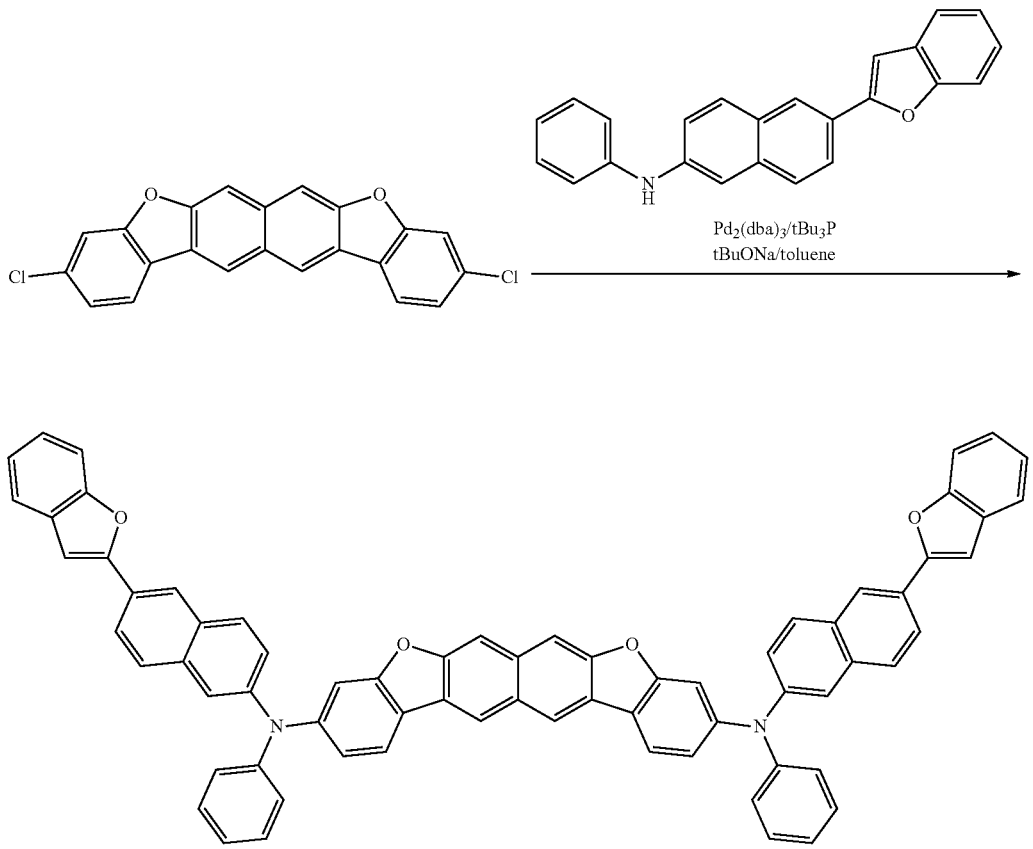

To 65 mg of crude mixture of 3-chloro and 3,10-dichloronaphtho[2,3-b;7,6-b']bisbenzofurans, N-phenyl-6-(2-benzofuranyl)-2-naphthalenylamine (0.144 g, 0.43 mmole) in toluene (50 ml) was added Pd$_2$(dba)$_3$ (0.016 g, 0.0172 mmole) and tri-tert-butyl-phosphine (0.0307 g, 0.0344 mmole) followed by addition of sodium tert-butoxide (0.083 g, 0.86 mmole). Resulting mixture was stirred with heating at 110° C. under nitrogen atmosphere overnight. After that the mixture was cooled down and absorbed on Celite® and subjected to chromatography purification on silica gel columns using gradient elution with mixtures of hexanes and dichloromethane to give 13 mg of bis-coupled product with purity 98% by HPLC. The product could be further purified by chromatography on basic alumina using toluene as eluent. $^1$H-NMR (toluene-d$_8$, 500 MHz): 6.72 (s, 2H), 6.97 (d, 2H, J=8 Hz), 7.10-7.22 (m, 14H), 7.34 (dd, 2H, J1=2 Hz, J2=9 Hz), 7.36 (d, 2H, J=9 Hz), 7.42 (d, 2H, J=2 Hz), 7.45-7.47 (m, 4H), 7.55 (d, 2H, J=2 Hz), 7.58 (d, 2H, J=9 Hz), 7.71-7.73 (m, 4H), 7.76 (d, 2H, J=9 Hz), 8.19 (s, 2H), 8.31 (s, 2H). MS: MH+=976. UV-vis in toluene, $\lambda_{max}$, nm (ε): 416 (186000), 359 (115000). Emission in toluene: 433 nm.

Synthesis Example 40

This example illustrates the preparation of a compound having Formula I, Compound IA-31.

Part 1. Synthesis of Naphthobisbenzofuran Precursor 29

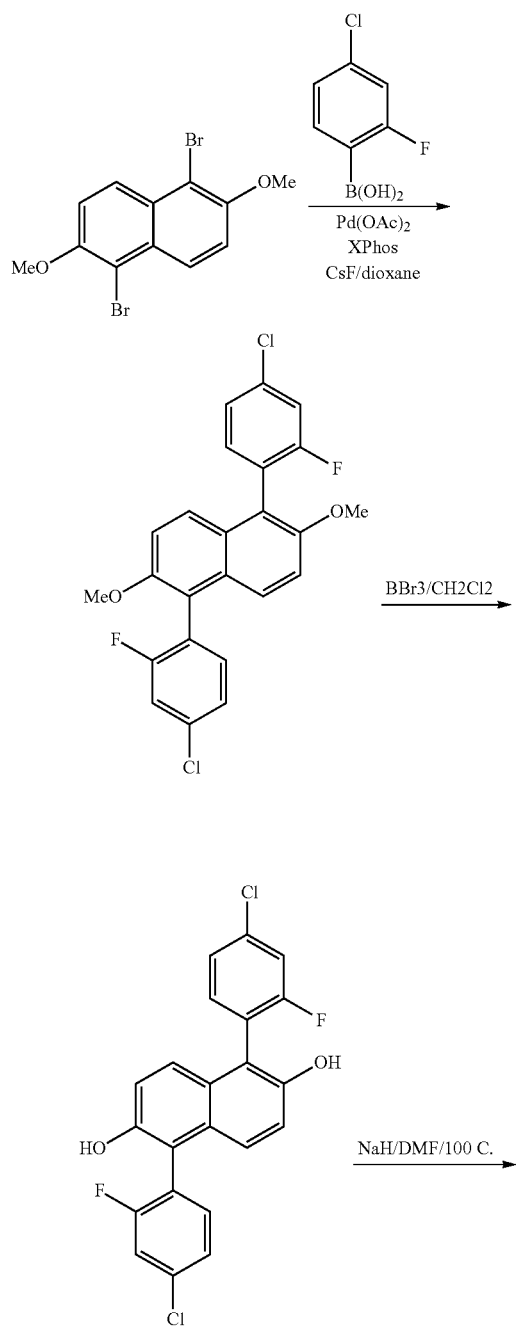

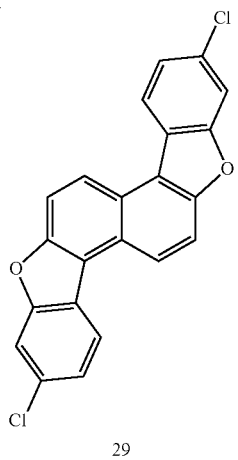

29

(a) 1,5-Bis(4-chloro-2-fluorophenyl)-2,6-dimethoxynaphthalene

A mixture of 1,5-dibromo-2,6-dimethoxynaphthalene (5 g, 14.45 mmole), 4-chloro-2-fluorophenylboronic acid (7.56 g, 43.35 mmole) were stirred cesium fluoride (11.05 g, 72.75 mmole) cesium fluoride (11.05 g, 72.75 mmole), palladium acetate (324 mg, 1.445 mmole) and XPhos (1.378 g, 2.89 mmole) in 1,4-dioxane (150 ml) was stirred at 110° C. for 7 hours under nitrogen atmosphere. After that reaction mixture cooled down, passed through a filter filled with basic alumina, Florisil®, silica gel and Celite® eluting with dichloromethane. The residue after evaporation of solvents using rotary evaporator was absorbed on Celite® and subjected to chromatography on silica gel column using gradient elution with mixtures of hexanes and dichloromethane. Fractions containing pure product combined, eluent evaporated to give 1.28 g of 1,5-bis(4-chloro-2-fluorophenyl)-2,6-dimethoxynaphthalene as a mixture of atropoisomers. ¹H-NMR (CDCl₃, 500 MHz): 3.82 (s, 6H), 7.28-7.30 (m, 8H), 7.49 (d, 2H, J=9 Hz). MS: MH+=445.

(b) 1,5-Bis(4-chloro-2-fluorophenyl)-2,6-dihydroxynaphthalene

To a solution of 1,5-bis(4-chloro-2-fluorophenyl)-2,6-dimethoxynaphthalene (mixture of diastereomers, 1.28 g, 2.88 mmole) in dichloromethane (10 ml) 1M solution of boron tribromide in dichloromethane (9 ml) added carefully under nitrogen atmosphere and the mixture stirred at ambient temperature until complete conversion. After that the mixture was poured into water (100 ml), dichloromethane (50 ml) added and the mixture stirred at ambient temperature for 2 days. After that 100 ml of dichloromethane added, precipitate filtered, dried to give 0.66 g of the product. Lower purity product (0.41 g) could also be isolated by evaporating dichloromethane to minimal volume and collecting precipitate. MS: MH+=417.

(c) 2,9-Dichloronaphtho[2,1-b:6,5-b']bisbenzofuran (29)

1,5-Bis(4-chloro-2-fluorophenyl)-2,6-dihydroxynaphthalene (0.66 g, 1.58 mmole) was dissolved in anhydrous dimethylformamide (25 ml) under nitrogen atmosphere at 100° C. followed by addition of sodium hydride (60% dispersion in mineral oil, 6.93 mmole) over 30 min and resulting mixture stirred for 10-15 min at 100° C. After that reaction mixture cooled down, quenched with methanol, precipitate filtered, washed with water, methanol, dried in vacuum to give 0.48 g of 2,9-dichloronaphtho[2,1-b:6,5-b']bisbenzofuran 29. ¹H-NMR (CD$_2$Cl$_2$, 500 MHz): 7.56 (d, 2H, J=9 Hz), 7.80 (s, 2H), 8.07 (d, 2H, J=9 Hz), 8.44 (d, 2H, J=8 Hz), 8.76 (d, 2H, J=8 Hz). MS: MH+=377.

Part 2. Synthesis of N2,N9-diphenyl-N2,N9-bis(9,9-dimethyl-9H-fluoren-2-yl)naphtho[2,1-b:6,5-b']bisbenzofuran-2,9-diamine, Compound IA-31

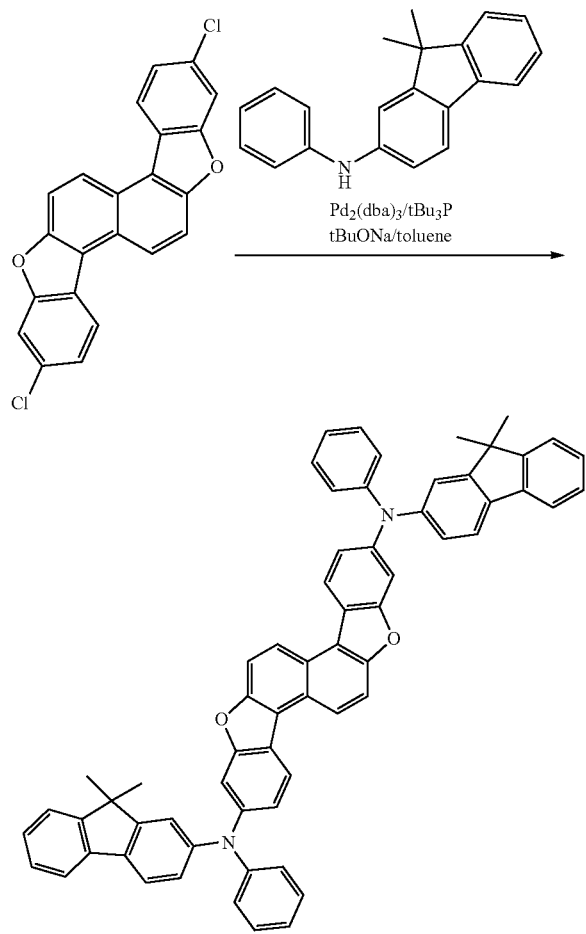

To a mixture of 2,9-dichloronaphtho[2,1-b:6,5-b']bisbenzofuran 29 (0.2 g, 0.531 mmole), 9,9-dimethyl-N-phenyl-9H-fluoren-2-amine (0.333 g, 1.167 mmole) in toluene (50 ml) was added Pd$_2$(dba)$_3$ (0.049 g, 0.053 mmole) and tri-tert-butyl-phosphine (0.021 g, 0.1062 mmole) followed by addition of sodium tert-butoxide (0.153 g, 1.593 mmole). Resulting mixture was stirred with heating at 110° C. under nitrogen atmosphere for 1.7 hours. After that the mixture was cooled down, stirred with water (50 ml) for 10 min. Organic phase passed through a filter filled with basic aluimna, Florisil®, silica gel and Celite® eluting with toluene. Toluene was concentrated to volume 10 ml, diluted with hexanes (20-30 ml), precipitate filtered, redissolved in hot 1,2-dichlorobenzene followed by addition of hexanes and subsequent chromatography on silica gel column using gradient elution with mixtures of hexanes and dichloromethane. Fractions containing product combined, eluent evaporated to minimal volume, precipitate collected by filtration and dried in vacuum to give 185 mg of product. ¹H-NMR (toluene-d$_8$, 500 MHz): 1.30 (s, 12H), 6.95 (t, 2H, J=8 Hz), 7.15-7.25 (m, 12H), 7.30 (d, 4H, J=8 Hz), 7.35 (dd, 2H, J1=2 Hz, J2=9 Hz), 7.46 (d, 2H, J=2 Hz), 7.51 (d, 2H, J=8 Hz), 7.55 (d, 2H, J=9 Hz), 7.61 (d, 2H, J=2 Hz), 7.73 (d, 2H, J=9 Hz), 8.00 (d, 2H, J=9 Hz), 8.40 (d, 2H, J=9 Hz). MS: MH+=875. UV-vis in toluene, $\lambda_{max}$, nm ($\varepsilon$): 422 (77900), 402 (57500), 346 (38200). Emission in toluene: 440 nm.

Synthesis Example 41

This example illustrates the preparation of a compound having Formula III, N2,N9-diphenyl-N2,N9-bis-(2-(6-(benzofuran-2-yl)naphthyl)-naphtho[2,1-b:6,5-b']bisbenzofuran-2,9-diamine, Compound III-14.

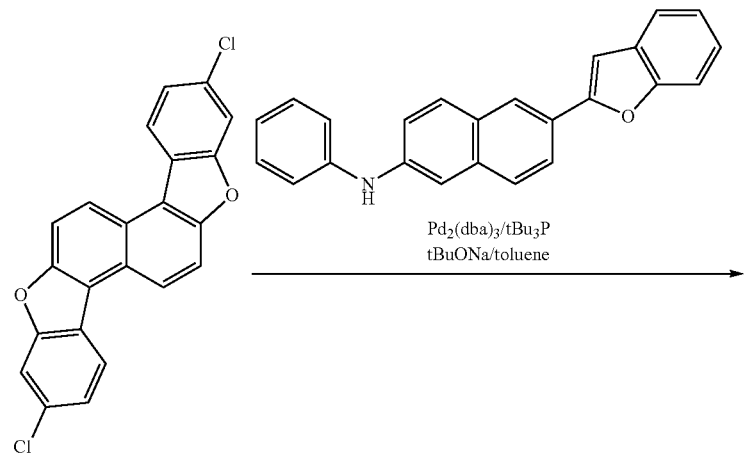

-continued

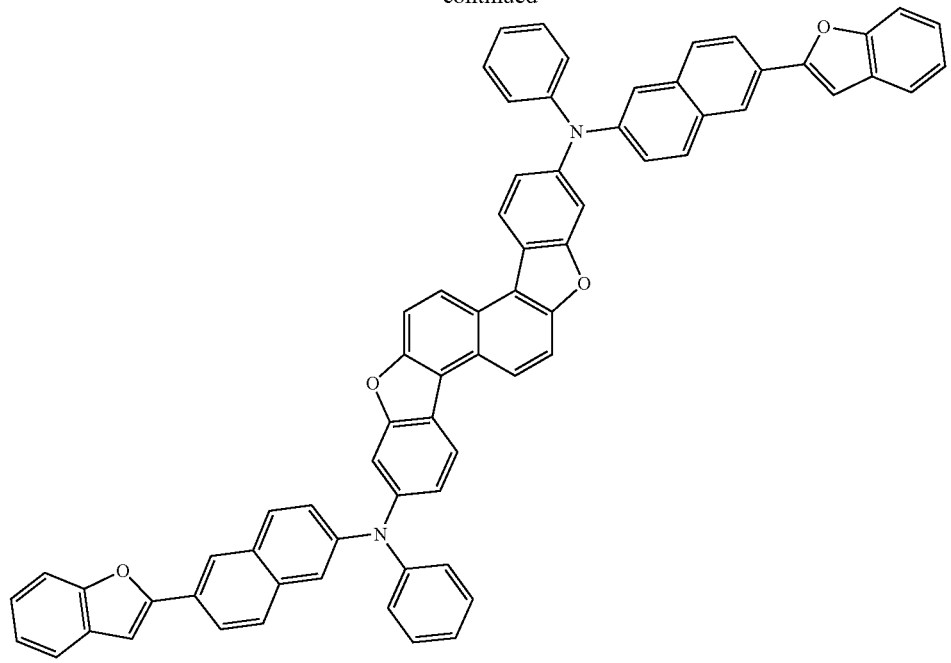

To a mixture of 2,9-dichloronaphtho[2,1-b:6,5-b']bisbenzofuran 29 (made as in Synthesis Example 40) (0.3 g, 0.795 mmole), N-phenyl-6-(2-benzofuranyl)-2-naphthalenylamine (0.587 g, 1.75 mmole) in toluene (100 ml) was added $Pd_2(dba)_3$ (0.073 g, 0.0795 mmole) and tri-tert-butyl-phosphine (0.032 g, 0.159 mmole) followed by addition of sodium tert-butoxide (0.229 g, 2.385 mmole). Resulting mixture was stirred with heating at 110° C. under nitrogen atmosphere for 1 day. After that the mixture was cooled down, stirred at ambient temperature for 3 hours, precipitated product collected by filtration, washed with toluene and dried to give 0.669 g of crude product. Crude product was dissolved in 1,2-dichlorobenzene (20 ml) at 180° C. under nitrogen atmosphere and hot solution passed through a filter filled with basic alumina, Florisil® and silica gel eluting with toluene and dichloromethane. Filtrated diluted with methanol, precipitates collected by filtration, dried in vacuum to give totally 0.372 g of product. $^1$H-NMR ($CD_2Cl_2$, 500 MHz): 7.17 (s, 2H), 7.19 (d, 2H, J=8 Hz), 7.25-7.33 (m, 8H), 7.36-7.41 (m, 4H), 7.44 (d, 2H, J=9 Hz), 7.48-7.50 (m, 2H), 7.51 (d, 2H, J=2 Hz), 7.55 (d, 2H, J=2 Hz), 7.59 (d, 2H, J=9 Hz), 7.65 (d, 2H, J=8 Hz), 7.71 (d, 2H, J=9 Hz), 7.90 (d, 4H, J=8 Hz), 7.99 (d, 2H, J=9 Hz), 8.35 (s, 2H), 8.38 (d, 2H, J=8 Hz), 8.69 (d, 2H, J=9 Hz). MS: MH+=975. UV-vis in toluene, $\lambda_{max}$, nm ($\varepsilon$): 424 (95200), 402 (79400), 358 (57700). Emission in toluene: 440 nm.

Synthesis Example 42

This example illustrates the preparation of a compound having Formula III, Compound III-22.

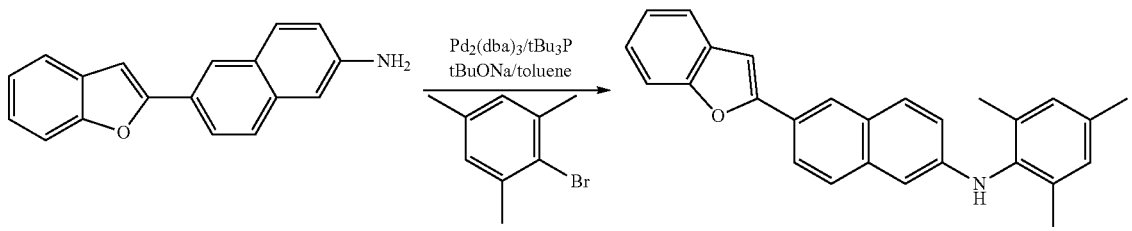

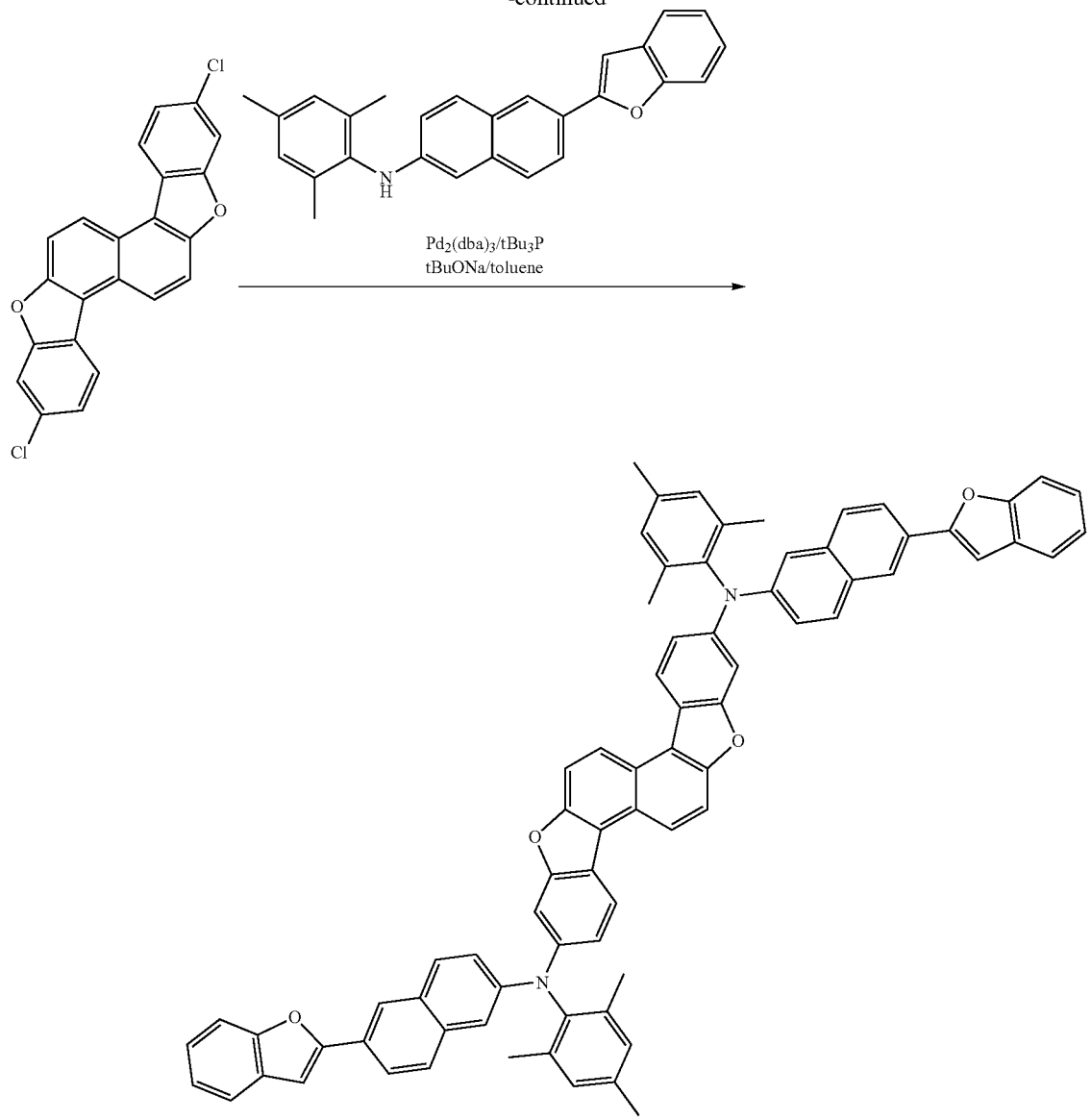

(a) N-(2,4,6-Trimethylphenyl)-6-(2-benzofuranyl)naphthylamine

To a mixture of 6-(2-benzofuranyl)naphthylamine (2 g, 7.72 mmole), 2-bromomesytilene (1.657 g, 8.33 mmole) in o-xylene (40 ml) was added a mixture of $Pd_2(dba)_3$ (0.354 g, 0.386 mmole) and tri-tert-butyl-phosphine (0.162 g, 0.801 mmole) in dry o-xylene (10 ml) followed by addition of sodium tert-butoxide (0.89 g, 9.26 mmole). Resulting mixture was stirred with heating at 130° C. under nitrogen atmosphere for 45 min. After that the mixture was cooled down, filtered through a filter filled with basic alumina, Florisil®, silica gel, Celite® eluting with toluene. Solids after evaporation of toluene were washed with hexanes and dried to give to give 1.795 g of the product with purity 99.82% by HPLC. $^1$H-NMR (toluene-$d_8$, 500 MHz): 2.11 (s, 6H), 2.23 (s, 3H), 4.62 (s, 1H), 6.52 (s, 1H), 6.64 (dd, 1H, J1=2 Hz, J2=9 Hz), 6.66 (s, 1H), 7.08-7.14 (m, 4H), 7.29 (d, 1H, J=8 Hz), 7.43 (d, 2H, J=8 Hz), 7.53 (d, 1H, J=9 Hz), 7.67 (dd, 1H, J1=2 Hz, J2=9 Hz), 8.25 (s, 1H). MS: MH+=378.

(b) N2,N9-bis-(2,4,6-trimethylbenzene)-N2,N9-bis-(2-(6-(benzofuran-2-yl)naphthyl)-naphtho[2,1-b:6,5-b']bisbenzofuran-2,9-diamine, Compound III-22

To a mixture of 2,9-dichloronaphtho[2,1-b:6,5-b']bisbenzofuran 29 (made as in Synthesis Example 40) (85 mg, 0.226 mmole), N-phenyl-6-(2-benzofuranyl)-2-naphthalenylamine (0.188 g, 0.497 mmole) in toluene (20 ml) was added $Pd_2(dba)_3$ (0.021 g, 0.023 mmole) and tri-tert-butyl-phosphine (0.0093 g, 0.046 mmole) followed by addition of sodium tert-butoxide (0.065 g, 0.68 mmole). Resulting mixture was stirred with heating at 100° C. under nitrogen atmosphere overnight. After that the mixture was cooled down, stirred at ambient temperature, precipitated product collected by filtration, washed with hexanes and water and dried in vacuum to give approximately 0.06 g of crude product. Crude product was absorbed on Celite® and subjected to chromatography purification on silica gel column using gradient elution with mixtures of hexanes and dichloromethane. Fractions containing the desired product combined, eluent evaporated to minimal volume, precipitate collected, dried to give 61 mg of product. The product can be additionally purified by passing toluene solution through a filter filled with basic alumina under nitrogen atmosphere followed by precipitation with methanol. $^1$H-NMR (toluene-d$_8$, 500 MHz): 2.16 (s, 12H), 2.26 (s, 6H), 6.71 (s, 2H), 6.91 (s, 4H), 7.10-7.16 (m, 8H), 7.27 (dd, 2H, J1=2 Hz, J2=8 Hz), 7.36 (d, 2H, J=9 Hz), 7.45-7.47 (m, 7H), 7.49 (d, 1H, J=2 Hz), 7.53 (d, 2H, J=2 Hz), 7.62 (d, 2H, J=9 Hz), 7.71 (dd, 2H, J1=2 Hz, J2=9 Hz), 7.79 (d, 2H, J=9 Hz), 7.98 (d, 2H, J=9 Hz), 8.32 (s, 2H), 8.46 (d, 2H, J=9 Hz). MS: MH+=1059. UV-vis in toluene, $\lambda_{max}$, nm (ε): 427 (164000), 405 (109000), 354 (63200). Emission in toluene: 439 nm.

Synthesis Example 43

This example illustrates the preparation of a compound having Formula I, Compound IA-42.

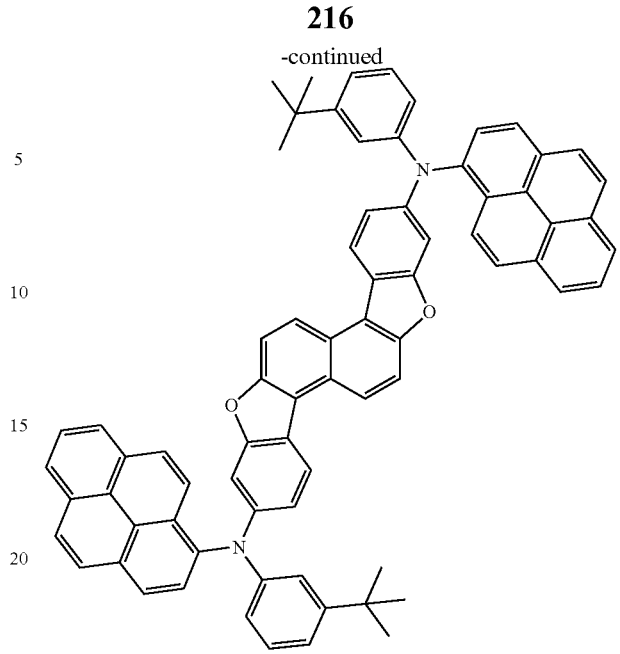

(a) N-(3-Tert-butylphenyl)-1-pyreneamine

To a mixture of 21-bromopyrene (21.2 g, 75.3 mmole), 3-tert-butylaniline (12.3 g, 82.4 mmole) in toluene (280 ml) was added Pd$_2$(dba)$_3$ (1.1 g, 1.2 mmole) and tri-tert-butyl-phosphine (0.49 g, 2.4 mmole) followed by addition of sodium tert-butoxide (8.7 g, 90.5 mmole). Resulting mixture was stirred at ambient temperature under nitrogen atmosphere overnight. After that the mixture was stirred with water (20 ml), organic phase passed through a filter filled with basic alumina, Florisil®, silica gel and Celite® eluting with toluene. Toluene evaporated, the reside dissolved in hexanes and precipitate collected after 1 day to give 24 g of the product that was used for the next step without further purification. $^1$H-NMR (toluene-d$_8$, 500 MHz): 1.29 (s, 9H), 5.69 (s, 1H), 6.77 (dd, 1H, J1=2 Hz, J2=8 Hz), 6.96 (d, 1H, J=8 Hz), 7.07 (t, 1H, J=1.5 Hz), 7.15 (t, 1H, J=8 Hz), 7.73-7.83 (m, 6H), 7.90 (d, 2H, J=8 Hz), 7.92 (d, 1H, J=9 Hz). MS: MH+=350.

(b) N2,N9-di(3-tertbutylphenyl)-N2,N9-bis-1-pyrenyl-naphtho[2,1-b:6,5-b']bisbenzofuran-2,9-diamine, Compound IA-42

To a mixture of 2,9-dichloronaphtho[2,1-b:6,5-b']bisbenzofuran 29 (made as in Synthesis Example 40) (0.1 g, 0.265 mmole), N-(3-tert-butylphenyl)-1-pyreneamine (0.204 g, 0.583 mmole) in toluene (25 ml) was added Pd$_2$(dba)$_3$ (0.025 g, 0.027 mmole) and tri-tert-butyl-phosphine (0.0011 g, 0.054 mmole) followed by addition of sodium tert-butoxide (0.076 g, 0.795 mmole). Resulting mixture was stirred with heating at 110° C. under nitrogen atmosphere for 3 hours. After that the mixture was cooled down, passed through a filter filled with silica gel, Florisil®, basic alumina and Celite® eluting with toluene. Toluene evaporated to volume 10 ml, precipitate filtered after 1 day, washed with toluene, hexanes, dried in vacuum to give 0.16 g of product. $^1$H-NMR (toluene-d$_8$, 500 MHz): 1.18 (s, 18H), 7.05-7.1

(signals overlapping with solvent peaks, 9H), 7.24 (dd, 2H, J1=2 Hz, J2=9 Hz), 7.53 (d, 2H, J=2 Hz), 7.62-7.64 (m, 3H), 7.68 (d, 2H, J=9 Hz), 7.71 (t, 2H, J=8 Hz), 7.79 (d, 2H, J=8 Hz), 7.82 (s, 3H), 7.34-7.94 (m, 7H), 8.32 (d, 2H, J=10 Hz), 8.42 (d, 2H, J=9 Hz). MS: MH+=1003.5. UV-vis in toluene, $\lambda_{max}$, nm ($\epsilon$): 425 (80500), 333 (39200), 320 (40700). Emission in toluene: 454 nm.

Synthesis Example 44

This example illustrates the preparation of a compound having Formula III, $N^3,N^9$-bis[4-(2,3-dihydro-1-benzofuran-2-yl)phenyl]-$N^3,N^9$-bis(3,4-dimethylphenyl)dibenzo[d,d']benzo[1,2-b:4,5-b']difuran-3,9-diamine, Compound III-23.

(a) Preparation of Core Precursor Material: $1^4,3^4$-dichloro-$1^2,3^2$-difluoro[$1^1,2^1:2^4,3^1$-terphenyl]-$2^2,2^5$-diol. B

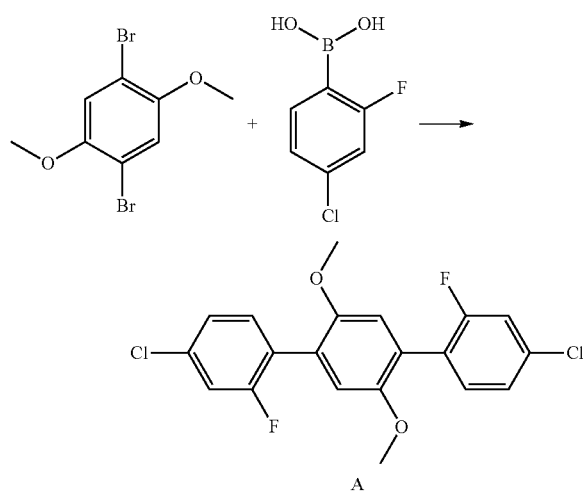

1,4-Dibromo-2,5-dimethoxybenzene (24.97 g, 84 mmol), 4-chloro-2-fluorophenylboronic acid (29.60 g, 170 mmol), 240 ml water, 700 ml toluene and potassium carbonate (60 g, 435 mmol) were sparged with nitrogen 40 minutes. Tetrakistriphenylphosphinepalladium(0) (2.77 g, 2.4 mmol) was quickly added to the mixture and refluxed overnight. The reaction was cooled and the water layer separated, solids were then filtered from the toluene layer for 21.9 grams of product material A. 65% yield.

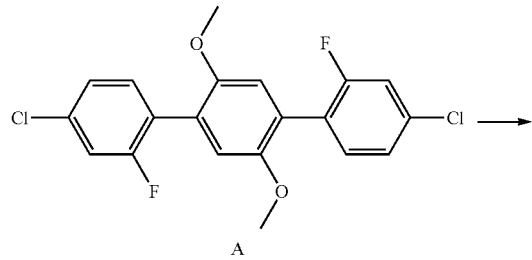

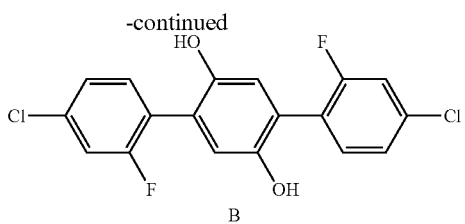

Material A was then demethylated using BBr₃ in methylene chloride. Under an inert atmosphere a methylene chloride solution of BBr₃ (33.48 ml, 1 mol/L) was added dropwise to compound A (7.34 g, 18.6 mmol) in 100 ml methylene chloride at 0° C. in an ice bath. The reaction was allowed to warm to ambient temperature overnight and quenched with excess water. The organic layer was collected, concentrated and product B was purified by recrystallization to give >95% yield.

(b) Preparation of Core Difuran: 3,9-dichlorodibenzo[d,d']benzo[1,2-b:4,5-b']difuran. C

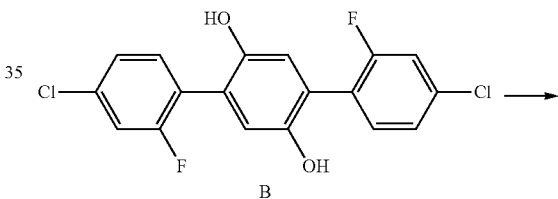

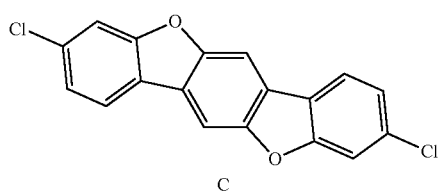

Product B from above (1.84 g, 0.005 mol), potassium carbonate (1.18 g, 0.0086 mol) and 45 mL 1-methyl-2-pyrrolidinone were combined in a nitrogen filled drybox and heated to 120° C. for 2 hours, cooled, diluted with water and the resultant solid filtered. The recovered filter cake was washed with acetonitrile and water and dried to give 1.39 g of poorly soluble product C. 85% yield.

(c) Preparation of N³,N⁹-bis[4-(2,3-dihydro-1-benzofuran-2-yl)phenyl]-N³,N⁹-bis(3,4-dimethylphenyl)dibenzo[d,d']benzo[1,2-b:4,5-b]difuran-3,9-diamine, Compound III-23

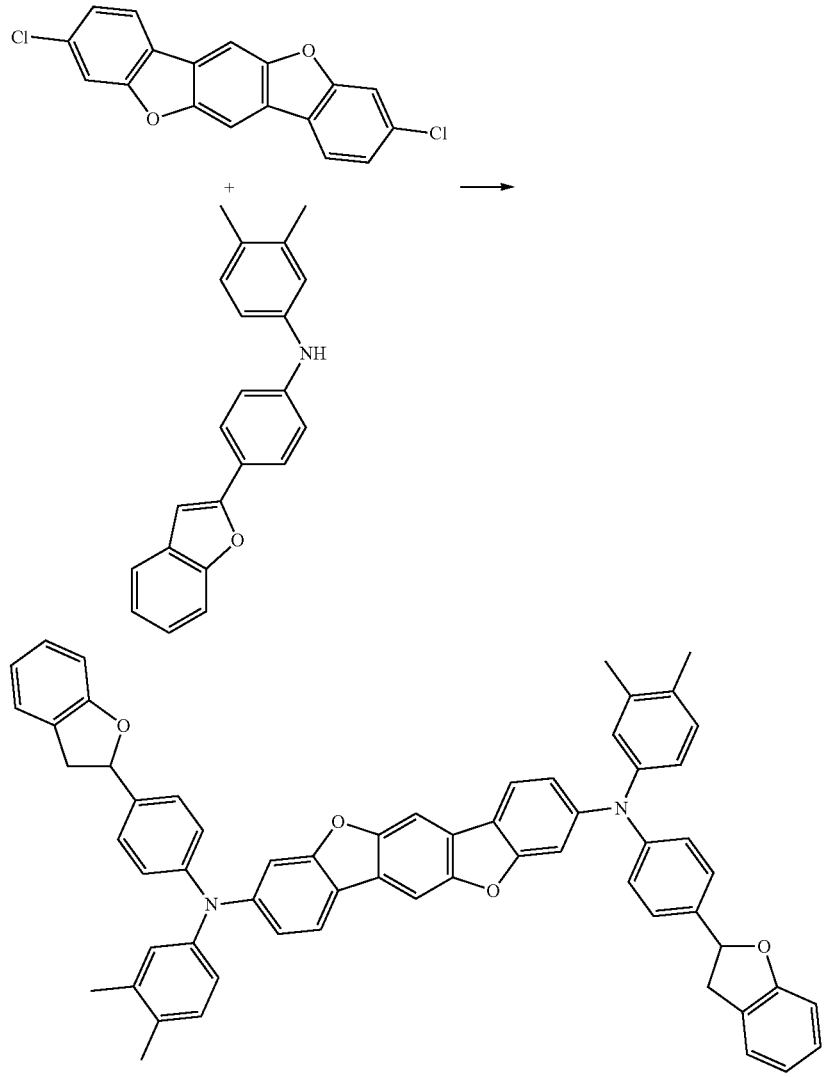

In a nitrogen filled drybox Pd$_2$DBA$_3$ (0.0630 g, 0.0688 mmol), tri-t-butylphosphine (0.0322 g, 0.1592 mmol), sodium-t-butoxide (0.3150 g, 3.277 mmol), product C from above (0.32 g, 0.965 mmol), secondary amine (0.65 g, 2.1 mmol) and 25 mL toluene were combined and heated to 90° C. for 4 hrs. The reaction mixture was eluted through basic alumina and Florisil® with toluene. Silica column chromatography eluting with toluene/hexanes, and recrystallization from toluene/n-propanol gave 280 mg of product. 30% yield identified by UPLC/MS and 1H-nmr spectroscopy.

Example 1

This example illustrates the photoluminescent properties of compounds having Formula I, Formula II, or Formula III.

The compounds were individually dissolved in a solvent. The solvent for Compound II-16 was o-dichlorobenzene. For all other compounds the solvent was toluene. The concentration was adjusted such that the optical density of the solution in a 1-cm quartz cell was preferably in the 0.2-0.4 range, at the excitation wavelengths between 300 and 360 nm. The photoluminescence spectrum was measured with a Spex Fluorolog spectrometer. The results are given in Table 1 below, where "PL" indicates photoluminescence;

"FWHM" stands for "full width half maximum" and is intended to mean the width of the emission profile at half the maximum intensity.

"PLQY" indicates photoluminescence quantum yield. Solution PLQY was measured in a manner similar to that described in R. W. Ricci and J. M. Nesta, J. Phys. Chem., 80, 9 (1976). The PLQY is shown as a percent relative to the reference emitter, quinine bisulfate in 1 N sulfuric acid. (See W. H. Melhuish, J. Phys. Chem., 1961, 65, 229.)

TABLE 1

PL Data

| Compound | Conc. µM | PL peak, nm | PL FWHM, nm | PLQY (%) |
|---|---|---|---|---|
| IA-7 | 3 | 446 | 41 | 89 |
| IA-17 | 3.75 | 446 | 41 | 89 |
| IA-46 | 3 | 436 | 17 | 90 |
| IB-1 | 3 | 443 | 39 | 90 |
| IB-3 | 2.5 | 438 | 42 | 84 |
| IB-5 | 3 | 444 | 40 | 88 |
| IB-7 | 3 | 438 | 40 | 91 |
| IC-1 | 3.75 | 446 | 51 | 93 |
| II-16 | 8 | 453 | 56 | 77 |
| II-17 | 1.5 | 438 | 39 | 83 |
| III-8 | 1.5 | 425 | 40 | 82 |
| III-15 | 1.25 | 433 | 26 | 87 |
| III-21 | 2.75 | 439 | 36 | 79 |
| III-22 | 1.8 | 439 | 39 | 94 |

Example 2

This example illustrates the degree of horizontal orientation of the compounds described herein in films co-deposited with a host material.

The host material was a deuterated diaryl-anthracene (Host-1 or Host-2, below) and the host:compound ratio was 30:1.

The orientation of the photoactive materials in films was determined as described in Frischeisen et al., Appl. Phyl. Lett., 96, 073301 (2010). The results are described as a percentage, where 100% represents total horizontal orientation of the transition dipole moments, i.e., parallel to the substrate. The results are given in Table 2.

TABLE 2

Orientation

| Compound | Horizontal Orientation (%) |
|---|---|
| IB-5 | 97 |
| IA-6 | 94 |
| IA-7 | 95 |
| IA-17 | 96 |
| IB-1 | 96 |
| IB-4 | 96 |

Device Examples (1) Materials
ET-1 is a benzimidazole-substituted anthracene.
ET-2 is an aryl phosphine oxide.
LiQ is lithium quinolate.
HAT-CN is 1,4,5,8,9,12-hexaazatriphenylenehexacarbonitrile.
HIJ-1 is a hole injection material which is made from an aqueous dispersion of an electrically conductive polymer and a polymeric fluorinated sulfonic acid.
Host-1 is a deuterated diaryl anthracene. Such materials have been described in published PCT Application WO 2011028216.
Host-2 is a deuterated diaryl anthracene. Such materials have been described in published PCT Application WO 2011028216.
Host-3 is a deuterated diaryl anthracene. Such materials have been described in published PCT Application WO 2011028216.
HTM-1 is a mono-arylamino phenanthrene.
HTM-2 is a polymeric diarylaminocarbazole.
HTM-3 is a polymeric triarylamine
HTM-3 is an arylamine.
NPD is N,N'-di(1-naphthyl)-N,N'-diphenyl-(1,1'-biphenyl)-4,4'-diamine.

(2) Devices
Both bottom-emitting and top-emitting devices were fabricated. The emissive layers were deposited by vapor deposition or by solution processing, as detailed below. In all cases, prior to use the substrates were cleaned ultrasonically in detergent, rinsed with water and subsequently dried in nitrogen.

(3) Device Characterization
The OLED devices were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The color coordinates were determined using either a Minolta CS-100 meter or a Photoresearch PR-705 meter.

Device Examples 1-3

These examples illustrate the use of a compound having Formula I or Formula II, as the emissive material in the photoactive layer of a device. The devices were top-emission devices made by thermal evaporation.

Top-emission devices were fabricated on glass substrates coated with patterned reflective anode, which comprised of a 7 nm ITO layer in the bottom, a 100 nm Silver-Palladium-Copper alloy layer in the center and a 7 nm ITO layer on the top. Cleaned substrates were loaded into a vacuum chamber. Once pressure reached $5 \times 10^{-7}$ Torr or below, they received thermal evaporations of the hole injection material, a first hole transport material, a second hole transport material, the photoactive and host materials, electron transport materials and electron injection material sequentially. The top-emission devices were thermally evaporated with transparent cathode—a 13 nm thick layer of Magnesium-Silver co-deposition at a volume ratio of 9:1, followed by a 60 nm thick light outcoupling layer. The chamber was then vented, and the devices were encapsulated using a glass lid, desiccant, and UV curable epoxy.

The device had the structure, in order (unless otherwise specified, all ratios are by weight and all percentages are by weight, based on the total weight of the layer):

Glass Substrate

Anode: ITO (7 nm)/Silver-Palladium-Copper alloy (100 nm)/ITO (7 nm)

HIL: HAT-CN (10 nm)

HTL1: NPD (137.5 nm)

HTL2: HTM-1 (5 nm)

EML: host and dopant as shown in Table 3, in a 30:1 ratio (20 nm)

ETL: ET-1:LiQ (2:3 weight ratio) (42 nm)

Cathode: Magnesium-Silver 9:1 (by volume) (13 nm)

Outcoupling layer: NPD (60 nm)

TABLE 3

Device Results

| Dev. Ex. | Host | Dopant Comp. | V | CIEx | CIEy | CE |
|---|---|---|---|---|---|---|
| 1 | Host-1 | IB-1 | 4.7 | 0.15 | 0.035 | 4.5 |
| 2 | Host-2 | IB-4 | 4.7 | 0.15 | 0.035 | 4.4 |
| 3 | Host-1 | II-16 | 4.9 | 0.15 | 0.041 | 4.3 |

All data at 1000 nits. V is the voltage; CIEx and CIEy are the x and y color coordinates according to the C.I.E. chromaticity scale (Commission Internationale de L'Eclairage, 1931); CE is the current efficiency in cd/A.

Device Examples 4-6

These examples illustrate the use of a compound having Formula I or Formula III, as the emissive material in the photoactive layer of a device. The devices were bottom-emission devices made by thermal evaporation.

Bottom-emission devices were fabricated on patterned indium tin oxide (ITO) coated glass substrates. Cleaned substrates were loaded into a vacuum chamber. Once pressure reached $5 \times 10^{-7}$ Torr or below, they received thermal evaporations of the hole injection material, a first hole transport material, a second hole transport material, the photoactive and host materials, electron transport materials and electron injection material sequentially. The bottom-emission devices were thermally evaporated with Al cathode material. The chamber was then vented, and the devices were encapsulated using a glass lid, desiccant, and UV curable epoxy.

The device had the structure, in order (unless otherwise specified, all ratios are by weight and all percentages are by weight, based on the total weight of the layer):

Glass substrate
Anode: ITO (50 nm)
HIL: HAT-CN (10 nm)
HTL1: NPD (185 nm)
HTL2: HTM-1 (20 nm)
EML: host and dopant as shown in Table 4, in a 30:1 weight ratio (25 nm)
ETL: ET-2:LiQ 1:1 (26.2 nm)
EIL: LiQ (3.5 nm)
Cathode: Al (100 nm)

TABLE 4

Device results

| Dev. Ex. | Host | Dopant Comp. | V | CIEx | CIEy | CE |
|---|---|---|---|---|---|---|
| 4 | Host-1 | IC-1 | 5.5 | 0.15 | 0.09 | 6 |
| 5 | Host-1 | III-12 | 5.9 | 0.15 | 0.079 | 5.9 |
| 6 | Host-1 | III-11 | 5.7 | 0.14 | 0.096 | 6.9 |

All data at 1000 nits. V is the voltage; CIEx and CIEy are the x and y color coordinates according to the C.I.E. chromaticity scale (Commission Internationale de L'Eclairage, 1931); CE is the current efficiency in cd/A.

Device Example 7-13

These examples illustrate the use of a compound having Formula I, Formula II, or Formula III, as the emissive material in the photoactive layer of a device. The devices were bottom-emission devices made by thermal evaporation.

The devices were made as described in Device Examples 4-6, except that the ETL was ET-1:LiQ in a 2:3 weight ratio and there was no EIL. The hosts and dopants are given in Table 5 below.

TABLE 5

Device Results

| Dev. Ex. | Host | Dopant Comp. | V | CIEx | CIEy | CE |
|---|---|---|---|---|---|---|
| 7 | Host-1 | III-13 | 5.2 | 0.15 | 0.091 | 7.1 |
| 8 | Host-1 | II-11 | 4.7 | 0.14 | 0.16 | 12.5 |
| 9 | Host-2 | IA-6 | 4.7 | 0.14 | 0.087 | 8.6 |
| 10 | Host-2 | IC-3 | 4.7 | 0.14 | 0.12 | 9.6 |
| 11 | Host-2 | IA-31 | 5 | 0.14 | 0.093 | 7.8 |
| 12 | Host-2 | IB-5 | 4.7 | 0.14 | 0.091 | 8.8 |
| 13 | Host-2 | IB-3 | 4.9 | 0.15 | 0.070 | 6.3 |

All data at 1000 nits. V is the voltage; CIEx and CIEy are the x and y color coordinates according to the C.I.E. chromaticity scale (Commission Internationale de L'Eclairage, 1931); CE is the current efficiency in cd/A.

Device Examples 14-16

These examples illustrate the use of a compound having Formula III as the emissive material in the photoactive layer of a device. The devices were top-emission devices made by solution deposition of the photoactive layer.

Top-emitting devices were fabricated on glass substrates coated with a patterned reflective anode. The reflective anode comprised of a 70 Å ITO layer in the bottom, a 1000 Å Silver-Palladium-Copper alloy layer in the center and a 70 Å ITO layer on the top. All substrates were cleaned ultrasonically in detergent, rinsed with water and subsequently dried in nitrogen.

To fabricate solution-processed top-emitting devices, a 700 Å thick hole injection layer was first spin coated as a dispersion in a mixture of glycol and glycol-ethers on previously cleaned substrates with reflective anode. The hole injection layer was then baked at 140° C. for 10 mins in inert nitrogen environment. After cooling, a 900~1000 Å thick hole transporting layer was spin coated from an aromatic solvent on top of the hole injection layer, followed by heating at 230° C. for 30 mins to harden the film. After cooling the substrates to room temperature, a ~400 Å thick emissive layer was spin coated from an aromatic solvent on the hole transport layer and baked at 140° C. for 15 mins to remove residue solvents.

Substrates were later transported into a vacuum chamber for vapor-deposition. A 200 Å thick electron transporting layer was first deposited at a pressure $<10^{-6}$ Torr, followed by Magnesium-Silver co-deposition at a volume ratio of 10:1 to form a 130 Å thick transparent cathode. After that, a 600 Å thick organic layer were deposited on top of the transparent cathode to facilitate light out-coupling.

Finally, the devices were hermetically encapsulated with glass lid, desiccant and UV curable epoxy.

The devices had the structure, in order (unless otherwise specified, all ratios are by weight and all percentages are by weight, based on the total weight of the layer):

Glass Substrate

Anode: ITO (7 nm)/Silver-Palladium-Copper alloy (100 nm)/ITO (7 nm)

HIL: HIJ-1 (70 nm)

HTL: HTM-2 (90-100 nm)

EML: host and dopant as shown in Table 6, in a 30:1 weight ratio (40 nm)

ETL: ET-2:LiQ 2:3 (20 nm)

Cathode: Magnesium-Silver 10:1 by volume (13 nm)

Outcoupling Layer: HTM-4 (60 nm)

TABLE 6

| | | Device Results | | | |
|---|---|---|---|---|---|
| Dev. Ex. | Host | Dopant Comp. | V | CIEx | CIEy | CE |
| 14 | Host-3 | III-9 | 6.4 | 0.15 | 0.048 | 3.1 |
| 15 | Host-3 | III-10 | 6.1 | 0.15 | 0.047 | 3.4 |
| 16 | Host-3 | III-5 | 6.5 | 0.14 | 0.051 | 3.6 |

All data at 1000 nits. V is the voltage; CIEx and CIEy are the x and y color coordinates according to the C.I.E. chromaticity scale (Commission Internationale de L'Eclairage, 1931); CE is the current efficiency in cd/A.

Device Examples 17-23

These examples illustrate the use of a compound having Formula I as the emissive material in the photoactive layer of a device. The devices were bottom-emission devices made by solution deposition of the photoactive layer.

Bottom-emitting devices were fabricated on substrates coated with patterned indium tin oxide (ITO). Previously cleaned substrates with patterned ITO were exposed to 10 mins of UV Ozone immediately before use. First, a 1000 Å thick hole injection layer was spin coated from a dispersion in glycol and glycol-ethers and baked at 70° C. for 5 mins in air. After cooling, a ~1000 Å thick hole transporting layer was spin coated from an aromatic solvent on top of the hole injection layer, followed by heating at 230° C. for 30 mins to harden the film. After cooling the substrates to room temperature, a ~400 Å thick emissive layer was spin coated from an aromatic solvent on the hole transport layer and baked at 140° C. for 15 mins to remove residue solvents.

Substrates were later transported into a vacuum chamber for vapor-deposition. A 200 Å thick electron transporting layer was first deposited at a pressure <$10^{-6}$ Torr. After that, a 1000 Å thick Aluminum was deposited to form electric contact and serve as cathode.

Finally, the devices were hermetically encapsulated with glass lid, desiccant and UV curable epoxy.

The devices had the structure, in order (unless otherwise specified, all ratios are by weight and all percentages are by weight, based on the total weight of the layer):

Glass Substrate

Anode: ITO (50 nm)

HIL: HIJ-1 (100 nm)

HTL: HTM-3 (100 nm)

EML: host and dopant as shown in Table 7, in a 30:1 weight ratio (40 nm)

ETL: ET-2:LiQ 3:4 (23 nm)

Cathode: Al (100 nm)

TABLE 7

| | | Device Results | | | |
|---|---|---|---|---|---|
| Dev. Ex. | Host | Dopant Comp. | V | CIEx | CIEy | CE |
| 17 | Host-1 | IA-7 | 6.4 | 0.14 | 0.069 | 4.3 |
| 18 | Host-1 | IA-17 | 6.0 | 0.14 | 0.077 | 4.1 |
| 19 | Host-1 | IA-43 | 6.4 | 0.14 | 0.067 | 4.0 |
| 20 | Host-1 | IA-44 | 6.1 | 0.14 | 0.074 | 4.0 |
| 21 | Host-1 | IA-45 | 7.0 | 0.14 | 0.081 | 3.9 |
| 22 | Host-1 | IB-6 | 6.4 | 0.15 | 0.063 | 3.9 |
| 23 | Host-1 | IB-2 | 6.4 | 0.14 | 0.082 | 3.9 |

All data at 1000 nits. V is the voltage; CIEx and CIEy are the x and y color coordinates according to the C.I.E. chromaticity scale (Commission Internationale de L'Eclairage, 1931); CE is the current efficiency in cd/A.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

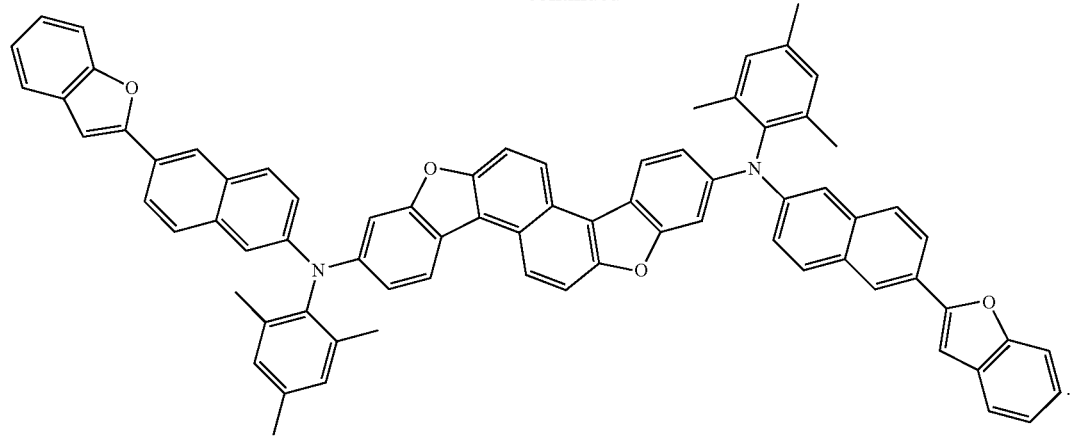

What is claimed is:

1. A compound having Formula I

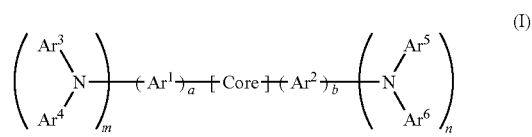

wherein:

$Ar^1$-$Ar^6$ are the same or different and are selected from the group consisting of hydrocarbon aryl groups, heteroaryl groups, and substituted derivatives thereof;

a and b are the same or different and are 0 or 1;
m and n are 1; and
Core is Formula IB or Formula IC

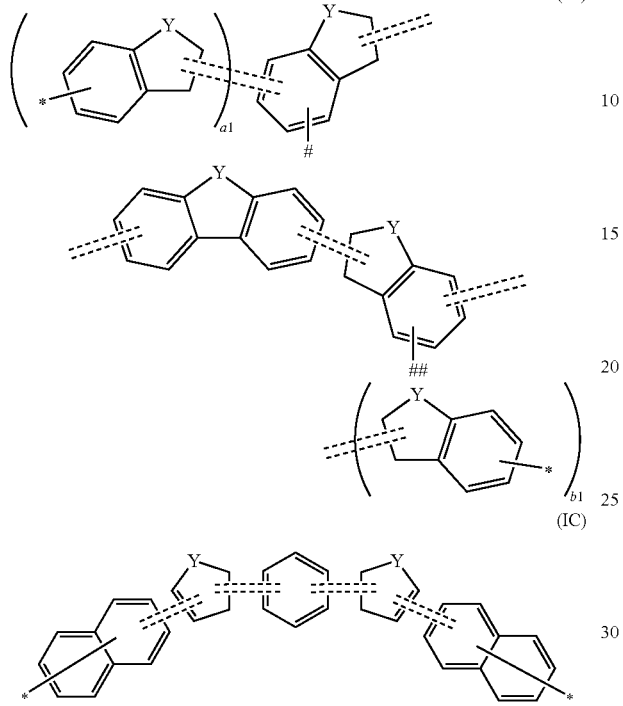

where:
Y is the same or different at each occurrence and is selected from the group consisting of O, S, Se, Te, $NR^2$, $CR^3R^4$, and $SiR^5R^6$;
$R^2$ is the same or different at each occurrence and is selected from the group consisting of alkyl, hydrocarbon aryl, heteroaryl, and substituted derivatives thereof;
$R^3$-$R^6$ are the same or different at each occurrence and are selected from the group consisting of alkyl, silyl, germyl, hydrocarbon aryl, heteroaryl, and substituted derivatives thereof, where $R^3$ and $R^4$ and/or $R^5$ and $R^6$ can be joined to form a cyclic group selected from the group consisting of cycloalkyl, silacycloalkyl, spirofluorenyl, silaspirofluorenyl, or a substituted derivative thereof;
a1 and b1 are the same or different and are 0 or 1;
a double dashed line between two rings indicates that the rings are fused together in any orientation;
* indicates a point of attachment in the identified formula; and
# and ## represent no bond or a point of attachment in the identified formula, such that when a1=0 then # is a point of attachment, when a1=1 then # is no bond, when b1=0 then ## is a point of attachment, and when b1=1 then ## is no bond;
and further wherein the Core may have one or more substituents selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

2. The compound of claim 1, wherein the Core is selected from the group consisting of Formula IB-1 through Formula IB-m

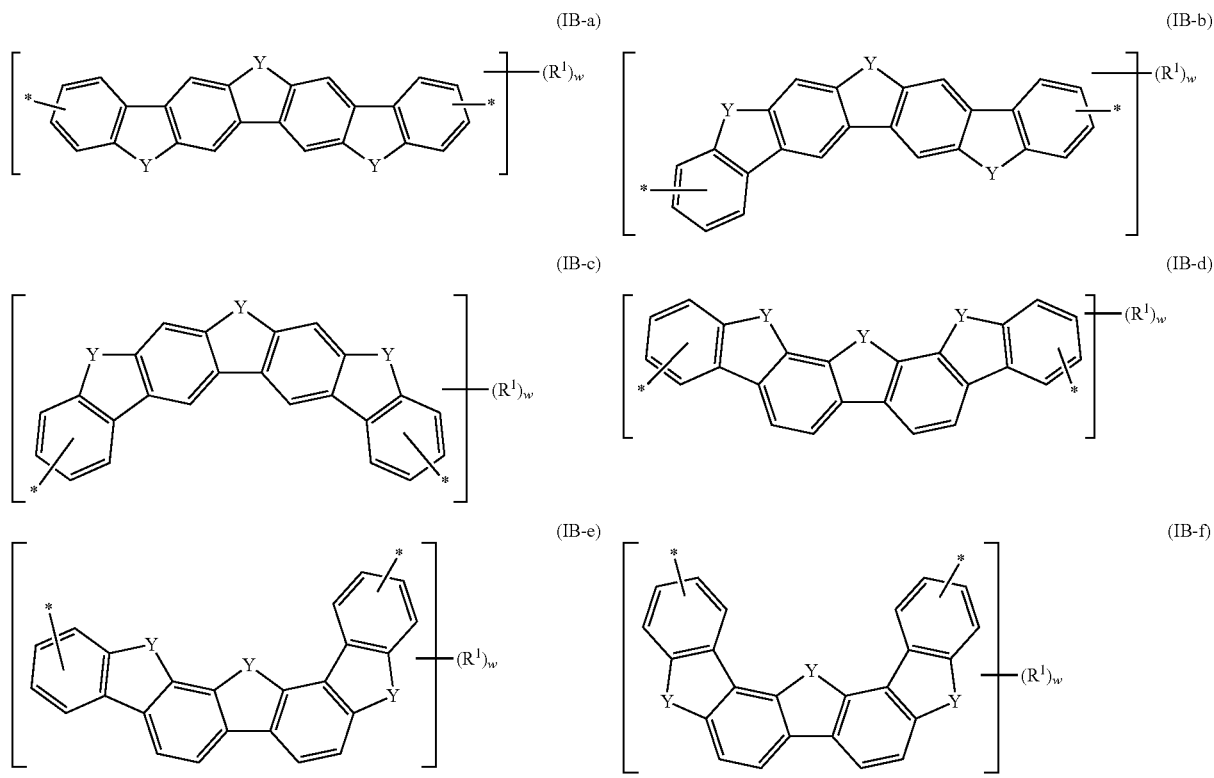

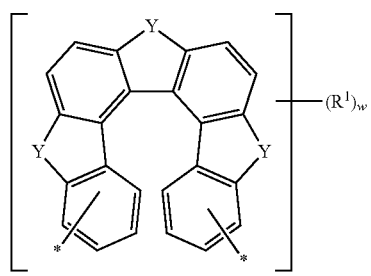 (IB-g)

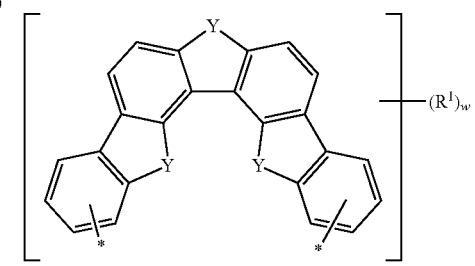 (IB-h)

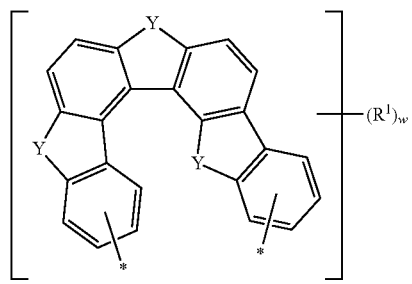 (IB-i)

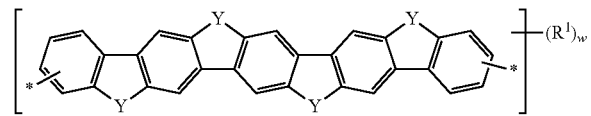 (IB-j)

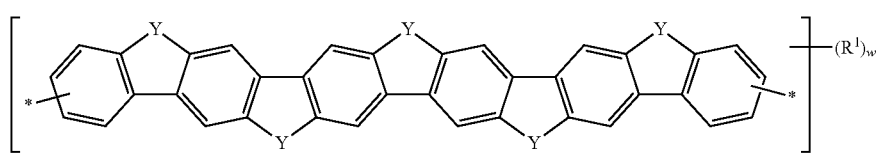 (IB-k)

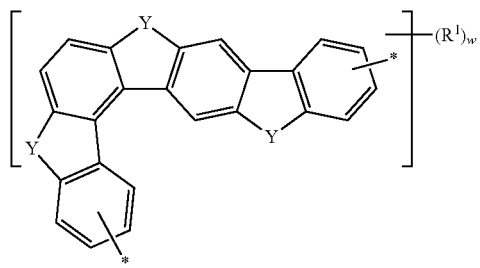 (IB-m)

where:
$R^1$ is the same or different at each occurrence and is selected from the group consisting of D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl deuterated silyl, deuterated siloxane, deuterated siloxy, and deuterated germyl;

w is an integer from 0 to a maximum number of bonding positions available.

3. The compound of claim 1, wherein the Core is selected from the group consisting of Formula IB-aa through Formula IB-mm

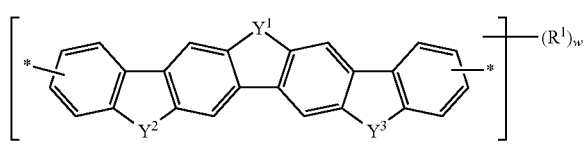 (IB-aa)

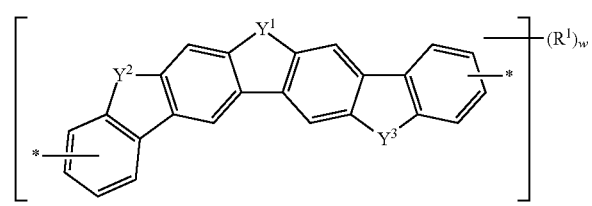 (IB-bb)

-continued
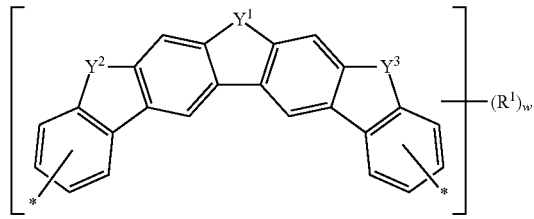 (IB-cc)
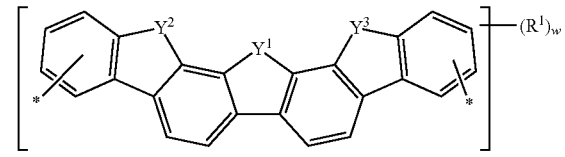 (IB-dd)
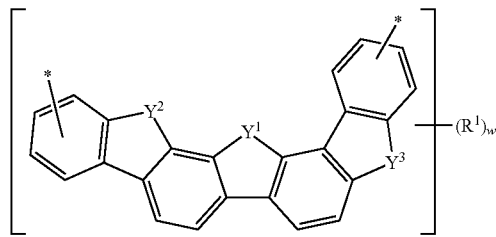 (IB-ee)
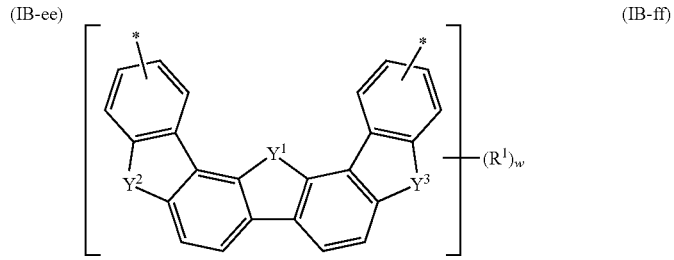 (IB-ff)
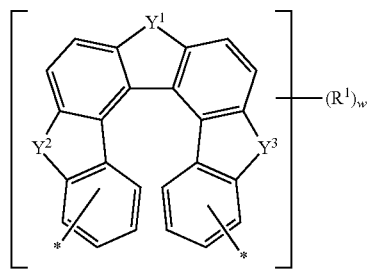 (IB-gg)
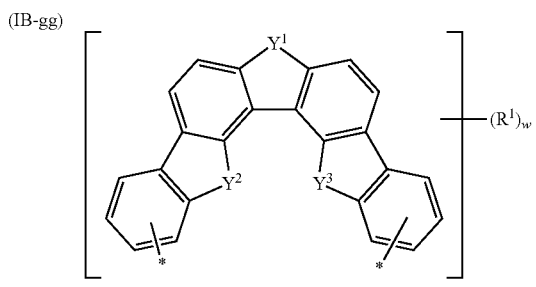 (IB-hh)
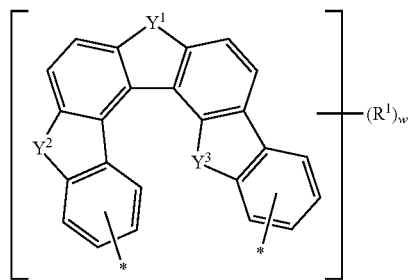 (IB-ii)
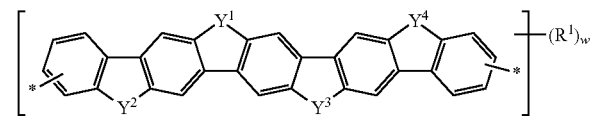 (IB-jj)
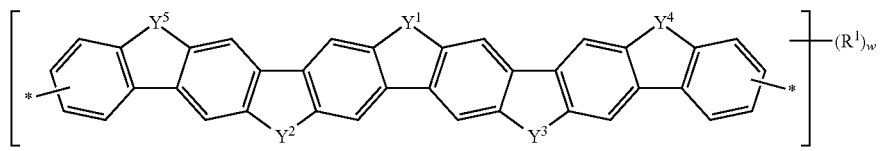 (IB-kk)
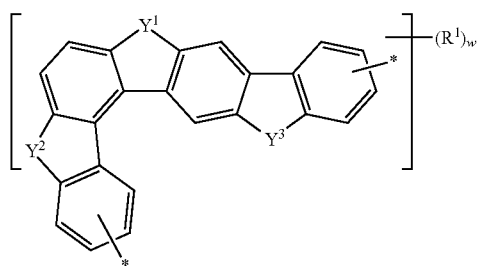 (IB-mm)

where:

$Y^1$ through $Y^5$ are the same or different and are selected from the group consisting of O, S, Se, Te, $NR^2$, $CR^3R^4$, and $SiR^5R^6$, wherein at least one of $Y^1$ through $Y^5$ is different from the other $Y^1$ through $Y^5$ groups;

$R^1$ is the same or different at each occurrence and is selected from the group consisting of D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl deuterated silyl, deuterated siloxane, deuterated siloxy, and deuterated germyl; and w is an integer from 0 to a maximum number of bonding positions available.

4. The compound of claim 1, wherein the Core is selected from the group consisting of Formula IC-a through IC-p

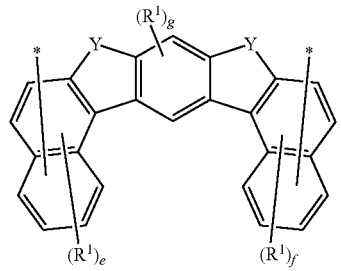
(IC-a)

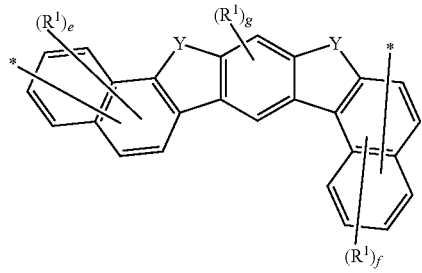
(IC-b)

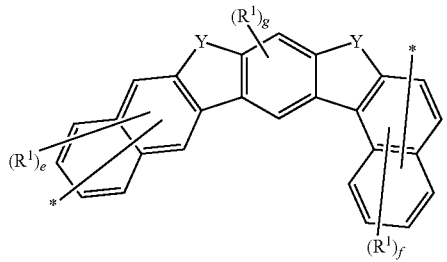
(IC-c)

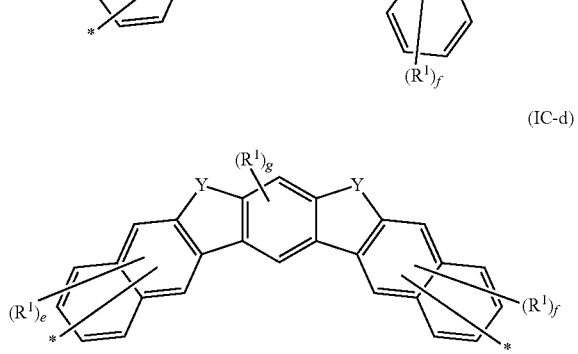
(IC-d)

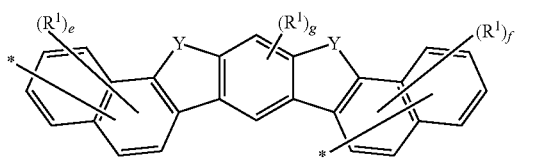
(IC-e)

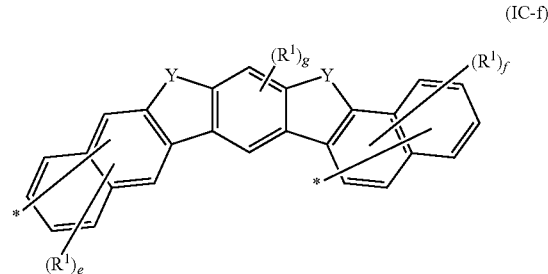
(IC-f)

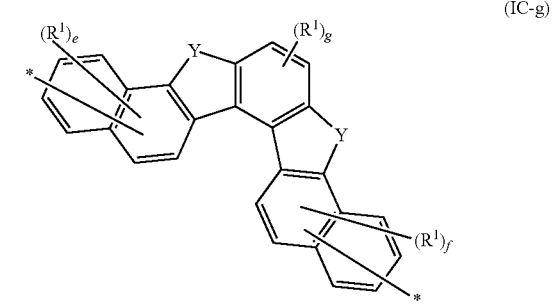
(IC-g)

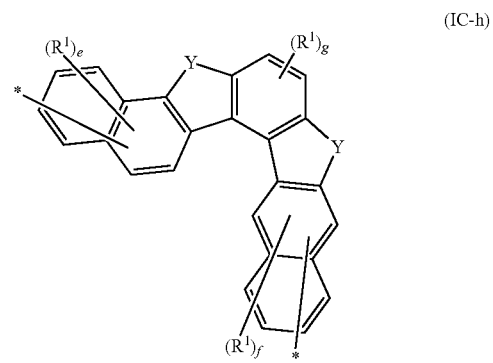
(IC-h)

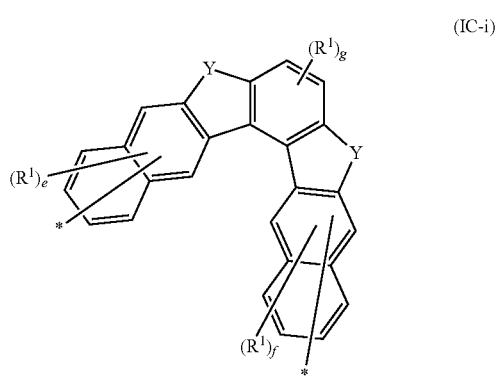
(IC-i)

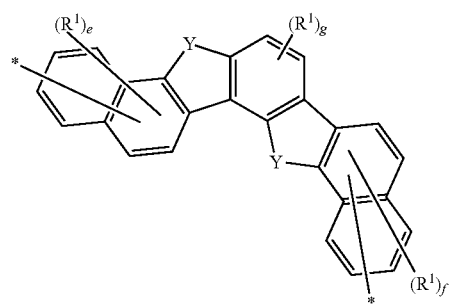
(IC-j)

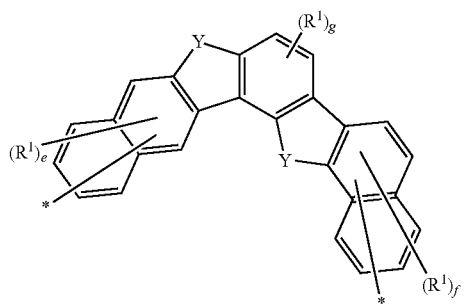
(IC-k)

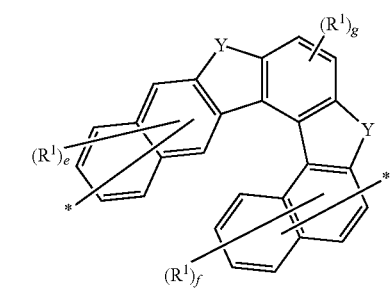
(IC-m)

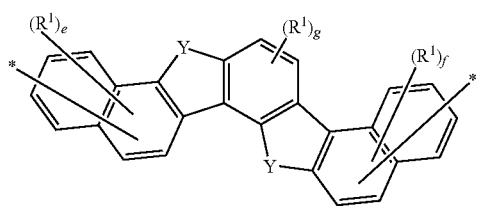
(IC-n)

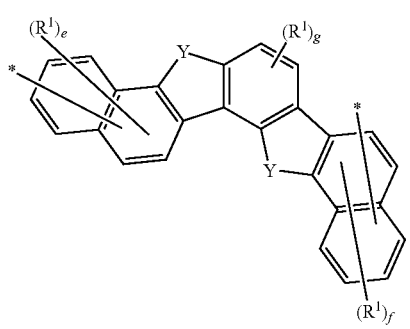
(IC-o)

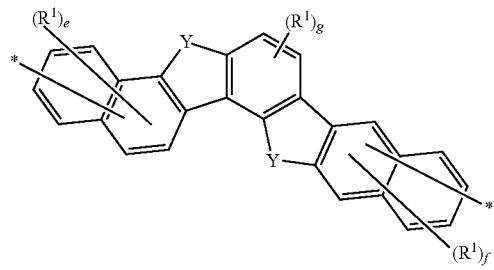
(IC-p)

where:
R$^1$ is the same or different at each occurrence and is selected from the group consisting of D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl deuterated silyl, deuterated siloxane, deuterated siloxy, and deuterated germyl;
e and f are the same or different and are an integer of 0-5; and
g is an integer of 0-2.

5. The compound of claim 4, wherein the Core is selected from the group consisting of Formula IC-a1 and Formula IC-a2

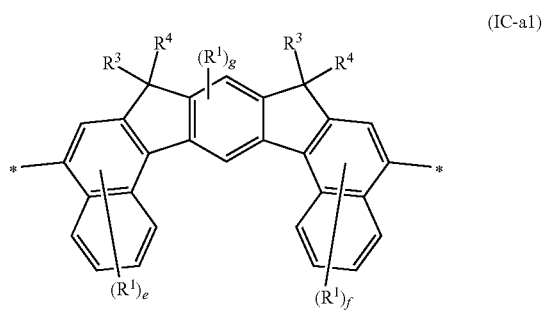
(IC-a1)

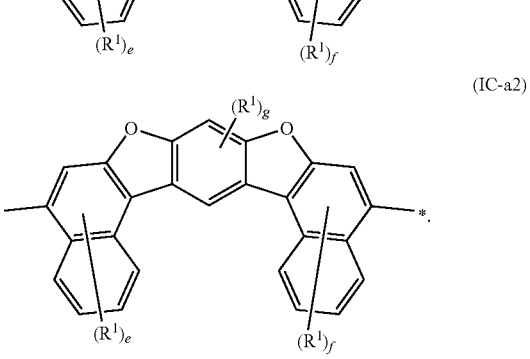
(IC-a2)

6. A compound having Formula II or Formula III

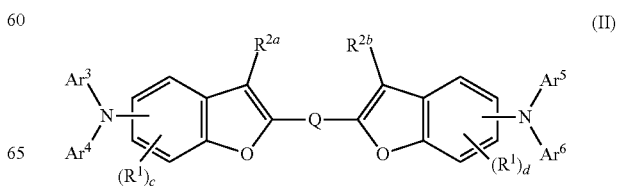
(II)

-continued (III)

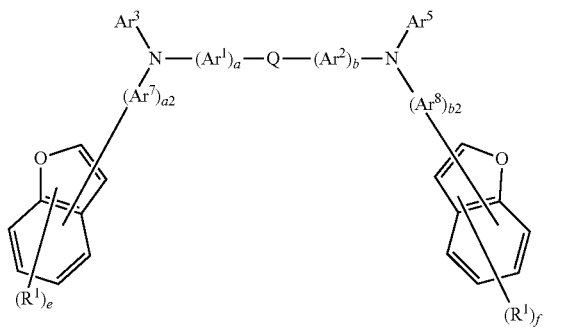

wherein:
Ar$^1$-Ar$^8$ are the same or different and are selected from hydrocarbon aryl groups, heteroaryl groups, and substituted derivatives thereof;
R$^1$ is the same or different at each occurrence and is selected from the group consisting of D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl, deuterated silyl, deuterated siloxane, deuterated siloxy, and deuterated germyl;
R$^{2a}$ and R$^{2b}$ are the same or different and are selected from the group consisting of H, D, F, CN, alkyl, alkoxy, fluoroalkyl, hydrocarbon aryl, aryloxy, heteroaryl, silyl, siloxane, siloxy, germyl, deuterated alkyl, deuterated partially-fluorinated alkyl, deuterated alkoxy, deuterated hydrocarbon aryl, deuterated aryloxy, deuterated heteroaryl, deuterated heteroaryl, deuterated silyl, deuterated siloxane, deuterated siloxy, and deuterated germyl;
Q is selected from the group consisting of naphthodifuran, Formula IA, Formula IB and Formula IC:

wherein:
Y is the same or different at each occurrence and is selected from the group consisting of O, S, Se, Te, NR$^2$, CR$^3$R$^4$, and SiR$^5$R$^6$;
R$^2$ is the same or different at each occurrence and is selected from the group consisting of alkyl, hydrocarbon aryl, heteroaryl, and substituted derivatives thereof;
R$^3$-R$^6$ are the same or different at each occurrence and are selected from the group consisting of alkyl, silyl, germyl, hydrocarbon aryl, heteroaryl, and substituted derivatives thereof, where R$^3$ and R$^4$ and/or R$^5$ and R$^6$ can be joined to form a cyclic group selected from the group consisting of cycloalkyl, silacycloalkyl, spirofluorenyl, silaspirofluorenyl, or a substituted derivative thereof;
a1 and b1 are the same or different and are 0 or 1;
a double dashed line between two rings indicates that the rings are fused together in any orientation;
* indicates a point of attachment in the identified formula;
# and ## represent no bond or a point of attachment in the identified formula, such that when a1=0 then # is a point of attachment, when a1=1 then # is no bond, when b1=0 then ## is a point of attachment, and when b1=1 then ## is no bond;
a, a2, b, and b2 are the same or different and are 0 or 1;
c and d are the same or different and are an integer of 0-3; and
e and f are the same or different and are an integer of 0-5.

7. An organic electronic device comprising a first electrical contact, a second electrical contact and a photoactive layer therebetween, wherein the photoactive layer comprises a compound according to claim 1.

8. The compound of claim 1, wherein the compound is any one selected from the group consisting of (IA)

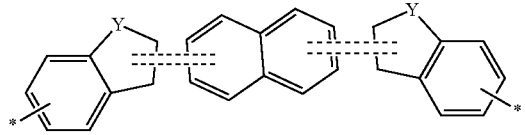

(IB)

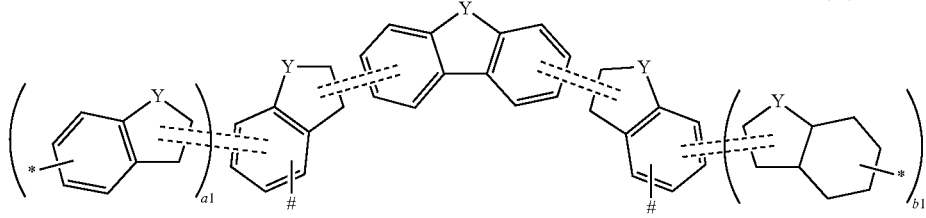

(IC)

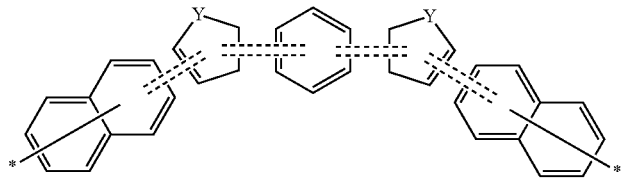

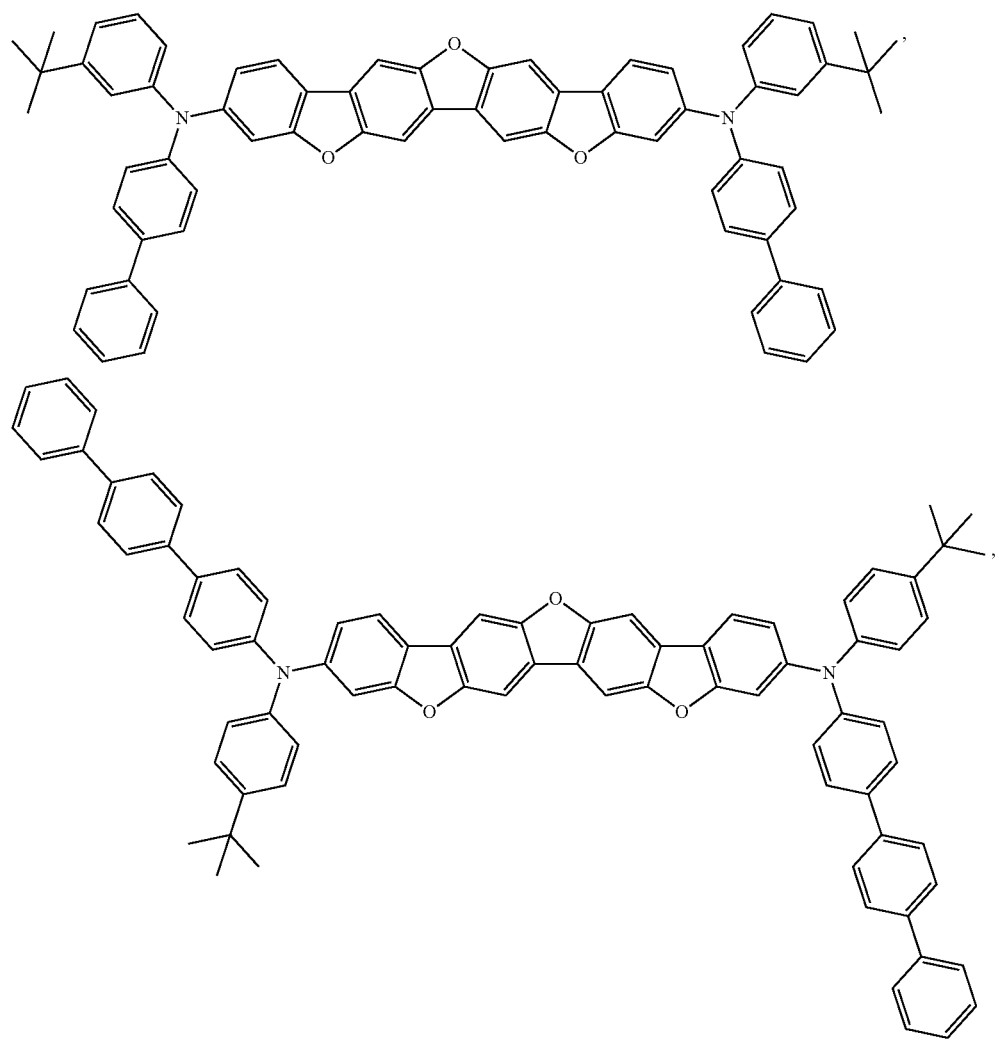
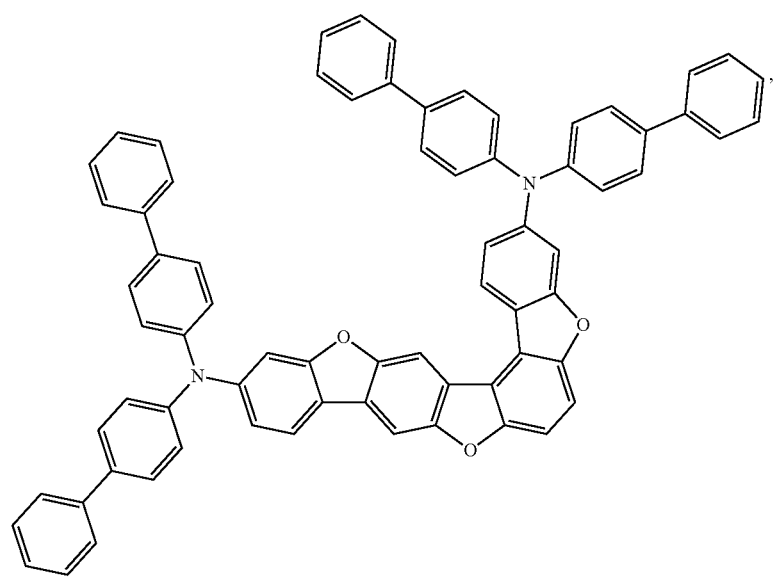

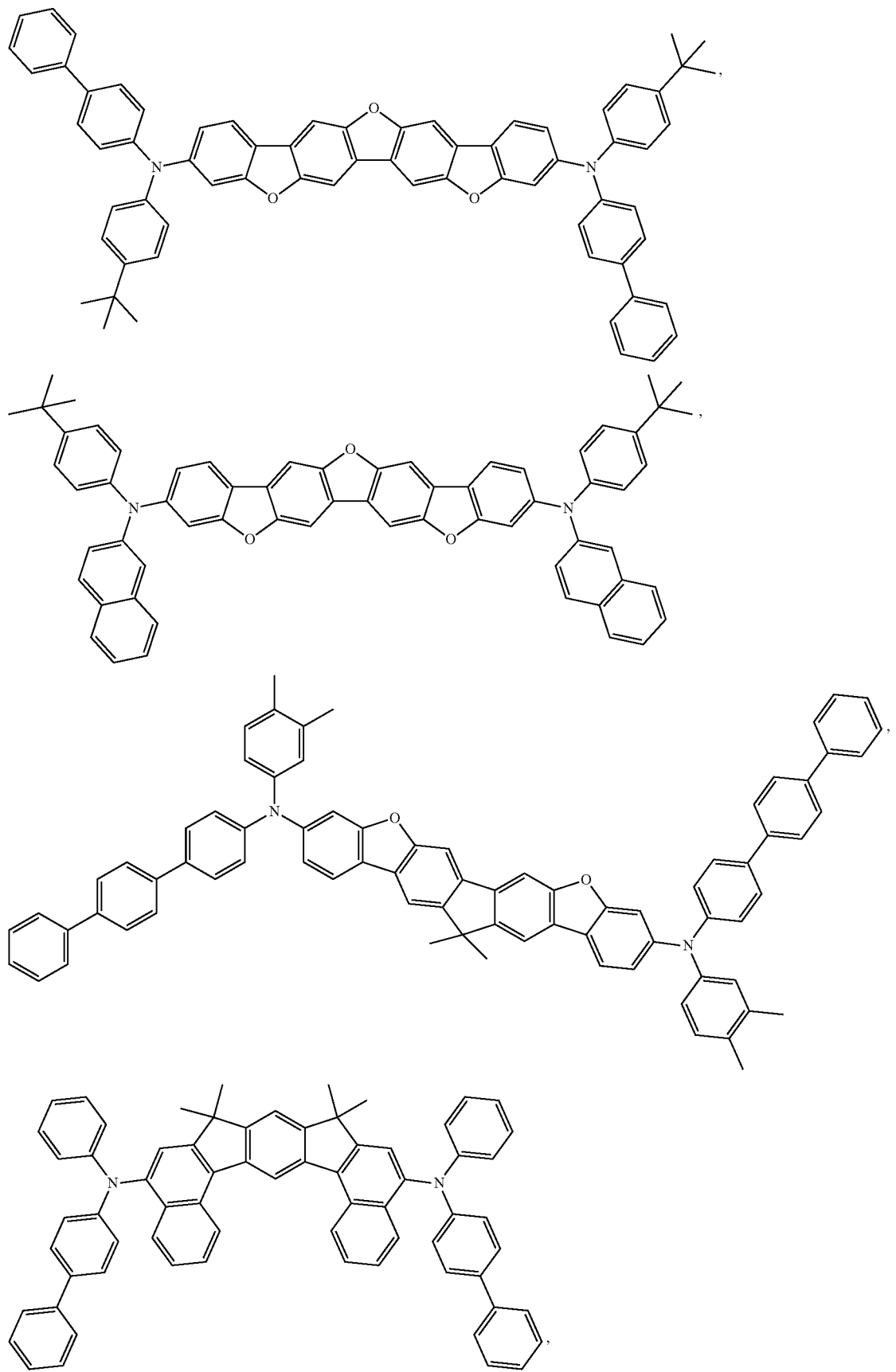

-continued
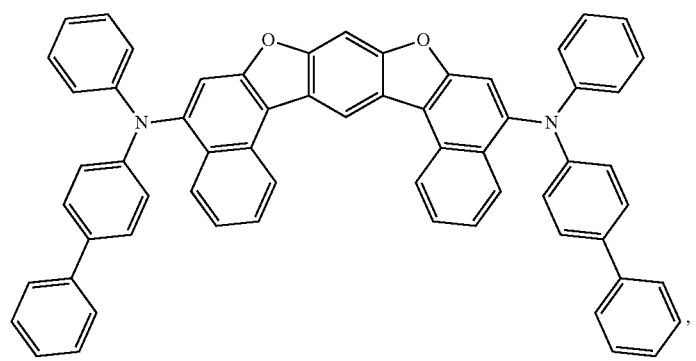
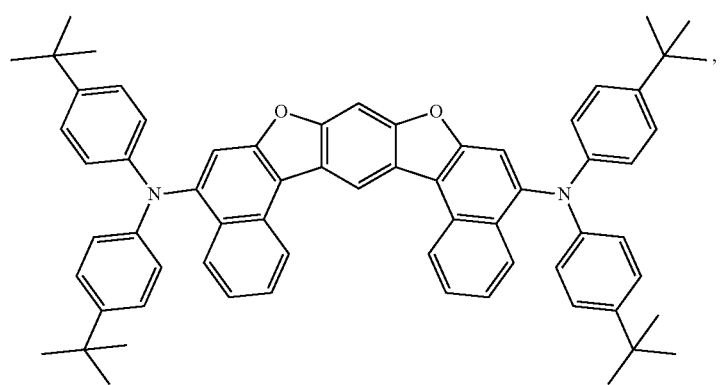
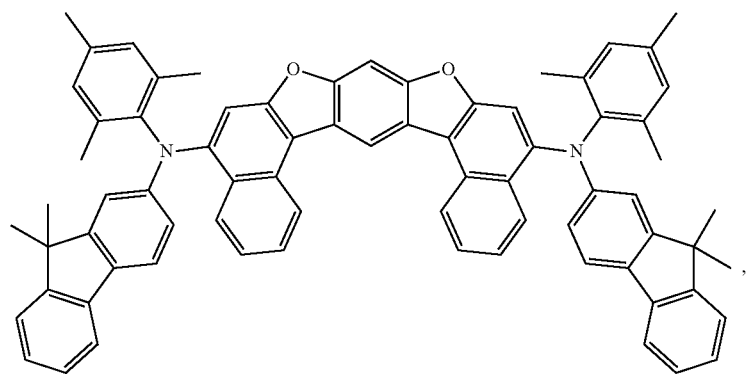
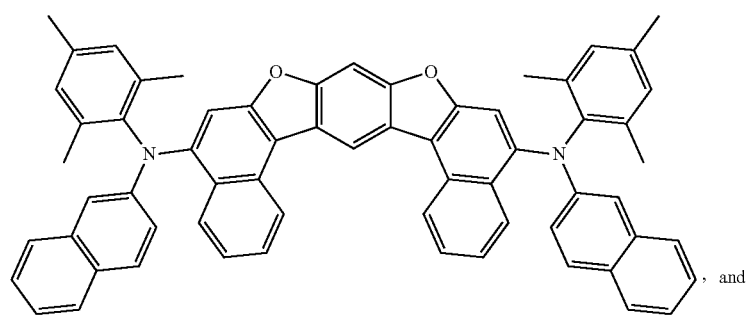
, and

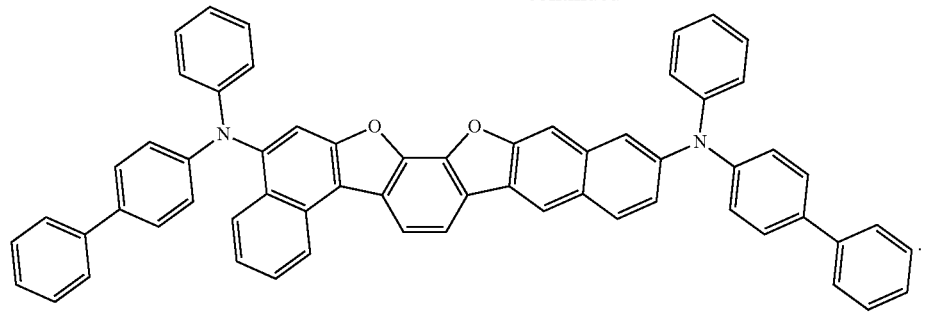
9. The compound of claim 8, wherein the compound is any one selected from the group consisting of
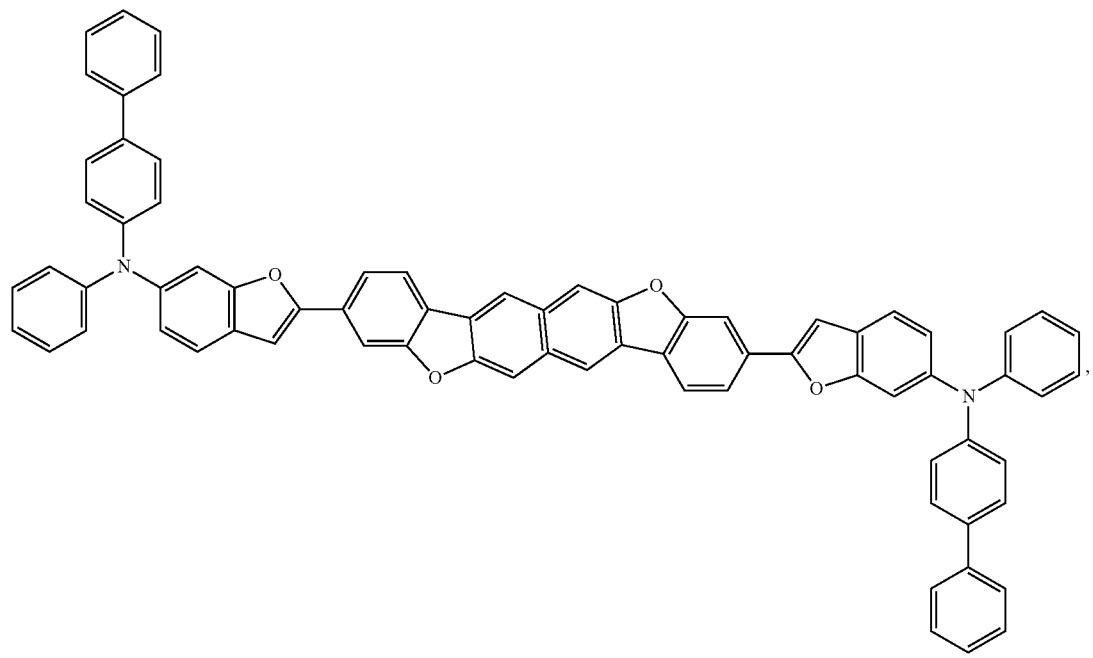
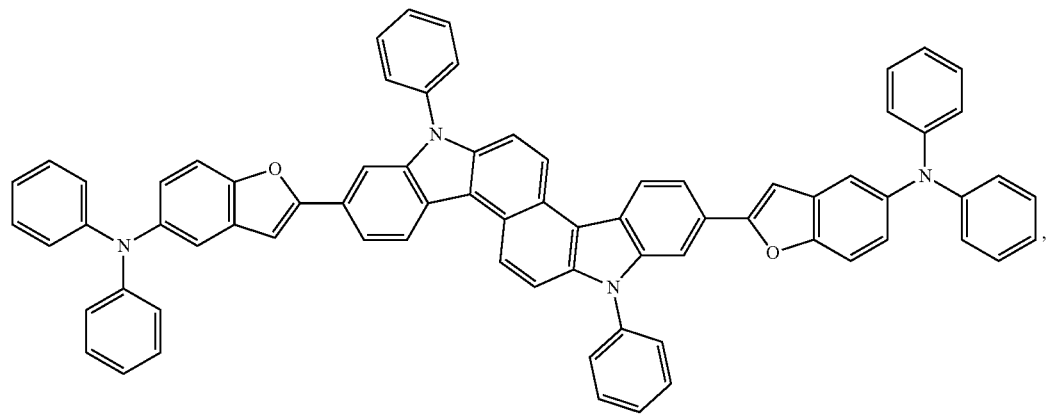

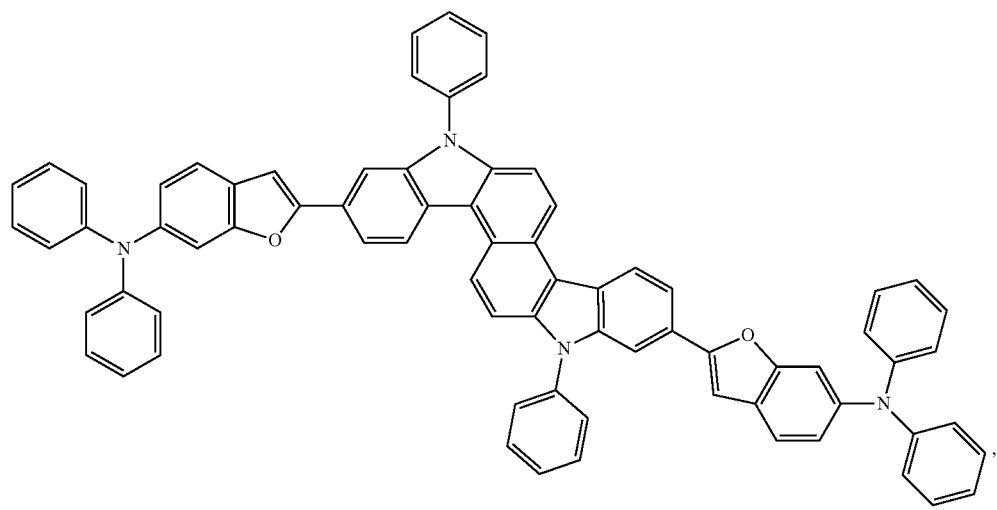
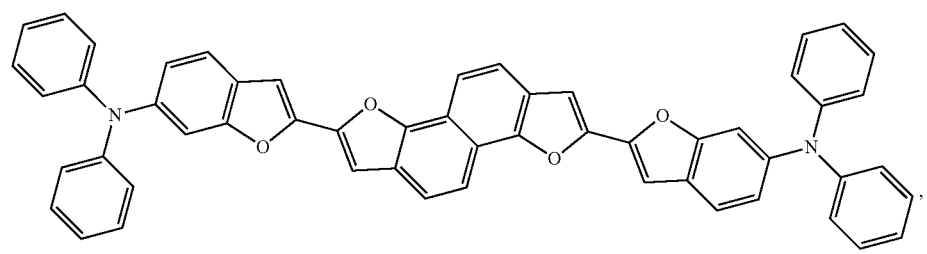
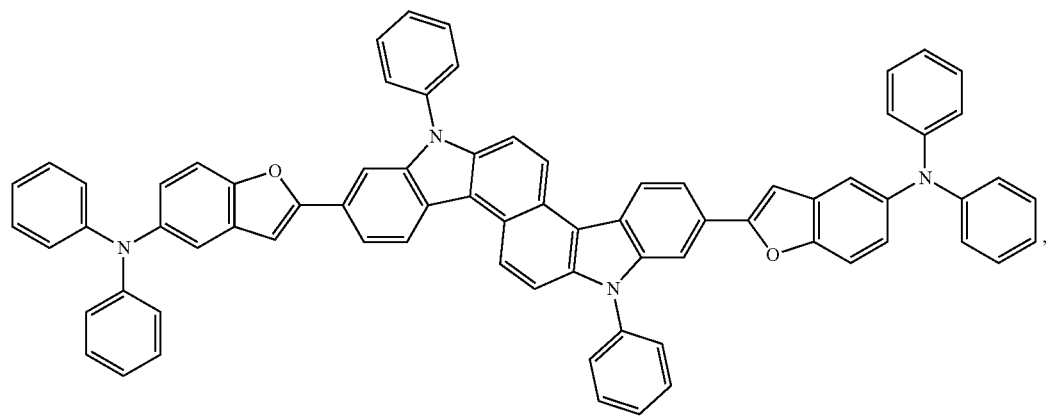
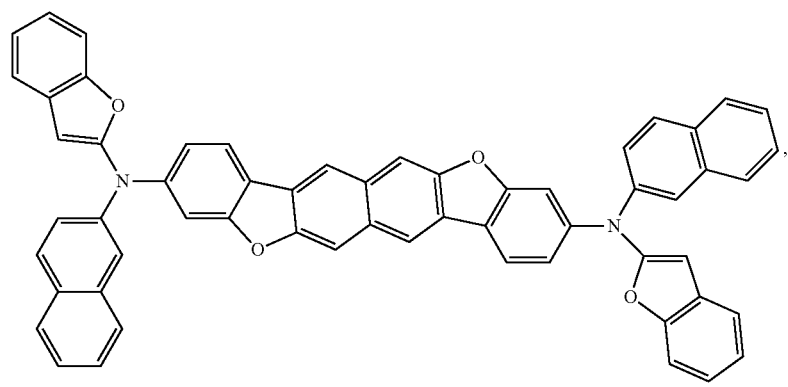

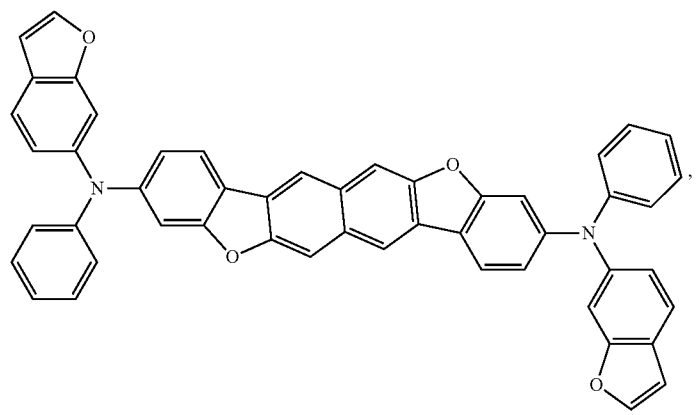
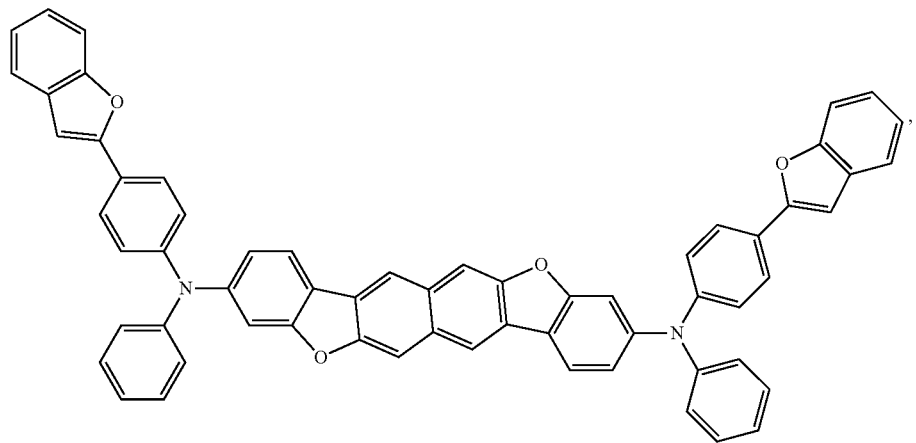
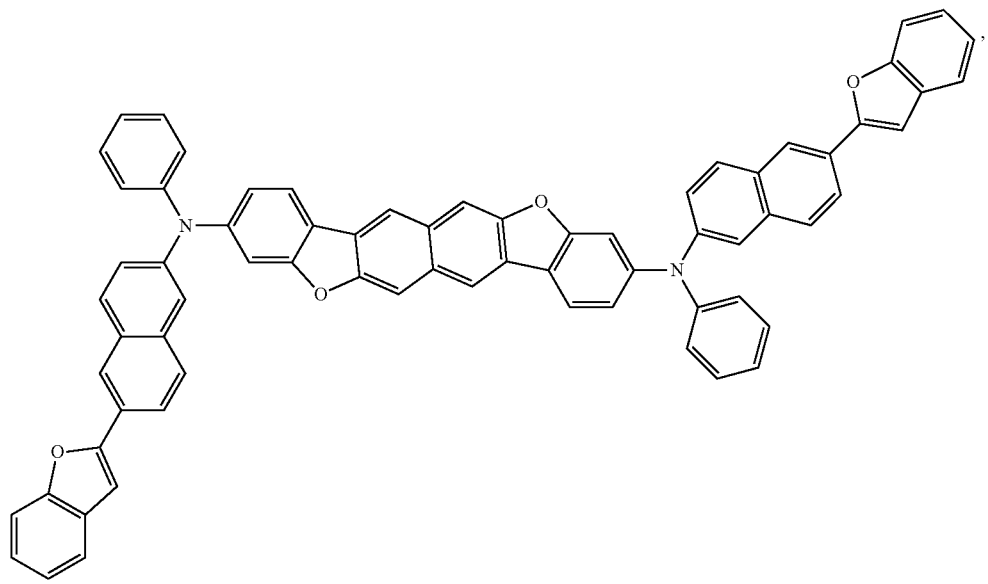

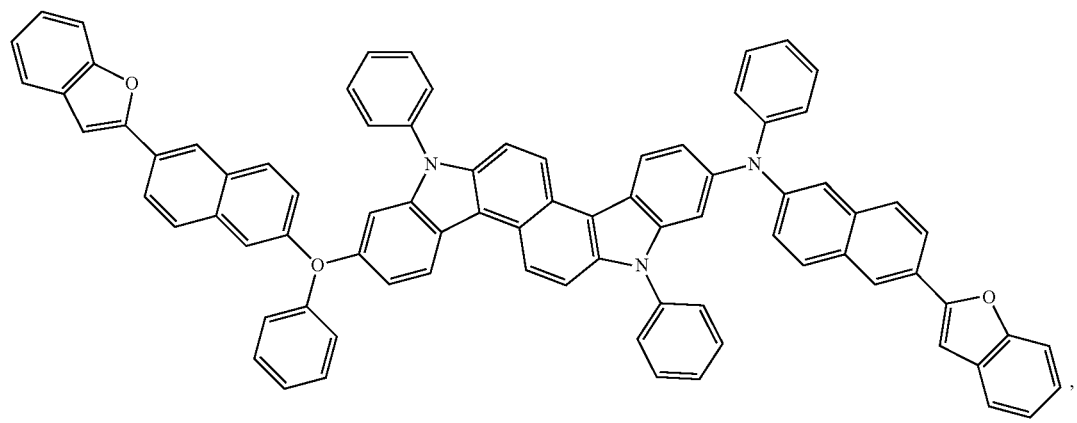
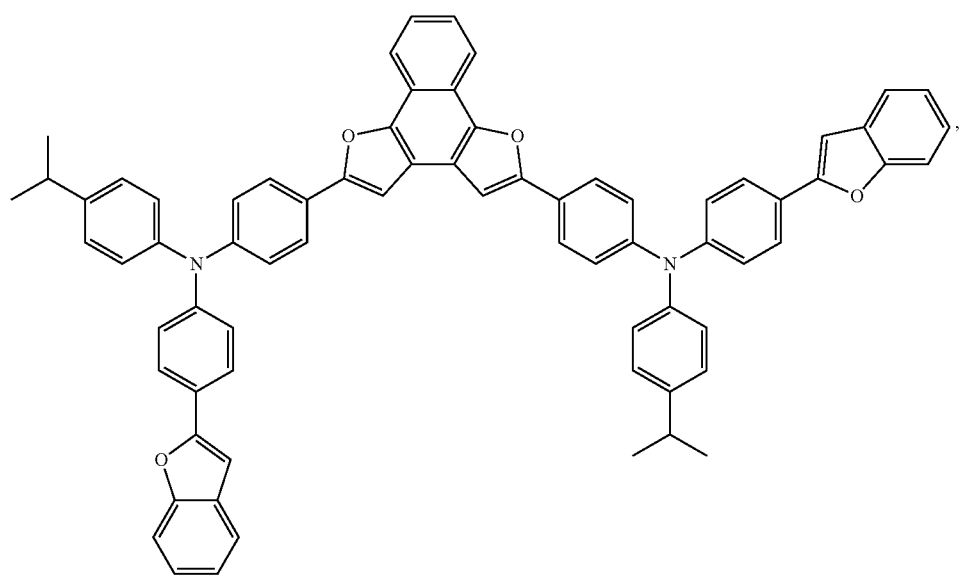
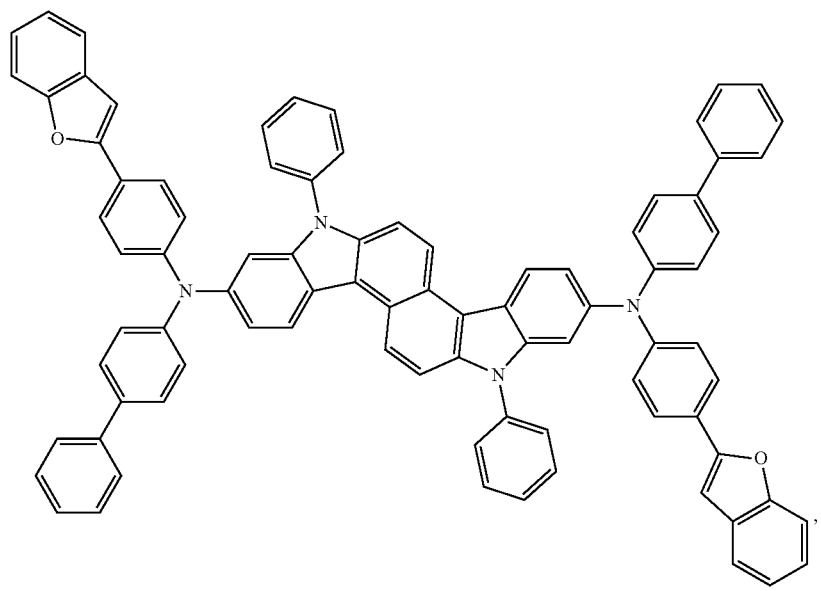

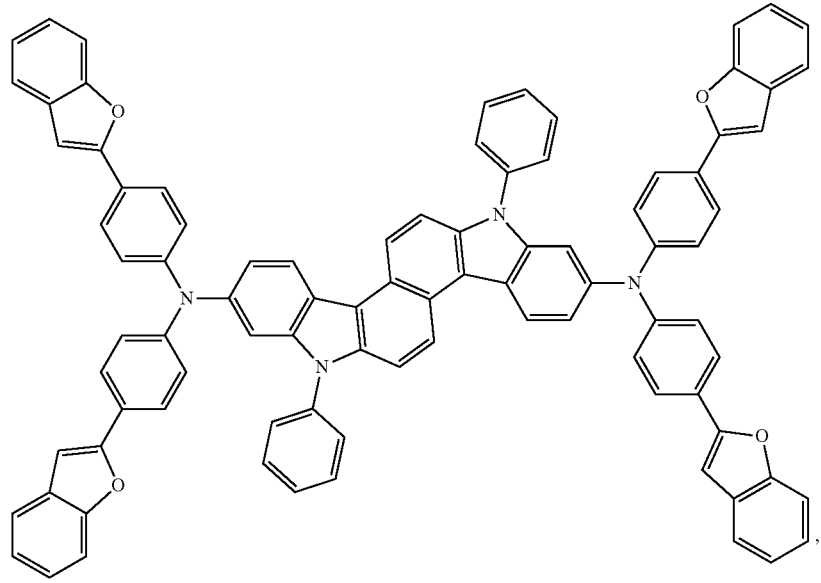
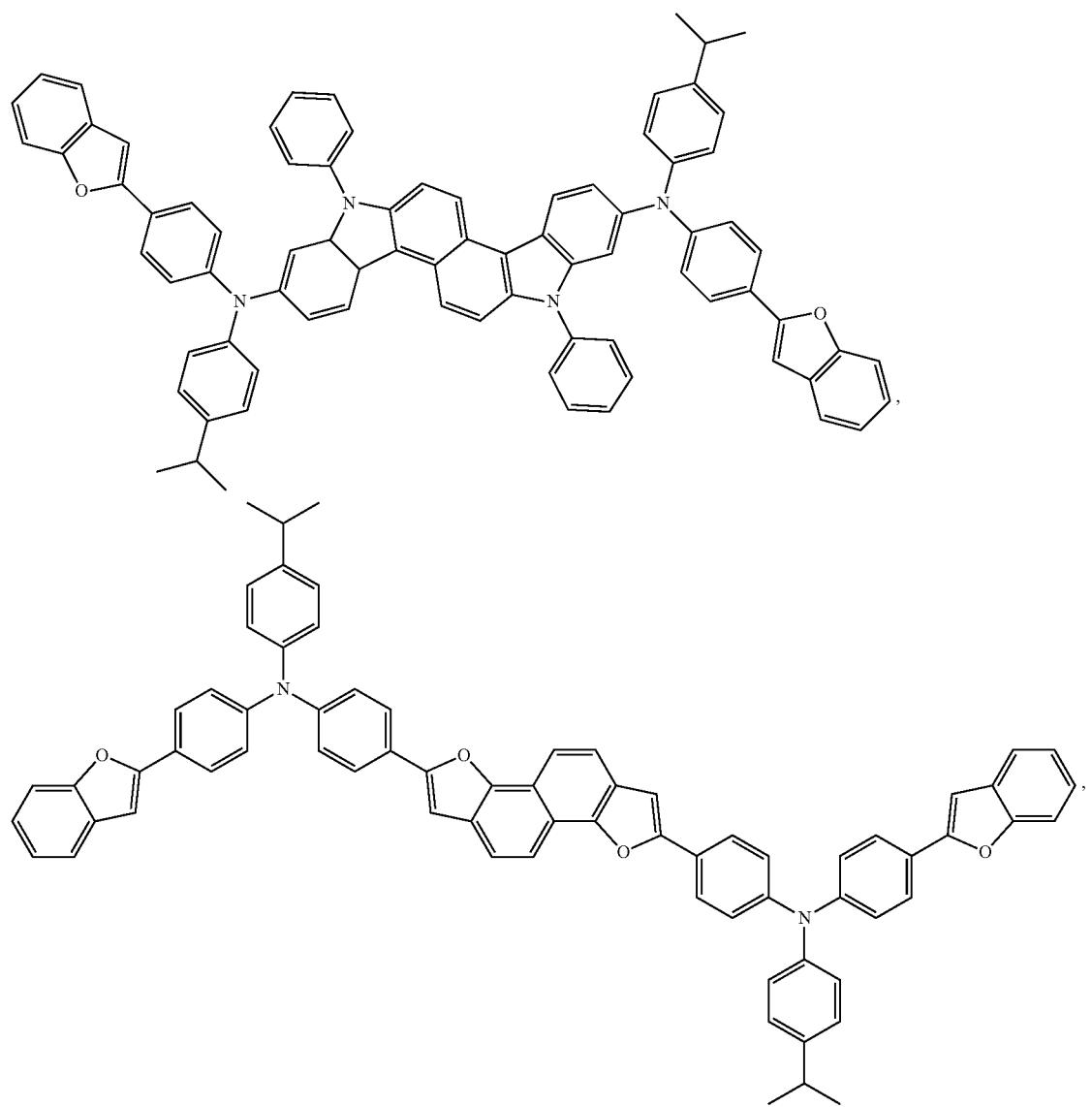

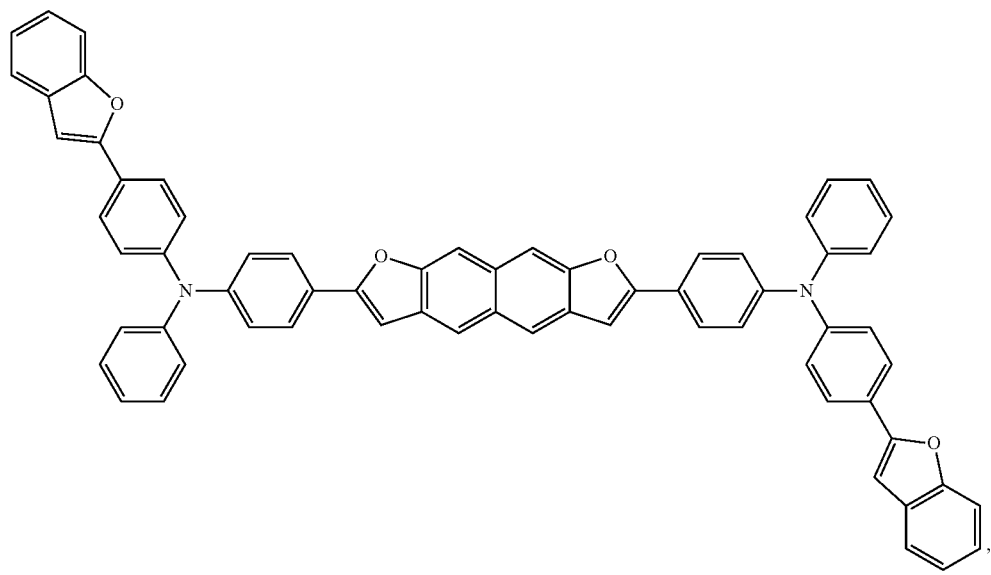
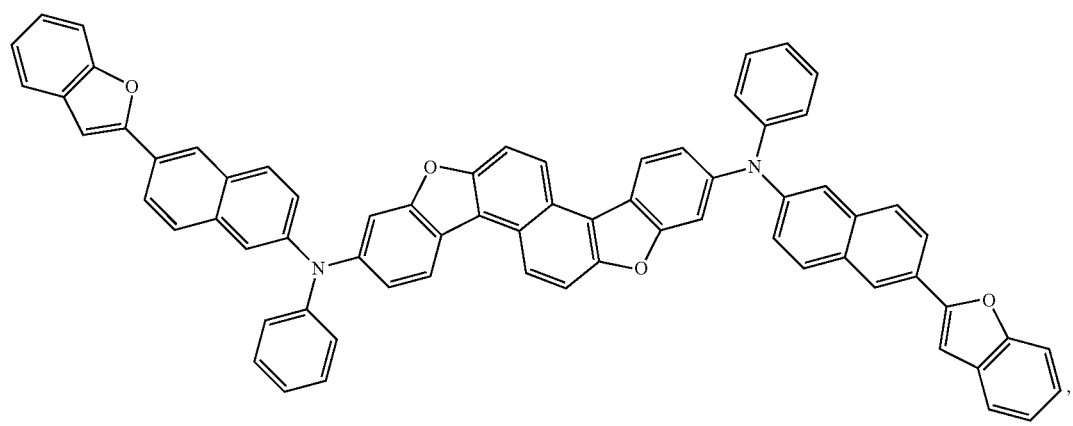
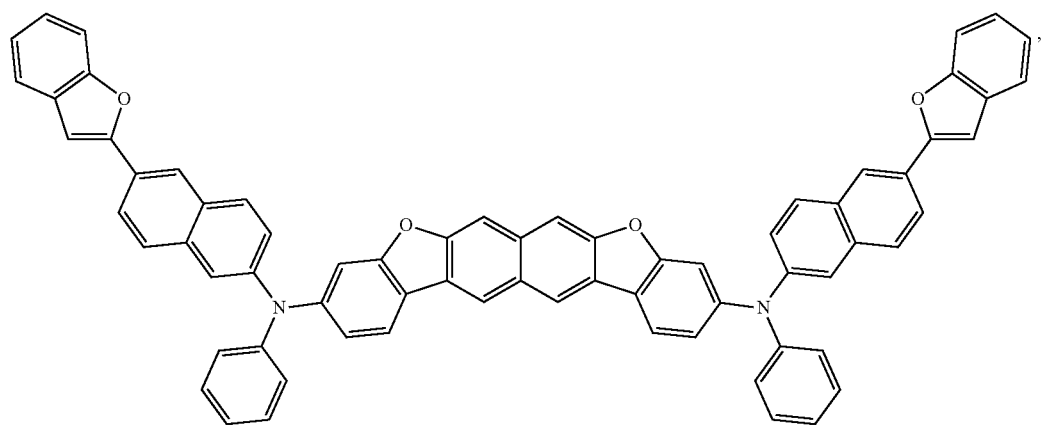

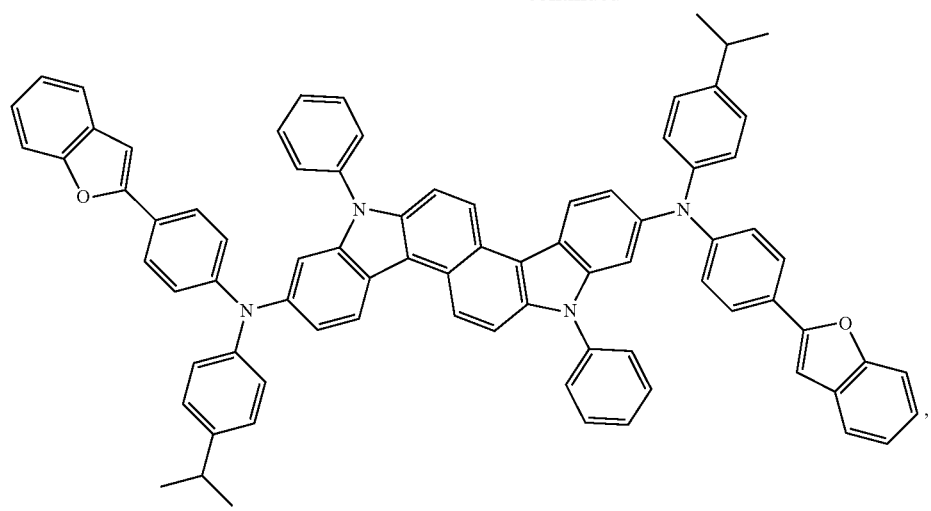
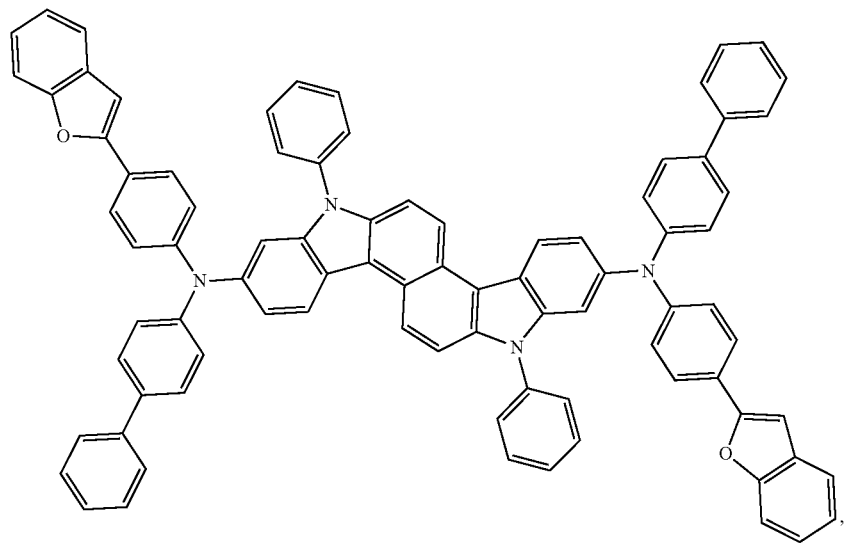
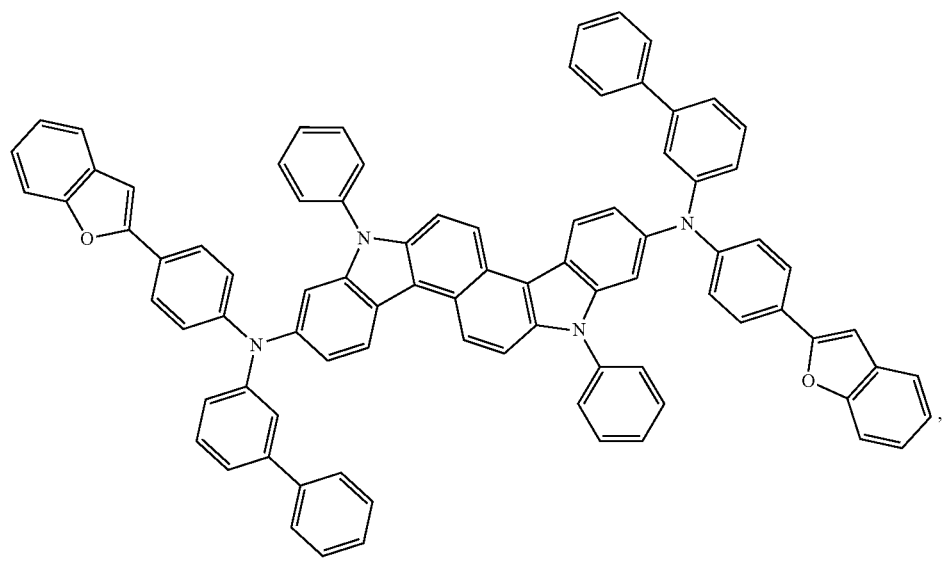

-continued
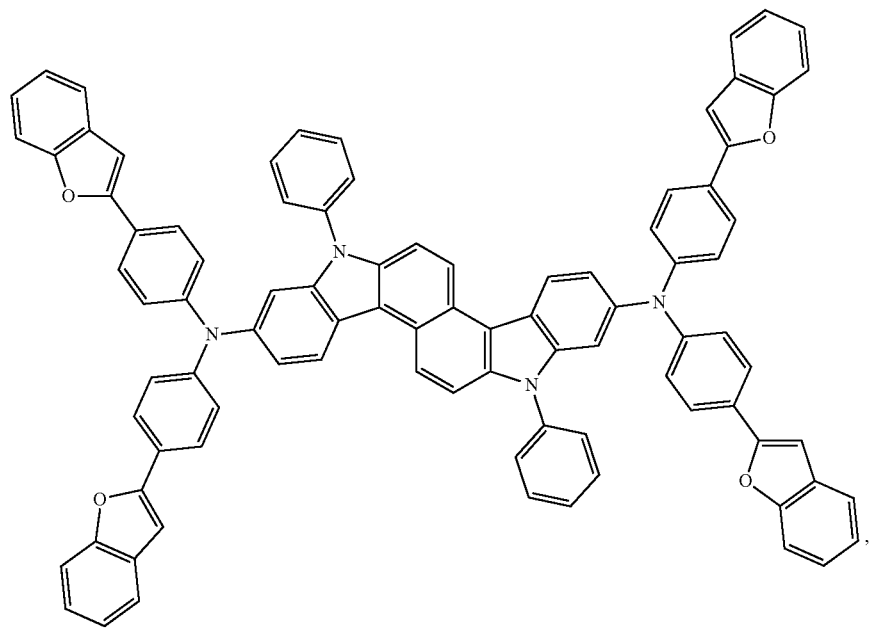
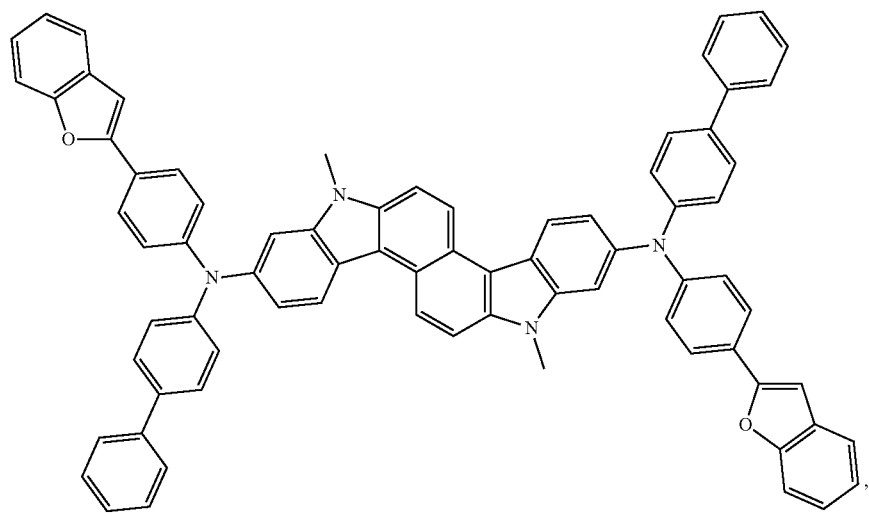
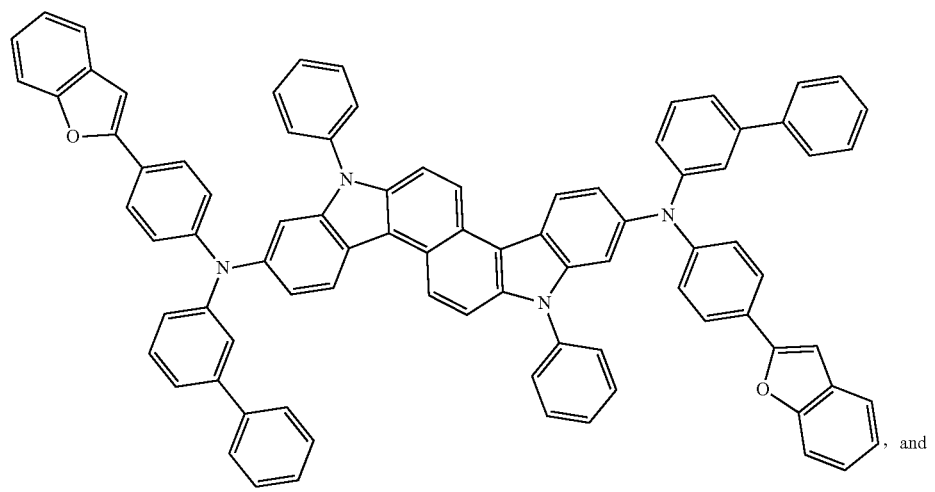
, and